United States Patent
Lee et al.

(10) Patent No.: US 11,088,330 B2
(45) Date of Patent: Aug. 10, 2021

(54) COMPOUND FOR ORGANIC ELECTRONIC ELEMENT, ORGANIC ELECTRONIC ELEMENT USING SAME, AND ELECTRONIC DEVICE COMPRISING SAME

(71) Applicant: DUK SAN NEOLUX CO., LTD, Cheonan-si (KR)

(72) Inventors: Yun Suk Lee, Seoul (KR); Seul-gi Kim, Daejeon (KR); Dae Sung Kim, Yongin-si (KR); Ki Ho So, Cheonan-si (KR); Dae Hwan Oh, Cheonan-si (KR); Jin Ho Yun, Cheonan-si (KR); Bum Sung Lee, Cheonan-si (KR); Seong Je Park, Busan (KR)

(73) Assignee: Duk San Neolux Co., Ltd

( * ) Notice: Subject to any disclaimer, the term of this patent is extended or adjusted under 35 U.S.C. 154(b) by 0 days.

(21) Appl. No.: 16/261,050

(22) Filed: Jan. 29, 2019

(65) Prior Publication Data
US 2019/0157560 A1    May 23, 2019

Related U.S. Application Data

(63) Continuation of application No. 15/323,052, filed as application No. PCT/KR2015/006784 on Jul. 1, 2015, now Pat. No. 10,297,758.

(30) Foreign Application Priority Data

Jul. 3, 2014    (KR) .................. 10-2014-0083017

(51) Int. Cl.
*H01L 51/50* (2006.01)
*H01L 51/00* (2006.01)
(Continued)

(52) U.S. Cl.
CPC .......... *H01L 51/006* (2013.01); *C07D 221/18* (2013.01); *C07D 401/04* (2013.01); *C07D 401/10* (2013.01); *C07D 401/12* (2013.01); *C07D 401/14* (2013.01); *C07D 405/04* (2013.01); *C07D 405/12* (2013.01);
(Continued)

(58) Field of Classification Search
None
See application file for complete search history.

(56) References Cited

U.S. PATENT DOCUMENTS 8,674,141 B2    3/2014  Stoessel et al.
2009/0134384 A1  5/2009  Stoessel et al.
(Continued)

FOREIGN PATENT DOCUMENTS

CN    103589420 A        2/2014
CN    103589421 A    *   2/2014    ............. C09K 11/06
(Continued)

OTHER PUBLICATIONS

International Search Report and Written Opinion for PCT/KR2015/006784, dated Jun. 23, 2016; ISA/KR.

*Primary Examiner* — Gregory D Clark
(74) *Attorney, Agent, or Firm* — Harness, Dickey & Pierce, P.L.C.

(57) ABSTRACT

The purpose of the present invention is to provide a compound that can improve the lifespan, low drive voltage and high luminous efficiency of an element, an organic electronic element using same, and an electronic device comprising same.

8 Claims, 1 Drawing Sheet

(51) Int. Cl.

| | | |
|---|---|---|
| *C07D 401/10* | (2006.01) | |
| *C09K 11/06* | (2006.01) | |
| *C07D 401/12* | (2006.01) | |
| *C07D 405/04* | (2006.01) | |
| *C07D 405/12* | (2006.01) | |
| *C07D 221/18* | (2006.01) | |
| *C07D 401/04* | (2006.01) | |
| *C07D 401/14* | (2006.01) | |
| *C07D 409/04* | (2006.01) | |
| *C07D 409/12* | (2006.01) | |
| *C07D 409/14* | (2006.01) | |

(52) U.S. Cl.
CPC ......... *C07D 409/04* (2013.01); *C07D 409/12* (2013.01); *C07D 409/14* (2013.01); *C09K 11/06* (2013.01); *H01L 51/0054* (2013.01); *H01L 51/0059* (2013.01); *H01L 51/0061* (2013.01); *H01L 51/0073* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1092* (2013.01); *H01L 51/0052* (2013.01); *H01L 51/0058* (2013.01); *H01L 51/0067* (2013.01); *H01L 51/0072* (2013.01); *H01L 51/0074* (2013.01); *H01L 51/5012* (2013.01); *H01L 51/5056* (2013.01); *Y02E 10/549* (2013.01)

(56) References Cited

U.S. PATENT DOCUMENTS

| | | | |
|---|---|---|---|
| 2013/0278147 A1* | 10/2013 | Vetsuypens | ....... G02F 1/133602 315/151 |
| 2013/0334518 A1 | 12/2013 | Park et al. | |
| 2014/0027747 A1 | 1/2014 | Mun et al. | |
| 2015/0048323 A1* | 2/2015 | Kim | .................... H01L 51/0072 257/40 |
| 2015/0069350 A1* | 3/2015 | Kim | ...................... C09K 11/06 257/40 |
| 2015/0322091 A1 | 11/2015 | Stoessel et al. | |

FOREIGN PATENT DOCUMENTS

| | | |
|---|---|---|
| CN | 103589421 A | 2/2014 |
| KR | 1020080012337 A | 2/2008 |
| KR | 1020110006915 A | 1/2011 |
| KR | 1020120081539 A | 7/2012 |

* cited by examiner

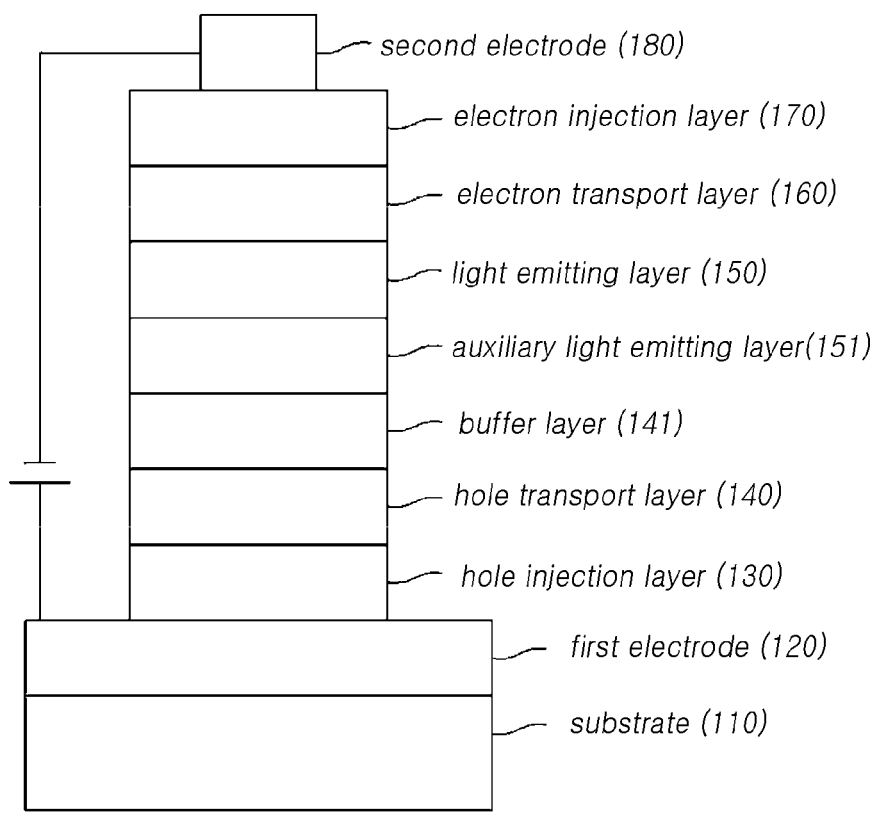

COMPOUND FOR ORGANIC ELECTRONIC ELEMENT, ORGANIC ELECTRONIC ELEMENT USING SAME, AND ELECTRONIC DEVICE COMPRISING SAME

CROSS-REFERENCE TO RELATED APPLICATIONS

This application is a continuation of U.S. patent application Ser. No. 15/323,052, filed on Dec. 29, 2016, which is a 371 U.S. National Stage of International Application No. PCT/KR2015/006784, filed on Jul. 1, 2015. This application also claims priority to Korean Application No. 10-2014-0083017, filed on Jul. 3, 2014. The entire disclosures of the above applications are incorporated herein by reference.

TECHNICAL FIELD

The present invention relates to a compound for an organic electronic element, an organic electronic element using the same, and an electronic device comprising the same.

BACKGROUND ART

In general, an organic light emitting phenomenon refers to a phenomenon in which electric energy is converted into light energy of an organic material using an organic material. An organic electronic element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electronic element, and for example, may include a hole injection layer, a hole transport layer, a light emitting layer, an electron transport layer, an electron injection layer, or the like.

A material used as an organic material layer in an organic electronic element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

When only one material is used as a light emitting material, there occur problems of shift of a maximum luminescence wavelength to a longer wavelength due to intermolecular interactions and lowering of the efficiency of a corresponding element due to the deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as the size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

That is, in order to allow the organic electronic element to sufficiently exhibit excellent characteristics, most of all, materials constituting an organic material layer in the element, for examples, a hole injection material, a hole transport material, a light emitting material, an electron transport material, an electron injection material, and the like need to be supported by stable and efficient materials, but the development of stable and efficient materials for the organic material layer for an organic electronic element is not sufficiently achieved. Therefore, the development of new materials is continuously required, and especially, the development of an electron transport material and a light emitting material is urgently required.

DETAILED DESCRIPTION OF THE INVENTION

Technical Problem

In order to solve the above-mentioned problems occurring in the prior art, an object of the present invention is to provide a compound capable of achieving high luminous efficiency, a low driving voltage, and an improved lifespan of an element, an organic electronic element using the same, and an electronic device comprising the same.

Technical Solution

In accordance with an aspect of the present invention, there is provided a compound represented by the following formula.

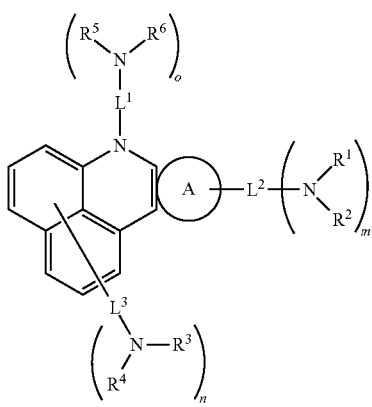

In another aspect of the present invention, there are provided an organic electronic element using the compound represented by the above formula, and an electronic device comprising the same.

Advantageous Effects

The use of the compound according to the present invention can achieve high luminous efficiency and a low driving voltage of an element and significantly improving an improved lifespan of an element.

BRIEF DESCRIPTION OF THE DRAWING

The FIGURE illustrates an example of an organic light emitting diode according to the present invention.

MODE FOR CARRYING OUT THE INVENTION

Hereinafter, some embodiments of the present invention will be described in detail with reference to the accompanying illustrative drawings.

In designation of reference numerals to components in respective drawings, it should be noted that the same elements would be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b), or the like may be used herein when describing components of the present invention. Each of these terminologies is not used to define an essence, order, or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine (F), bromine (Br), chlorine (Cl), and iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl group" or "halogen alkyl group" as used herein means an alkyl group substituted with halogen.

The term "heteroalkyl group" as used herein means an alkyl group of which at least one of carbon atoms is substituted with a hetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an alkyl group to which oxygen radical is attached, but not limited to, and, unless otherwise stated, has 1 to 60 carbon atoms.

The term "alkenoxyl group", "alkenoxy group", "alkenyloxyl group", or "alkenyloxy group" as used herein means an alkenyl group to which oxygen radical is attached, but not limited to, and, unless otherwise stated, has 2 to 60 carbon atoms.

The term "aryloxyl group" or "aryloxy group" as used herein means an aryl group to which oxygen radical is attached to, but not limited to, and has 6 to 60 carbon atoms.

Unless otherwise stated, the terms "aryl group" and "arylene group" each have 6 to 60 carbon atoms, but not limited thereto. The aryl group or arylene group herein means a monocyclic or polycyclic aromatic group, and includes an aromatic ring that is formed in conjunction with an adjacent substituent linked thereto or participating in the reaction. Examples of the aryl group may include a phenyl group, a biphenylyl group, a terphenylyl group, a naphthyl group, an anthracenyl group, a fluorene group, a spirofluorene group, and a spirobifluorene group.

The prefix "aryl" or "ar" means a radical substituted with an aryl group. For example, an arylalkyl group may be an alkyl group substituted with an aryl group, and an arylalkenyl group may be an alkenyl group substituted with an aryl group, and a radical substituted with an aryl group has a number of carbon atoms defined as herein.

Also, when prefixes are named subsequently, it means that substituents are listed in the order described first. For example, an arylalkoxy group means an alkoxy group substituted with an aryl group, an alkoxylcarbonyl group means a carbonyl group substituted with an alkoxyl group, and an arylcarbonylalkenyl group also means an alkenyl group substituted with an arylcarbonyl group, wherein the arylcarbonyl group may be a carbonyl group substituted with an aryl group.

Unless otherwise stated, the term "heteroalkyl" as used herein means alkyl containing one or more heteroatoms. Unless otherwise stated, the term "heteroaryl group" or "heteroarylene group" as used herein means, but not limited to, an aryl or arylene group having 2 to 60 carbon atoms and containing one or more heteroatoms, includes at least one of monocyclic and polycyclic rings, and may also be formed in conjunction with an adjacent group.

Unless otherwise stated, the term "heterocyclic group" as used herein contains one or more heteroatoms, has 2 to 60 carbon atoms, includes at least one of homocyclic and heterocyclic rings, and may also be formed in conjunction with an adjacent group.

Unless otherwise stated, the term "heteroatom" as used herein represents N, O, S, P, or Si.

In addition, the "heterocyclic group" also may include a ring containing SO2 instead of carbon forming the ring. For examples, the "heterocyclic group" includes the following compound.

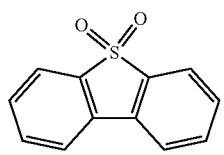 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the formulas used in the present invention are defined as in the index definition of the substituent of the following Formula.

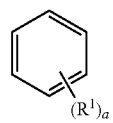

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$'s may be the same and different, and are linked to the benzene ring as follows. When a is an integer of 4 to 6, the substituents $R^1$'s may be the same and different, and are linked to the benzene ring in a similar manner to that when a is an integer of 2 or 3, hydrogen atoms linked to carbon constituents of the benzene ring being not represented as usual.

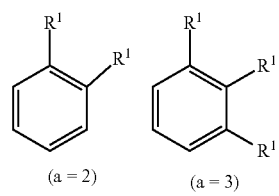

The FIGURE illustrates an organic electronic element according to an embodiment of the present invention.

Referring to the FIGURE, an organic electronic element 100 according to an embodiment of the present invention includes a first electrode 120 formed on a substrate 110, a second electrode 180, and an organic material layer between the first electrode 120 and the second electrode 180, which contains the compound of the present invention. Here, the first electrode 120 may be an anode (positive electrode), and the second electrode 180 may be a cathode (negative electrode). In the case of an inverted organic electronic element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an auxiliary light emitting layer 151, a buffer layer 141, etc., and the electron transport layer 160 and the like may serve as the hole blocking layer.

Although not shown, the organic electronic element according to an embodiment of the present invention may further include a protective layer or a light efficiency improving layer (capping layer) formed on at least one of the sides the first and second electrodes, which is a side opposite to the organic material layer.

The compound of the present invention employed in the organic material layer may be used as a host material, a dopant material, or a light efficiency layer material in the hole injection layer 130, the hole transport layer 140, the electron transport layer 160, the electron injection layer 170, the auxiliary light emitting layer 151, or the light emitting layer 150. Preferably, the compound of the present invention may be used for the hole transport layer 140 and the auxiliary light emitting layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

Accordingly, in the present invention, energy levels and T1 values and inherent material properties (mobility, interfacial properties, etc.), and the like among the respective layers included in the organic material layer are optimized by forming a hole transport layer and an auxiliary light emitting layer using the compound represented by formula 1, and thus the life span and efficiency of the organic electronic element can be improved at the same time.

An organic light emitting diode according to an embodiment of the present invention may be manufactured using a physical vapor deposition (PVD) method. For example, the organic electronic element may be manufactured by depositing a metal, a metal oxide having conviducive, or an alloy thereof, on the substrate to form the anode 120, forming the organic material layer including the hole injection layer 130, the hole transport layer 140, the auxiliary light emitting layer 151, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electronic element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a color conversion material (CCM) structure in which electroluminescence from a blue (B) organic light emitting layer, and photoluminescence from an inorganic luminescent using the electroluminescence are combined. The present invention is applicable to these WOLEDs.

Further, the organic electronic element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electronic element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

<Formula 1>

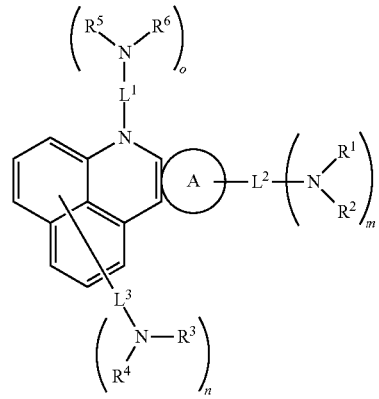

In Formula 1, ring A is a $C_6$-$C_{60}$ monocyclic or polycyclic ring. In other words, ring A may be a monocyclic or polycyclic ring bound with *1 and *2 of

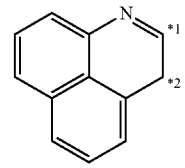 [SMILES: C1=Nc2cccc3cccc(c23)C1]

in Formula 1. In this regard, Formulas 2 to 5 may be referred to.

$R^1$ to $R^6$ may be the same or different from each other, and may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_3$-$C_{60}$ aliphatic group and a $C_6$*$C_{60}$ aromatic group, a $C_1$-$C_{50}$ alkyl group, a $C_2$-$C_{20}$ alkenyl group, a $C_2$-$C_{20}$ alkynyl group, $C_1$-$C_{30}$ alkoxyl group, a $C_6$-$C_{30}$ aryloxy group, and -L'-N($R_a$) ($R_b$). For example, $R^1$ to $R^6$ may be each independently a phenyl group, a naphthyl group, a biphenyl group, a terphenyl group, a fluorenyl group, an anthryl group, a phenanthryl group, or the like.

In addition, $R^1$ and $R^2$, $R^3$ and $R^4$, or $R^5$ and $R^6$ may bind to each other to form a ring. Here, $R^1$ to $R^6$ that do not form the ring may be each defined as above. The ring formed in this case may be a $C_6$-$C_{30}$ aliphatic ring, a $C_6$-$C_{60}$ aromatic ring, a $C_2$-$C_{60}$ hetero ring, a $C_3$-$C_{60}$ cycloaliphatic ring, or a fused ring composed of a combination thereof, may be a monocyclic or polycyclic ring, and may be a saturated or unsaturated ring.

L' may be selected from the group consisting of a single bond, a $C_6$-$C_{60}$ arylene group, a fluorenylene group, a fused ring group of a $C_3$-$C_{60}$ aliphatic group and a $C_6$-$C_{60}$ aromatic group, and a $C_2$-$C_{60}$ heterocyclic group.

$R_a$ and $R_b$ may be each independently selected from the group consisting of a $C_6$-$C_{60}$ aryl group, a fluorenyl group, a fused ring group of a $C_3$-$C_{60}$ aliphatic group and a $C_6$-$C_{60}$ aromatic group, and a $C_2$-$C_{60}$ heterocyclic group containing at least one heteroatom of O, N, S, Si, and P.

o, m, and n may be each independently 0 or 1, and m+n+o≥1.

As described later, in consideration of characteristics of the compound represented by Formula 1 at the time of application to an organic electronic element, when ring A is benzene, both n and o are 0, and m is 1, $R^1$ and $R^2$ may be each except for biphenyl, dibenzofuran, dibenzothiophene, and fluorene. Here, the meaning that $R^1$ and $R^2$ are each except for biphenyl, dibenzofuran, dibenzothiophene, and fluorene is that one or both of $R^1$ and $R^2$ are except for biphenyl, dibenzofuran, dibenzothiophene, and fluorene. In other words, one of $R^1$ and $R^2$ may be except for biphenyl, dibenzofuran, dibenzothiophene, and fluorene, or both of $R^1$ and $R^2$ may be except for biphenyl, dibenzofuran, dibenzothiophene, and fluorene.

As for $L^1$ to $L^3$, when o, m, and n are each 0, $L^1$, $L^2$, and $L^3$ may be each independently selected from the group consisting of hydrogen, an aryl group, a fluorenyl group, and a $C_2$-$C_{60}$ heterocyclic group containing at least one heteroatom of O, N, S, Si, and P. For example, when o, m, and n are each 0, $L^1$, $L^2$, and $L^3$ may be a phenyl group, a naphthyl group, a fluorenyl group, a heterocyclic group. Herein, the meaning of "when o, m, and n are each 0, $L^1$, $L^2$, and $L^3$" is that "$L^1$ when o is 0, $L^2$ when m is 0, and $L^3$ when n is 0" and includes both a case where only one of o, m, and n is 0 and a case where two of o, m, and n are 0.

Alternatively, when o, m, and n are each 1, $L^1$, $L^2$, and $L^3$ may be each independently selected from the group consisting of a single bond, a arylene group, a fluorenylene group, a fused ring group of a $C_3$-$C_{60}$ aliphatic group and a $C_6$-$C_{60}$ aromatic group, and a $C_2$-$C_{60}$ divalent heterocyclic group containing at least one heteroatom of O, N, S, Si, and P. For example, when o, m, and n are each 1, $L^1$, $L^2$, and $L^3$ may be a single bond, a phenylene group, a biphenylene group, a naphthyl group, a fluorenyl group, a heterocyclic group. Herein, the meaning of "when o, m, and n are each 1, $L^1$, $L^2$, and $L^3$" is that "$L^1$ when o is 1, $L^2$ when m is 1, and $L^3$ when n is 1" and includes both a case where only one of o, m, and n is 1 and a case where two of o, m, and n are 1.

The aryl group, fluorenyl group, heterocyclic group, fused ring group, alkyl group, alkenyl group, alkynyl group, alkoxyl group, aryloxy group, arylene group, and fluorenylene group may be each substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Here, ring A may be benzene or naphthalene, but is not limited thereto, may be a $C_6$-$C_{30}$ monocyclic or polycyclic ring. In other words, the meaning that ring A is benzene or naphthalene is that ring A is benzene or naphthalene bounded or combined with *1 and *2 of

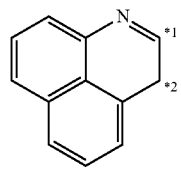

in Formula 1.

Here, the aryl group may be an aryl group having 6-60 carbon atoms, preferably 6-40 carbon atoms, and more preferably 6-30 carbon atoms;

the heterocyclic group may be a heterocyclic group having 2-60 carbon atoms, preferably 2-30 carbon atoms, and more preferably 2-20 carbon atoms;

the arylene group may be an arylene group having 6-60 carbon atoms, preferably 6-30 carbon atoms, and more preferably 6-20 carbon atoms; and the alkyl group may be an alkyl group having 1-50 carbon atoms, preferably 1-30 carbon atoms, more preferably 1-20 carbon atoms, and especially preferably 1-10 carbon atoms.

Specifically, ring A of the compound represented by Formula 1 may be benzene or naphthalene.

In addition, specifically, the compound represented by Formula 1 may be represented by one of the following formulas:

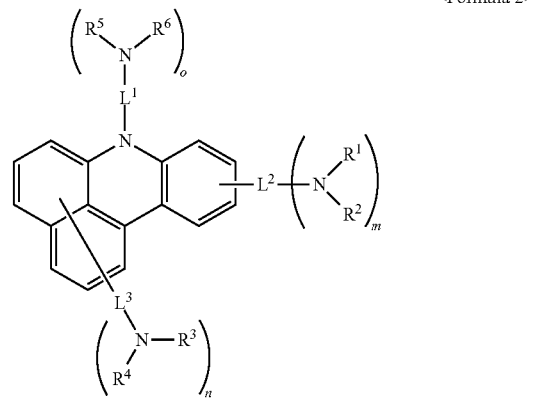

<Formula 2>

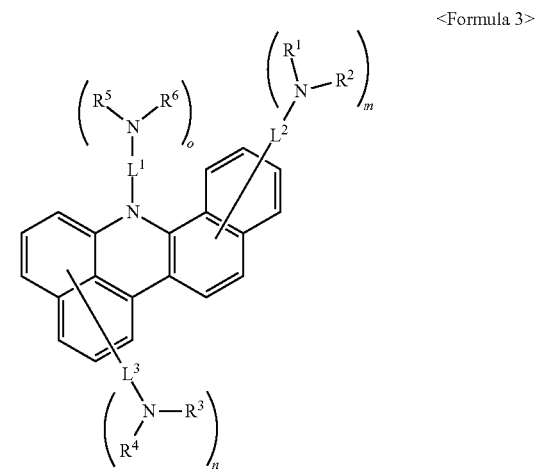

<Formula 3>

<Formula 4>
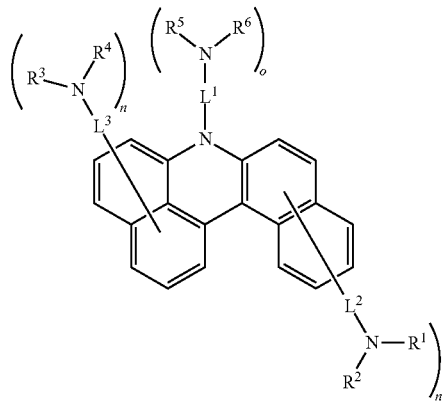
<Formula 5>
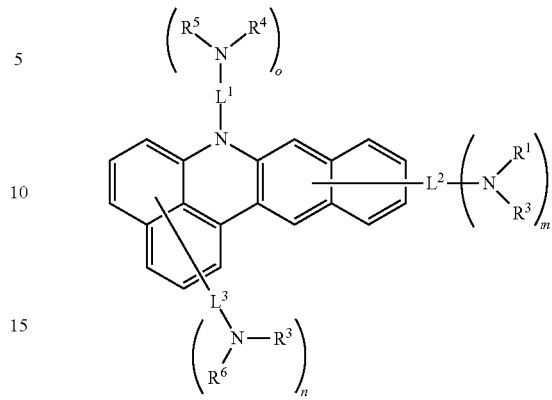
In Formulas 2 to 5,
R¹ to R⁶, L¹ to L³, m, n and o may be identical to R¹ to R⁶, L¹ to L³, m, n and o defined in formula 1.
More specifically, the compounds represented by Formulas 1 to 5 may be any one of the following compounds:
P1-1
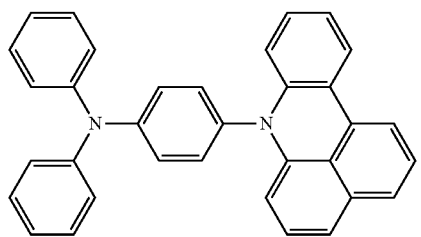
P1-2
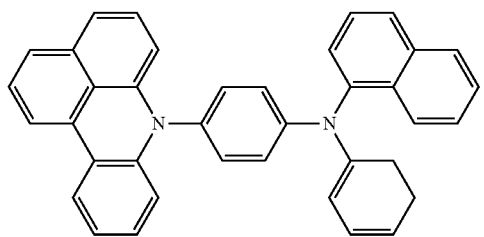
P1-3
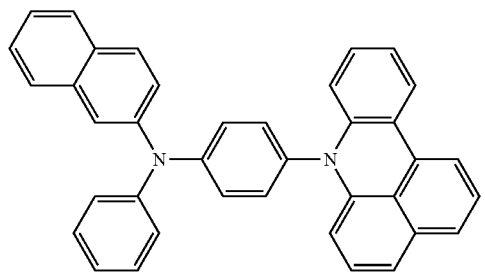
P1-4
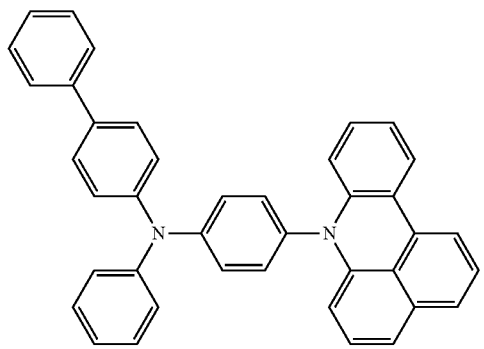
P1-5
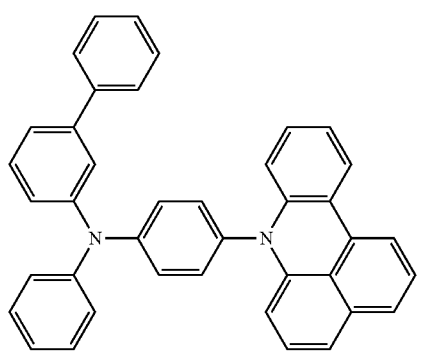
P1-6
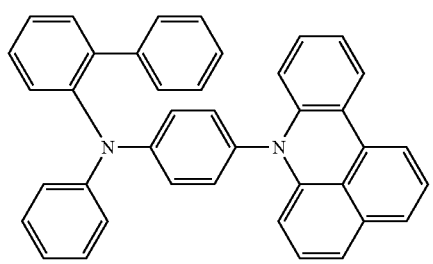

-continued
P1-7
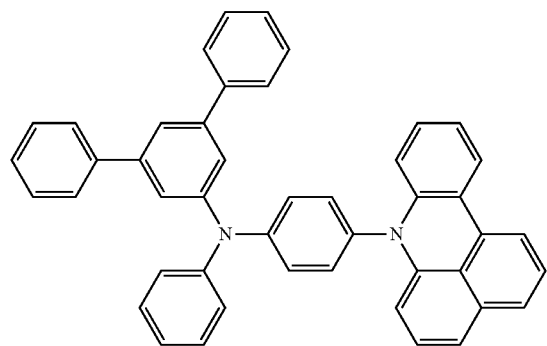
P1-8
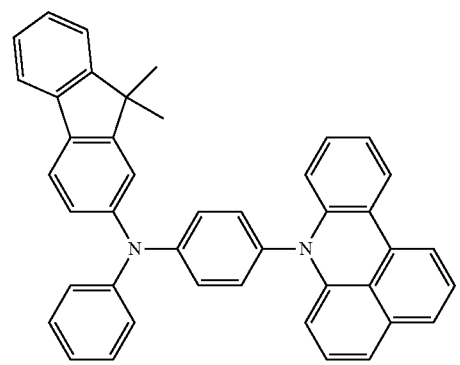
P1-9
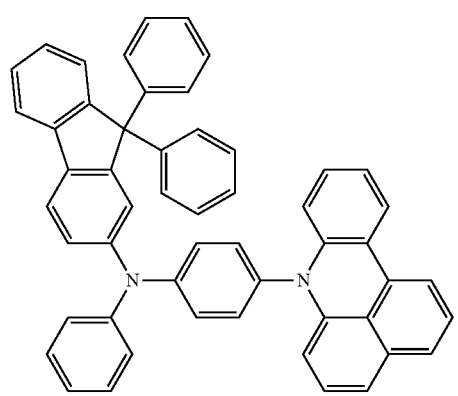
P1-10
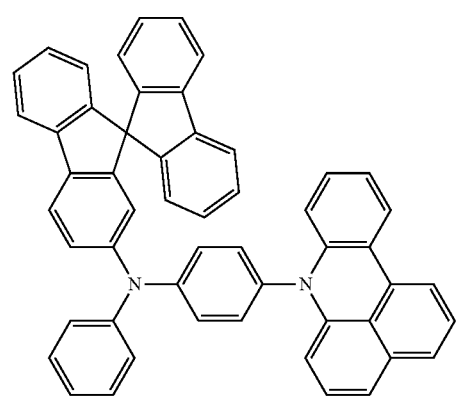
P1-11
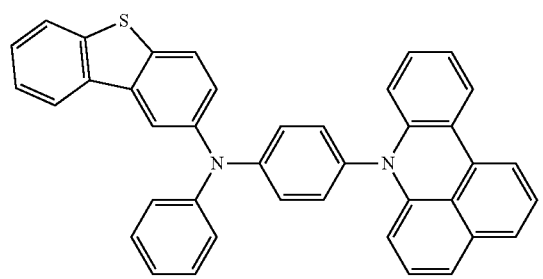
P1-12
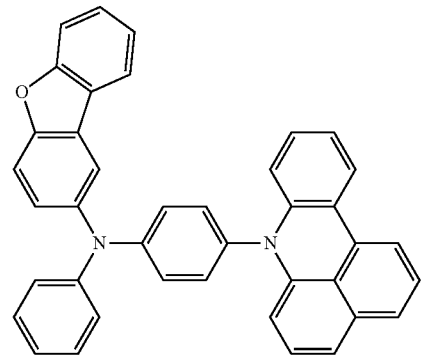
P1-13
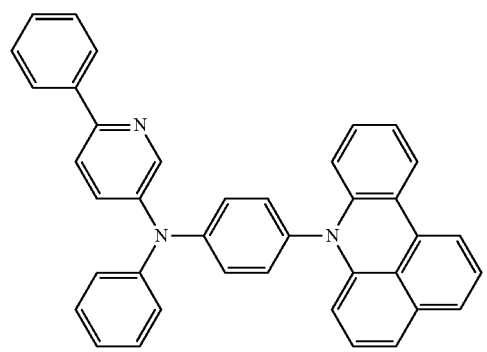
P1-14
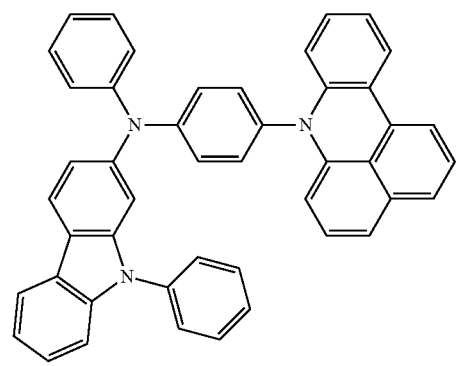

-continued
P1-15
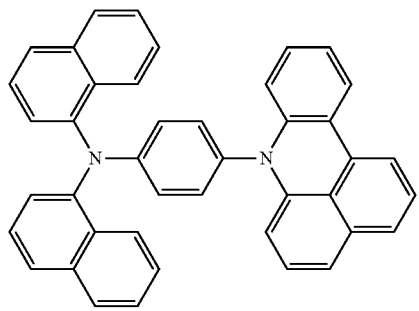
P1-16
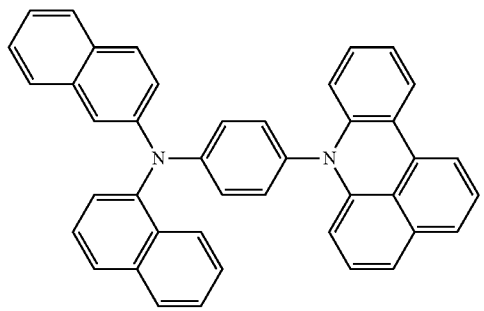
P1-17
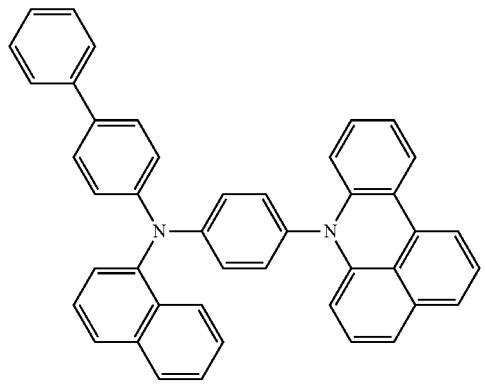
P1-18
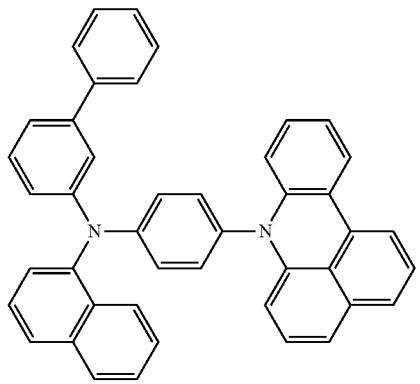
P1-19
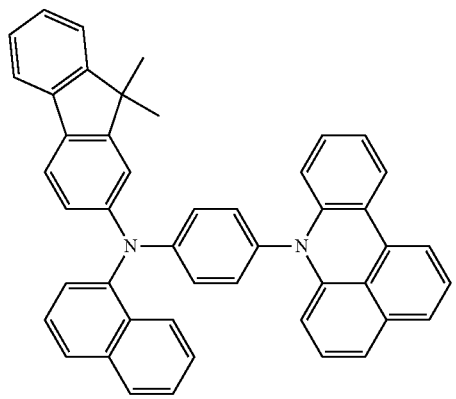
P1-20
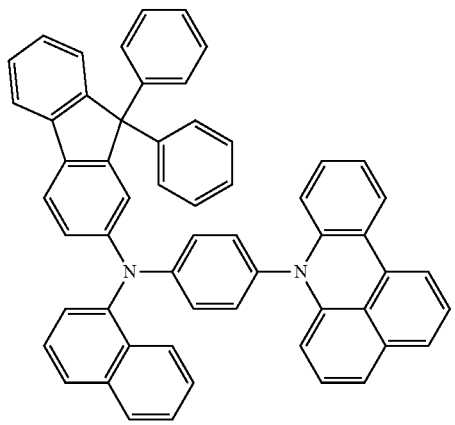
P1-21
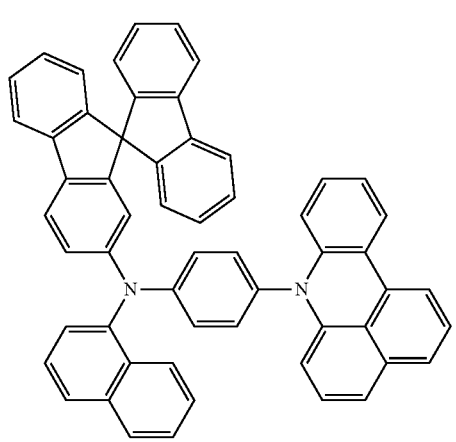
P1-22
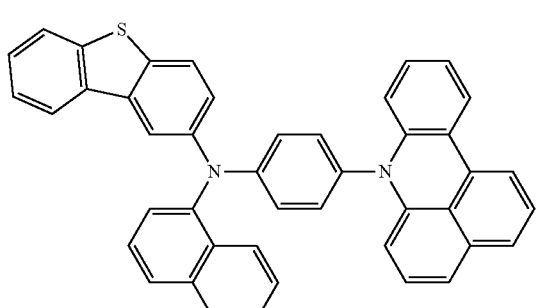

-continued
P1-23
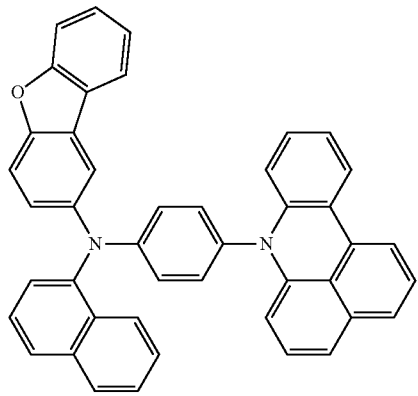
P1-24
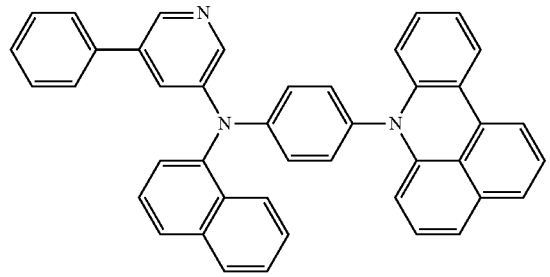
P1-25
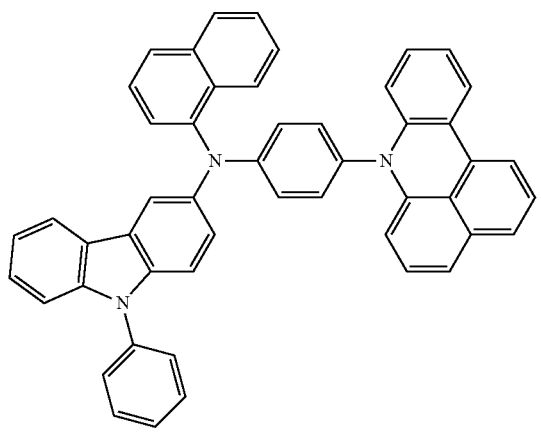
P1-26
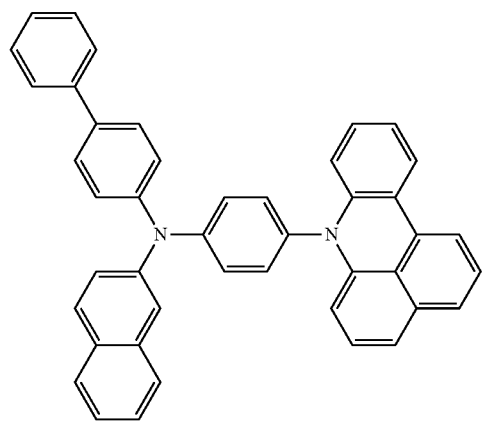
P1-28
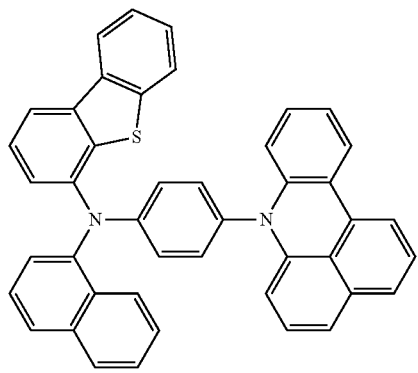
P1-27
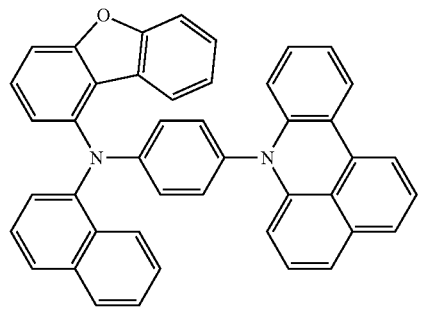
P1-29
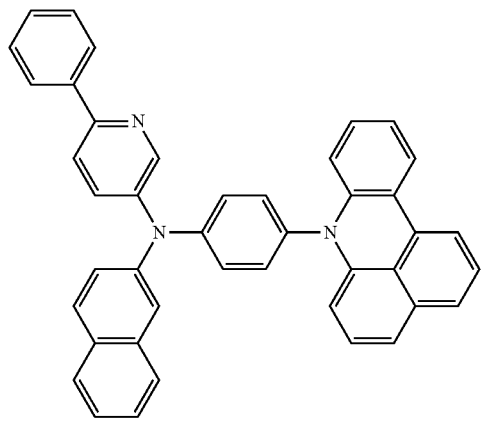
P1-30
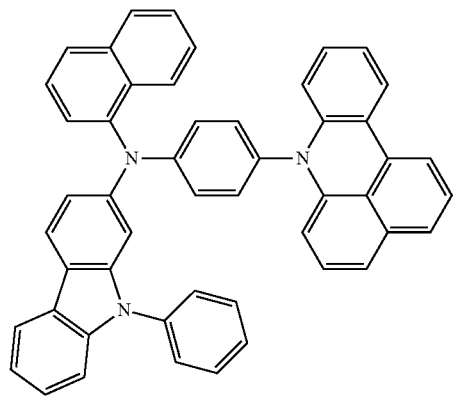

-continued
P1-31
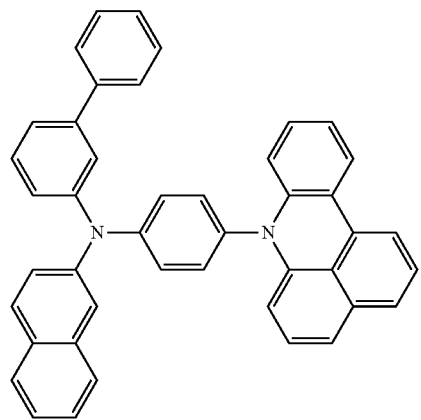
P1-32
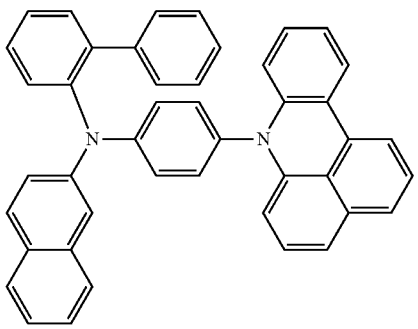
P1-33
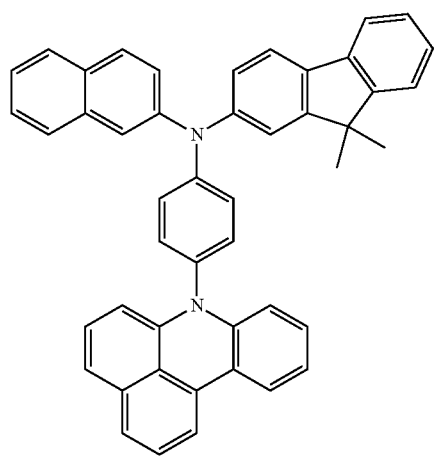
P1-34
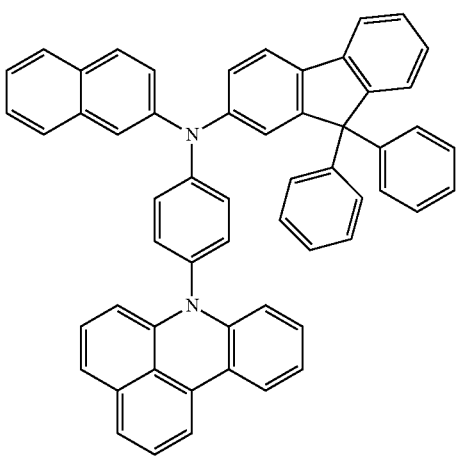
P1-35
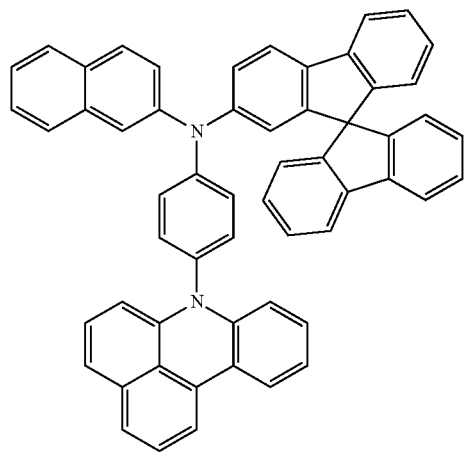
P1-36
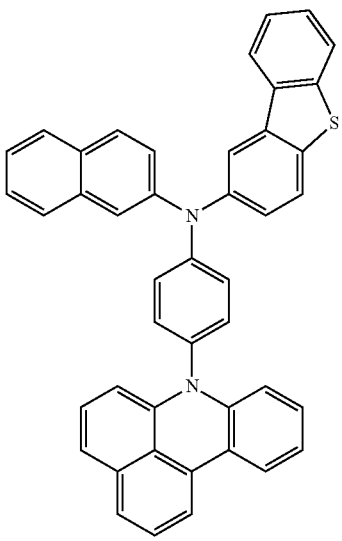

-continued
P1-37
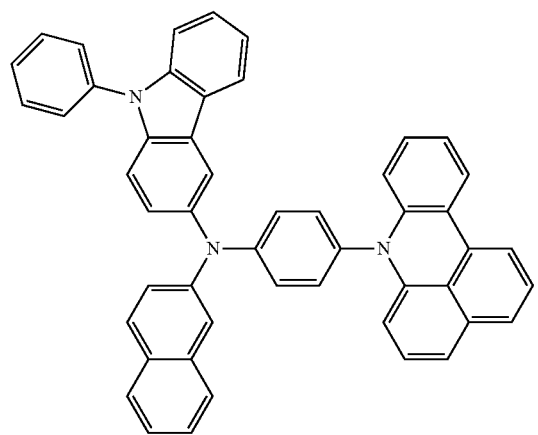
P1-38
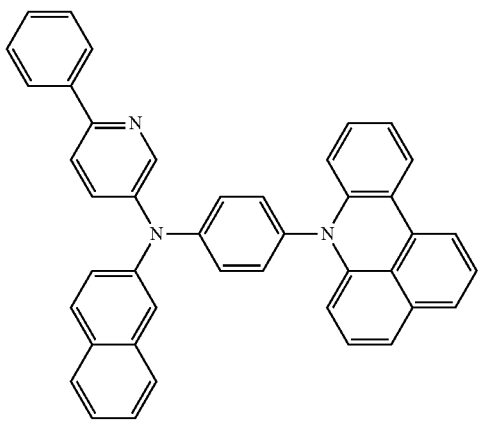
P1-39
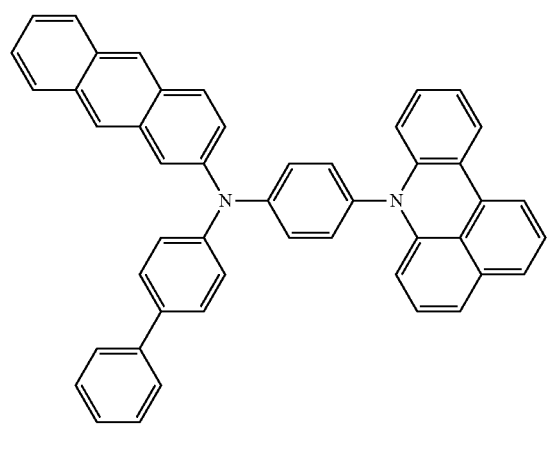
P1-40
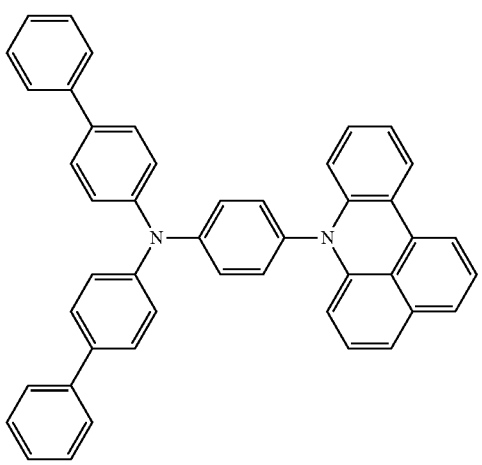
P1-41
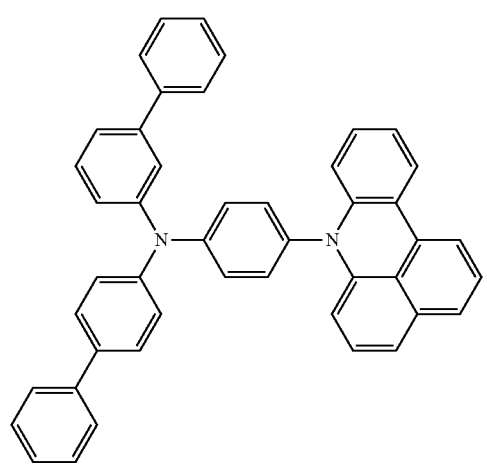
P1-42
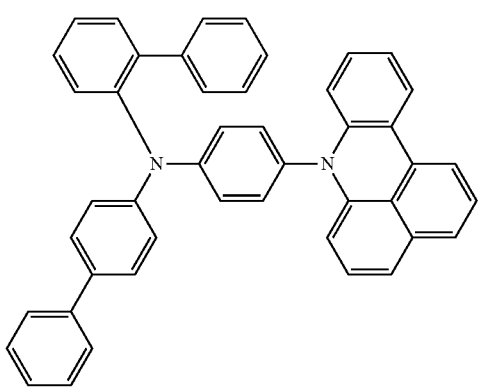

-continued
P1-43
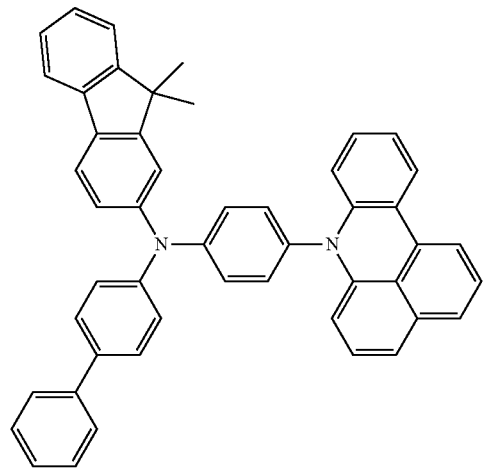
P1-44
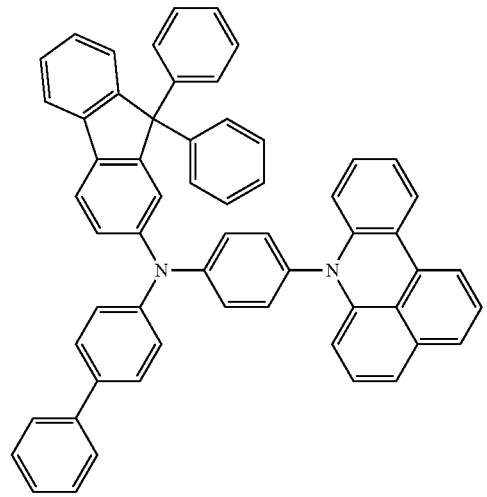
P1-45
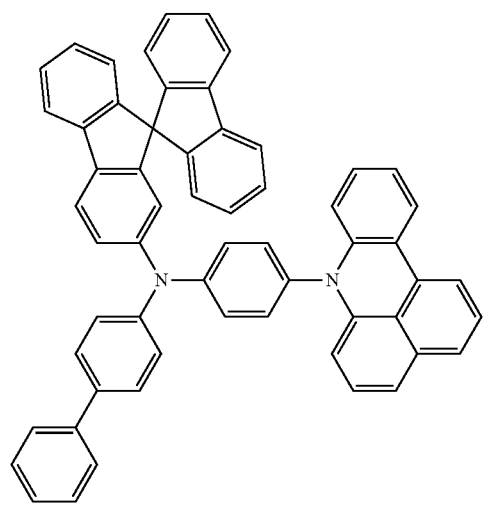
P1-46
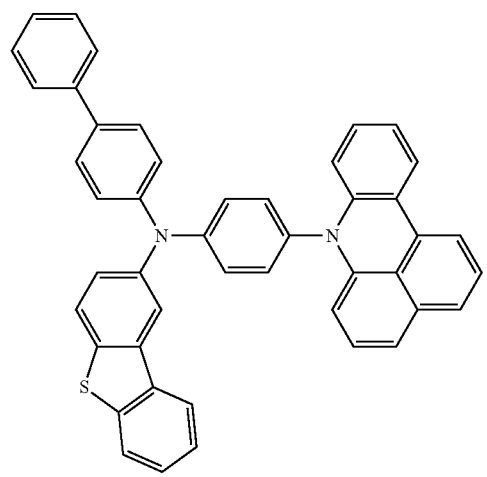
P1-47
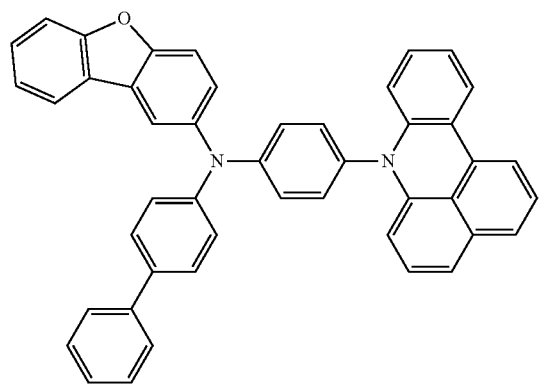
P1-48
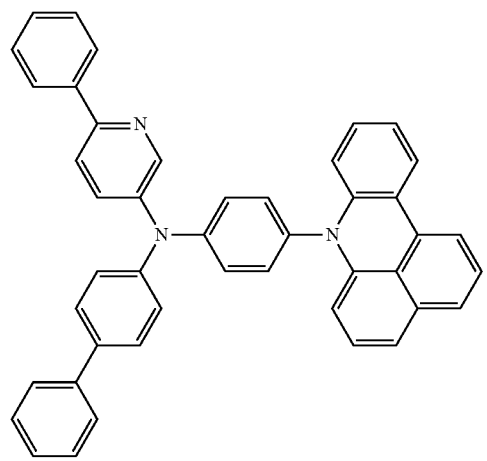

-continued
P1-49 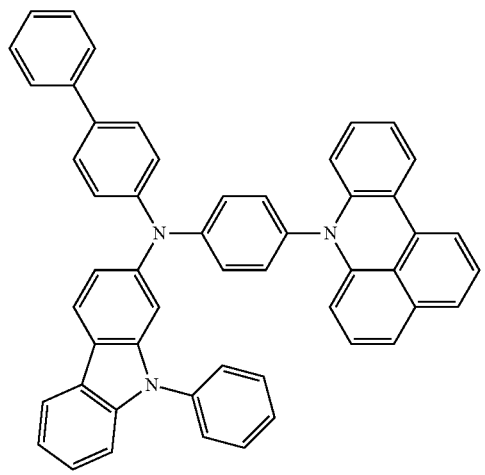
P1-50 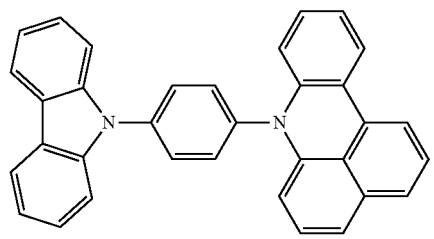
P1-51 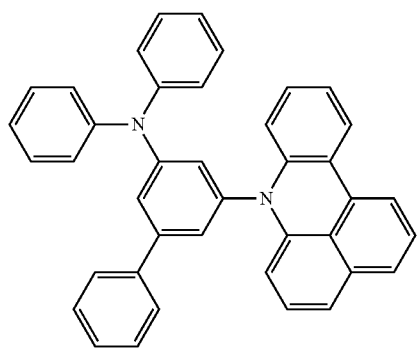
P1-52 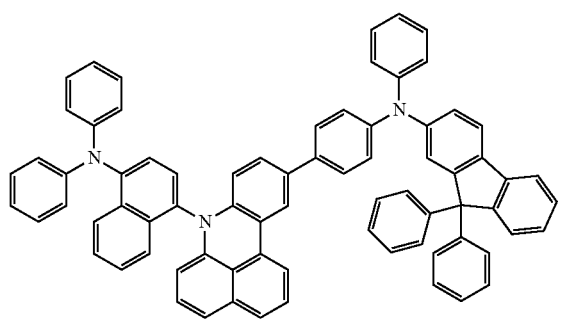
P1-53 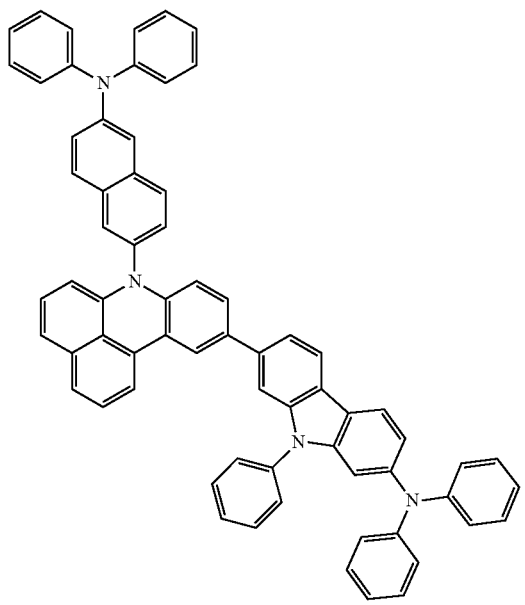
P1-54 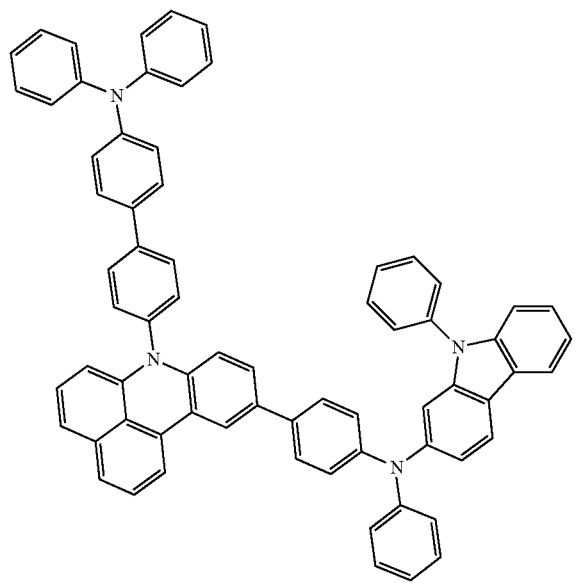

-continued
P1-55
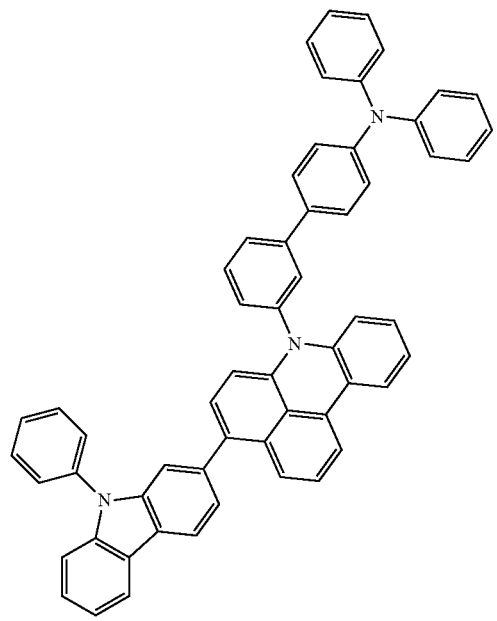
P1-56
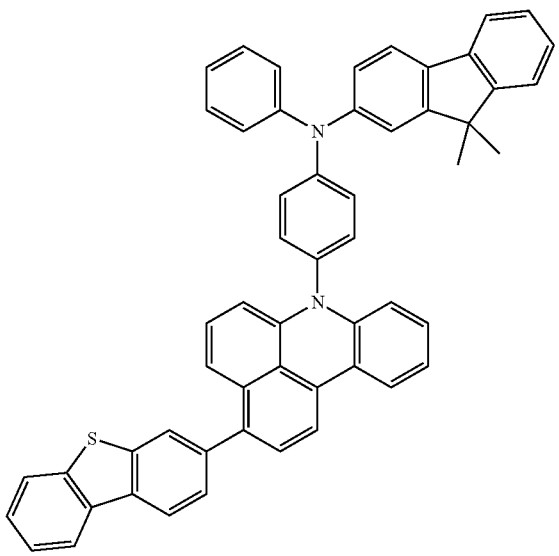
P1-57
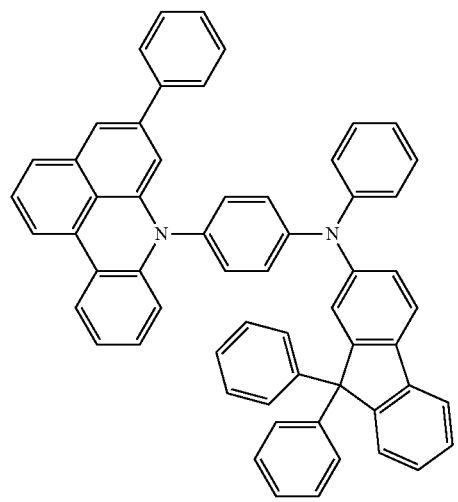
P1-58
P1-59
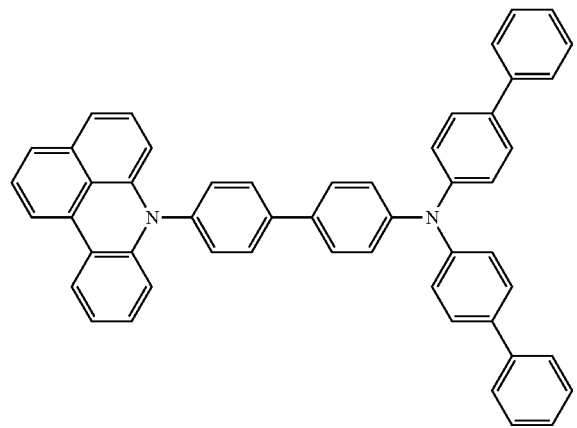
P1-60
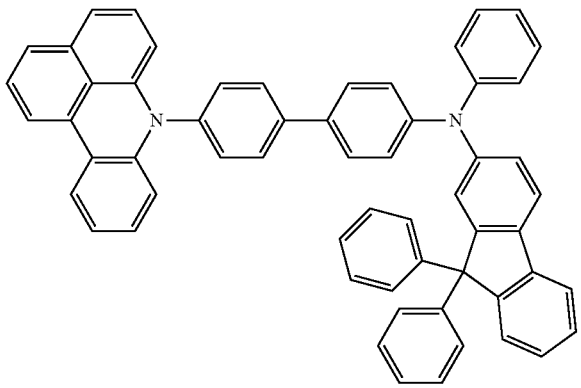

-continued
P1-61
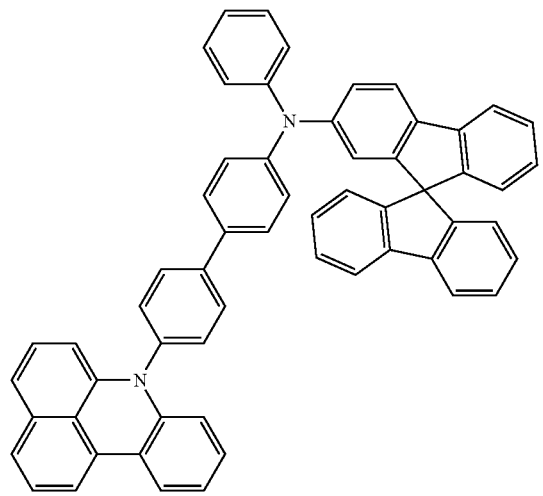
P1-62
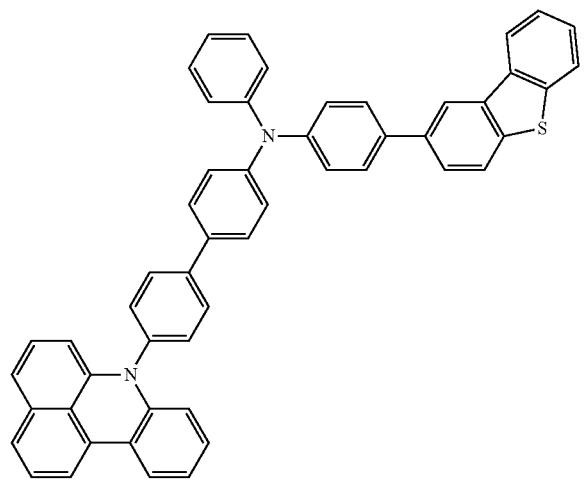
P1-63
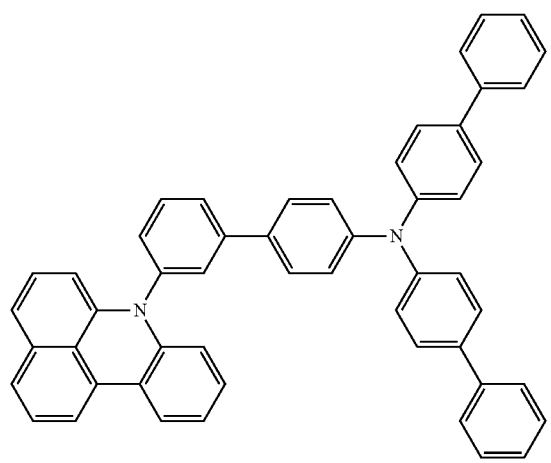
P1-64
P1-65
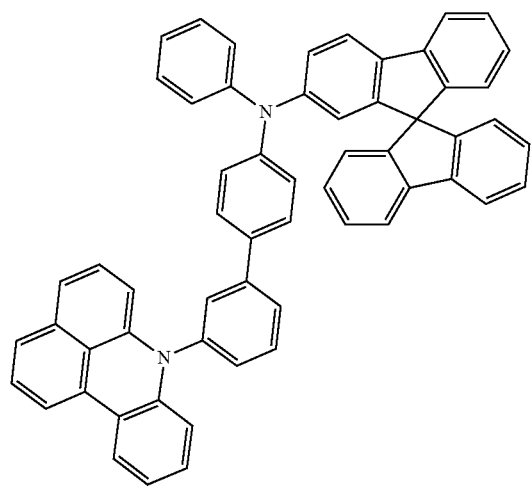
P1-66
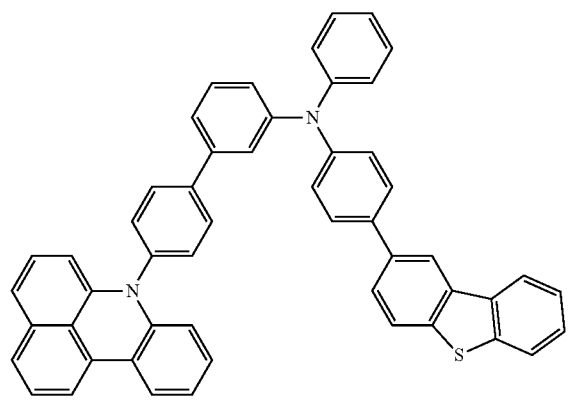

P1-67
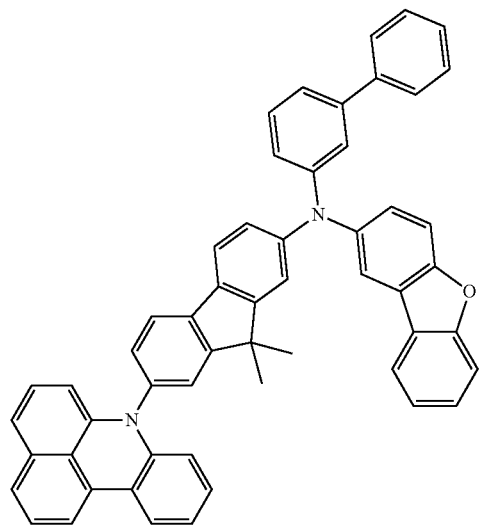
P1-68
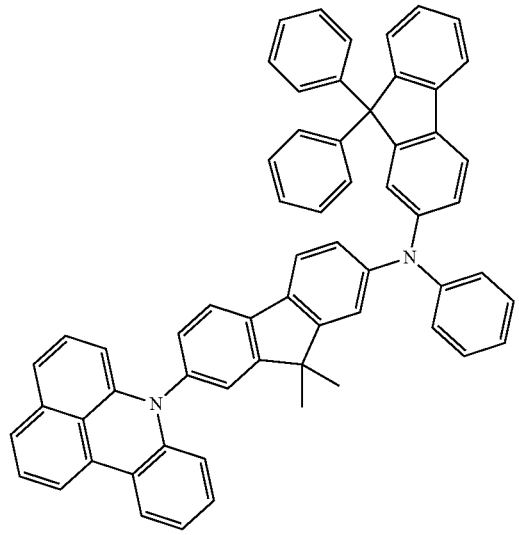
P1-69
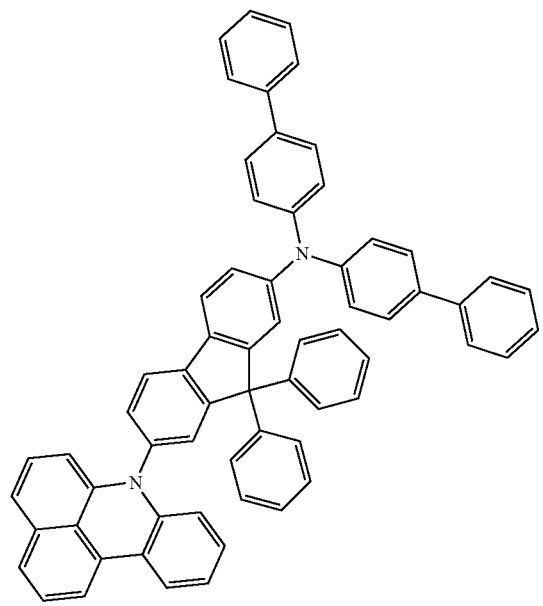
P1-70
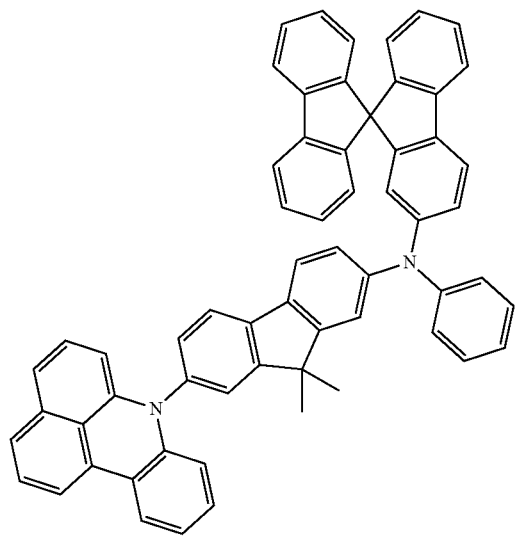

-continued
P1-71
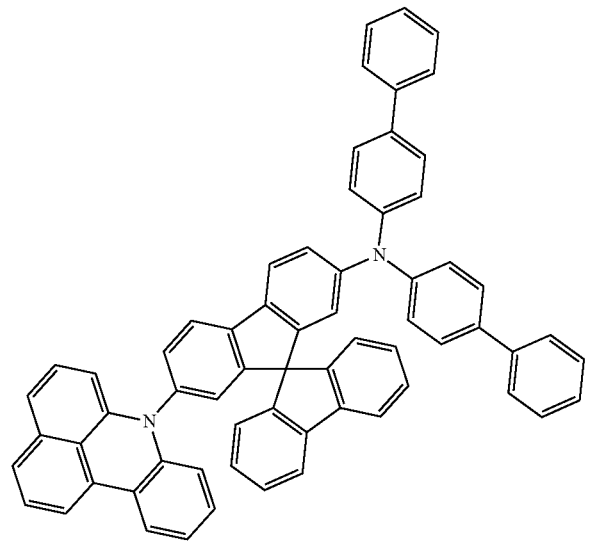
P1-72
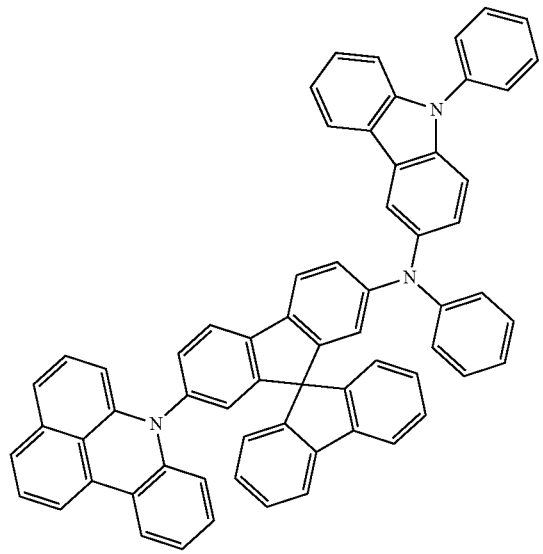
P1-73
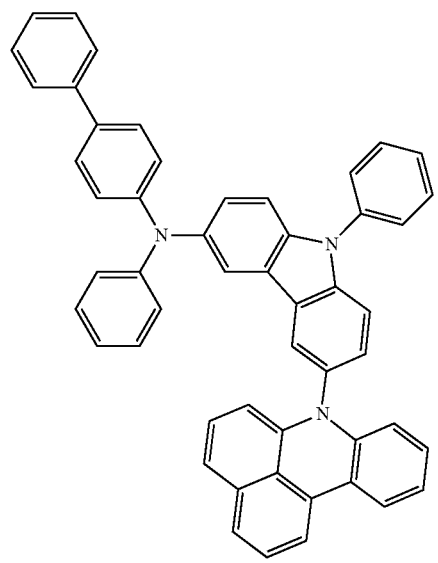
P1-74
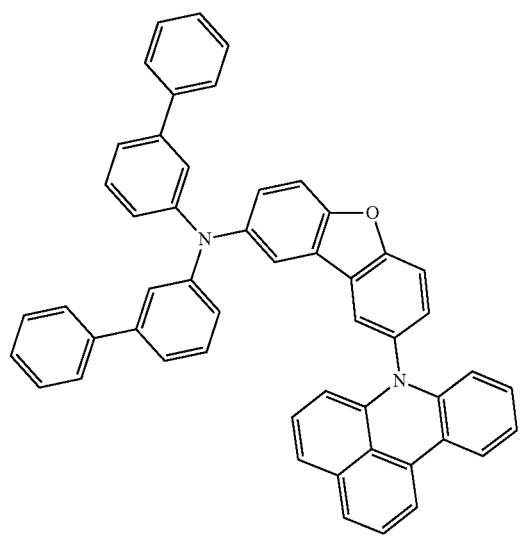

P1-75 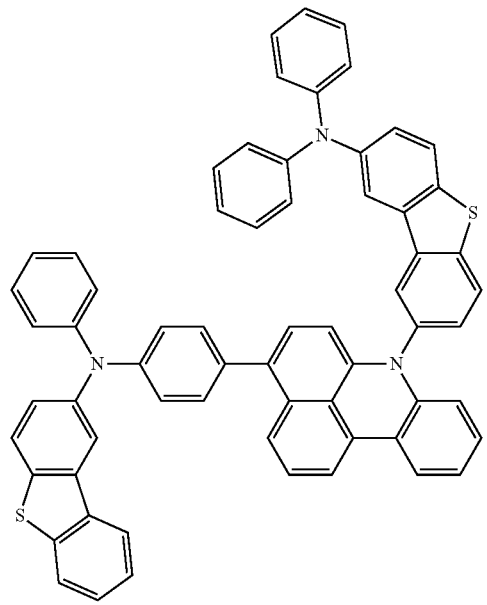
P1-76 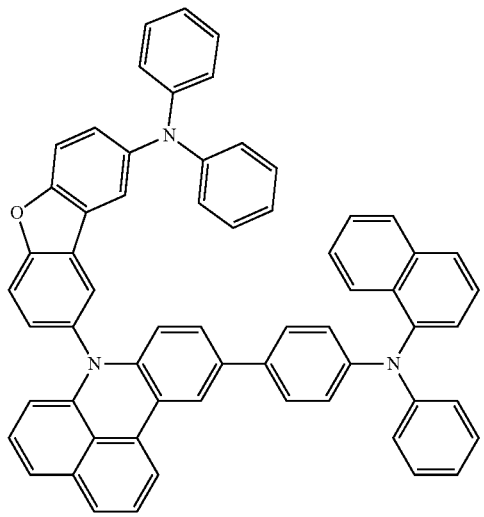
P1-77 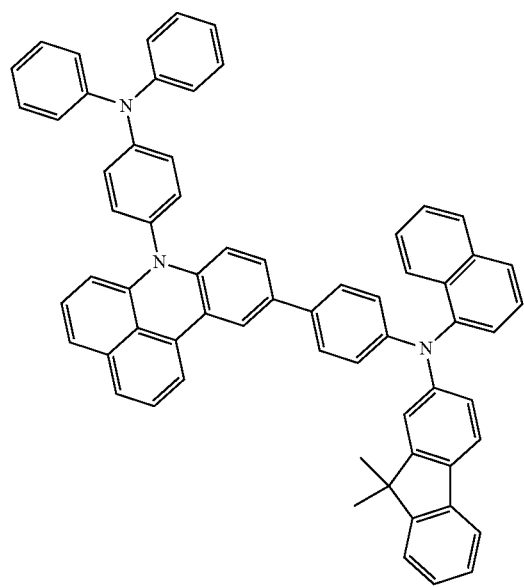
P1-78 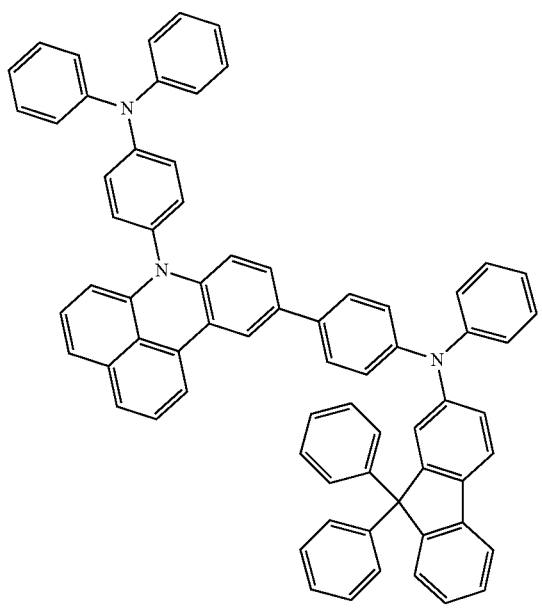

-continued
P1-79
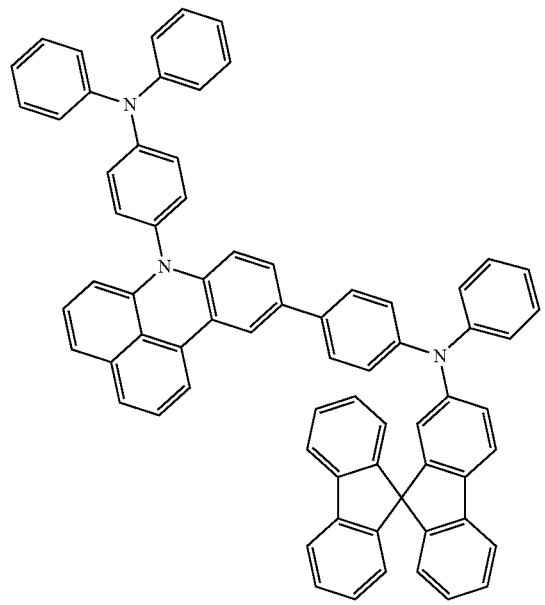
P1-80
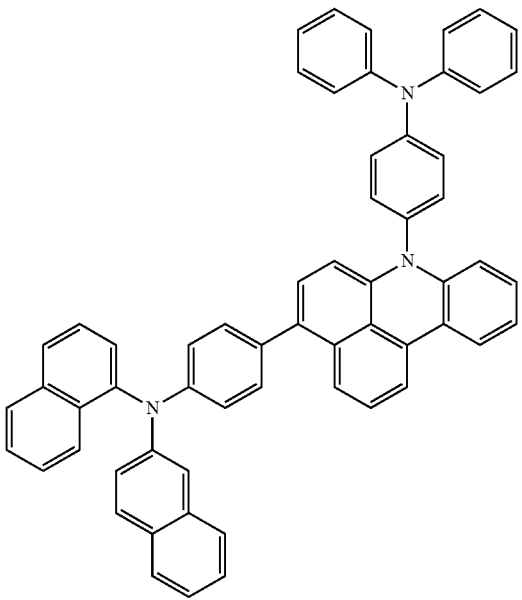
P1-81
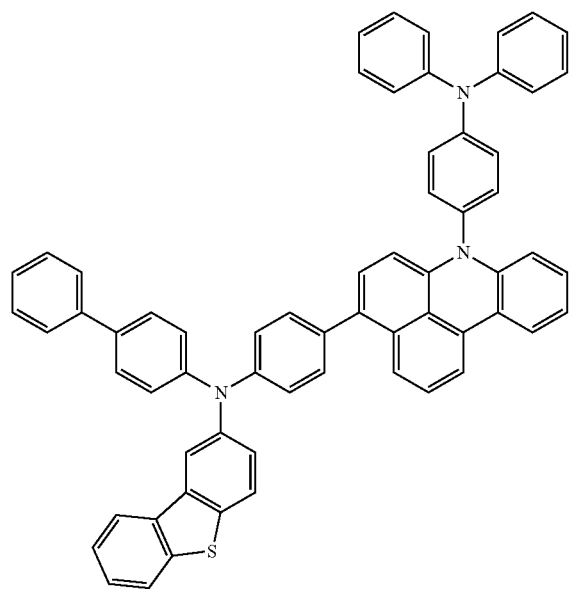
P1-82
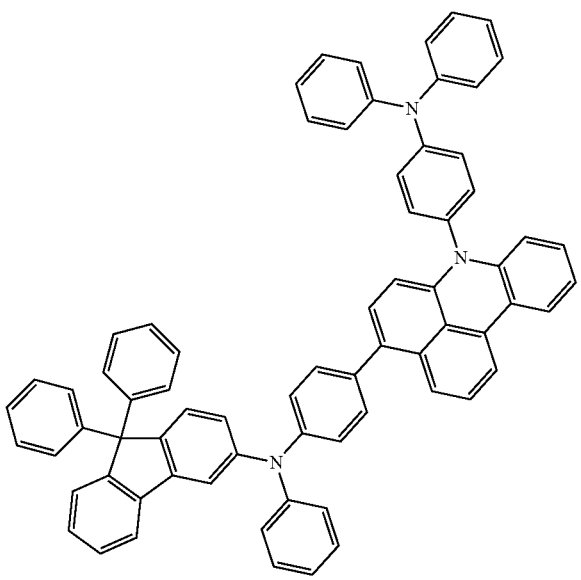

-continued
P1-83
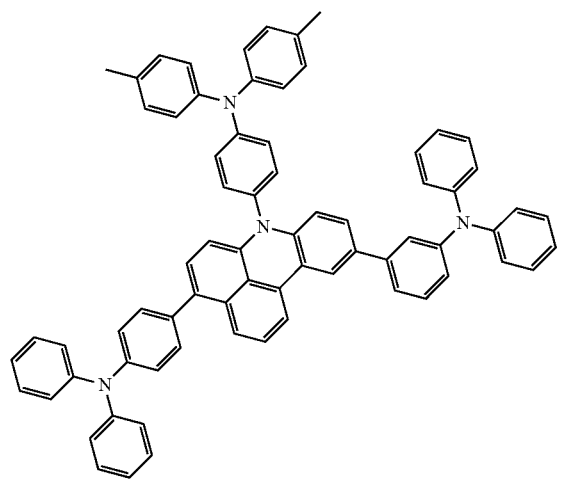
P1-84
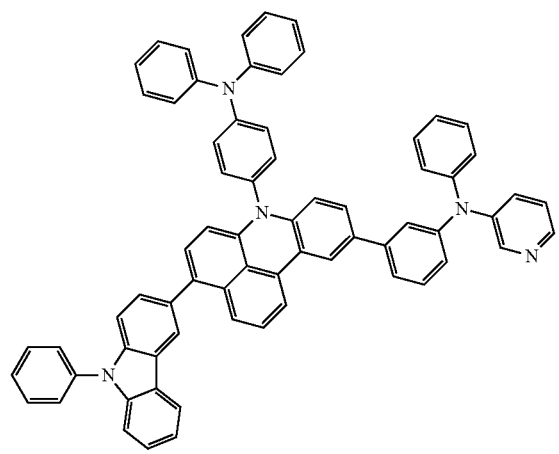
P2-1
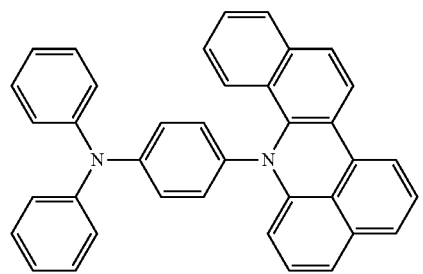
P2-2
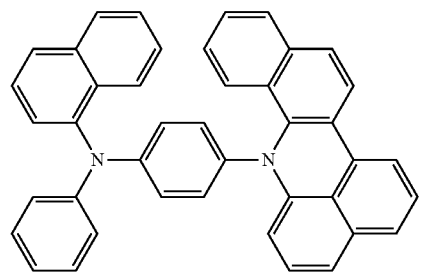
P2-3
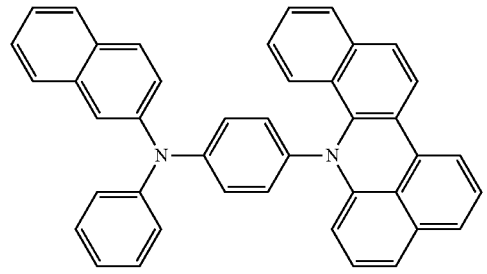
P2-4
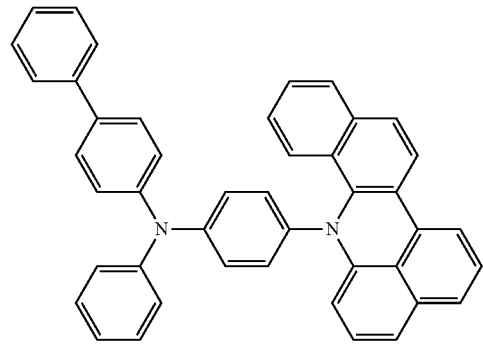
P2-5
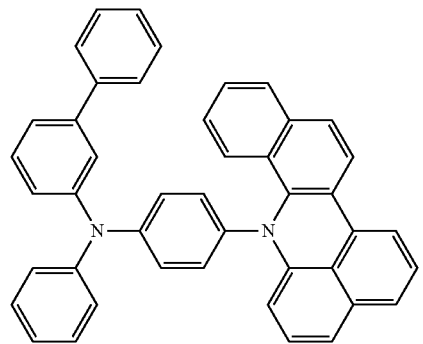
P2-6
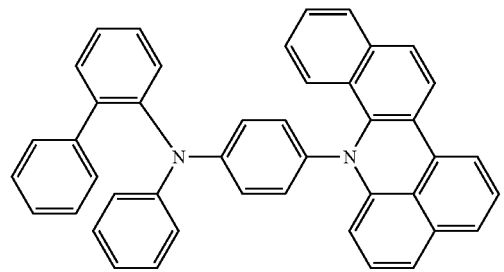

-continued
P2-7
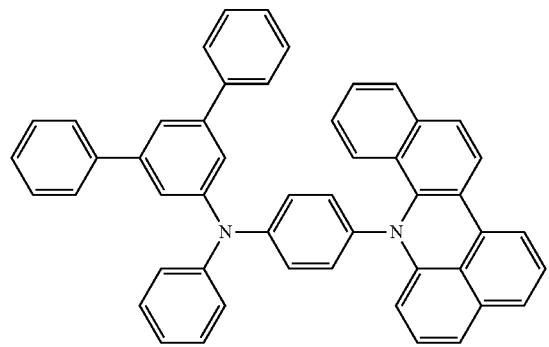
P2-8
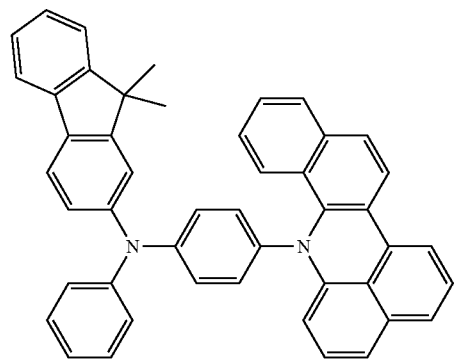
P2-9
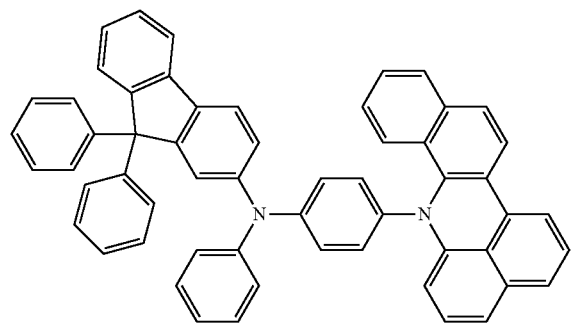
P2-10
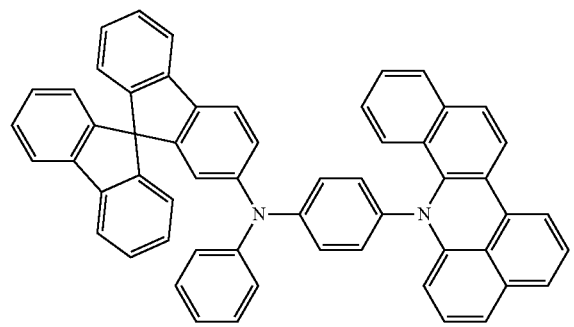
P2-11
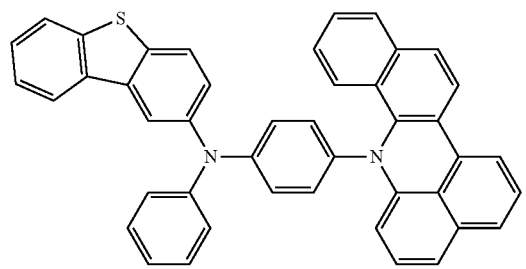
P2-12
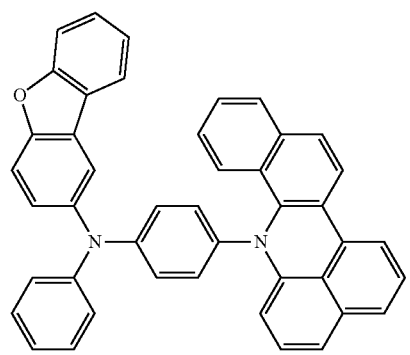
P2-13
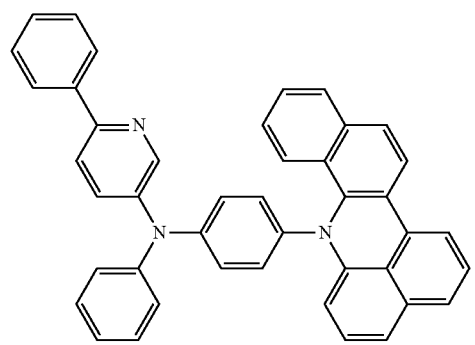
P2-14
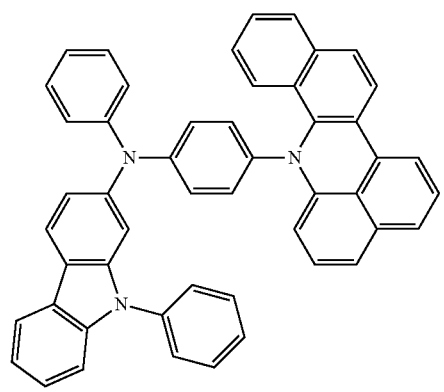

-continued
P2-15
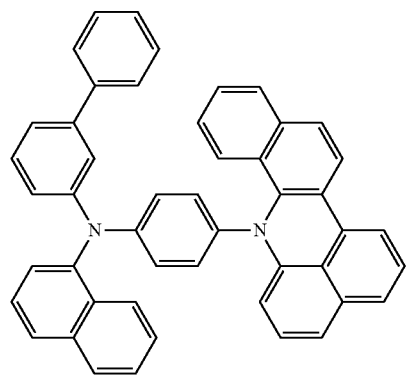
P2-16
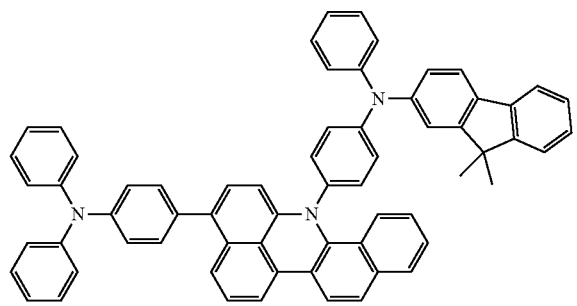
P2-17
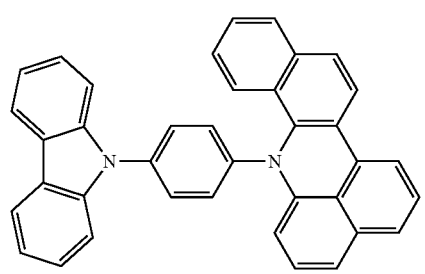
P2-18
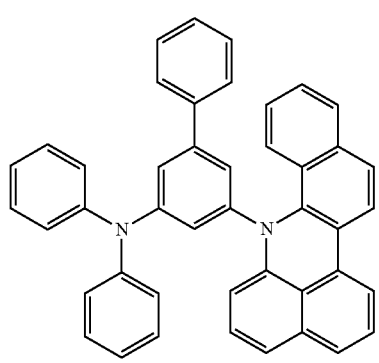
P1-19
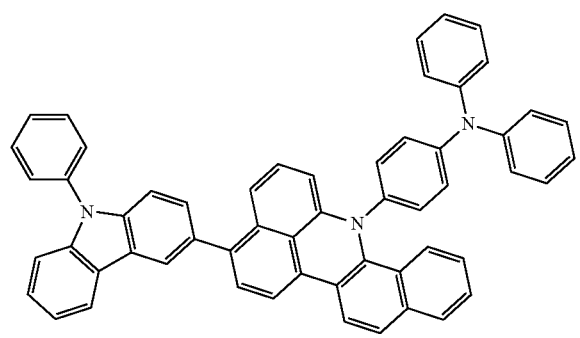
P2-20
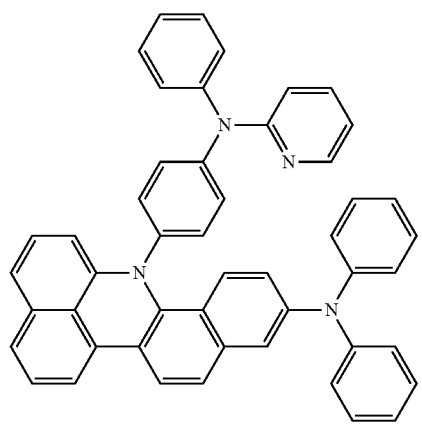

-continued
P2-21
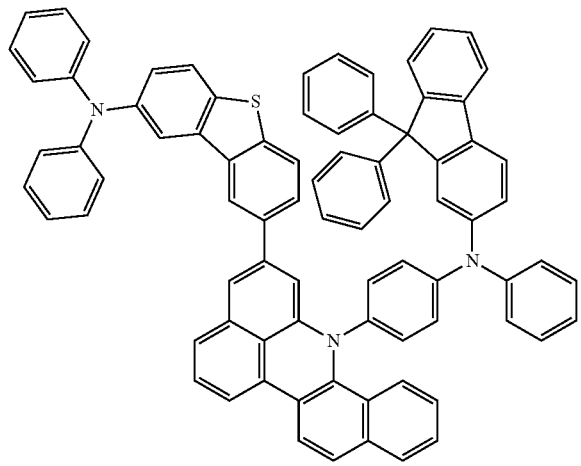
P2-22
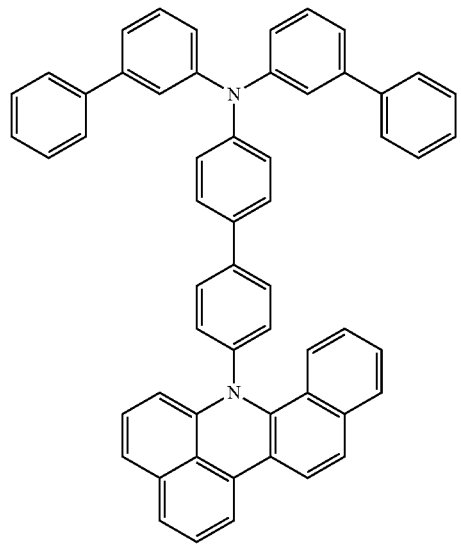
P2-23
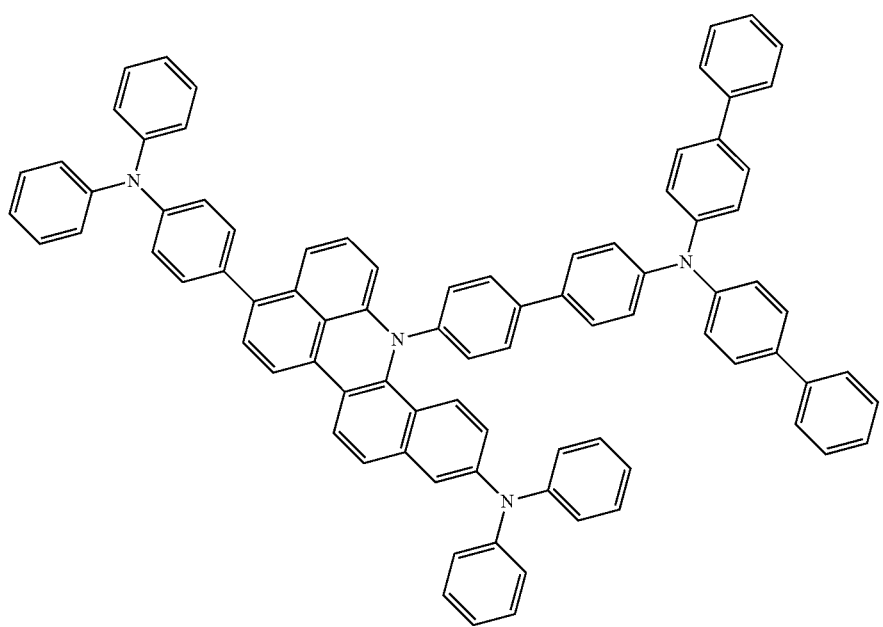

-continued
P2-24
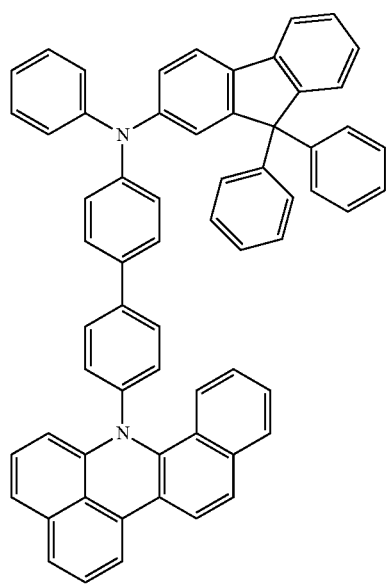
P2-25
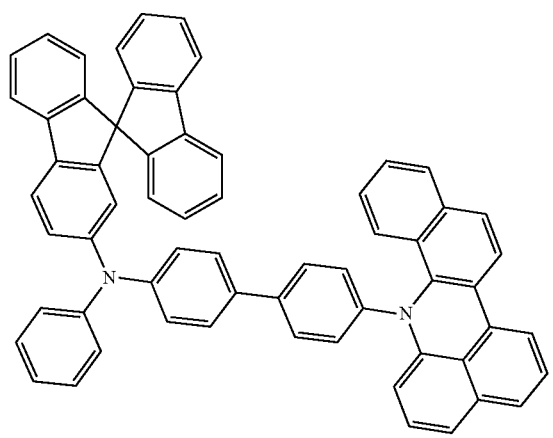
P2-26
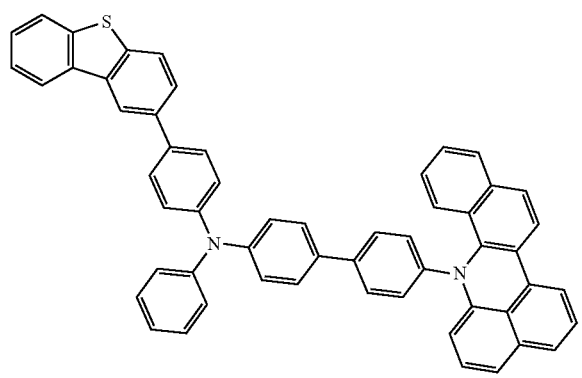
P2-27
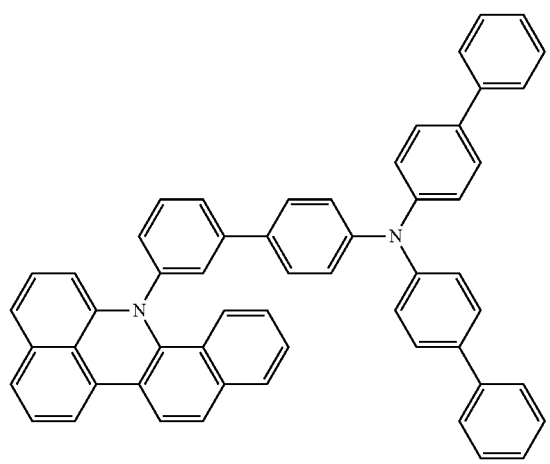
P2-28
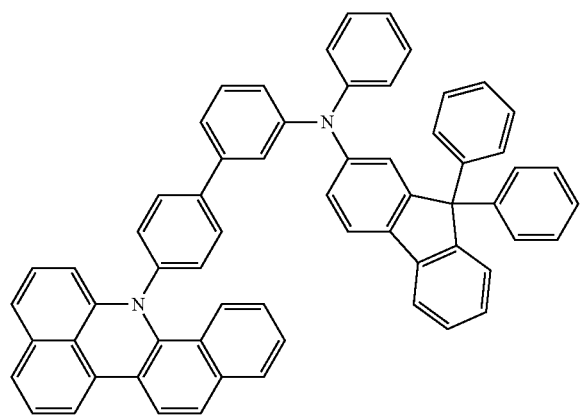
P2-29
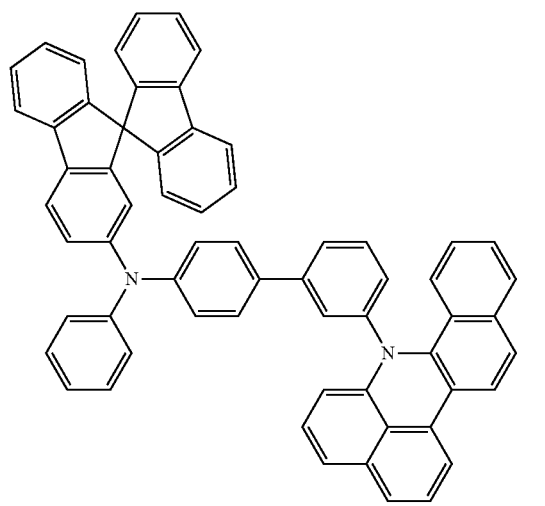

-continued
P2-30
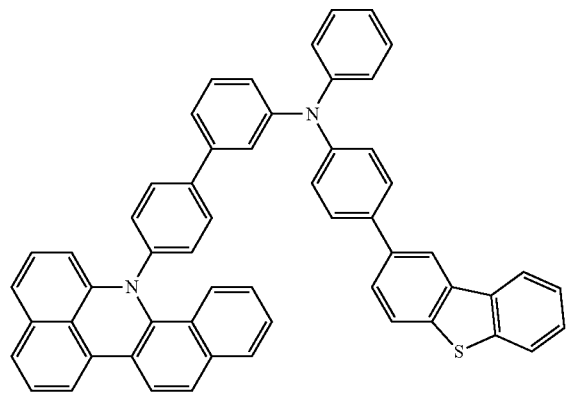
P2-31
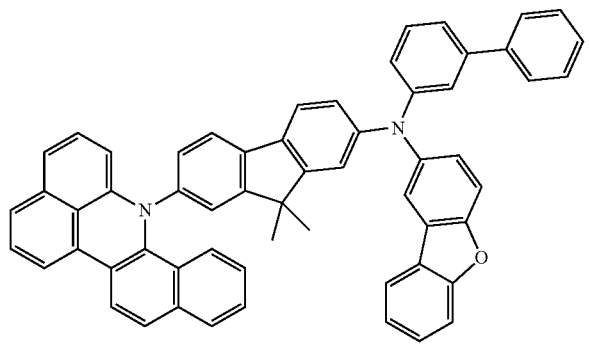
P2-32
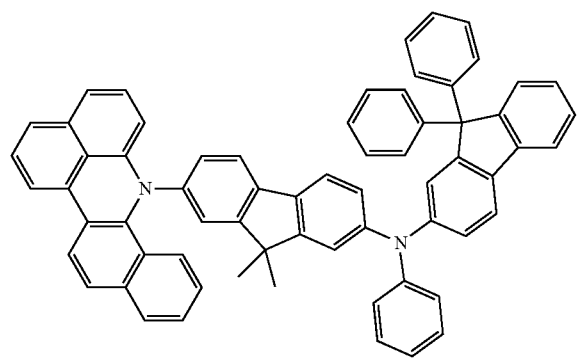
P2-33
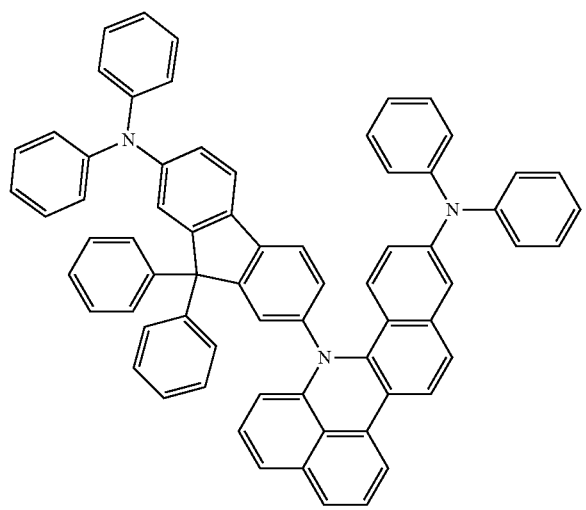
P2-34
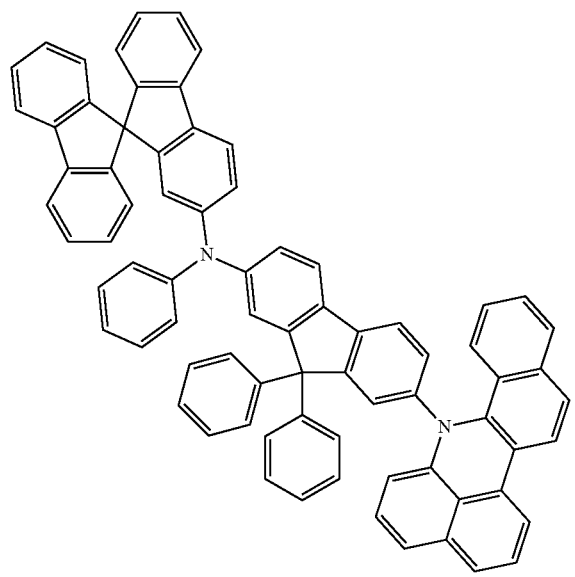
P2-35
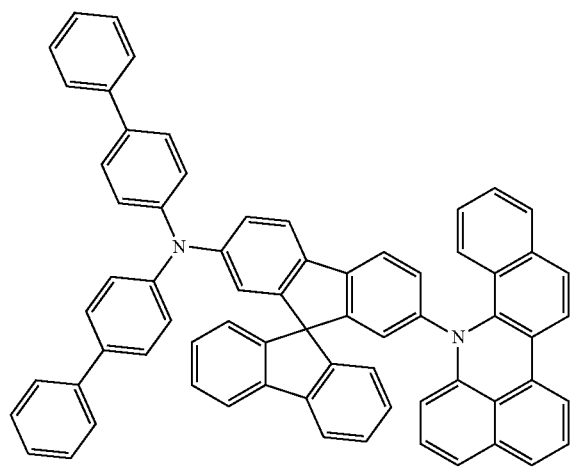

-continued
P2-36
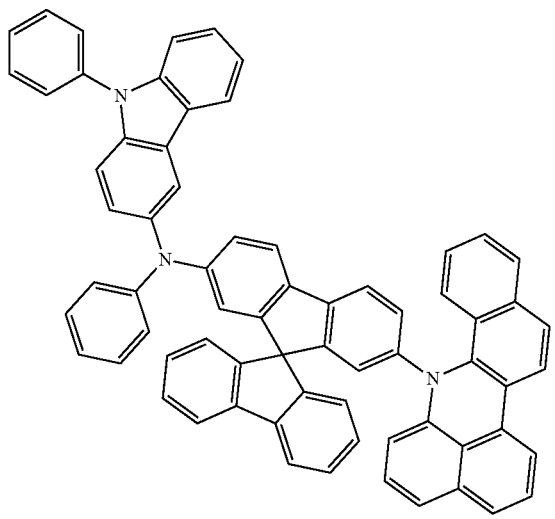
P2-37
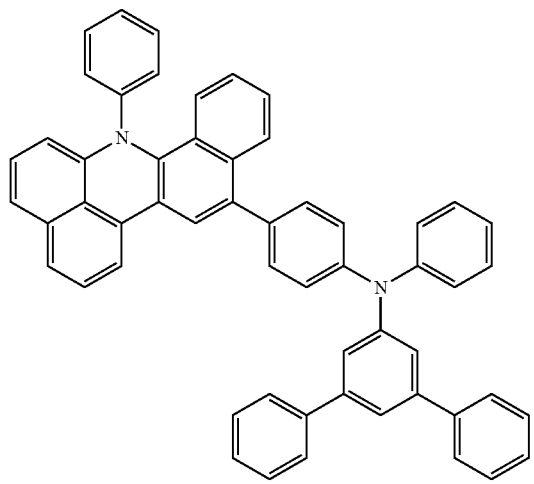
P2-38
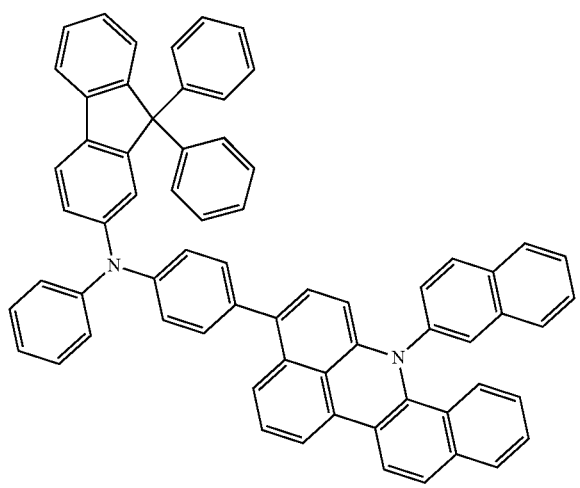
P2-39
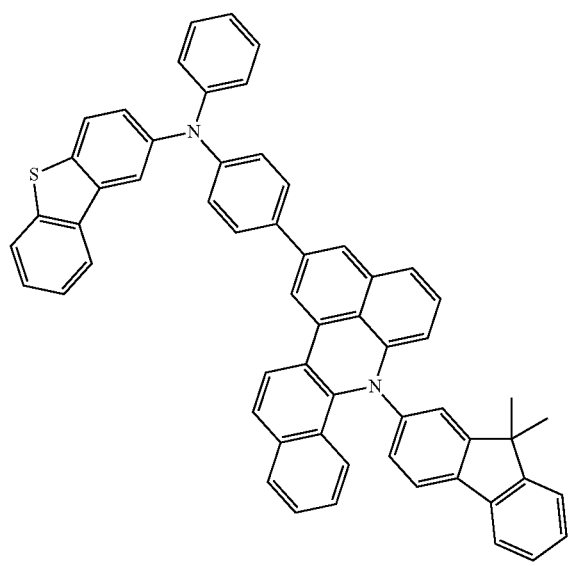
P2-40
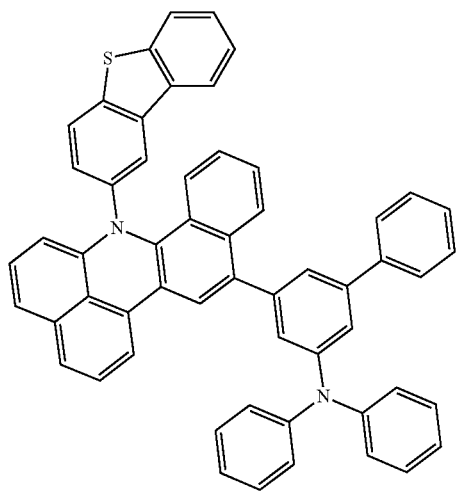
P3-1
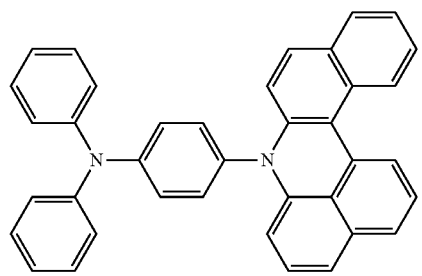

-continued
| P3-2 | P3-3 |
|---|---|
| 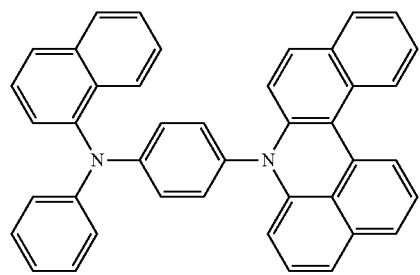 | 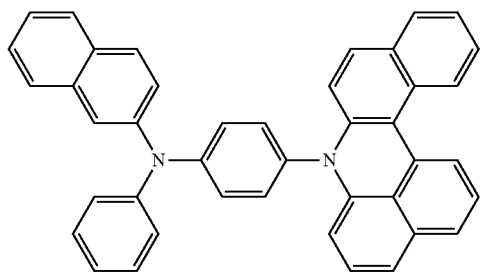 |
| P3-4 | P3-5 |
|---|---|
| 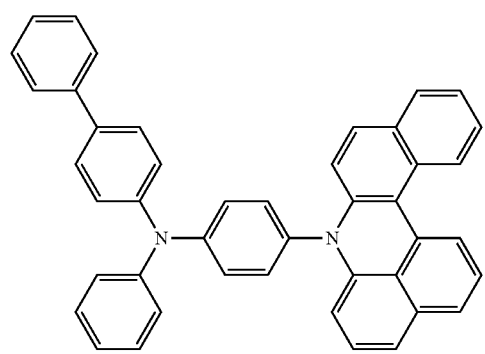 | 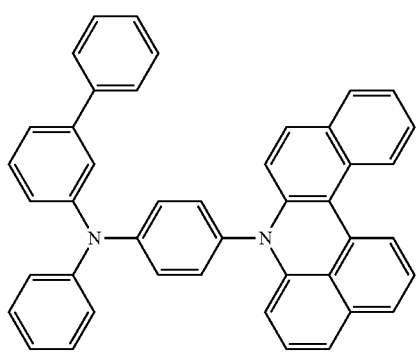 |
| P3-6 | P3-7 |
|---|---|
| 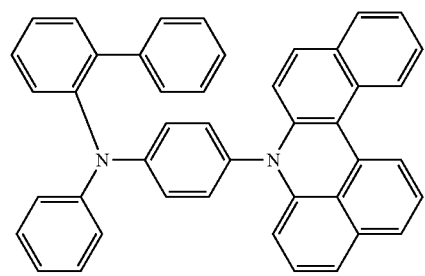 | 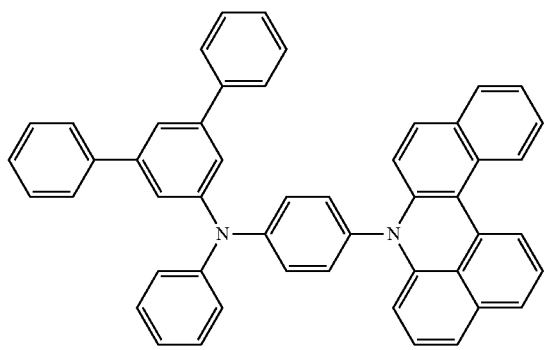 |
| P3-8 | P3-9 |
|---|---|
| 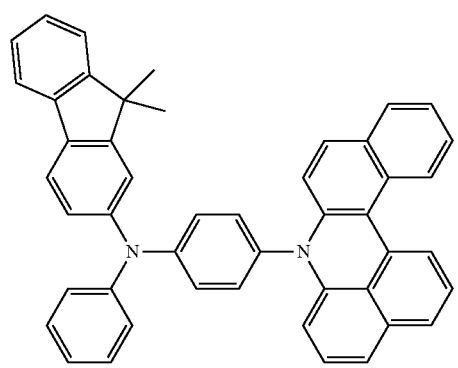 | 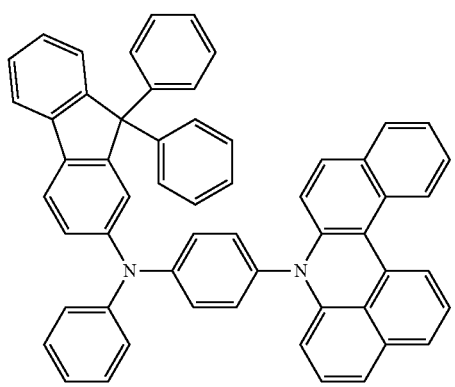 |

-continued
P3-10
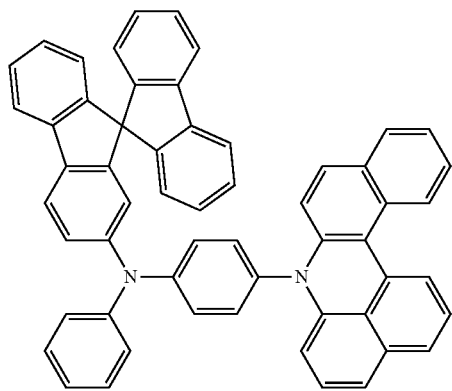
P3-11
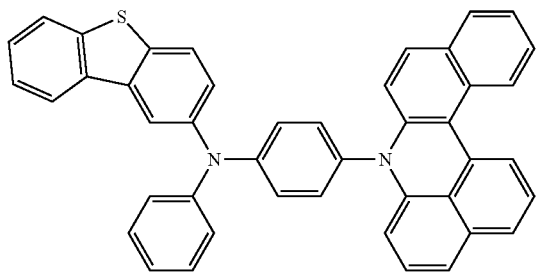
P3-12
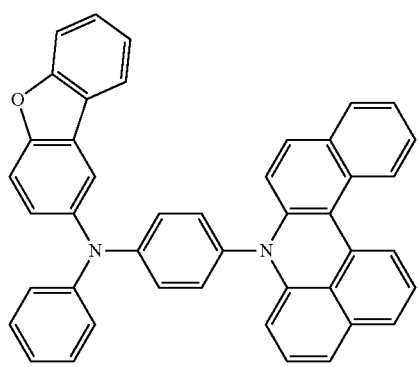
P3-13
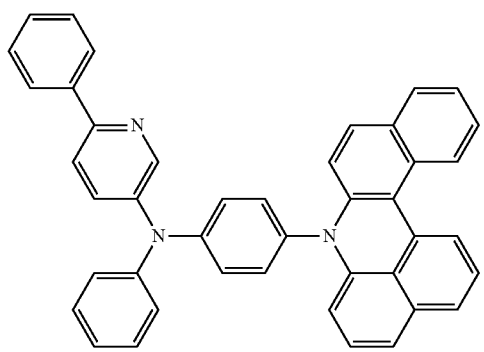
P3-14
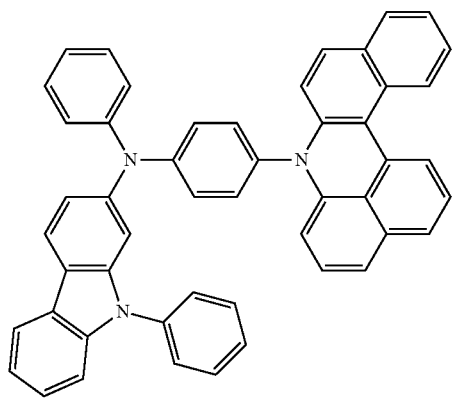
P3-15
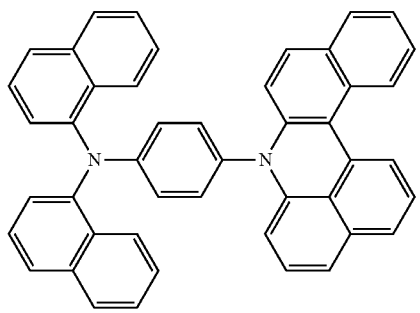
P3-16
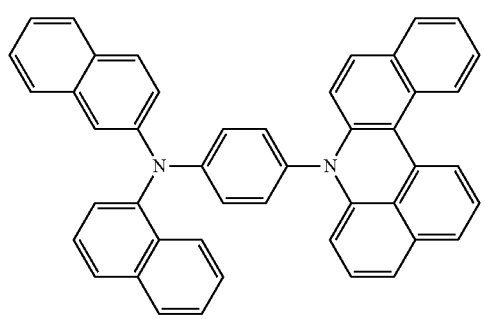
P3-17
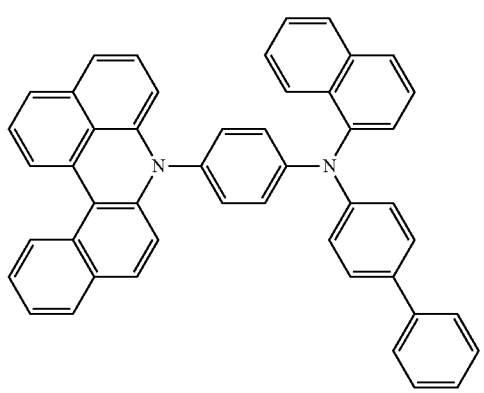

-continued
P3-18
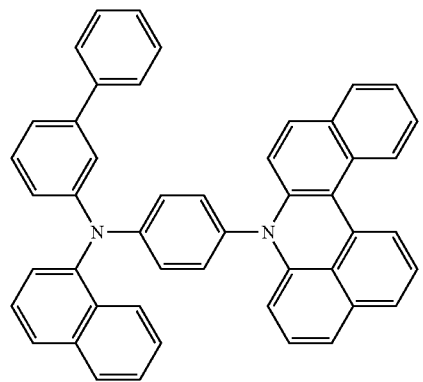
P3-19
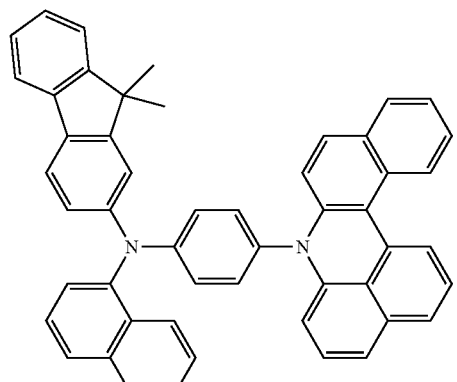
P3-20
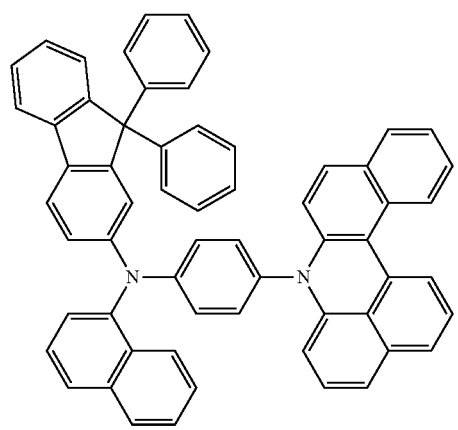
P3-21
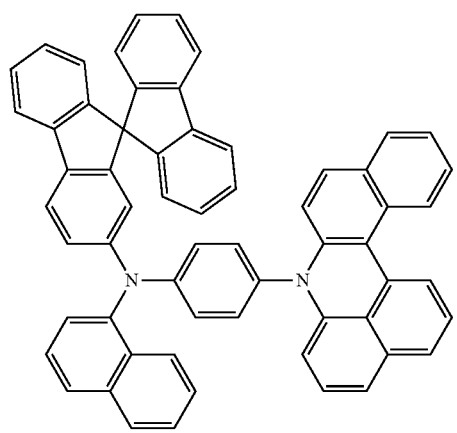
P3-22
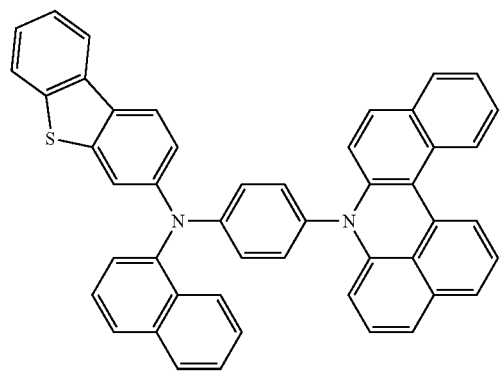
P3-23
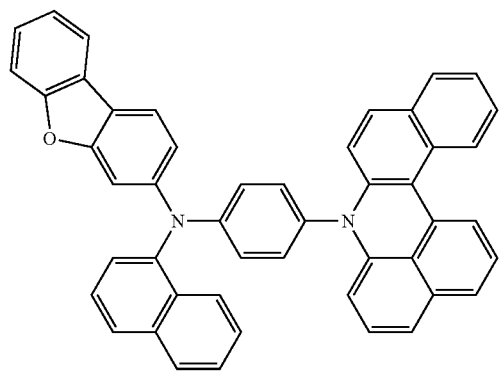
P3-24
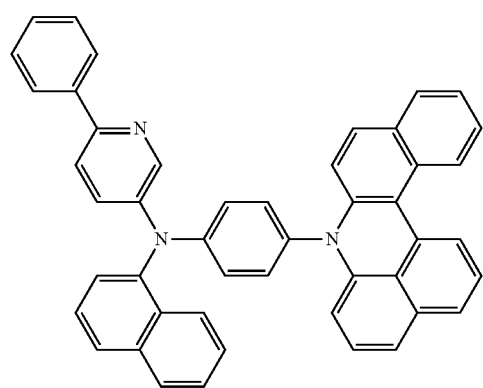
P3-25
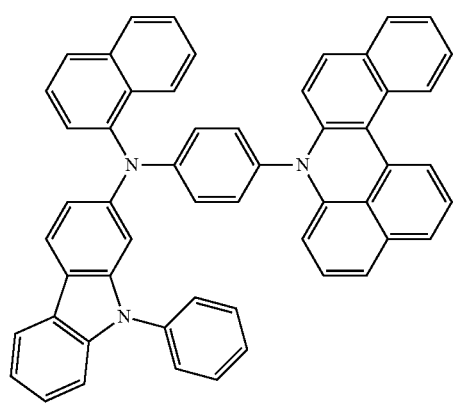

-continued
P3-26
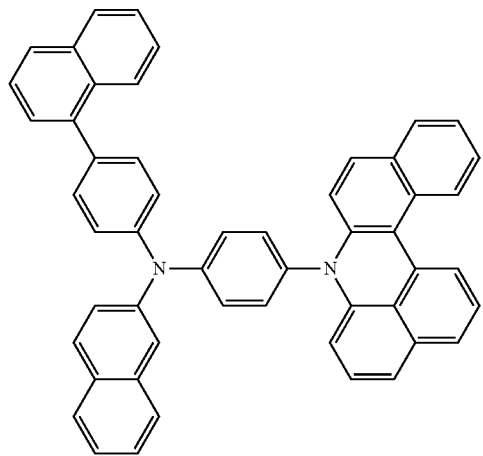
P3-27
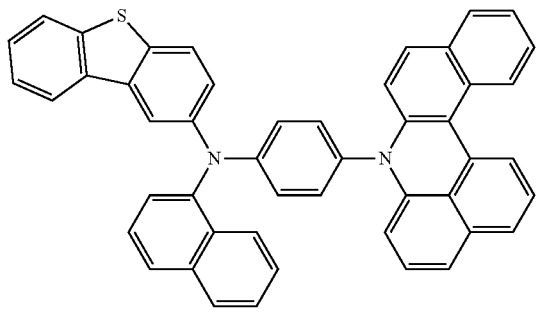
P3-28
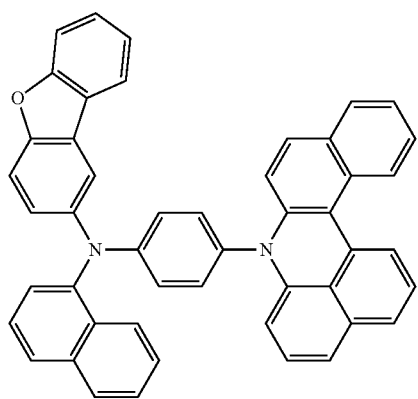
P3-29
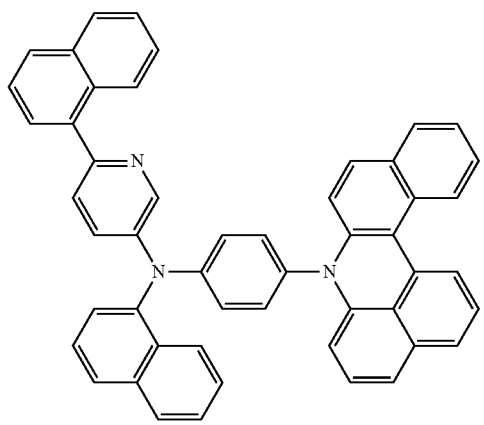
P3-30
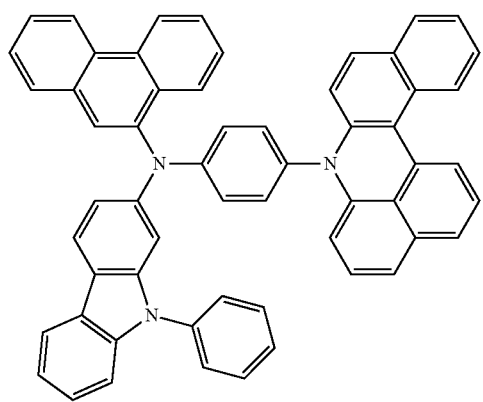
P3-31
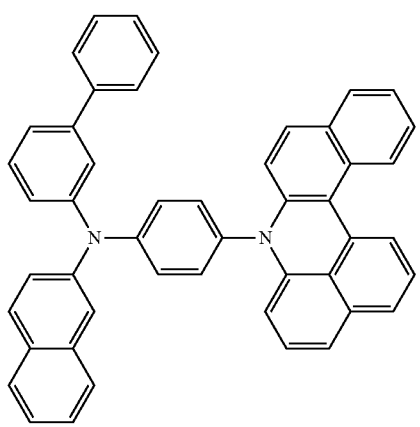

-continued
P3-32
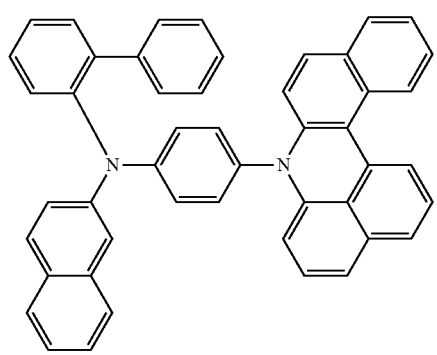
P3-33
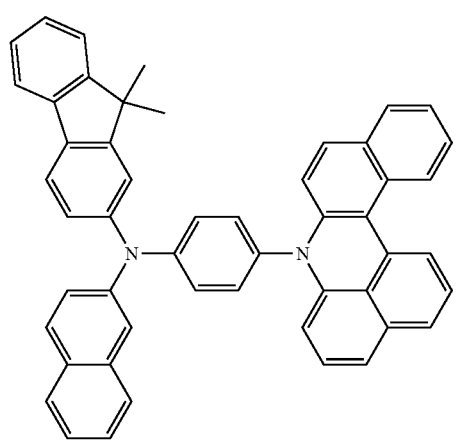
P3-34
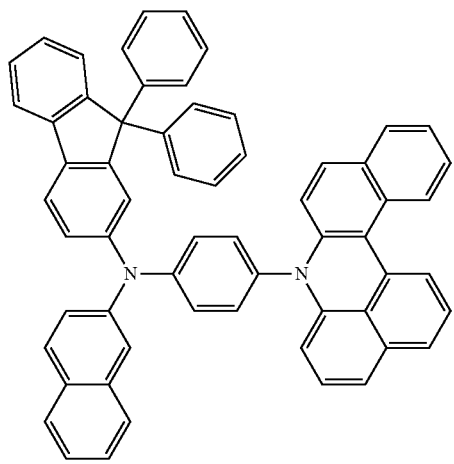
P3-35
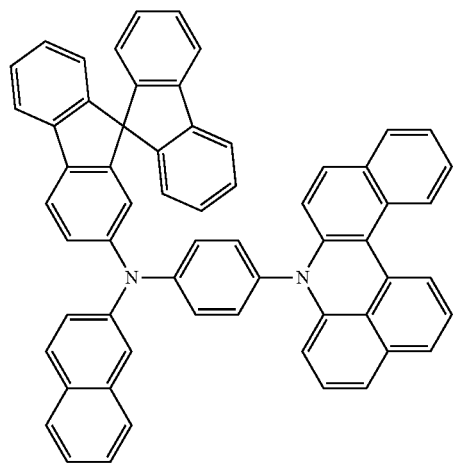
P3-36
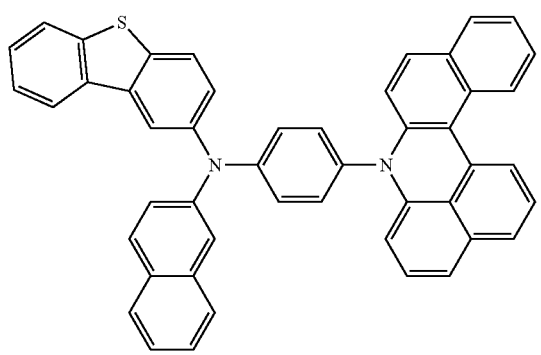
P3-37
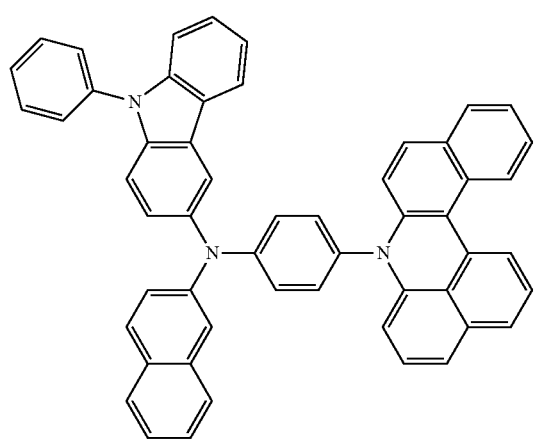

-continued
P3-38
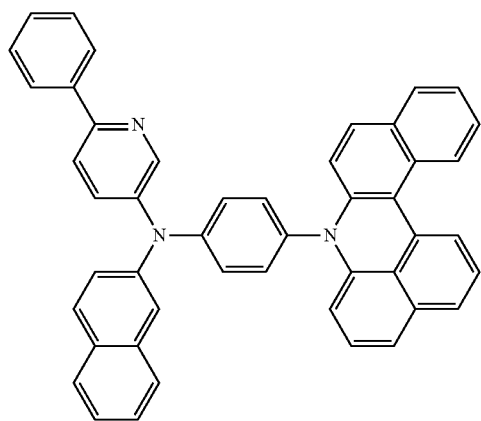
P3-39
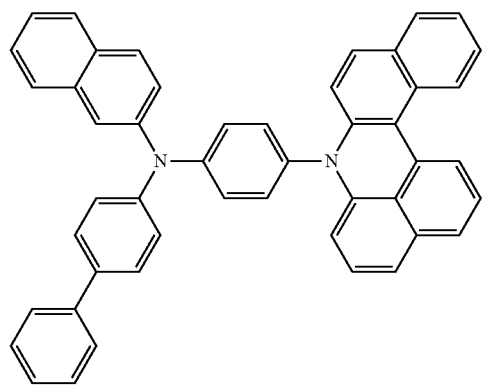
P3-40
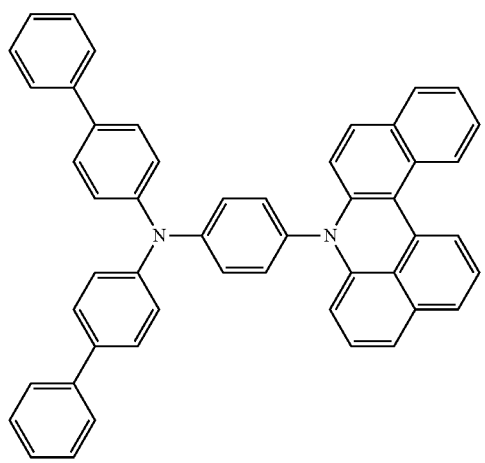
P3-41
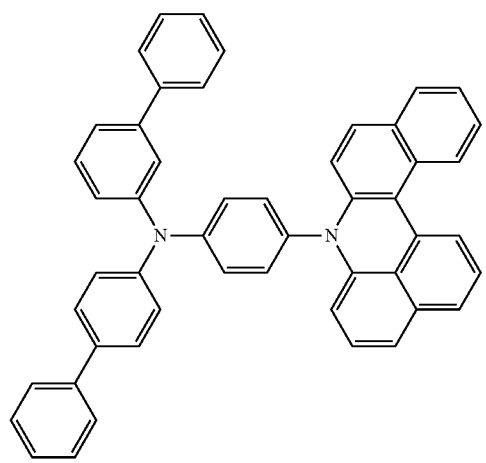
P3-42
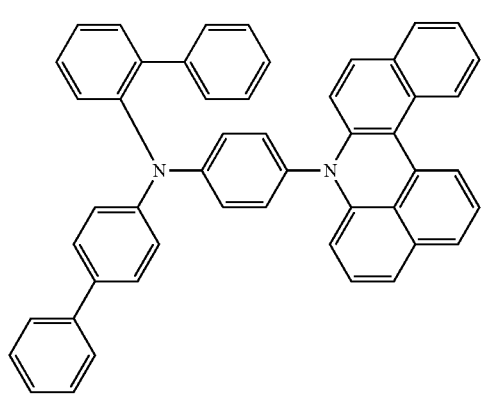
P3-43
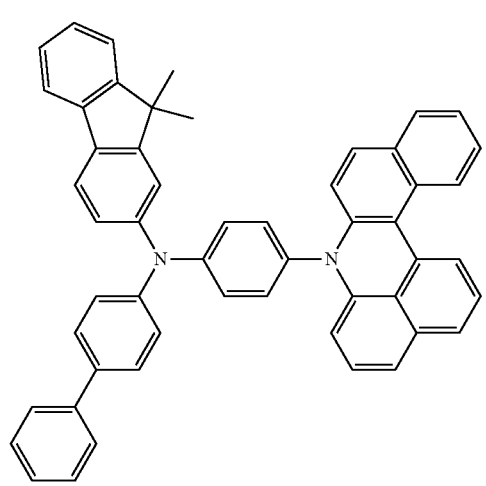

-continued
P3-44
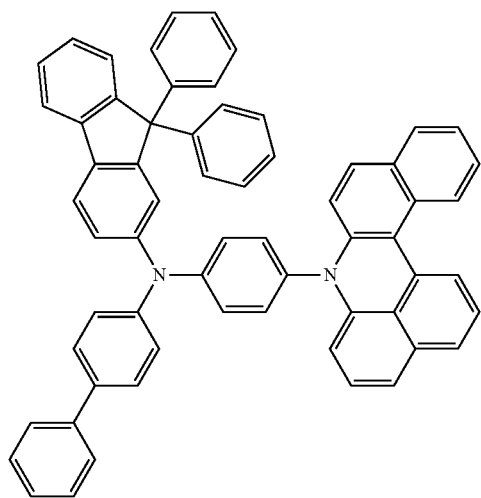
P3-45
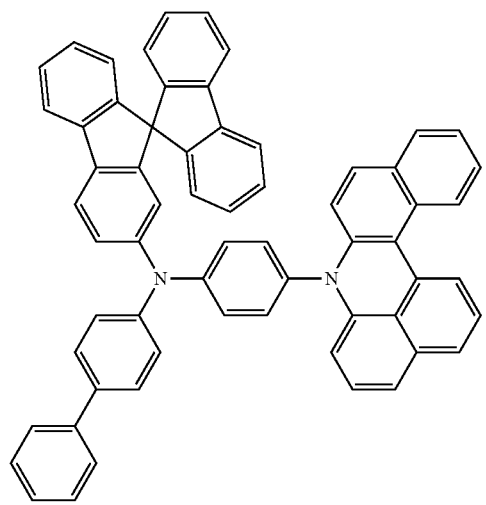
P3-46
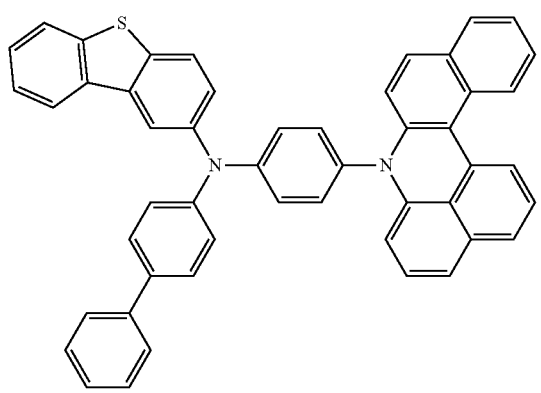
P3-47
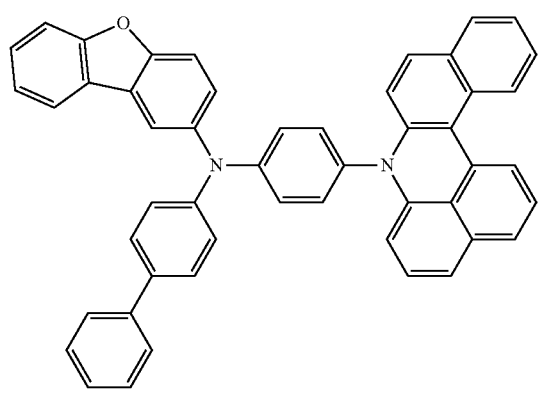
P3-48
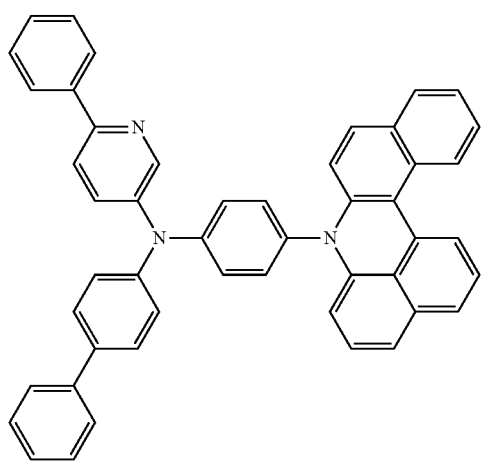
P3-49
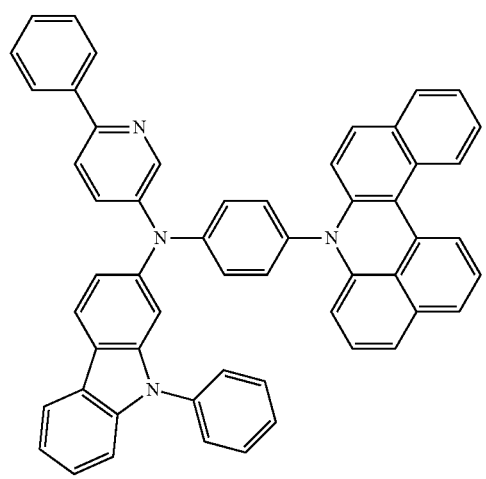

-continued
P3-50
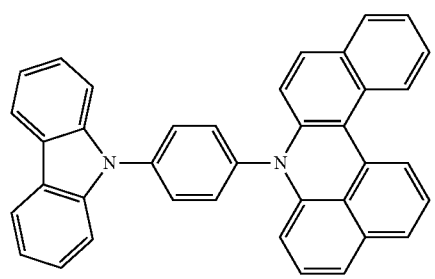
P3-51
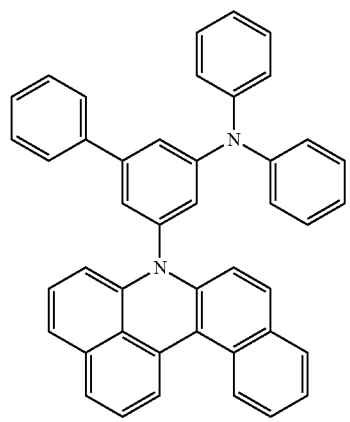
P3-52
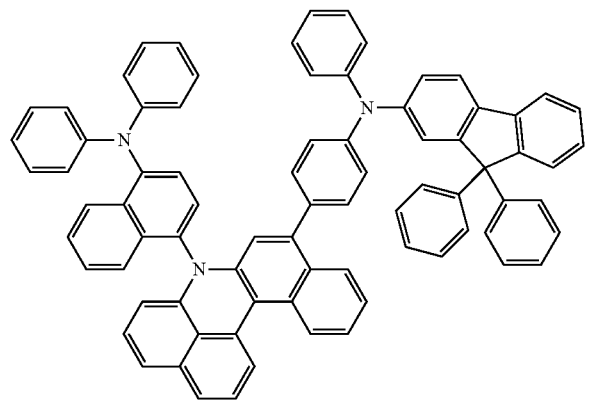
P3-53
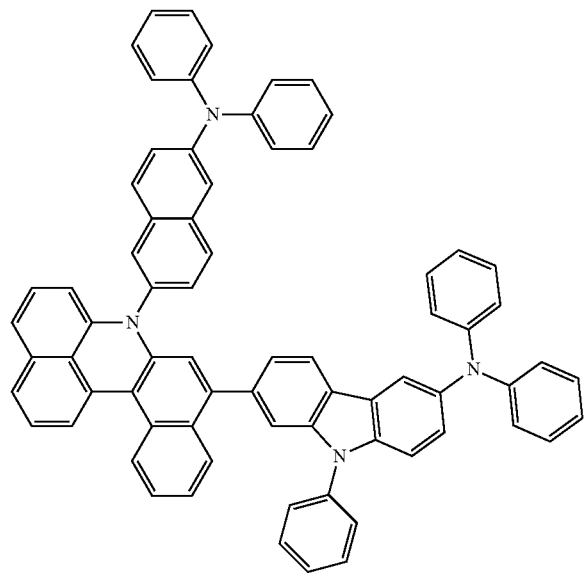
P3-54
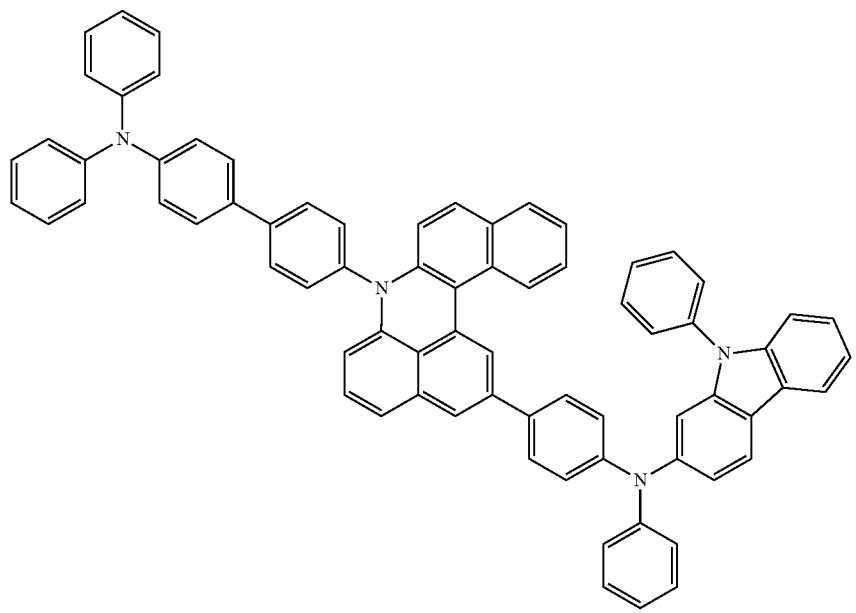

-continued
P3-55
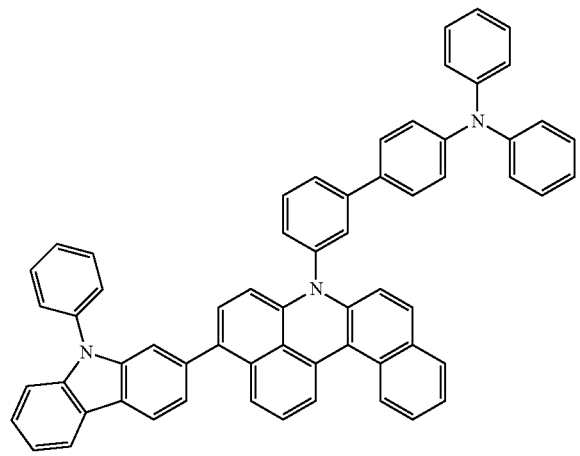
P3-56
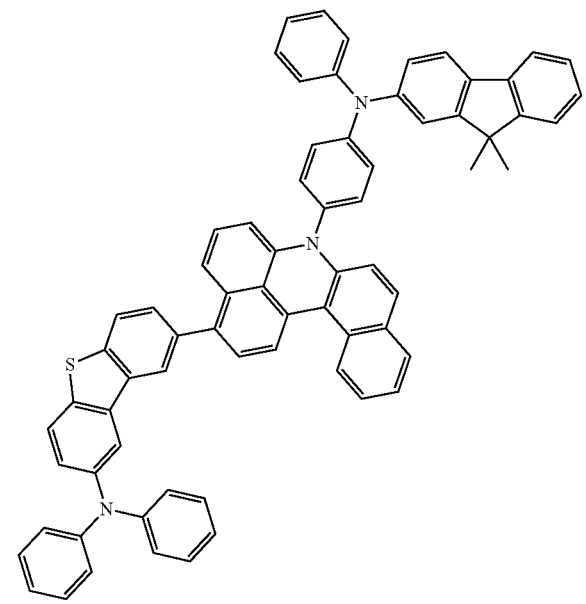
P3-57
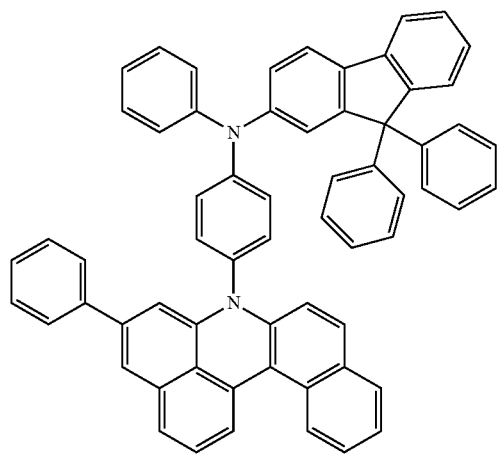
P3-58
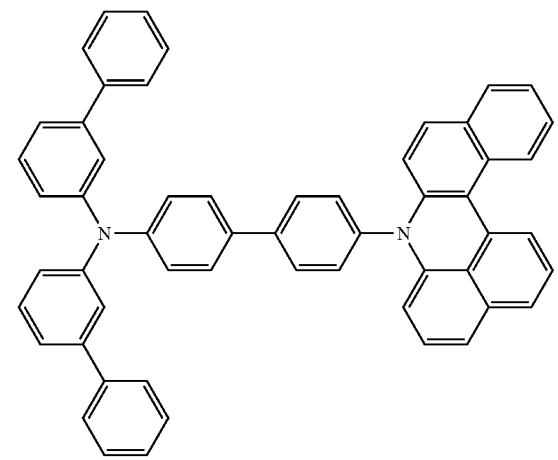
P3-59
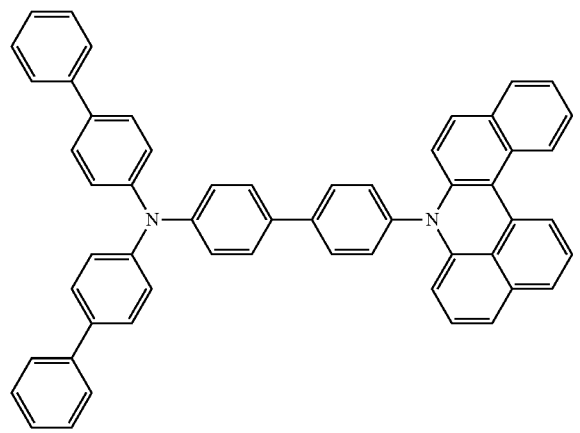
P3-60
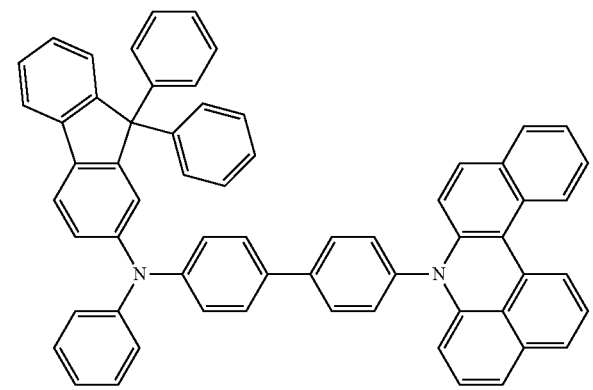

-continued
P3-61
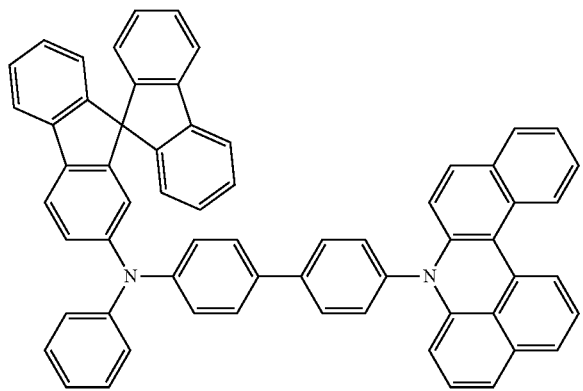
P3-62
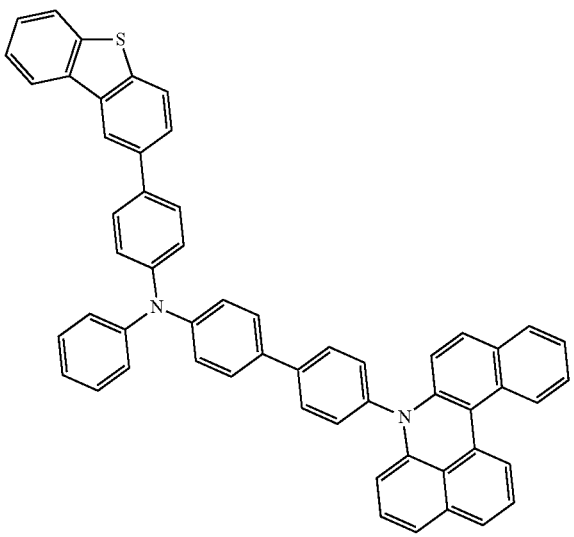
P3-63
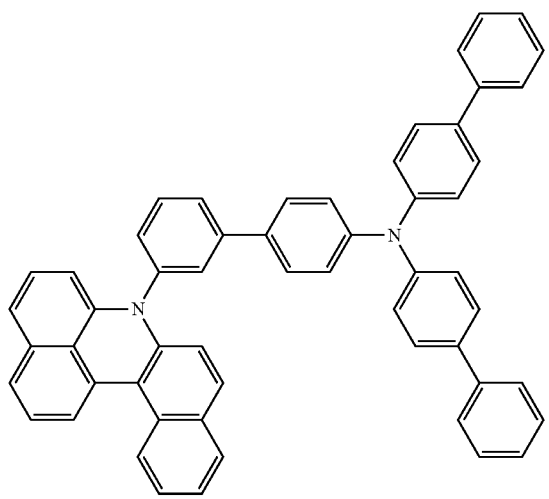
P3-64
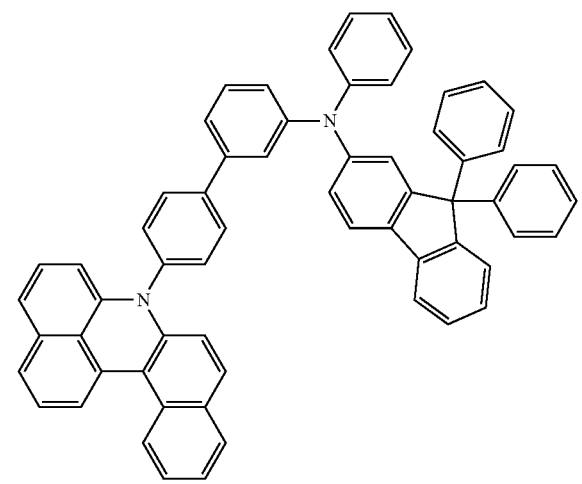
P-65
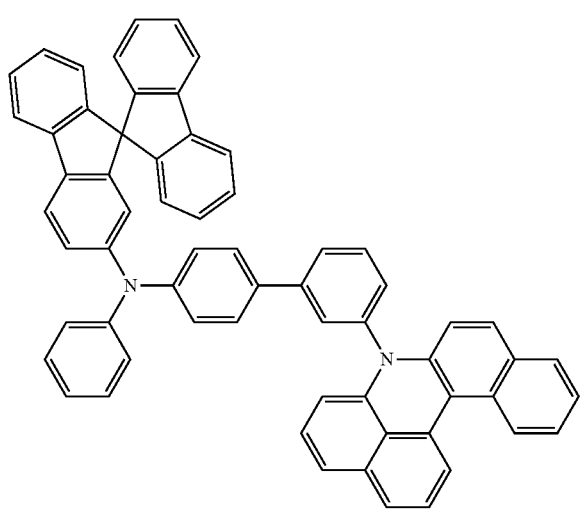
P3-66
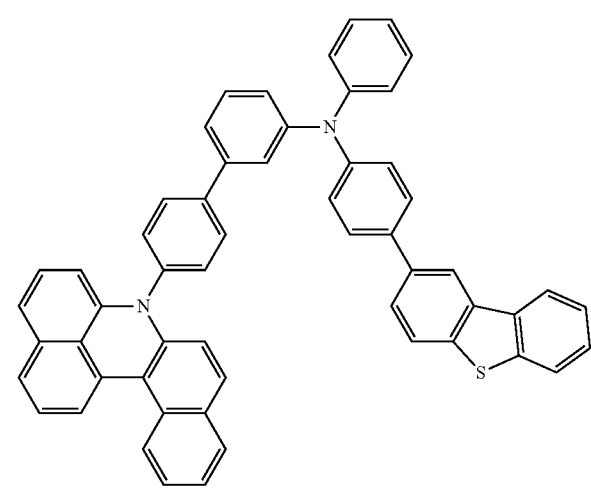

-continued
P3-67
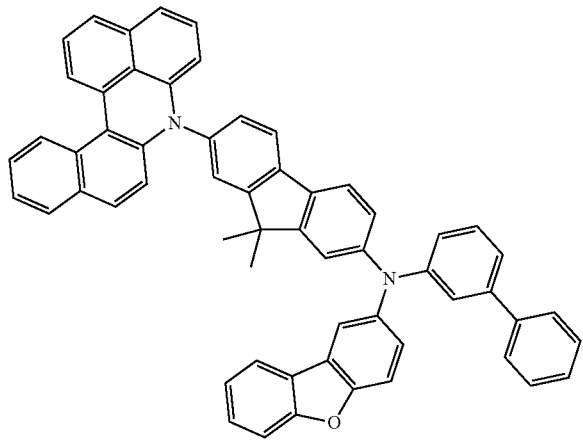
P3-68
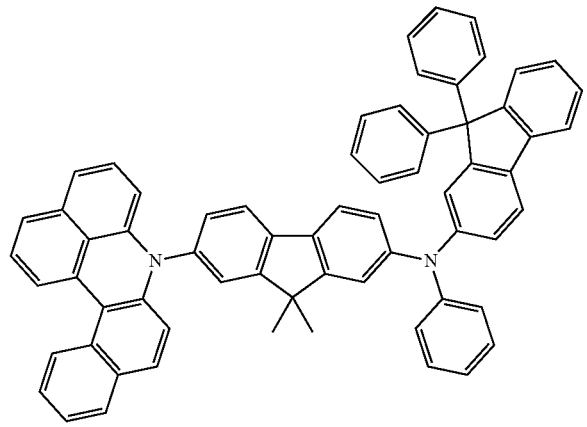
P3-69
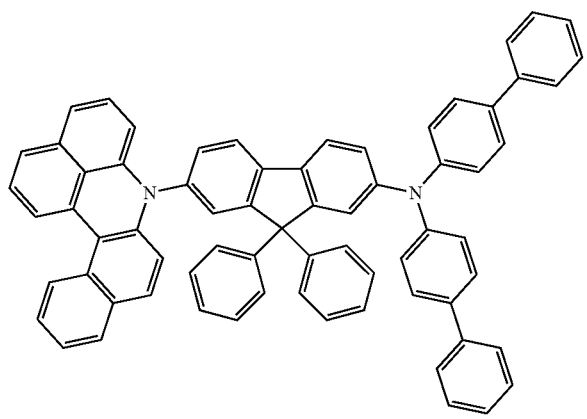
P3-70
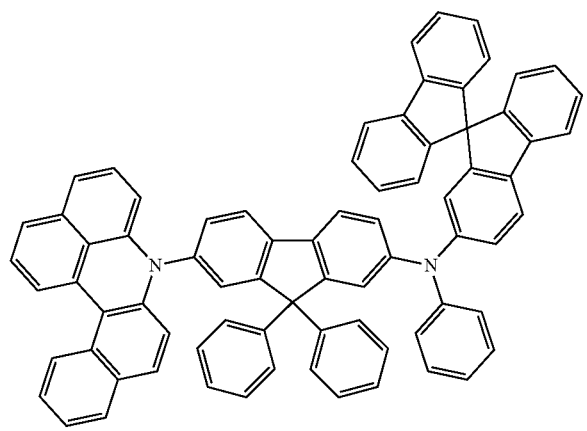
P3-71
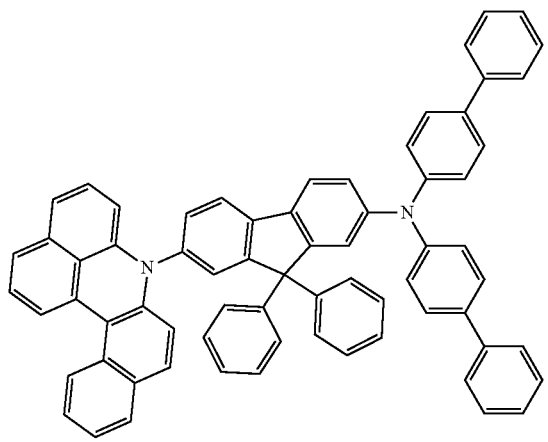
P3-72
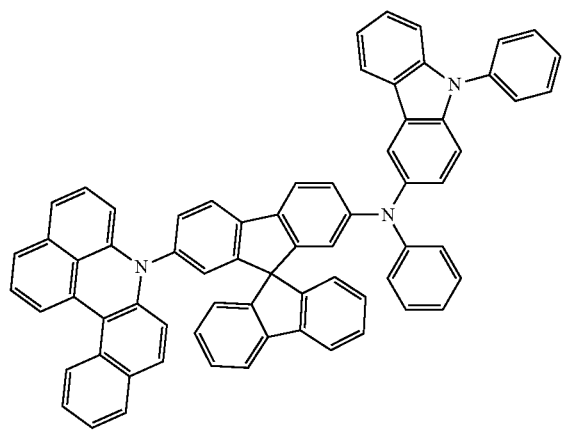

-continued
P3-73
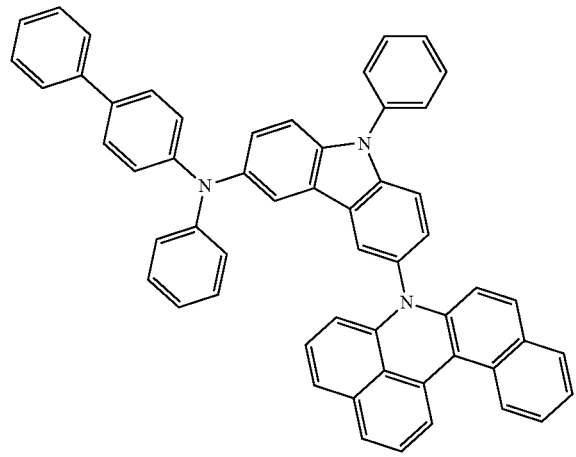
P3-74
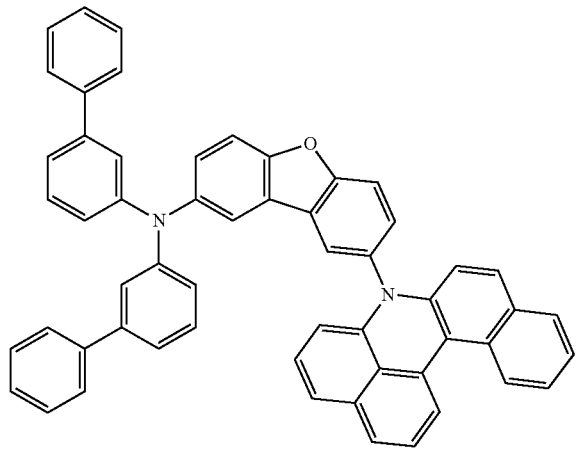
P3-75
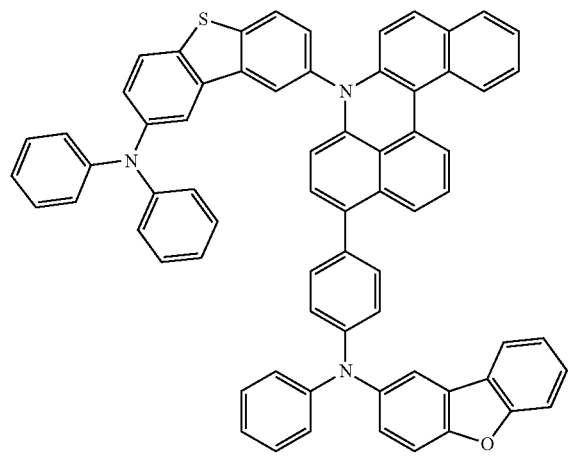
P3-76
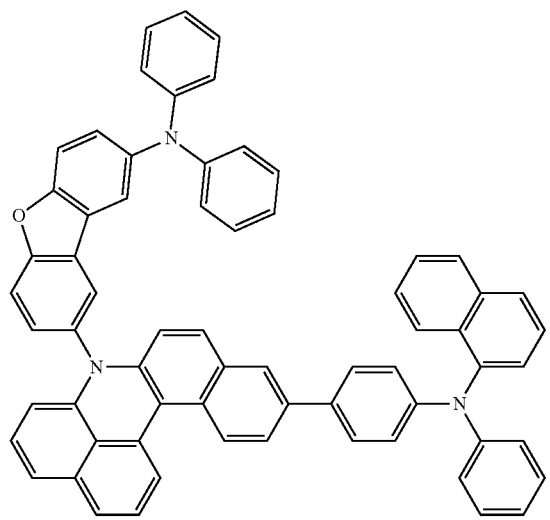
P3-77
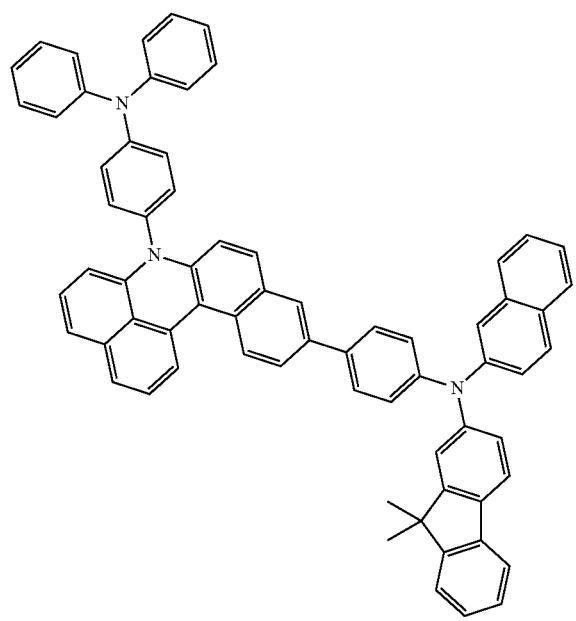
P3-78

-continued
P3-79
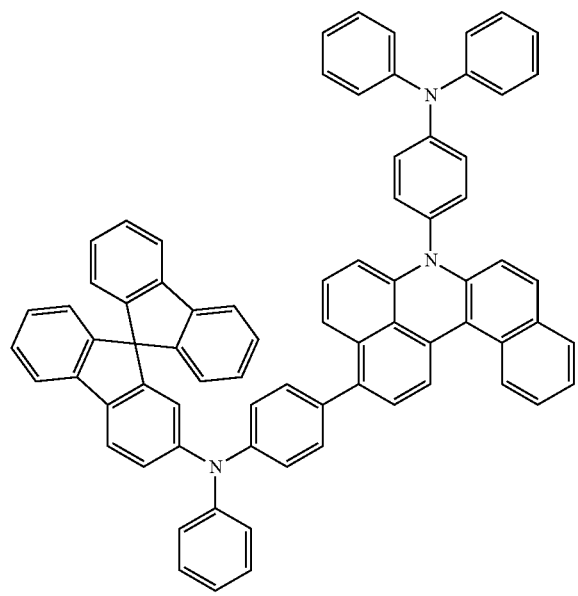
P3-80
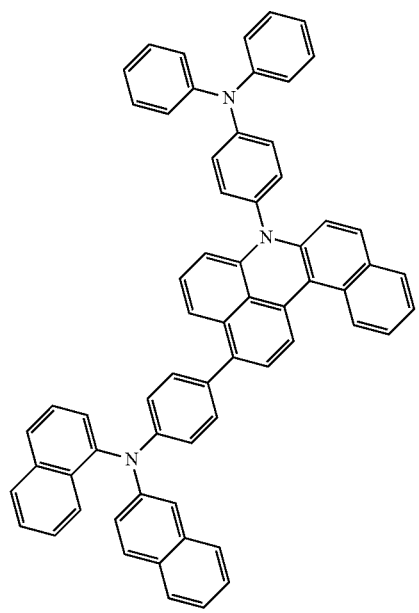
P3-81
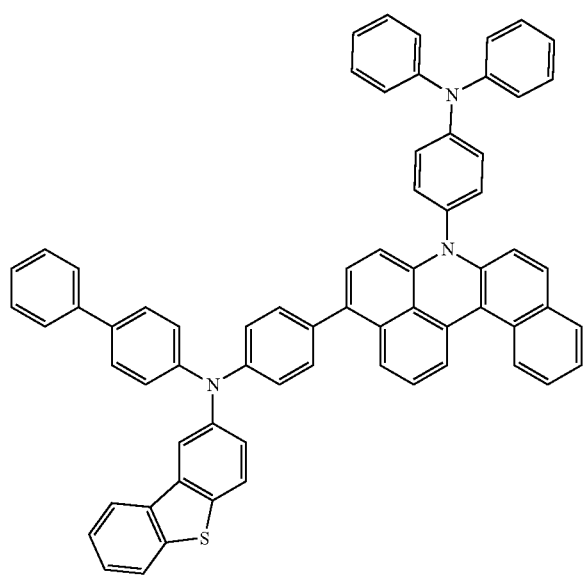
P3-82
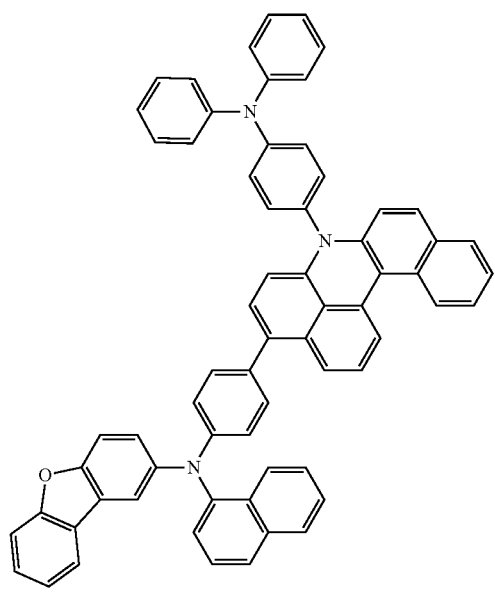

-continued
P3-83
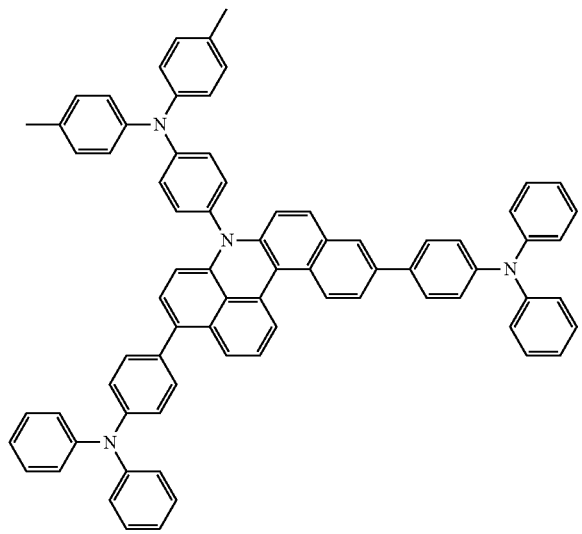
P3-84
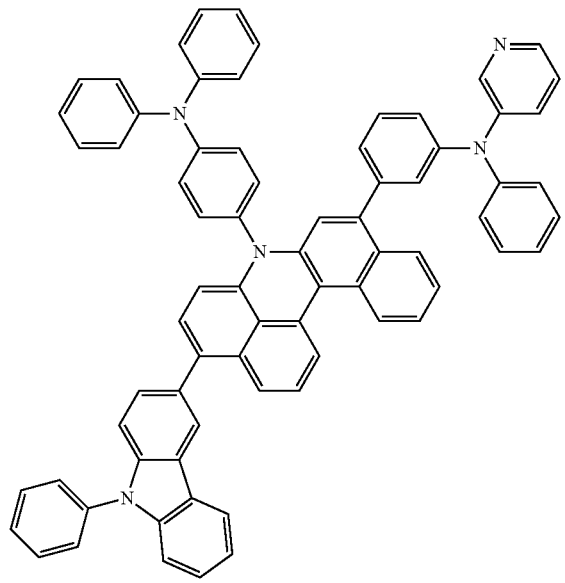
P3-85
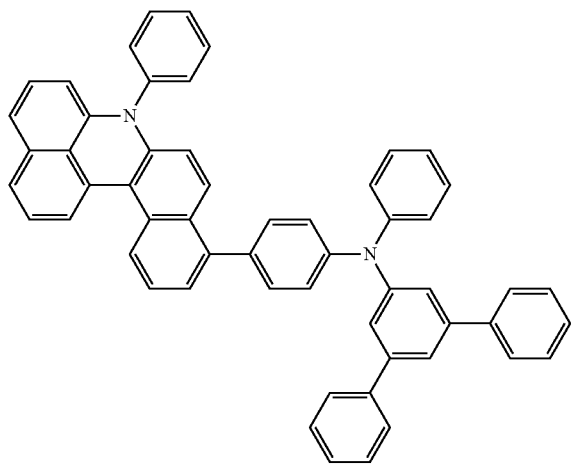
P3-86
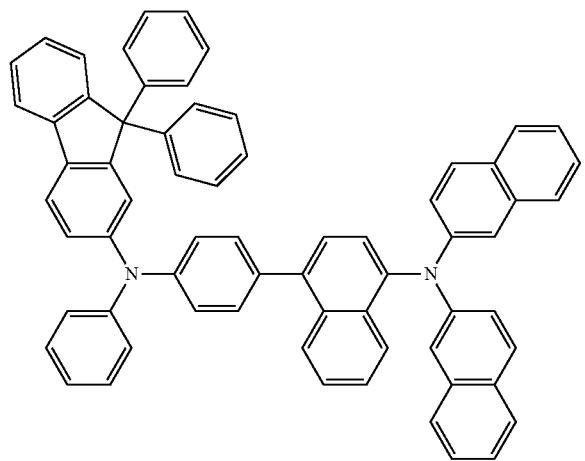
P3-87
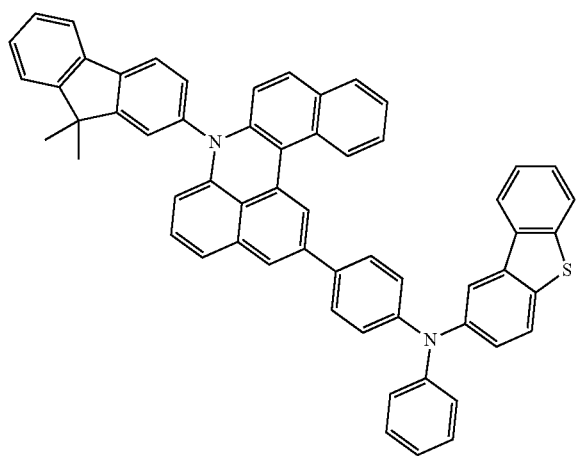
P3-88
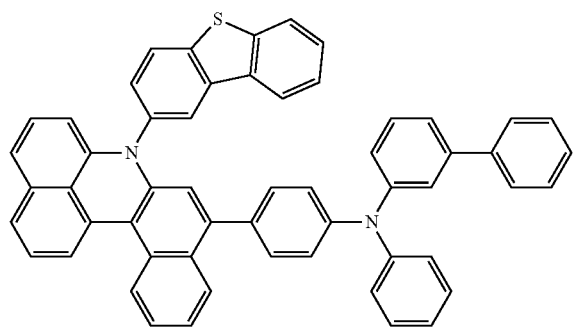

-continued
P4-1
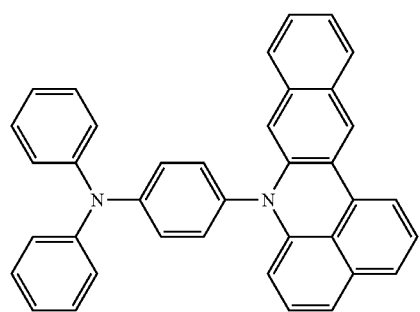
P4-2
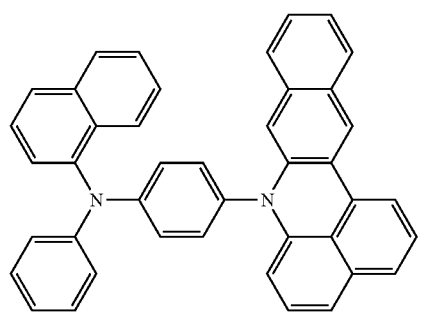
P4-3
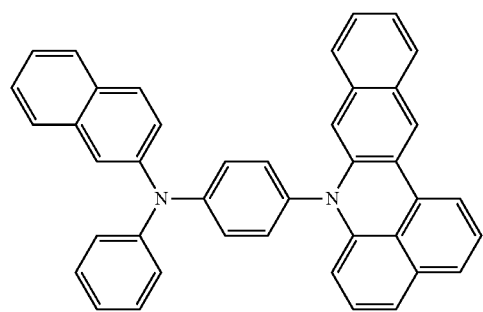
P4-4
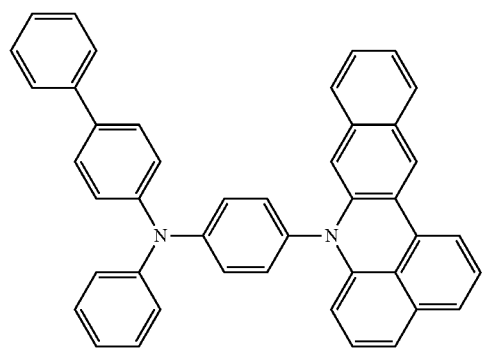
P4-5
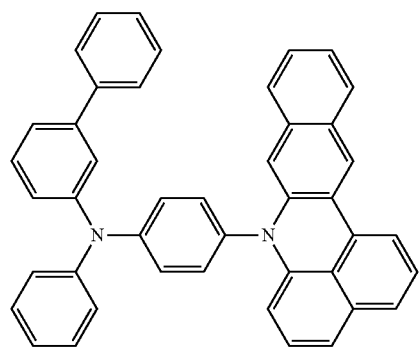
P4-6
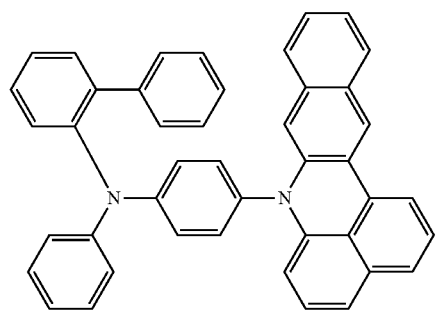
P4-7
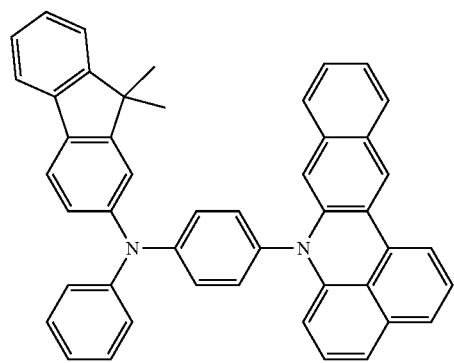
P4-8
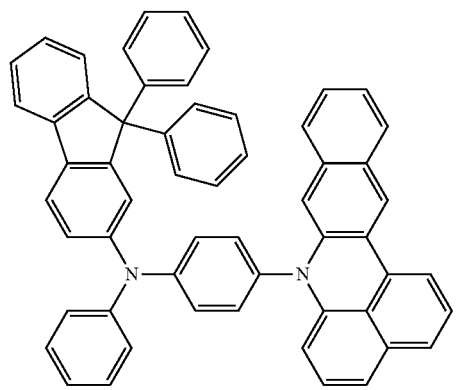

-continued
P4-9
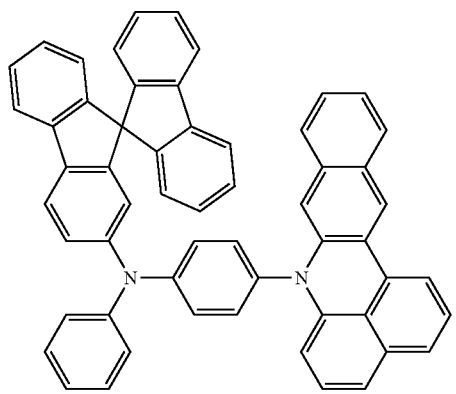
P4-10
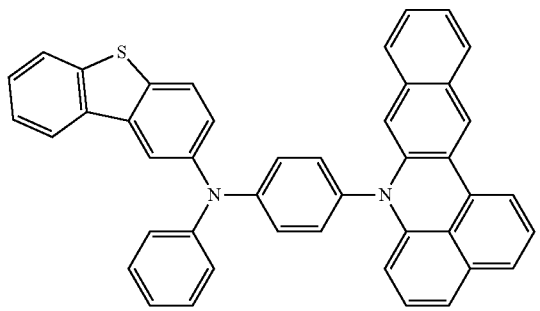
P4-11
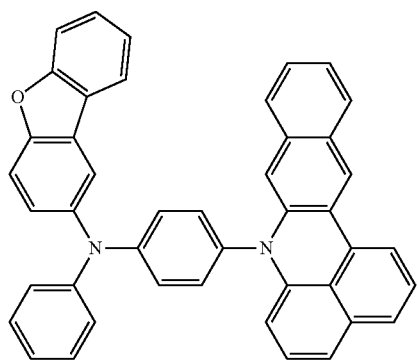
P4-12
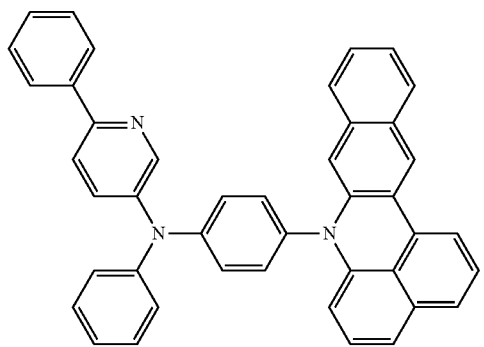
P4-13
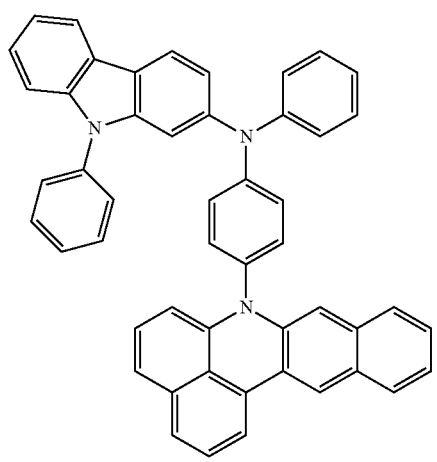
P4-14
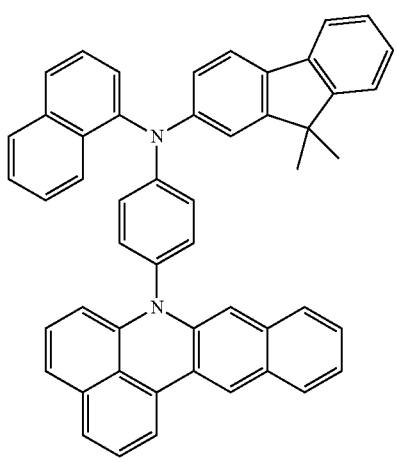

-continued
P4-15
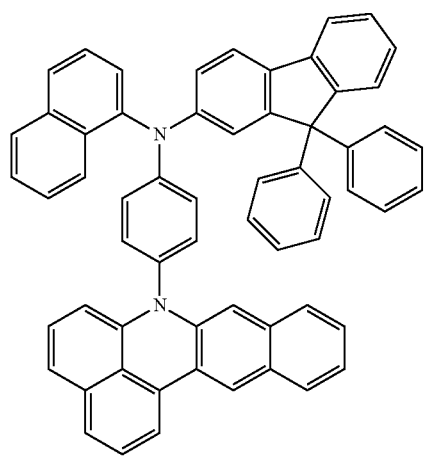
P4-16
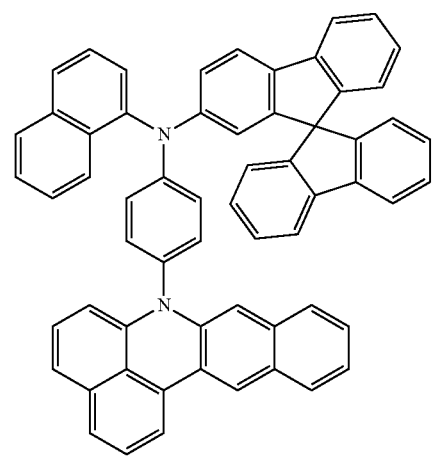
P4-17
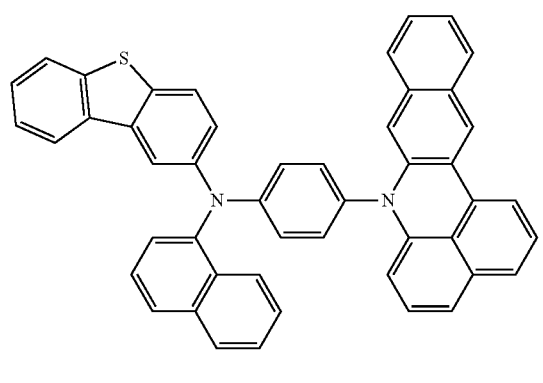
P4-18
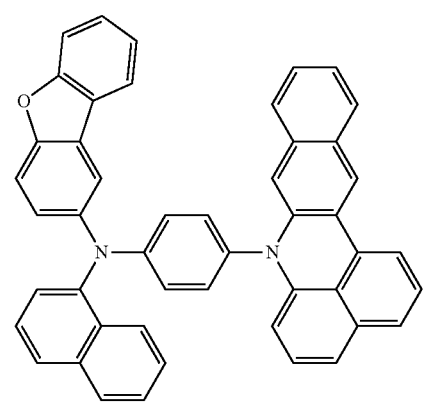
P4-19
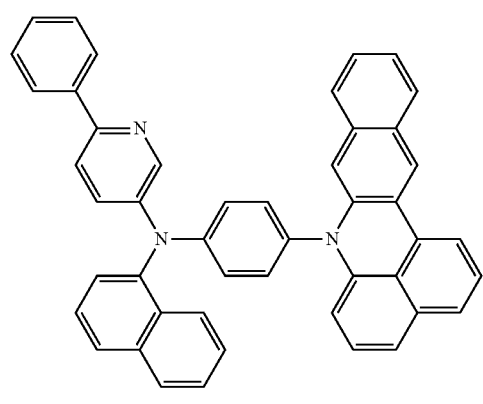
P4-20
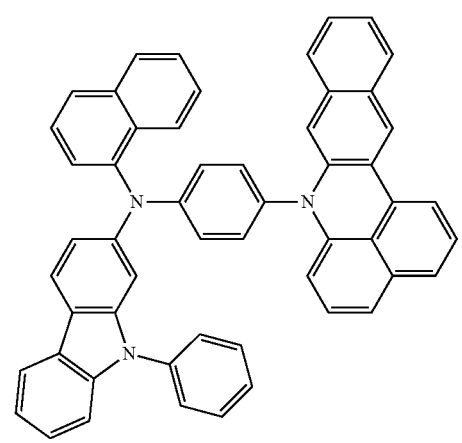

-continued
P4-21
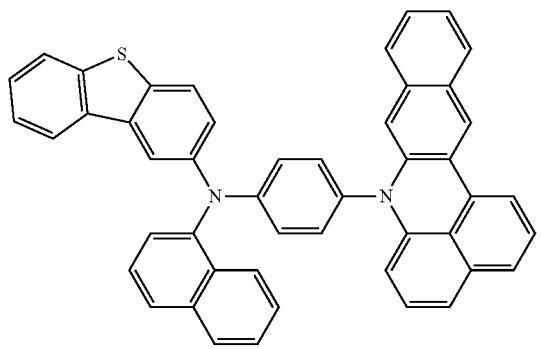
P4-22
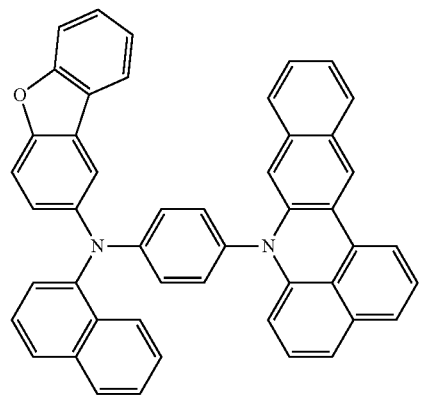
P4-23
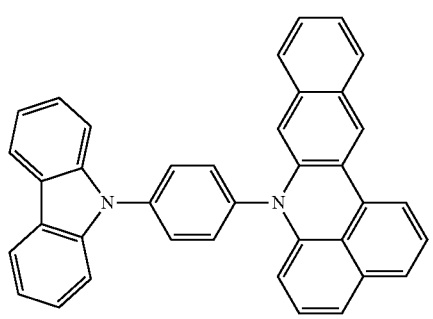
P4-24
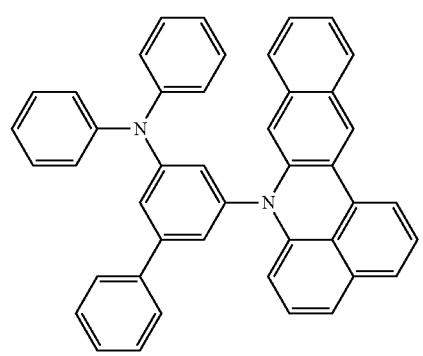
P4-25
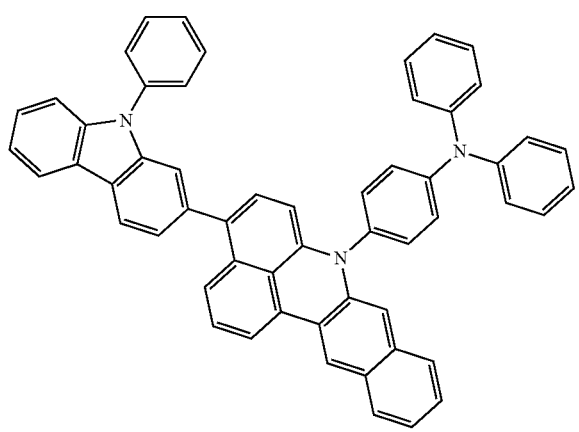
P4-26
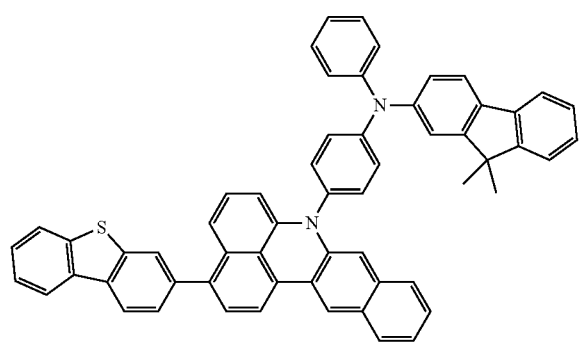

-continued
P4-27
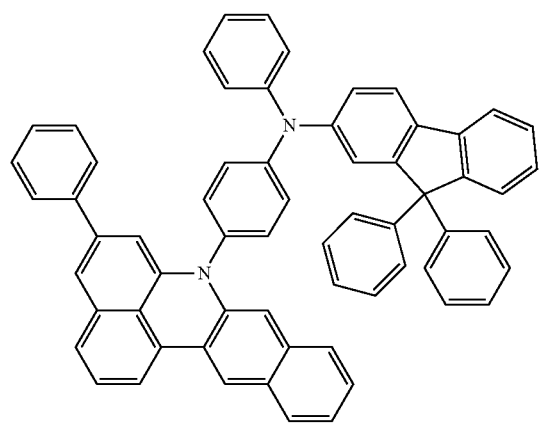
P4-28
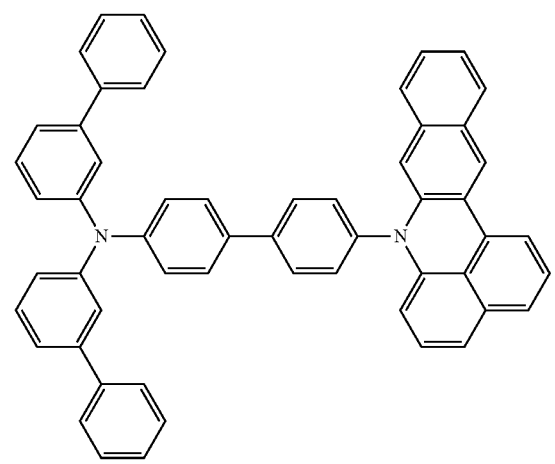
P4-29
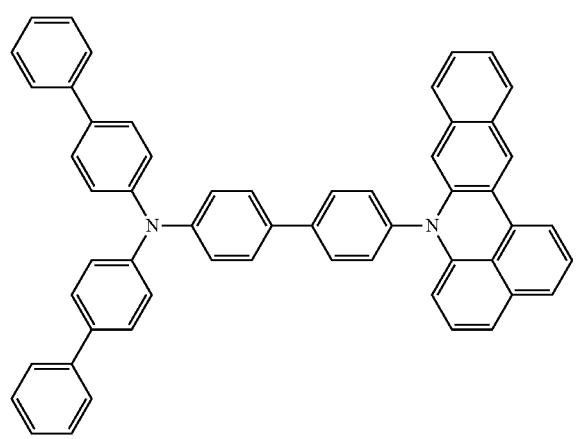
P4-30
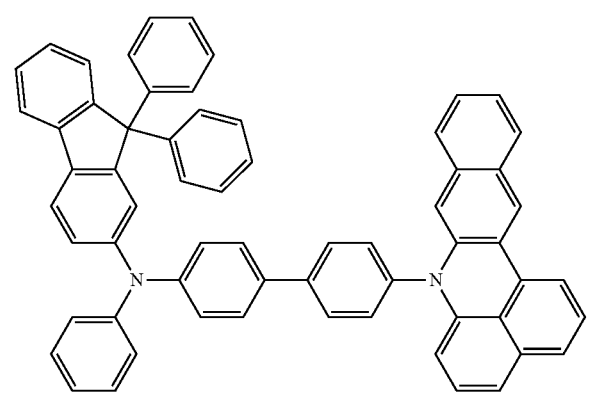
P4-31
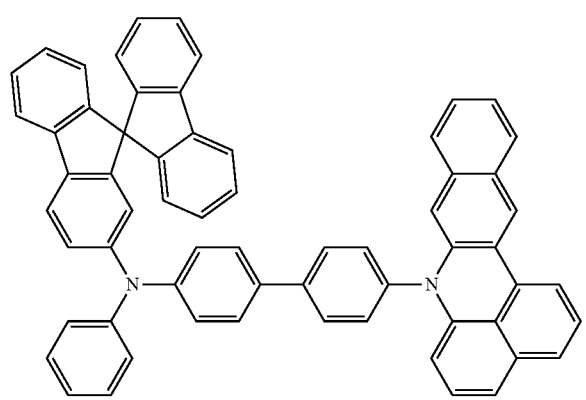
P4-32
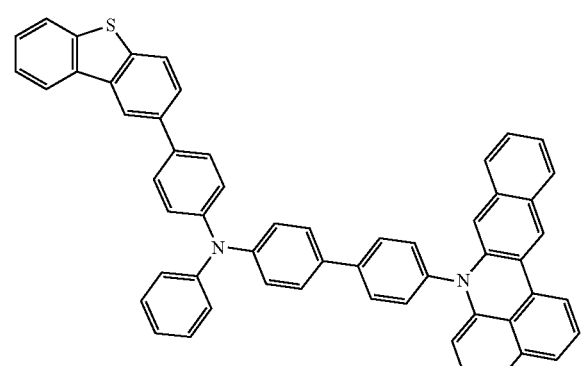

-continued
P4-33
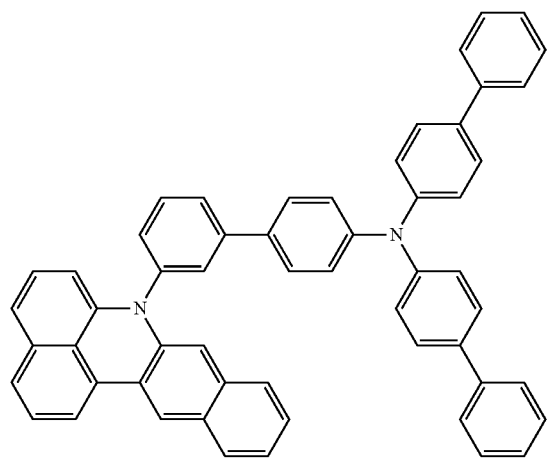
P4-34
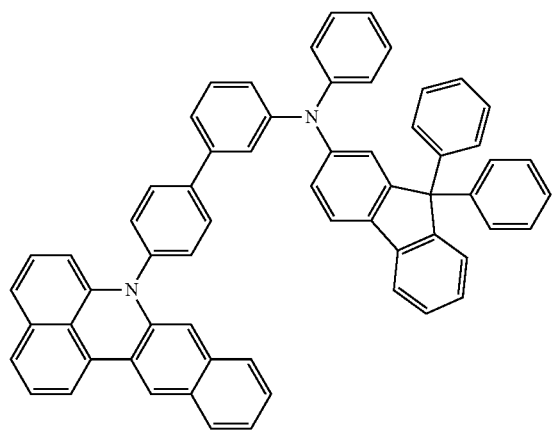
P4-35
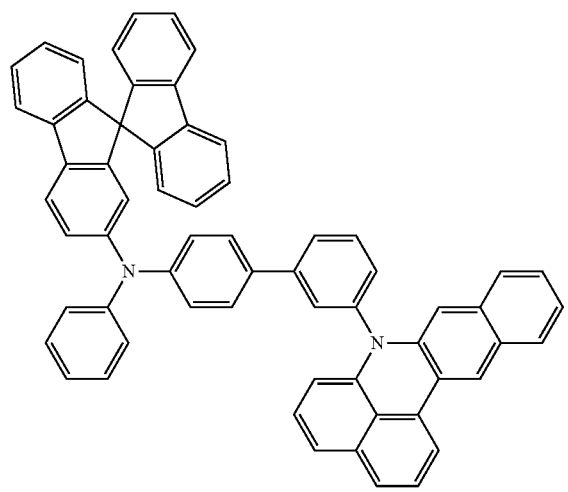
P4-36
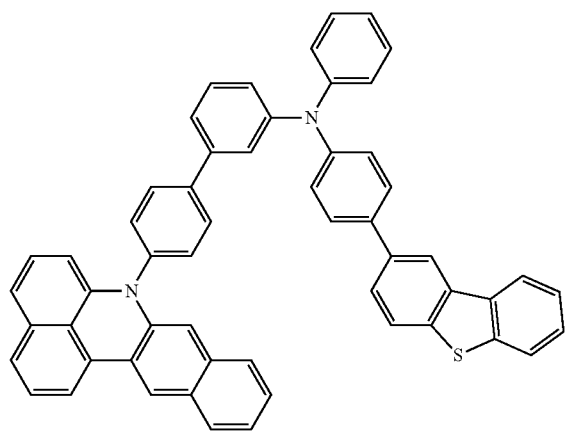
P4-37
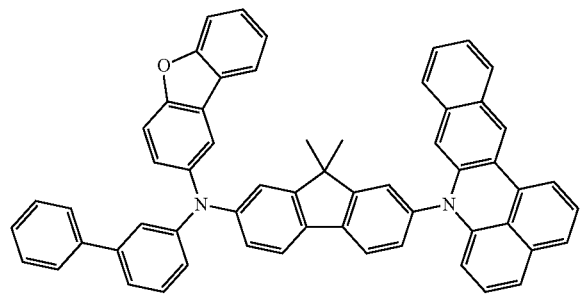
P4-38
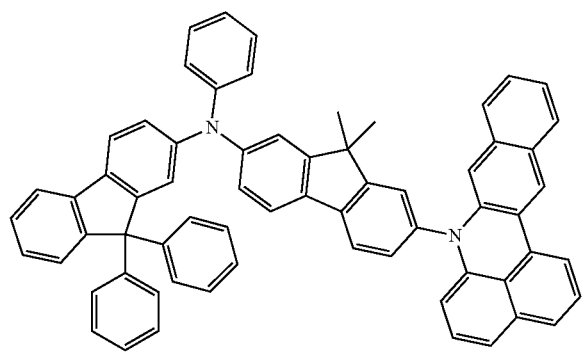

-continued
P4-39
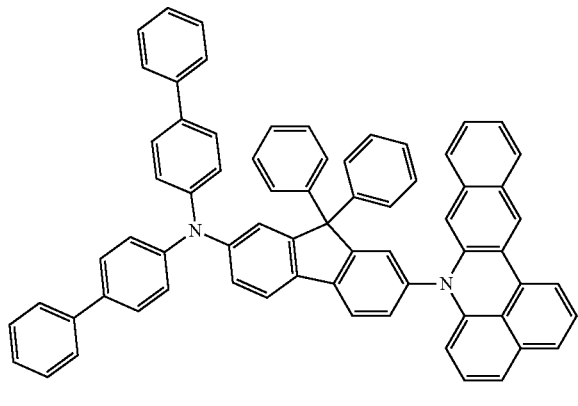
P4-40
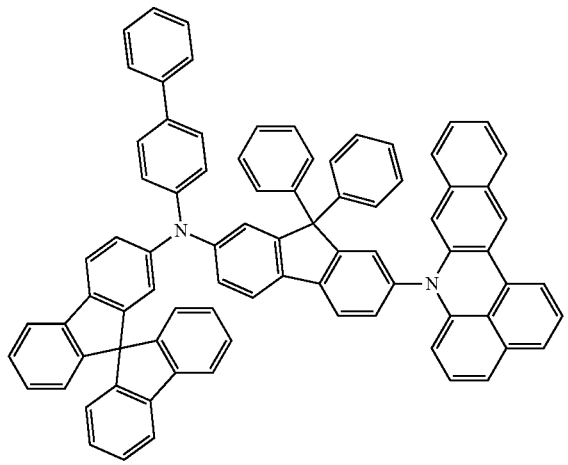
P4-41
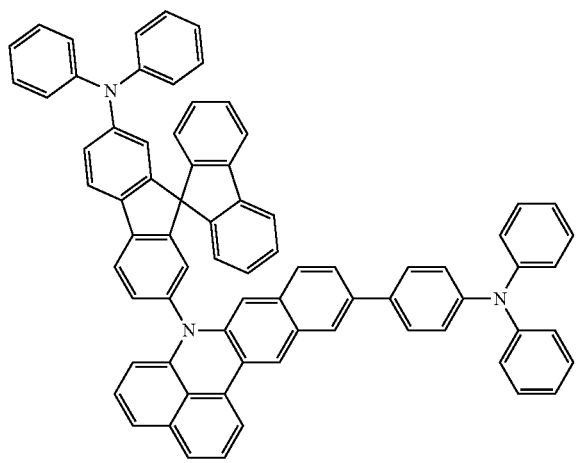
P4-42
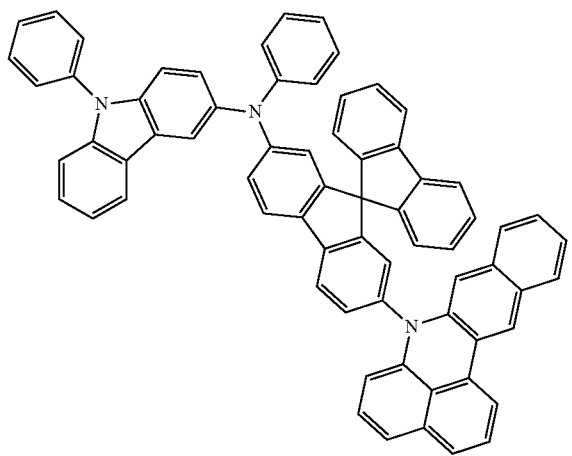
P4-43
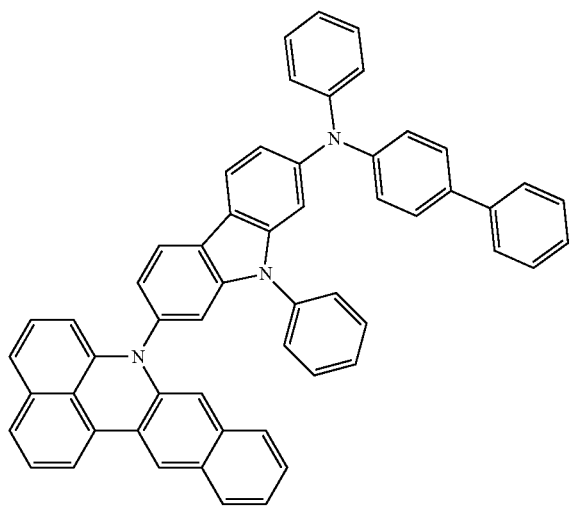
P4-44
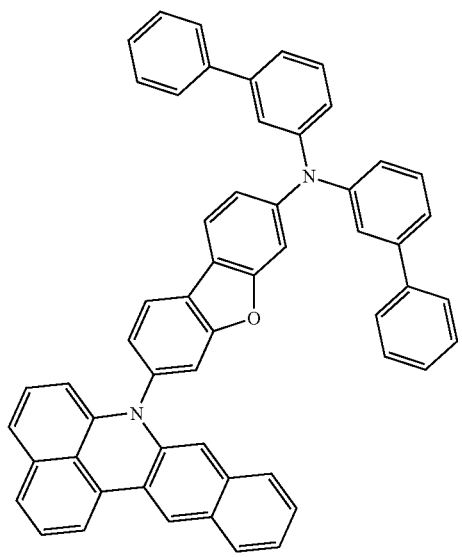

-continued
P4-45
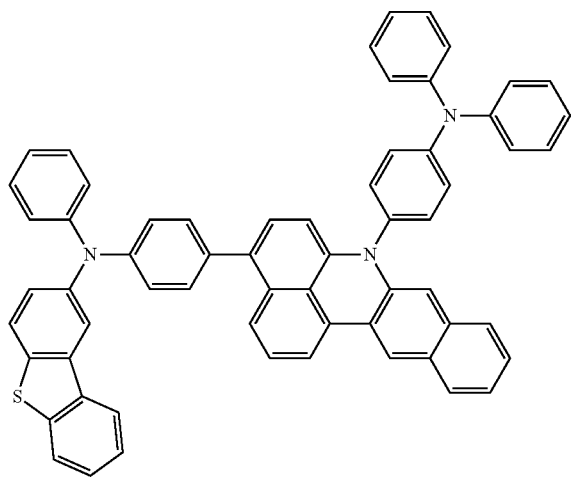
P4-46
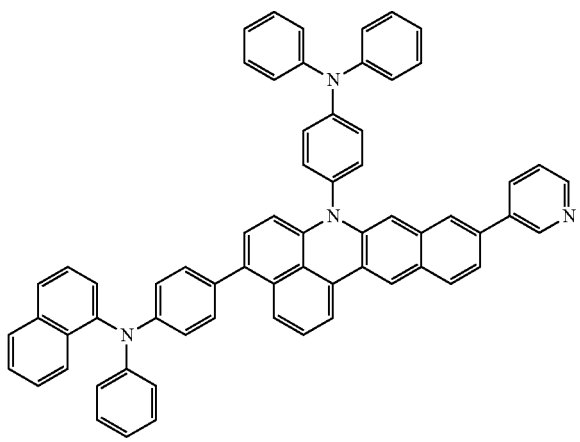
P4-47
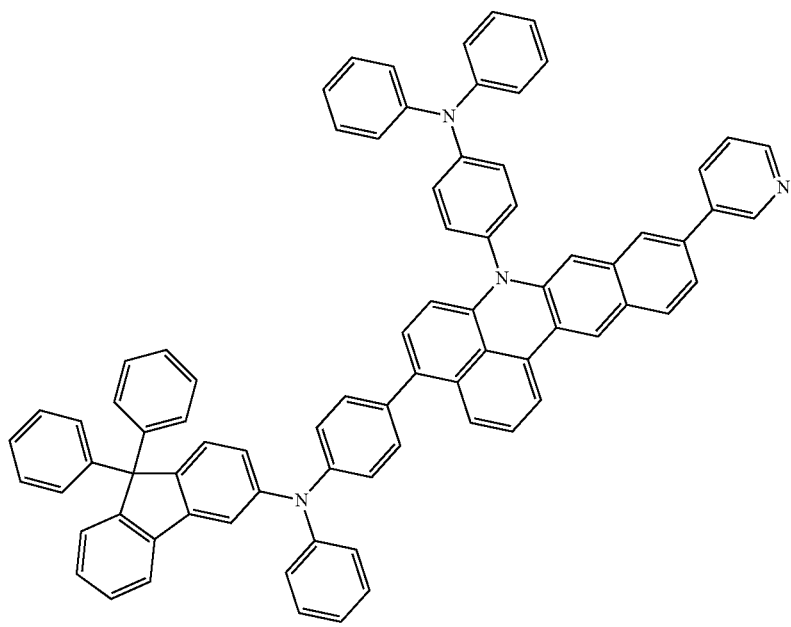
P4-48
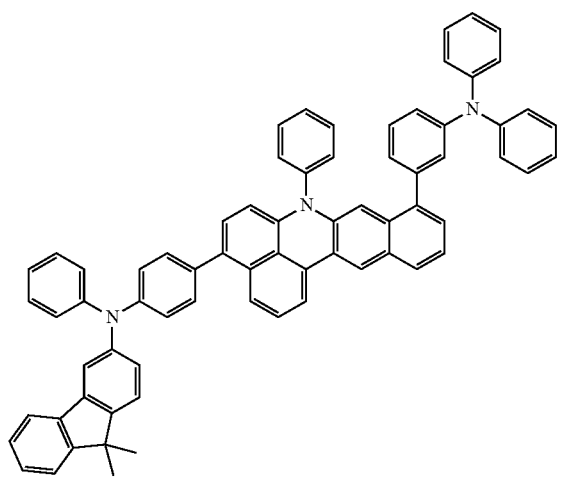
P4-49
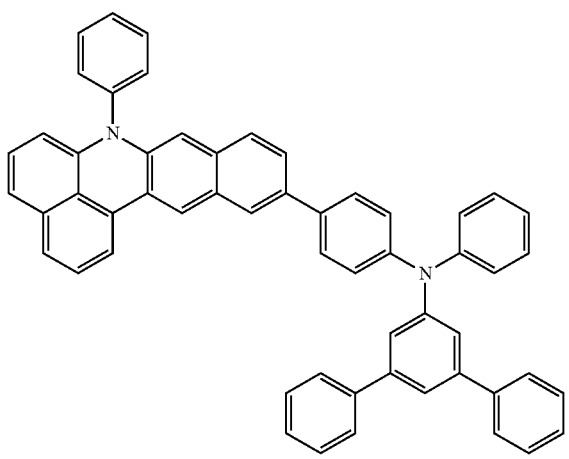

P4-50

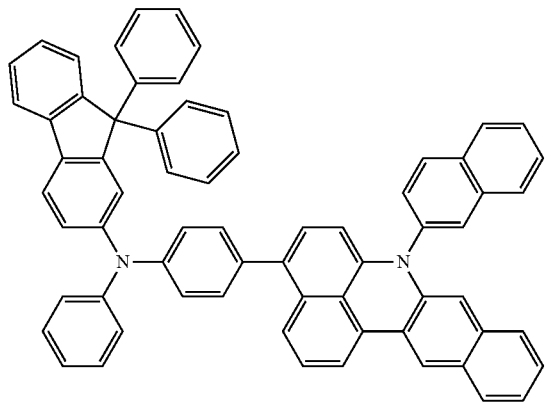

P4-51

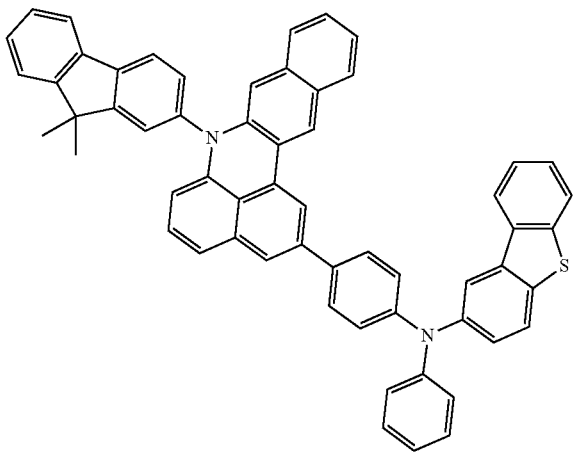

P4-52

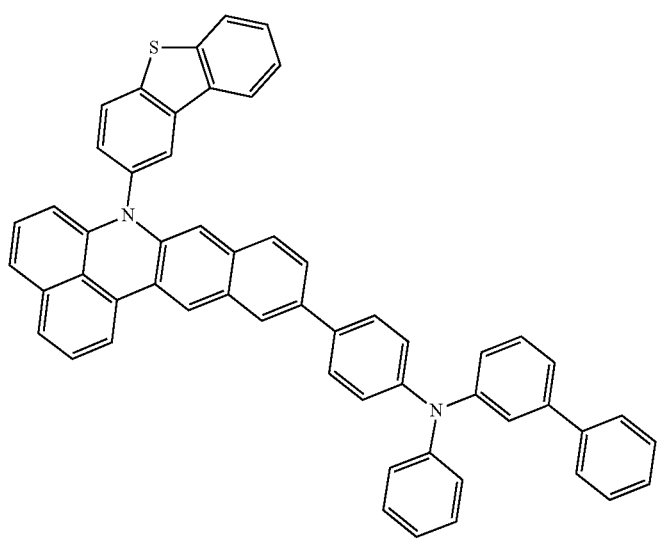

In another embodiment, the present invention provides a compound for an organic electronic element, represented by Formula 1.

In still another embodiment, the present invention provides an organic electronic element containing the compound represented by Formula 1.

Here, the organic electronic element may include: a first electrode; a second electrode; and an organic material layer positioned between the first electrode and the second electrode, wherein the organic material layer may contain a compound represented by Formula 1, and the compound represented by Formula 1 may be contained in at least one of a hole injection layer, a hole transport layer, an auxiliary light emitting layer, a light emitting layer, an electron transport layer, and an electron injection layer of an organic material layer. Especially, the compound represented by Formula 1 may be contained in the hole transport layer and the auxiliary light emitting layer.

That is, the compound represented by Formula 1 may be used as a material for a hole injection layer, a hole transport layer, an auxiliary light emitting layer, a light emitting layer, an electron transport layer, or an electron injection layer. Especially, the compound represented by Formula 1 may be used as a material for the hole transport layer and the auxiliary light emitting layer. The present invention provides, specifically, an organic electronic element including the organic material layer containing one of the compounds represented by Formulas 2 to 5, and more specifically, an organic electronic element including the organic material layer containing the compound represented by the above individual formula (P 1-1 to P 1-84, P 2-1 to P 2-40, P 3-1 to P 3-88, and P 4-1 to 4-52).

In still another embodiment, the present invention provides an organic electronic element, in which the compound is contained alone, two or more different kinds of the compounds are contained as a combination, or the compound is contained together with other compounds as a combination of two or more in at least one of the hole injection layer, the hole transport layer, the auxiliary light emitting layer, the light emitting layer, the electron transport layer, and the electron injection layer of the organic material layer. In other words, the compounds corresponding to Formulas 1 to 5 may be contained alone, a mixture of two or more kinds of compounds of Formulas 1 to 5 may be contained, or a mixture of the compound of claims 1 to 4 and a compound not corresponding to the present invention may be contained in each of the layers. Here, the compounds that do not correspond to the present invention may be a single compound or two or more kinds of compounds. Here, when the compound is contained together with other compounds as a combination of two or more kinds of compounds, another compound may be a compound that is already known for each organic material layer, or a compound to be developed in the future. Here, the compounds contained in the organic material layer may be composed of only the same kind of compounds, or a mixture of two or more kinds of different compounds represented by formula 1.

In still another embodiment of the present invention, the present invention provides an organic electronic element further including a light efficiency improvement layer, which is formed on at least one of one side of one surface of the first electrode, which is opposite to the organic material layer, and one side of one surface of the second electrode, which is opposite to the organic material layer.

Hereinafter, synthesis examples of the compound represented by Formula 1 and manufacturing examples of the organic electronic element according to the present invention will be described in detail by way of example. However, the following examples are only for illustrative purposes and are not intended to limit the scope of the invention.

SYNTHESIS EXAMPLES

The final products represented by Formula 1 according to the present invention are synthesized by a reaction of Sub 1 and Sub 2 via Reaction Scheme 1, but are not limited thereto.

<Reaction Scheme 1>

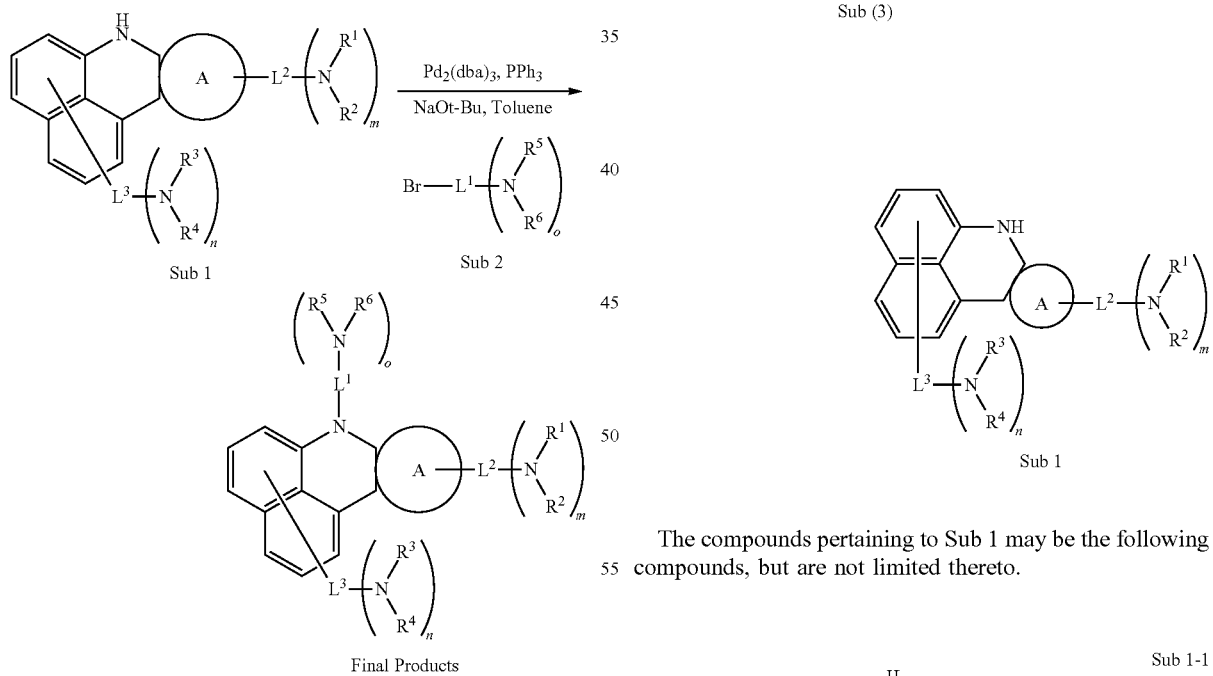

Final Products (A, $L^1$ to $L^3$, $R^1$ to $R^6$, m, n and o are defined as in Formula 1).

I. Synthesis of Sub 1

Sub 1 of Reaction Scheme 1 above may be synthesized by a reaction pathway of Reaction Scheme 2, but is not limited thereto.

<Reaction Scheme 2>

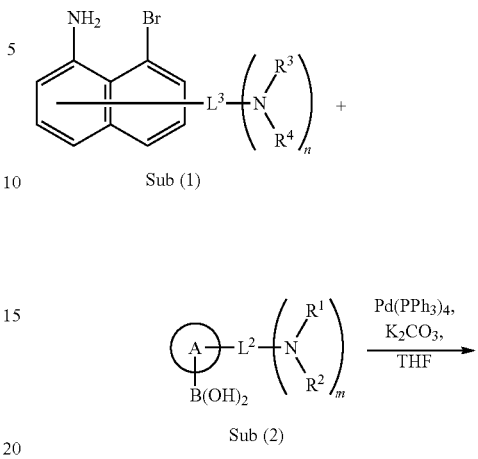

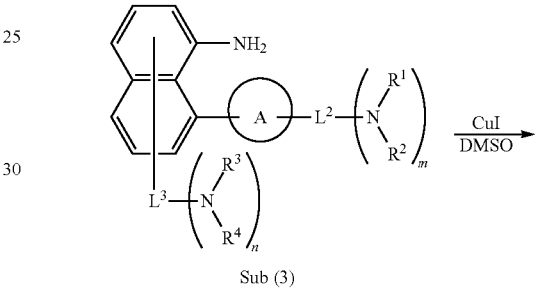

The compounds pertaining to Sub 1 may be the following compounds, but are not limited thereto.

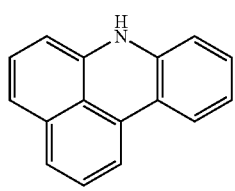

Sub 1-1

101
-continued
Sub 1-2
Sub 1-3
Sub 1-4
Sub 1-5
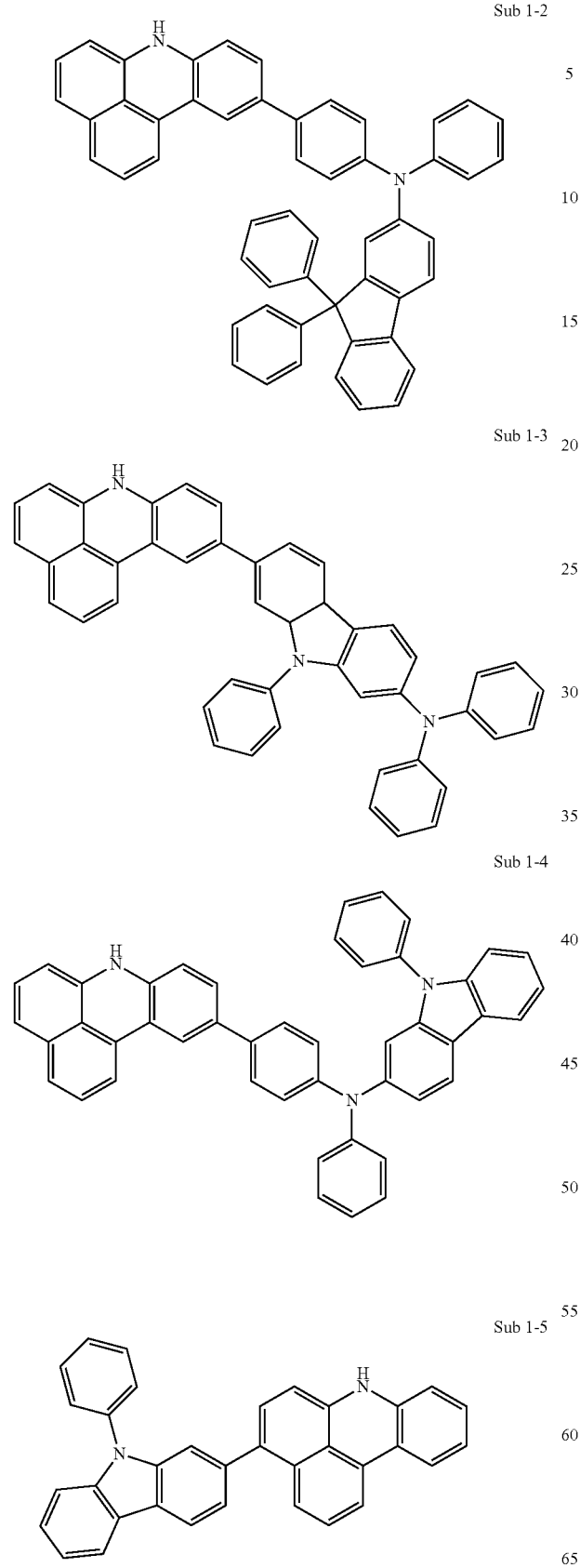
102
-continued
Sub 1-6
Sub 1-7
Sub 1-8
Sub 1-9
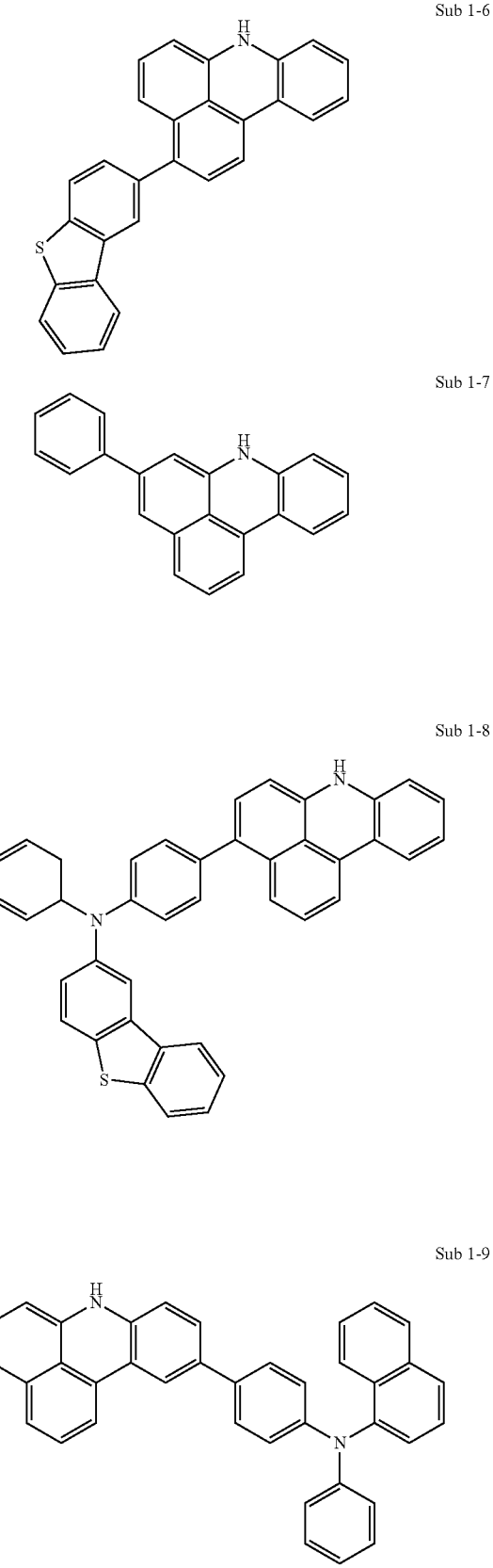

Sub 1-10
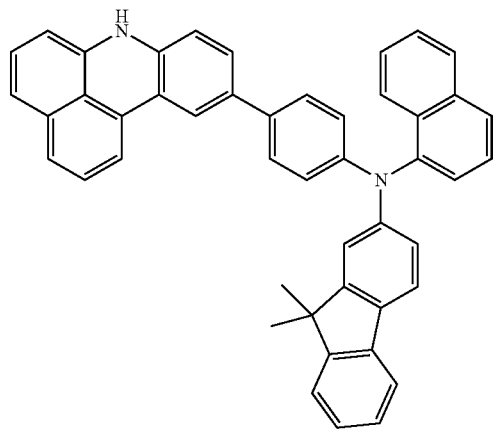
Sub 1-11
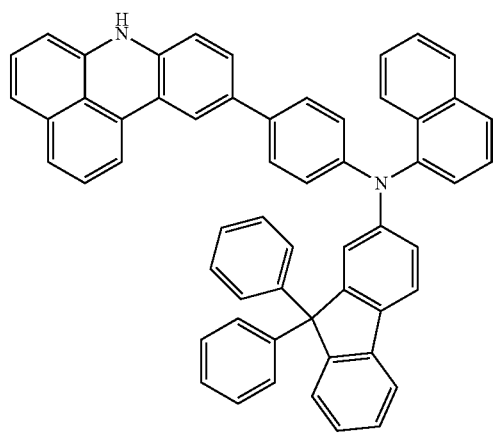
Sub 1-12
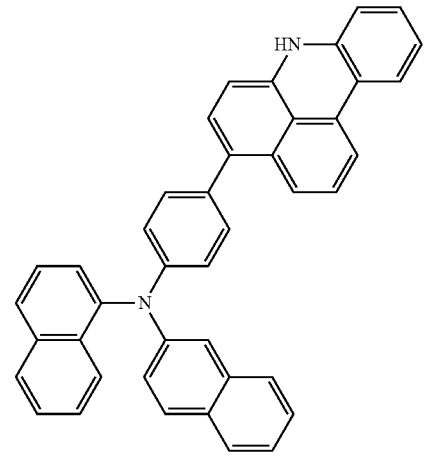
Sub 1-13
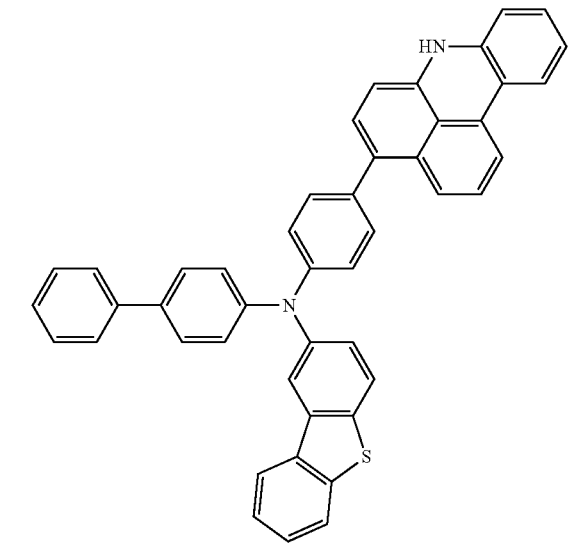
Sub 1-14
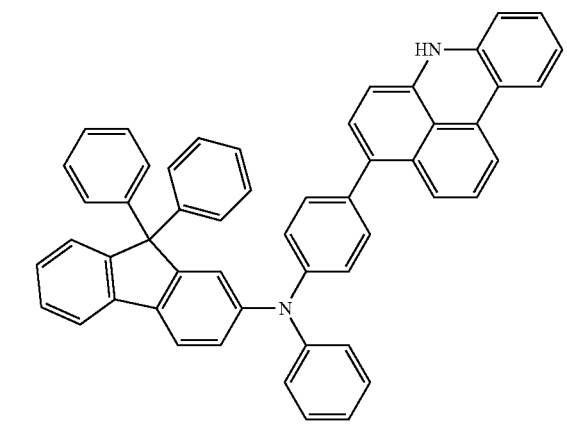
Sub 1-15
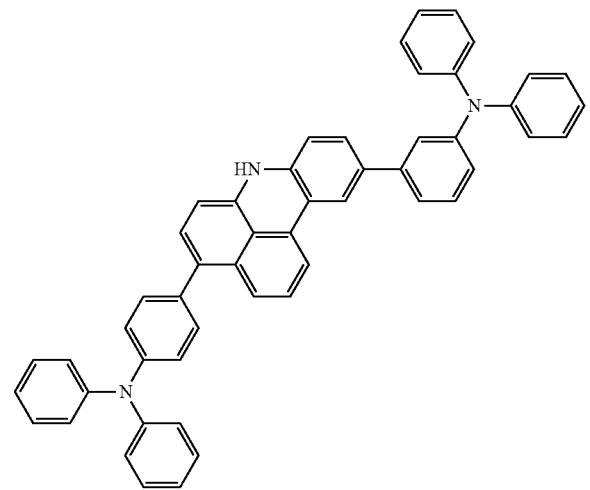

Sub 1-16
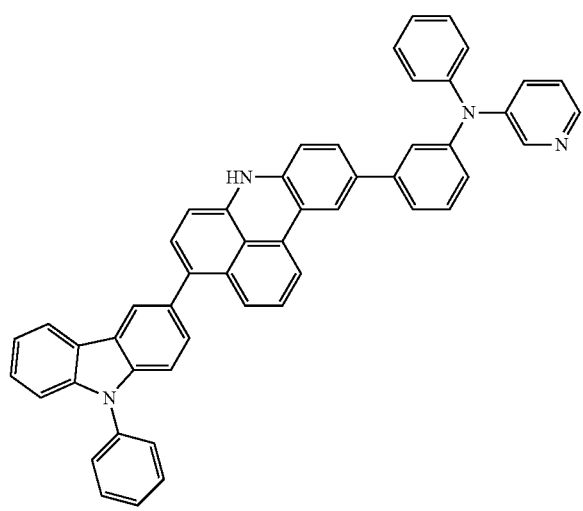
Sub 1-17
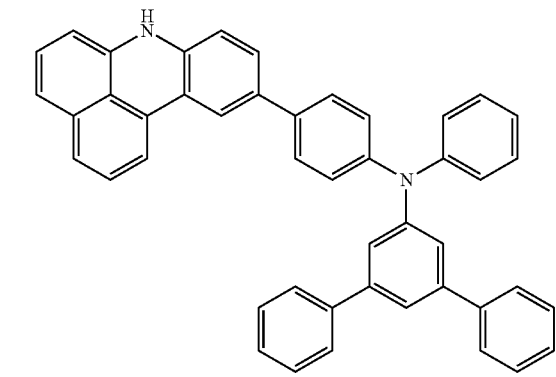
Sub 1-18
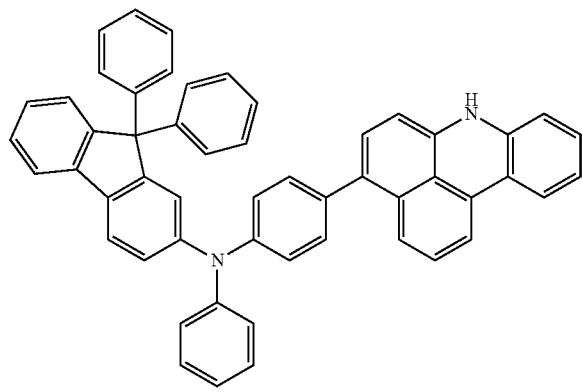
Sub 1-19
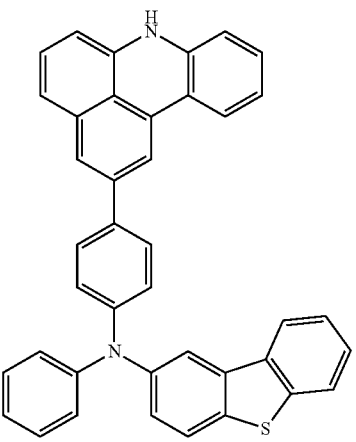
Sub 1-20
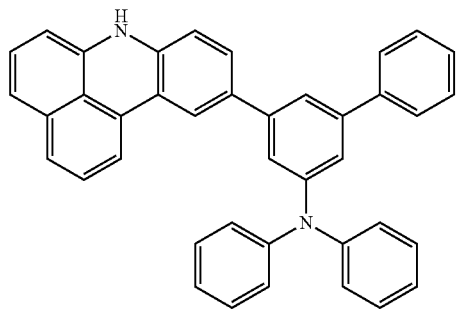
Sub 1-21
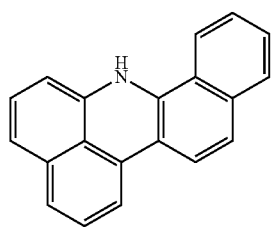
Sub 1-22

Sub 1-23
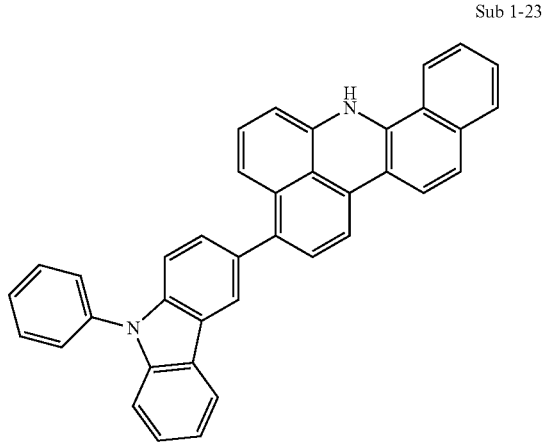
Sub 1-24
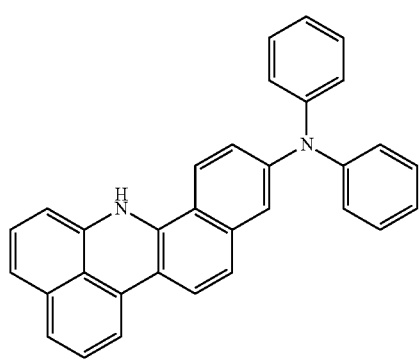
Sub 1-25
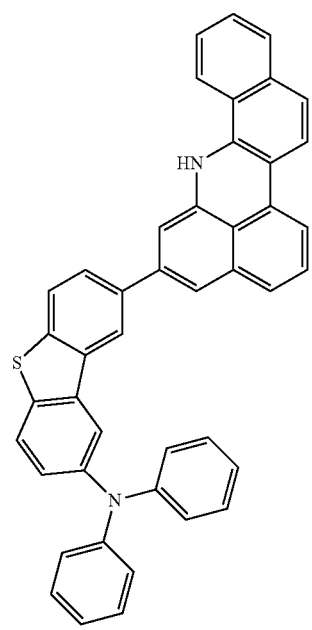
Sub 1-26
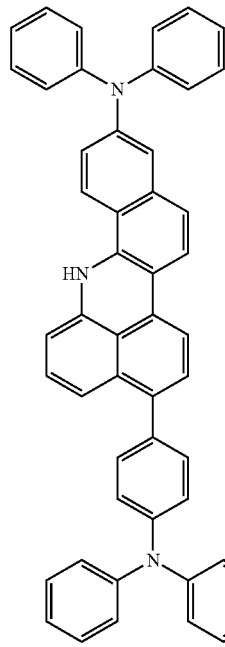
Sub 1-27
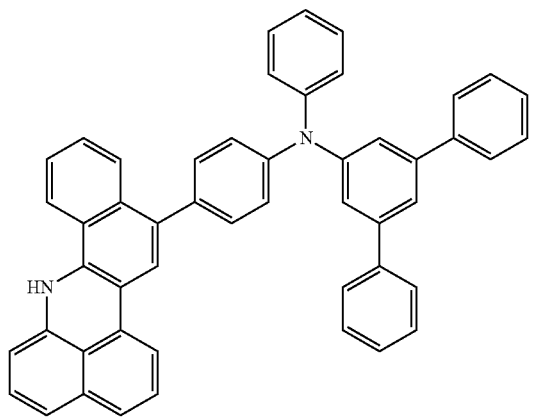
Sub 1-28
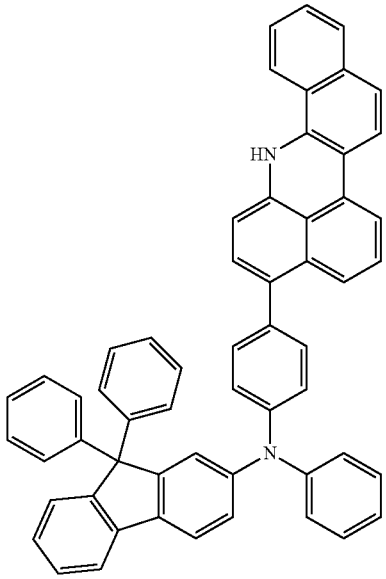

Sub 1-29
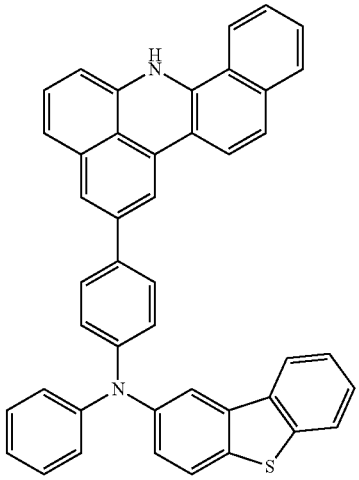
Sub 1-33
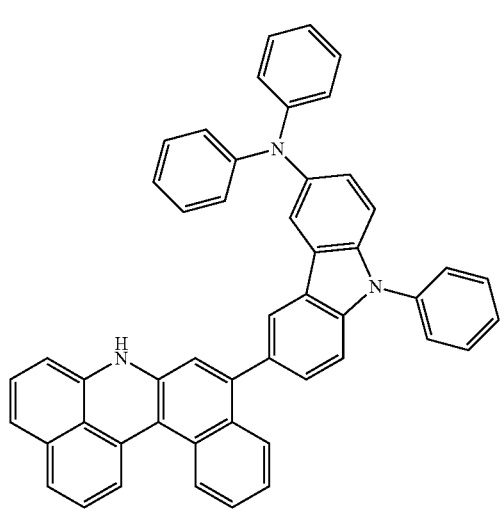
Sub 1-30
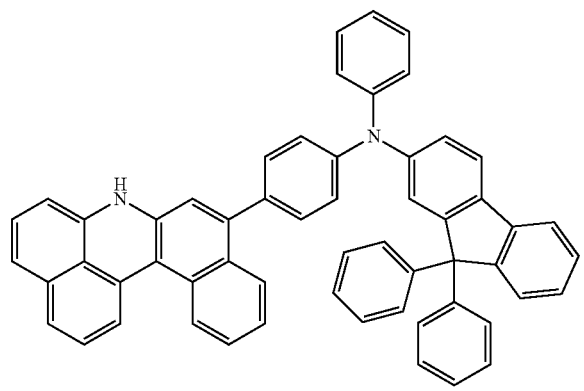
Sub 1-34
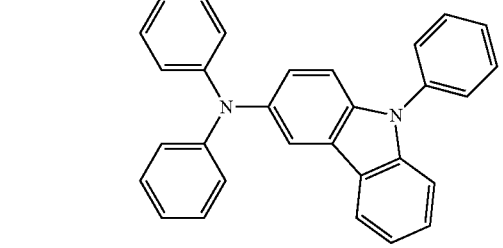
Sub 1-31
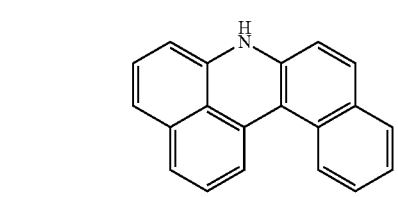
Sub 1-32
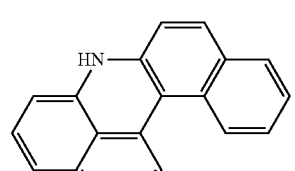
Sub 1-35
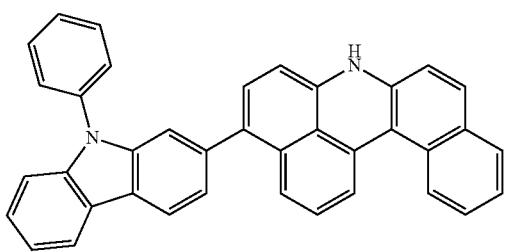

111
-continued
Sub 1-36
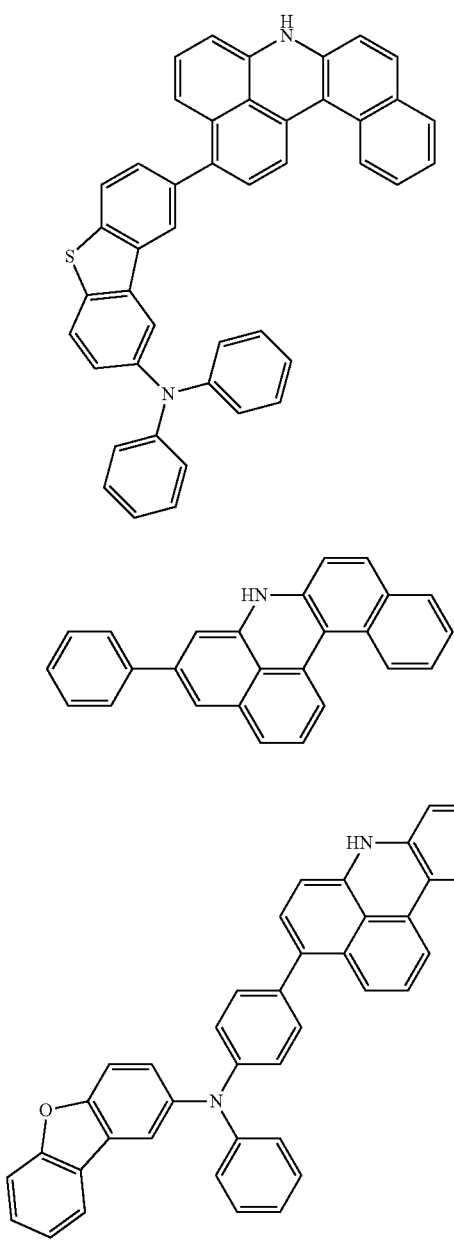
Sub 1-37
Sub 1-38
Sub 1-39
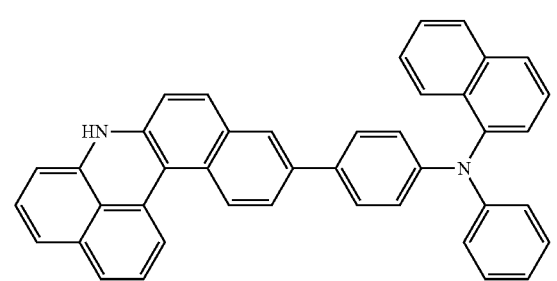
112
-continued
Sub 1-40
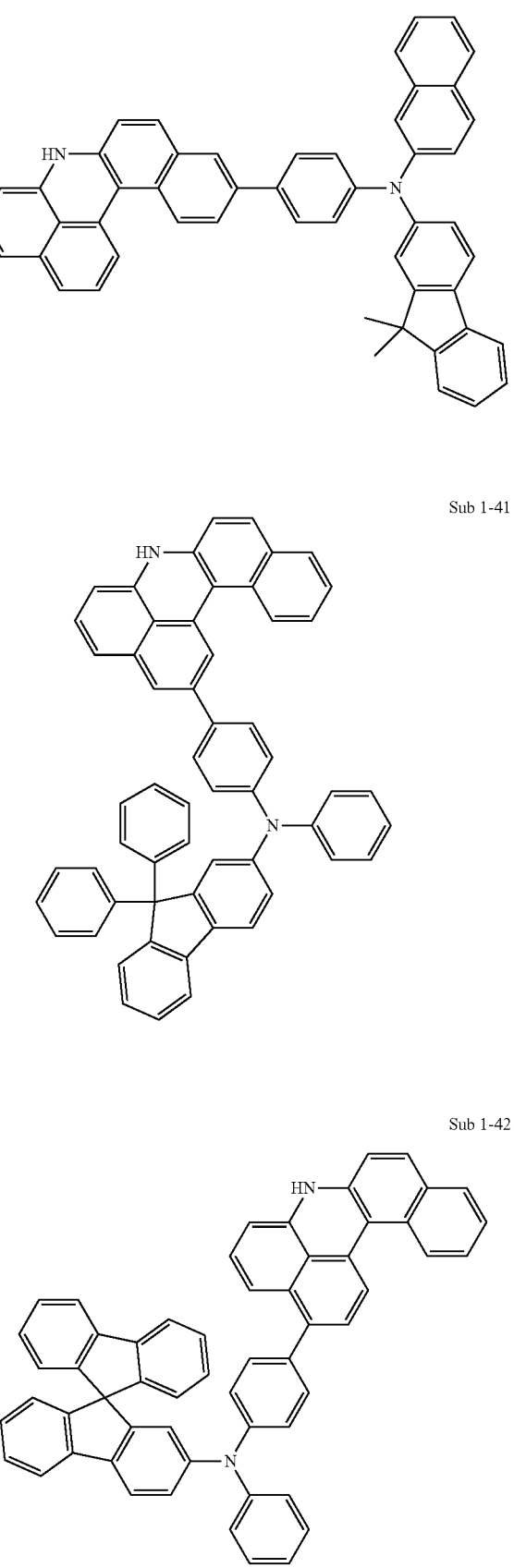
Sub 1-41
Sub 1-42

Sub 1-43
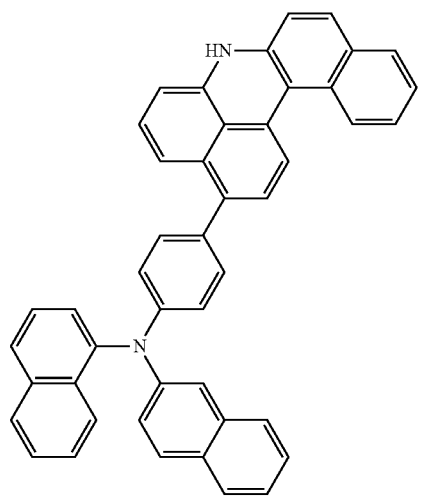
Sub 1-44
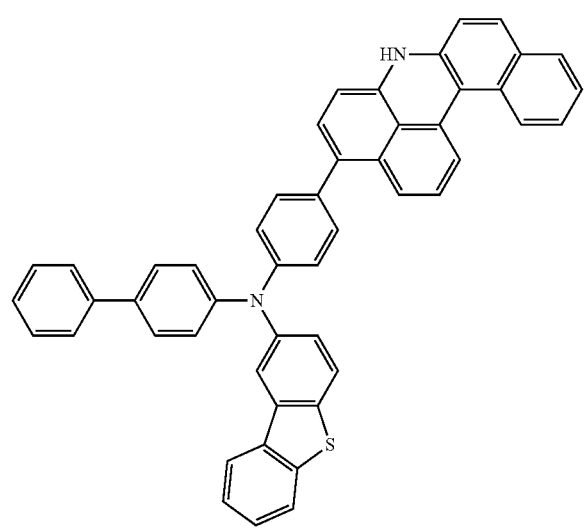
Sub 1-46
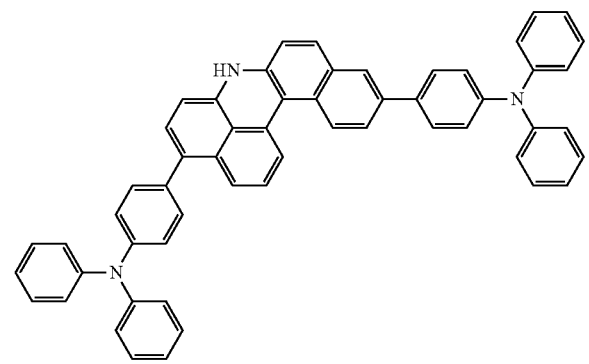
Sub 1-47
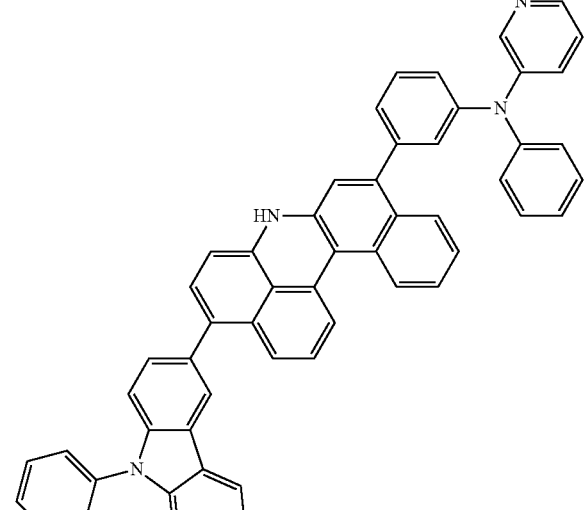
Sub 1-45
Sub 1-48
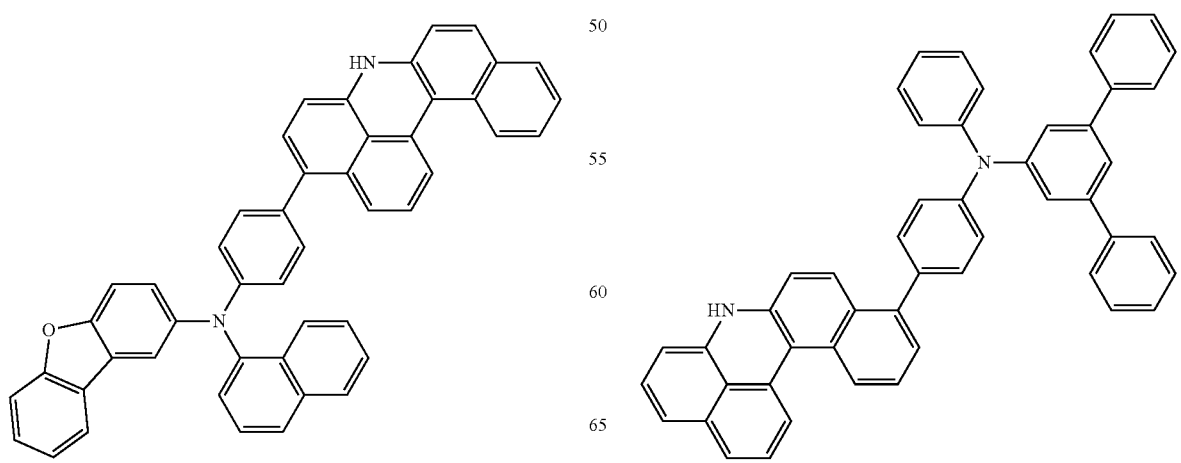

Sub 1-49
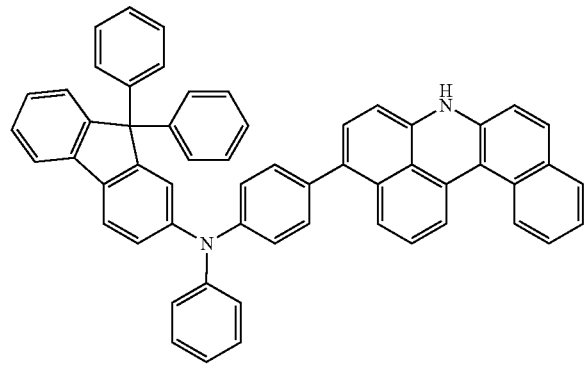
Sub 1-50
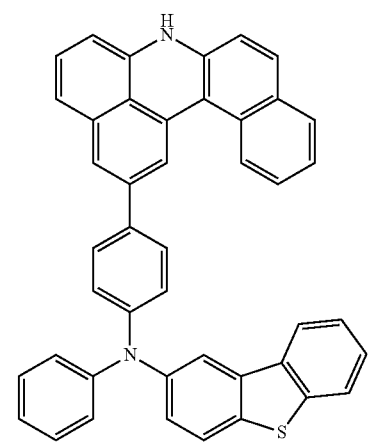
Sub 1-51
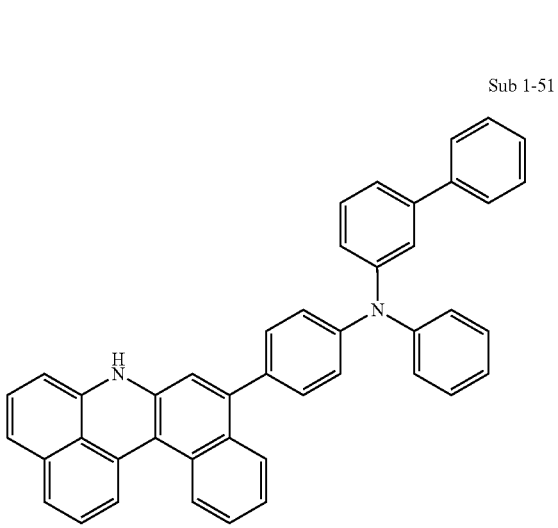
Sub 1-52
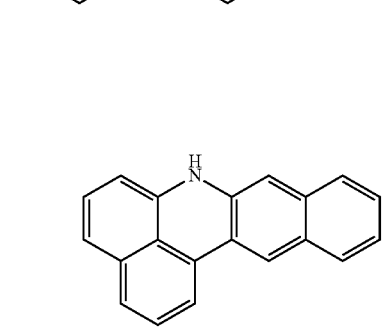
Sub 1-53
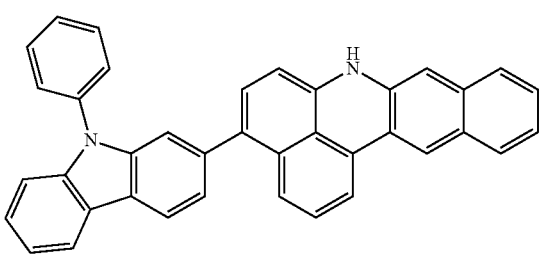
Sub 1-54
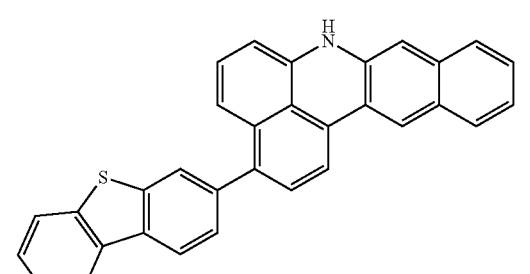
Sub 1-55
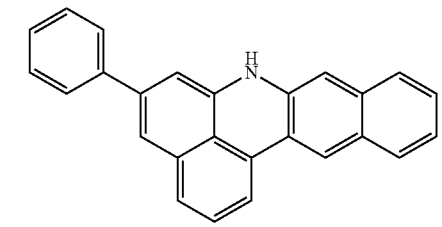
Sub 1-56
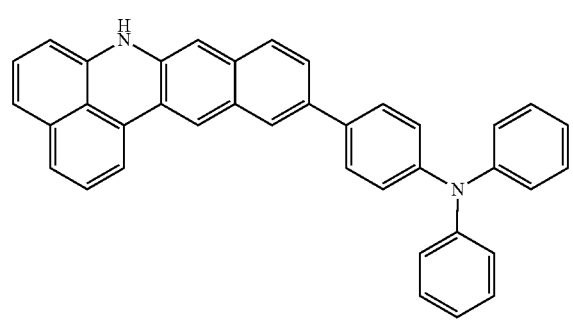

Sub 1-57
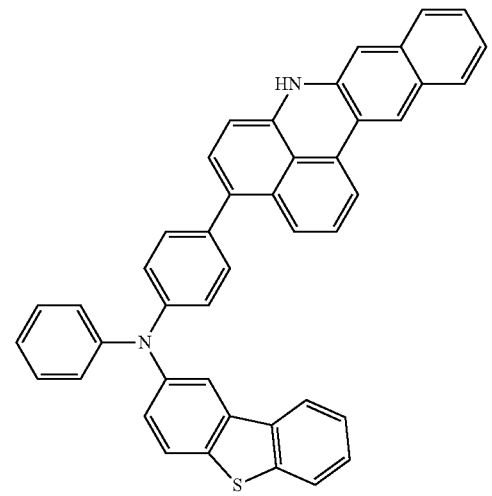
Sub 1-58
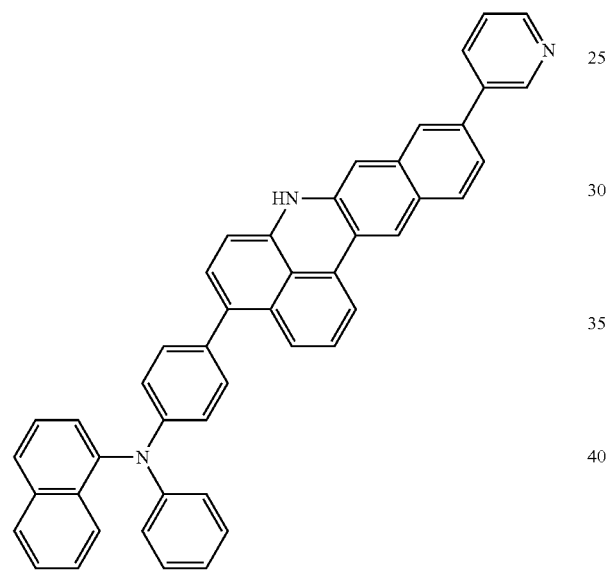
Sub 1-59
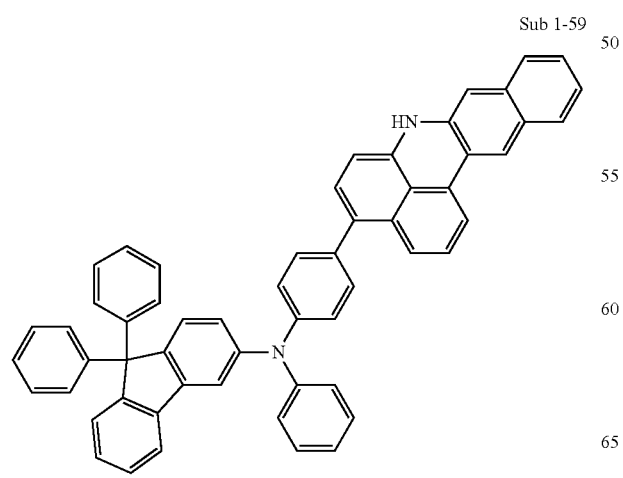
Sub 1-60
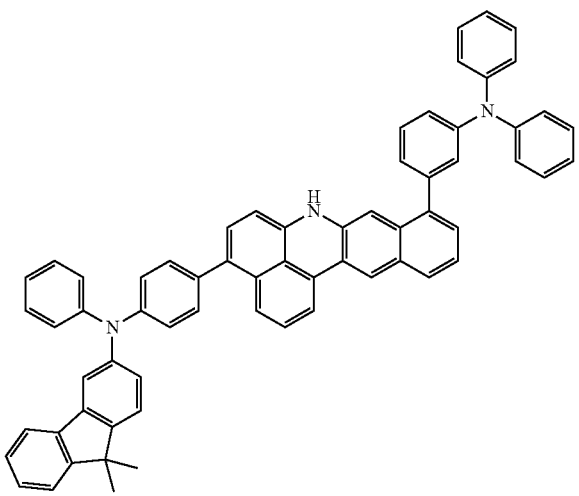
Sub 1-61
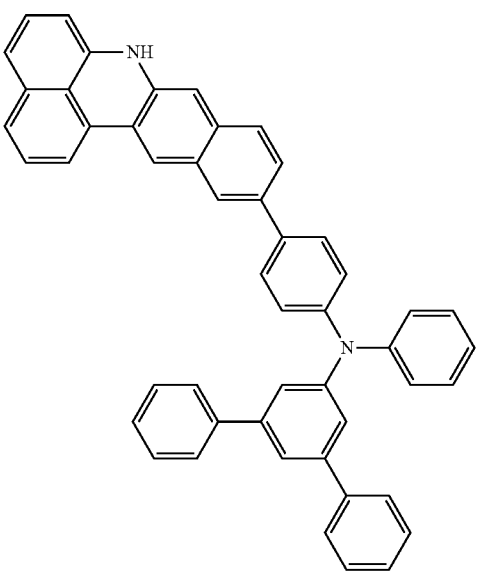

-continued

Sub 1-62

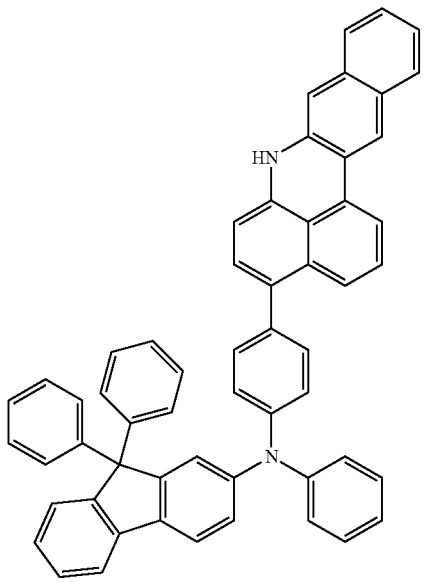

Sub 1-63

Sub 1-64

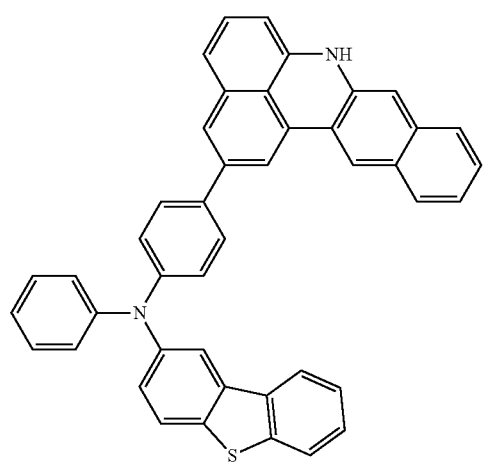

1. Synthesis Example of Sub 1-1

<Reaction Scheme 3>

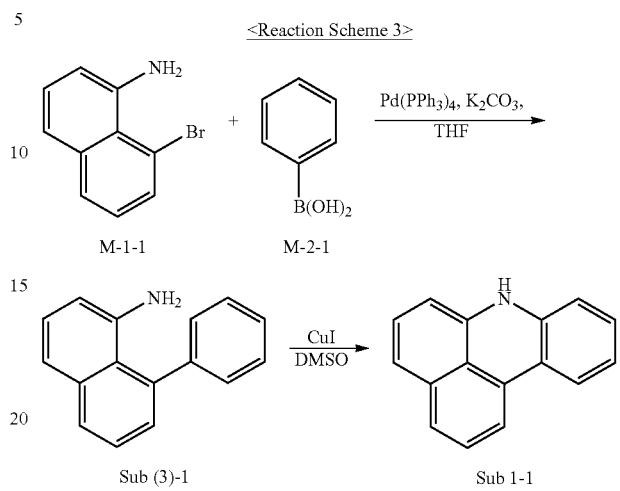

$L^2$ and $L^3$ = H, n = 0, and m = 0

(1) Synthesis of Sub (3)-1

After M-1-1 (6.66 g, 30 mmol) was dissolved in THF (132 mL), M-2-1 (3.66 g, 30 mmol), Pd(PPh$_3$)$_4$ (1.04 g, 0.9 mmol), NaOH (3.6 g, 90 mmol), and water (66 mL) were added, and then the mixture was stirred under reflux. Upon completion of the reaction, the reaction product was extracted with ether and water. The organic layer was dried over MgSO$_4$ and concentrated, and then the resulting organic material was subjected to silica gel column chromatography and recrystallization to give a product 4.93 g (yield: 75%).

(2) Synthesis of Sub 1-1

After Sub (3)-1 (4.93 g, 22.5 mmol) was dissolved in DMSO (112 mL), CuI (6.4 g, 33.7 mmol) was added, and then the mixture was boiled in the atmospheric conditions at 150° C. for 12 hours. Upon completion of the reaction, the reaction product was filtered and extracted with ether and water. The organic layer was dried over MgSO$_4$ and concentrated, and then the resulting organic material was subjected to silica gel column chromatography and recrystallization to give a product 2 g (yield: 41%).

2. Synthesis Example of Sub 1-13

<Reaction Scheme 4>

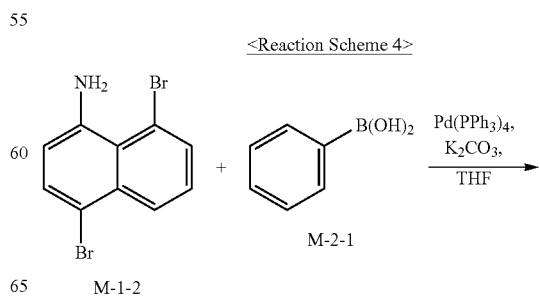

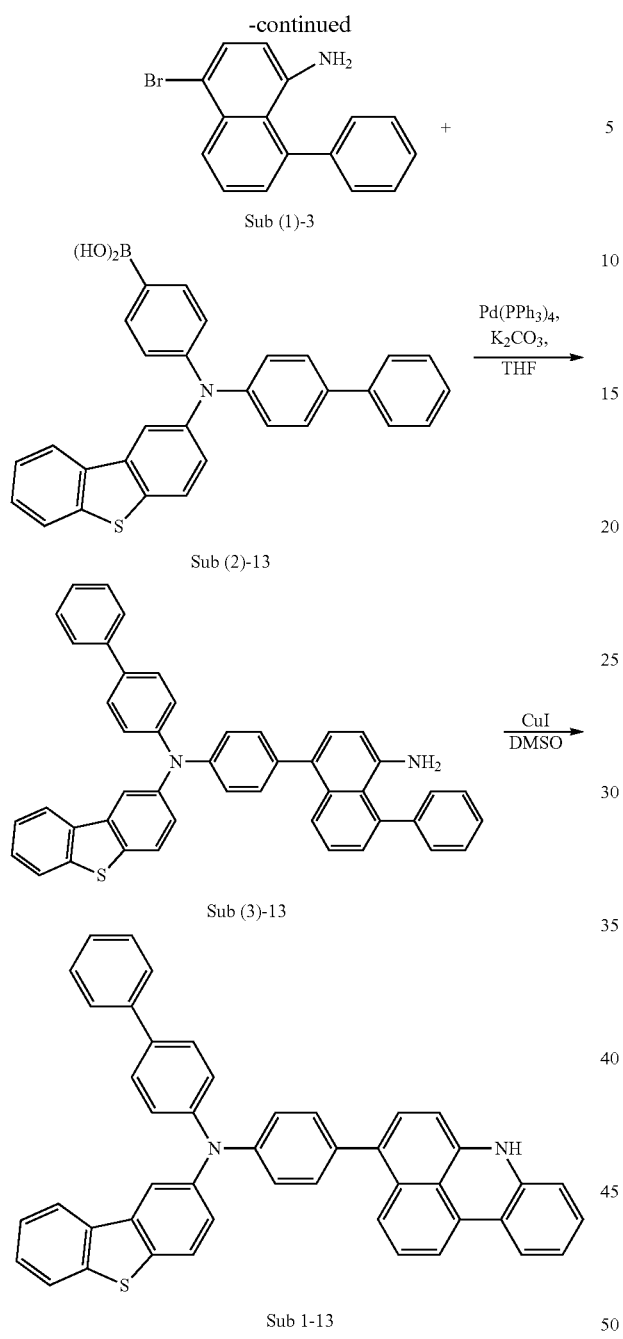

Sub 1-13

$L^2$ = H, n = 1, and m = 0

(1) Synthesis of Sub (1)-3

M-1-2 (9.03 g, 30 mmol), M-2-1 (3.66 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 6.17 g (yield: 69%).

(2) Synthesis of Sub (3)-13

Sub (1)-3 (6.17 g, 20.7 mmol), Sub (2)-13 (9.75 g, 20.7 mmol), Pd(PPh₃)₄ (0.72 g, 0.62 mmol), K₂CO₃ (2.48 g, 62 mmol), anhydrous THF (91 mL), and a little water (45 mL) were subjected to the synthesis method for Sub (3)-1 to give a product 9.07 g (yield: 68%).

(3) Synthesis of Sub 1-13

Sub (3)-13 (9.07 g, 14 mmol), DMSO (70 mL), and CuI (4 g, 21 mmol) were subjected to the synthesis method for Sub 1-1 to give 1.16 g (yield: 38%).

3. Synthesis Example of Sub 1-20

<Reaction Scheme 5>

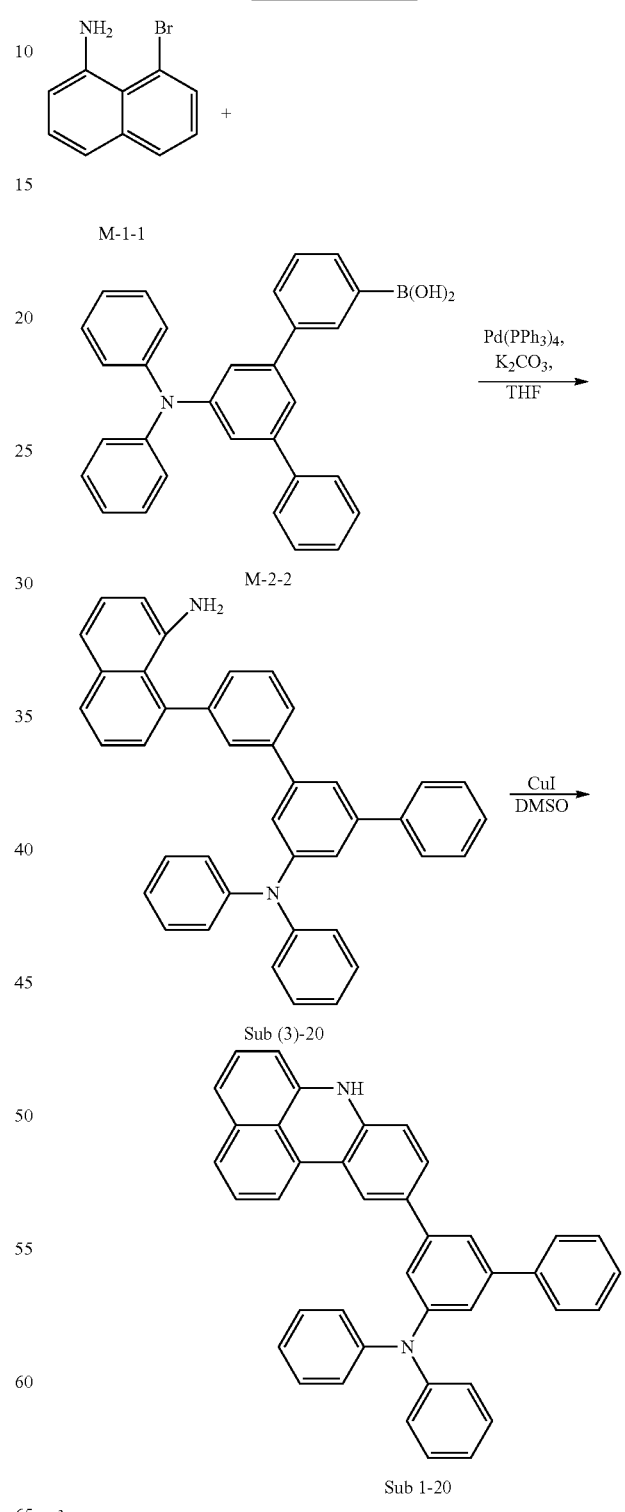

Sub 1-20

$L^3$ = H, n = 0, and m = 1

(1) Synthesis of Sub (3)-20

M-1-2 (6.66 g, 30 mmol), M-2-2 (13.2 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 10.2 g (yield: 63%).

(2) Synthesis of Sub 1-20

Sub (3)-20 (10.2 g, 14 mmol), DMSO (95 mL), and CuI (5.4 g, 28.4 mmol) were subjected to the synthesis method for Sub 1-1 to give 3.56 g (yield: 35%).

4. Synthesis Example of Sub 1-16

<Reaction Scheme 6>

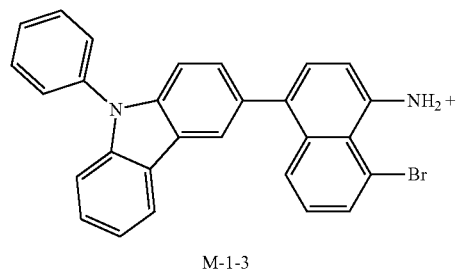

M-1-3

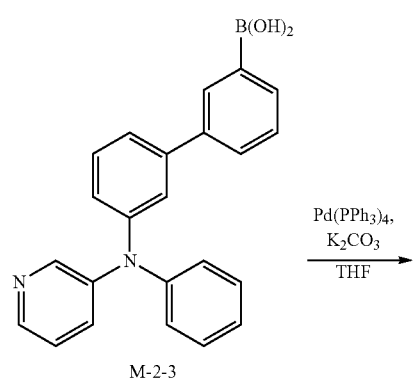

M-2-3

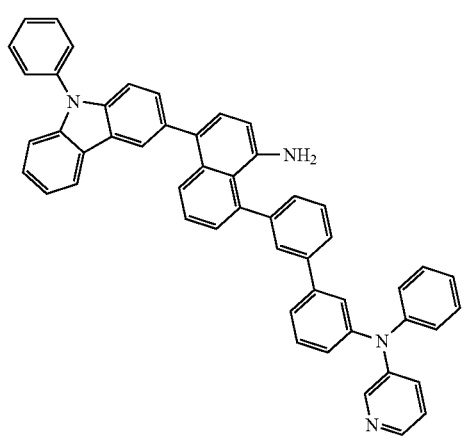

Sub (3)-16

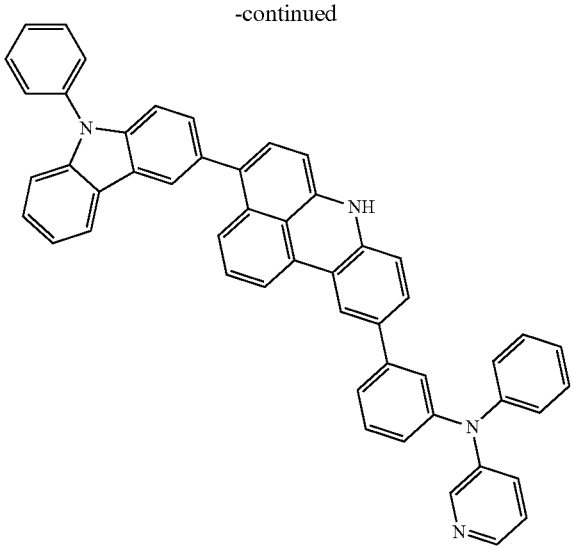

Sub 1-16 n = 1 and m = 1

(1) Synthesis of Sub (1)-16

M-1-3 (13.9 g, 30 mmol), M-2-3 (11 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 14.38 g (yield: 68%).

(2) Synthesis of Sub 1-16

Sub (3)-16 (14.38 g, 20.4 mmol), DMSO (102 mL), and CuI (5.83 g, 30.6 mmol) were subjected to the synthesis method for Sub 1-1 to give 5.6 g (yield: 39%).

5. Synthesis Example of Sub 1-21

<Reaction Scheme 7>

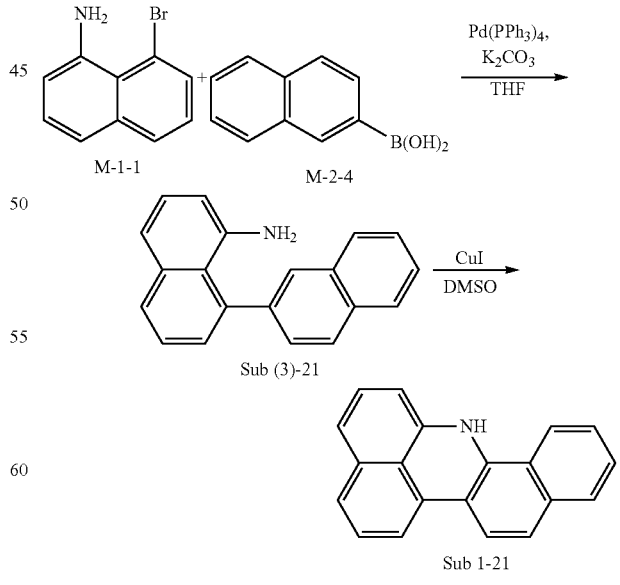

$L^2$, $L^3$ = H, n = 0, and m = 0

(1) Synthesis of Sub (3)-21

M-1-1 (6.66 g, 30 mmol), M-2-4 (5.16 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 5.25 g (yield: 65%).

(2) Synthesis of Sub 1-21

Sub (3)-21 (5.25 g, 19.5 mmol), DMSO (97 mL), and CuI (5.57 g, 29.2 mmol) were subjected to the synthesis method for Sub 1-1 to give 1.77 g (yield: 34%).

6. Synthesis Example of Sub 1-23

<Reaction Scheme 8>

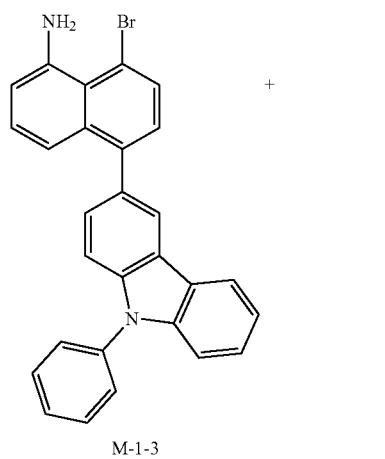

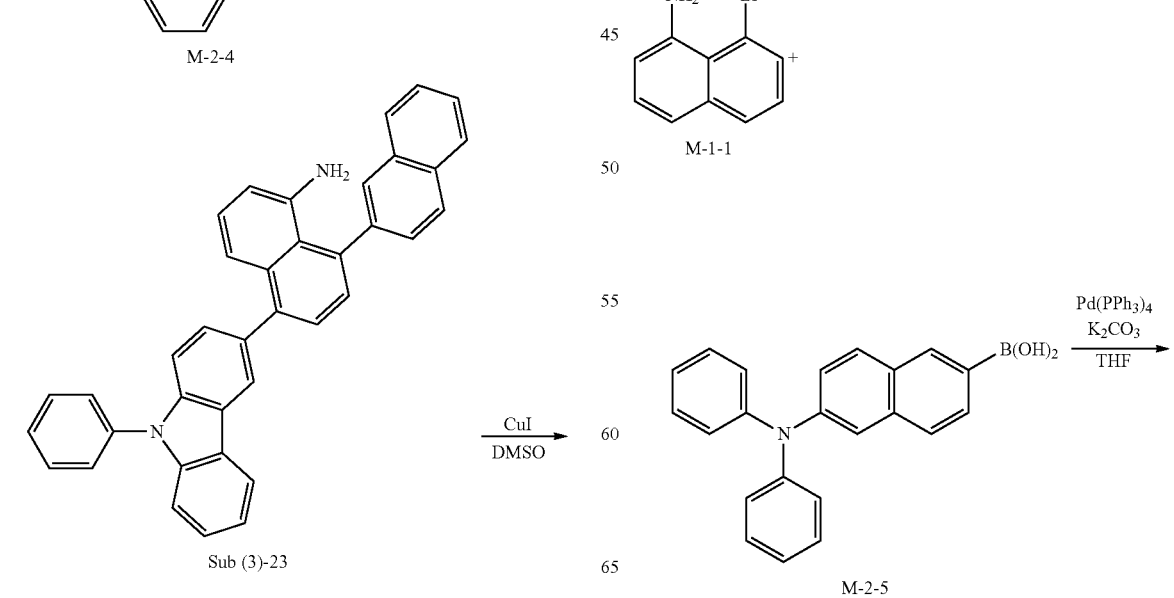

Sub 1-23

$L^2$ = H, n = 1, and m = 0

(1) Synthesis of Sub (3)-23

M-1-3 (13.96 g, 30 mmol), M-2-4 (5.16 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 11.2 g (yield: 73%).

(2) Synthesis of Sub 1-23

Sub (3)-23 (11.2 g, 22 mmol), DMSO (110 mL), and CuI (6.27 g, 33 mmol) were subjected to the synthesis method for Sub 1-1 to give 4.8 g (yield: 43%).

7. Synthesis Example of Sub 1-24

<Reaction Scheme 9>

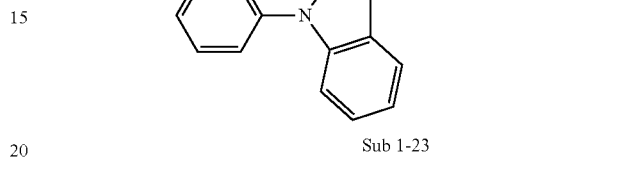

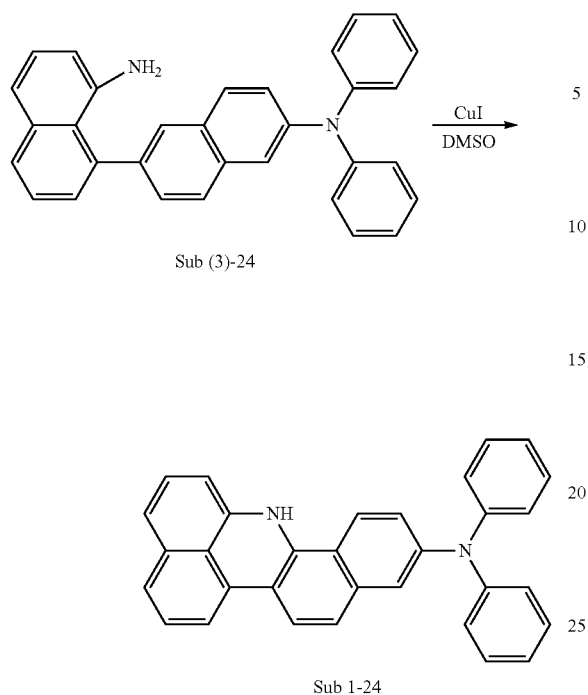
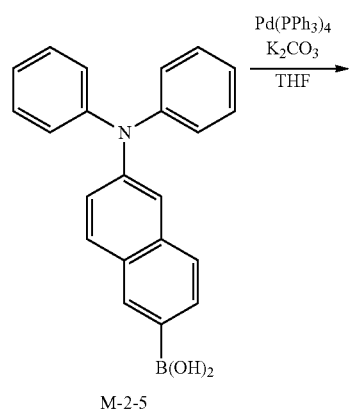
Sub (3)-24
Sub 1-24
$L^3$ = H, n = 0, and m = 1
(1) Synthesis of Sub (3)-24
M-1-1 (6.66 g, 30 mmol), M-2-5 (10.18 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 8.77 g (yield: 67%).
(3) Synthesis of Sub 1-24
Sub (3)-24 (8.77 g, 20 mmol), DMSO (100 mL), and CuI (5.74 g, 30 mmol) were subjected to the synthesis method for Sub 1-1 to give 2.97 g (yield: 34%).
8. Synthesis Example of Sub 1-26
<Reaction Scheme 10>
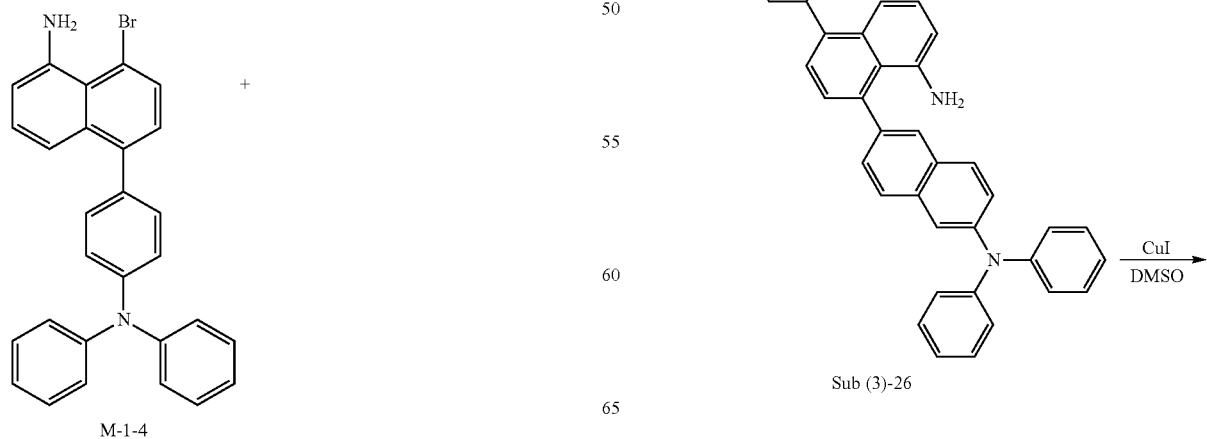
M-1-4
M-2-5
Sub (3)-26

-continued

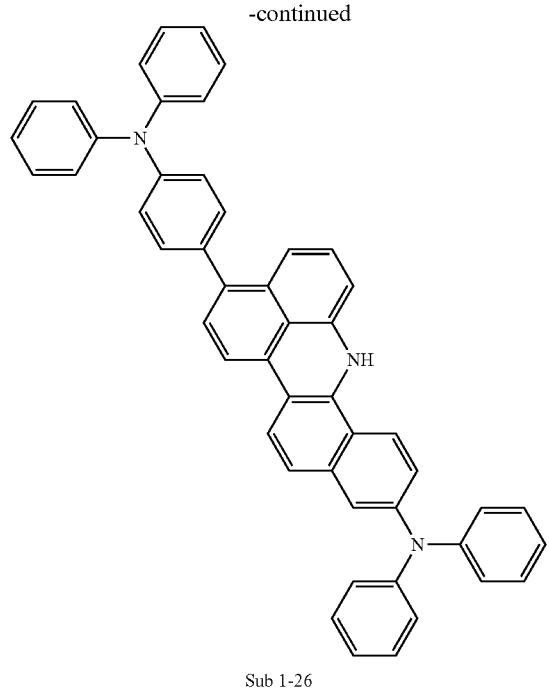

Sub 1-26 n = 1 and m = 1

(1) Synthesis of Sub (3)-26
M-1-4 (14 g, 30 mmol), M-2-5 (10.18 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 14.4 g (yield: 71%).
(3) Synthesis of Sub 1-26
Sub (3)-26 (14.5 g, 21.3 mmol), DMSO (106 mL), and CuI (6.09 g, 32 mmol) were subjected to the synthesis method for Sub 1-1 to give 5.2 g (yield: 36%).

9. Synthesis Example of Sub 1-31

<Reaction Scheme 11>

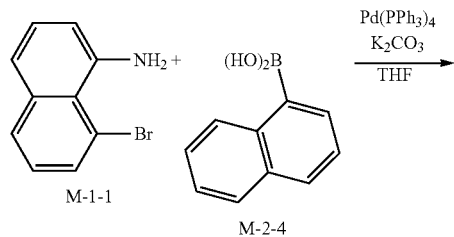

-continued

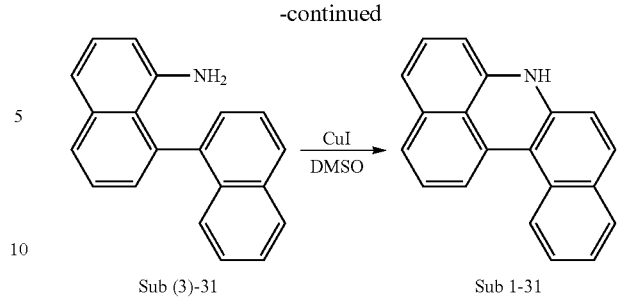

$L^2$ and $L^3$ = H, n = 0, and m = 0

(1) Synthesis of Sub (3)-31
M-1-1 (6.66 g, 30 mmol), M-2-4 (5.16 g, 30 mmol), Pd(PPh₃)₄ (1.04 g, 0.9 mmol), K₂CO₃ (3.6 g, 90 mmol), anhydrous THF (132 mL), and a little water (66 mL) were subjected to the synthesis method for Sub (3)-1 to give a product 5.5 g (yield: 68%).

(2) Synthesis of Sub 1-31
Sub (3)-31 (5.5 g, 20.4 mmol), DMSO (102 mL), and CuI (5.83 g, 30.6 mmol) were subjected to the synthesis method for Sub 1-1 to give 2.07 g (yield: 38%).

10. Synthesis Example of Sub 1-38

<Reaction Scheme 12>

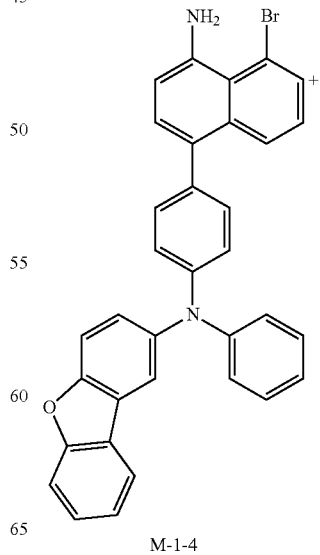

M-1-4

-continued

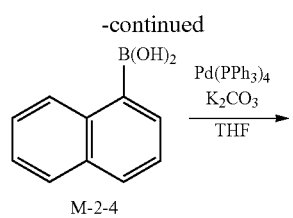

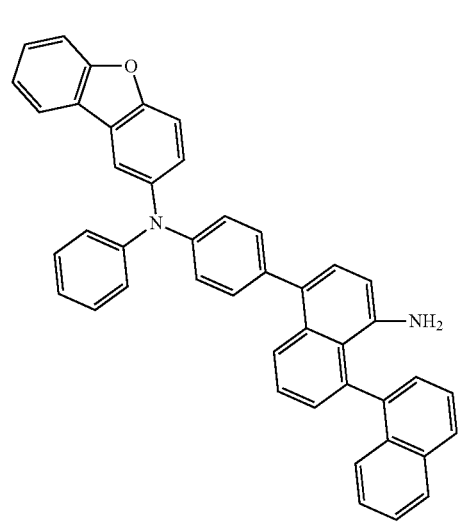

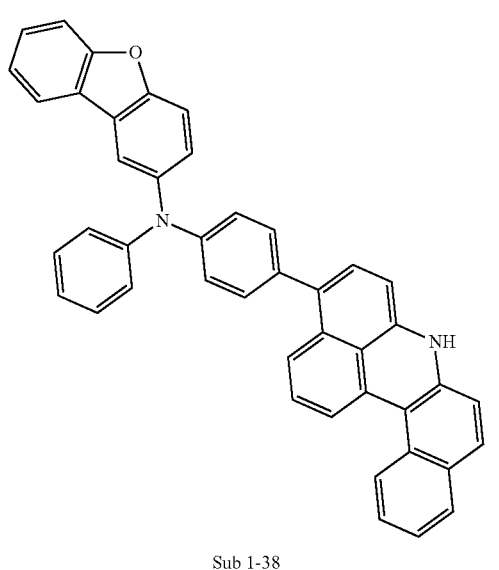

$L^2$ = H, n = 1, and , m = 0

(1) Synthesis of Sub (3)-38

M-1-4 (12.2 g, 22 mmol), M-2-4 (3.78 g, 22 mmol), Pd(PPh$_3$)$_4$ (0.76 g, 0.66 mmol), K$_2$CO$_3$ (2.63 g, 65.9 mmol), anhydrous THF (96 mL), and a little water (48 mL) were subjected to the synthesis method for Sub (3)-1 to give a product 8.34 g (yield: 63%).

(2) Synthesis of Sub 1-38

Sub (3)-38 (8.34 g, 13.8 mmol), DMSO (70 mL), and CuI (3.95 g, 20.8 mmol) were subjected to the synthesis method for Sub 1-1 to give 2.91 g (yield: 35%).

11. Synthesis Example of Sub 1-32

<Reaction Scheme 13>

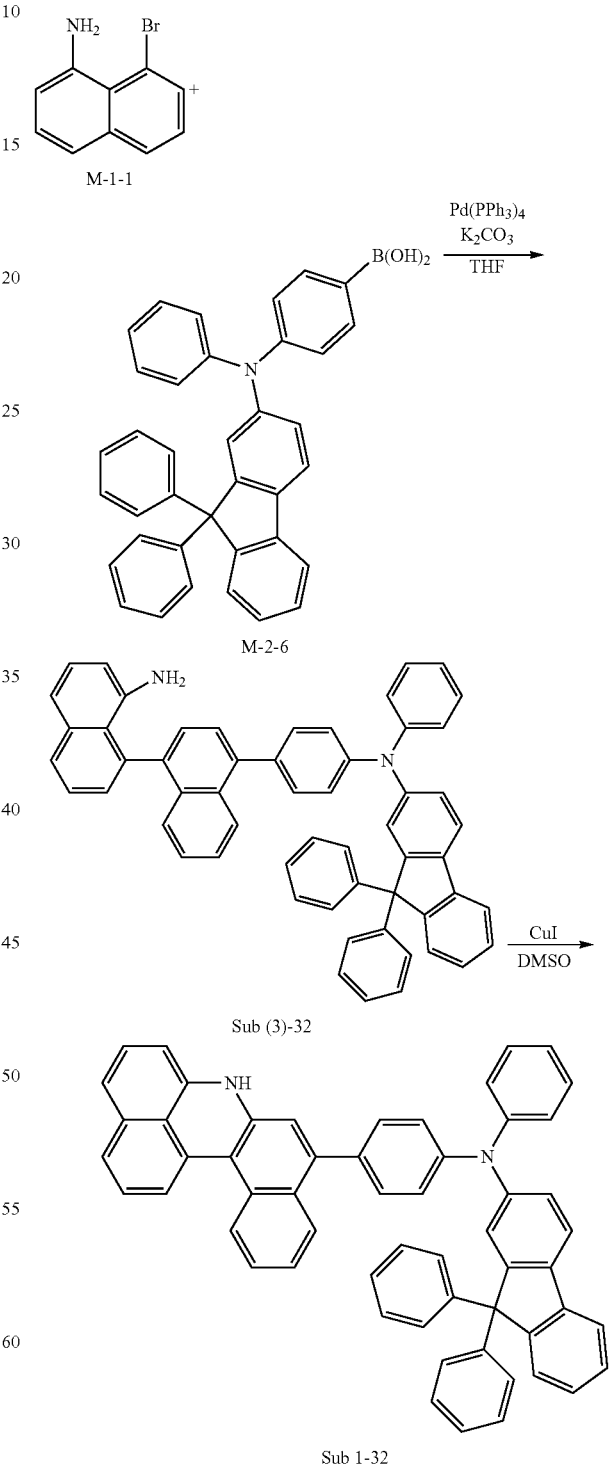

$L^3$ = H, n = 0, and m = 1

(1) Synthesis of Sub (3)-32

M-1-1 (6.66 g, 30 mmol), M-2-6 (15.9 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 14.7 g (yield: 65%).

(2) Synthesis of Sub 1-32

Sub (3)-32 (14.7 g, 19.5 mmol), DMSO (98 mL), and CuI (5.58 g, 29.3 mmol) were subjected to the synthesis method for Sub 1-1 to give 6.01 g (yield: 41%).

12. Synthesis Example of Sub 1-46

<Reaction Scheme 14>

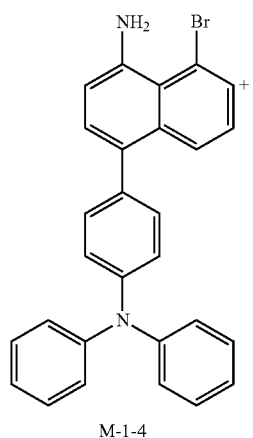

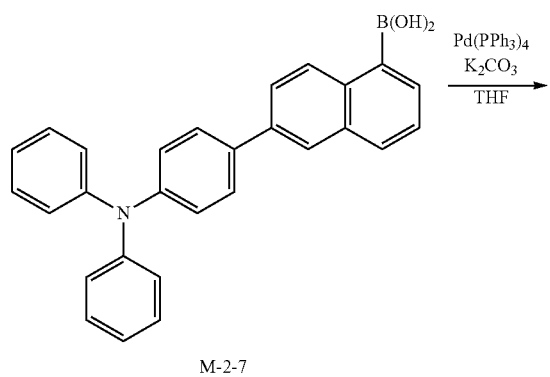

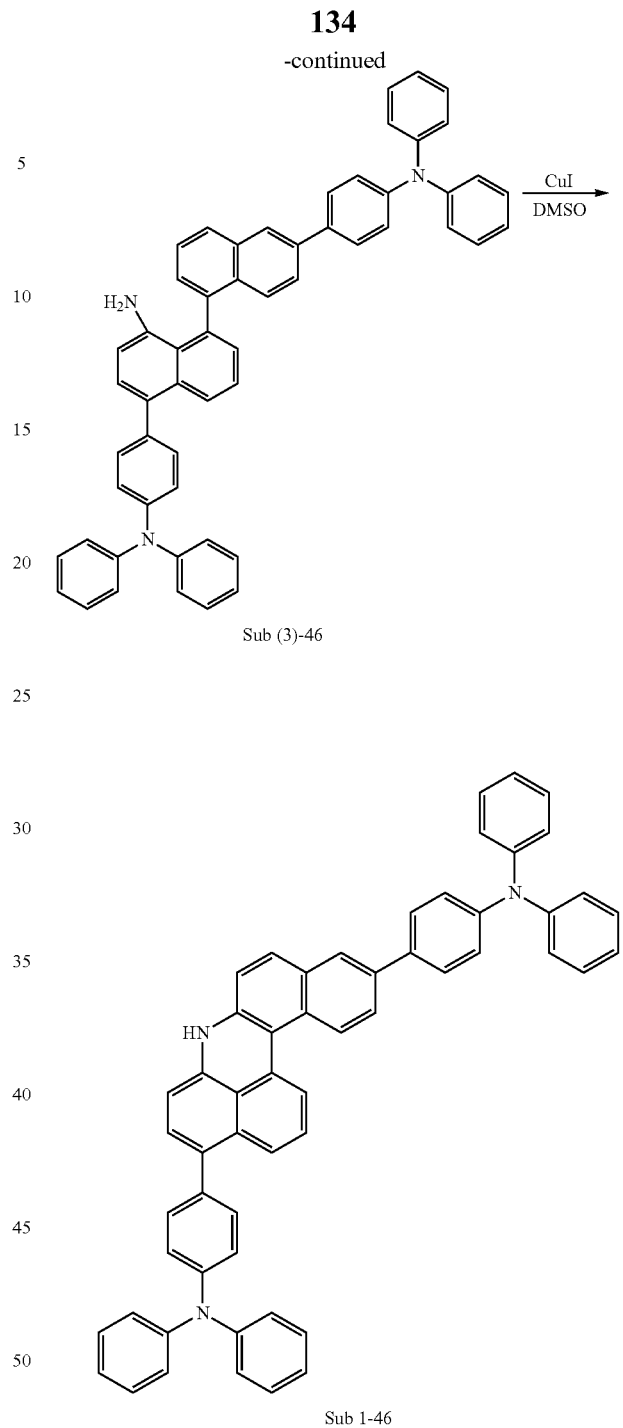

n = 1 and m = 1

(1) Synthesis of Sub (3)-46

M-1-4 (14 g, 30 mmol), M-2-7 (12.46 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 15.2 g (yield: 67%).

(2) Synthesis of Sub 1-46

Sub (3)-46 (15.2 g, 20.1 mmol), DMSO (100 mL), and CuI (5.74 g, 30.2 mmol) were subjected to the synthesis method for Sub 1-1 to give 6.52 g (yield: 43%).

13. Synthesis Example of Sub 1-52
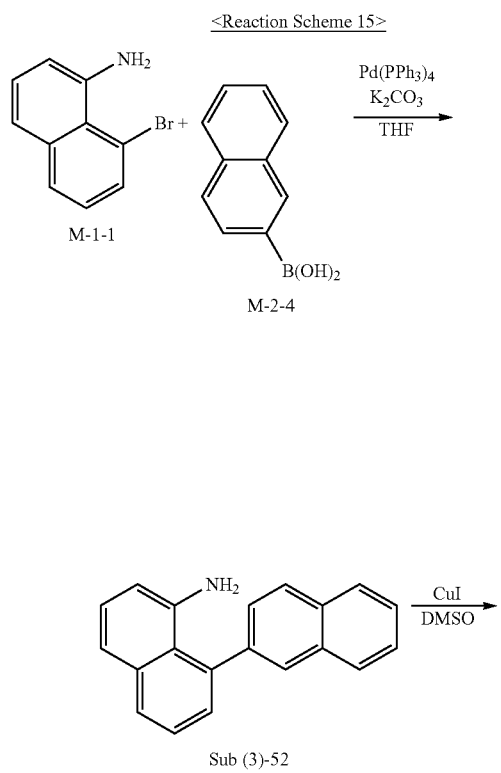
$L^2$ and $L^3$ = H, n = 0, and m = 0
(1) Synthesis of Sub (3)-52
M-1-1 (6.66 g, 30 mmol), M-2-4 (5.16 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 5.74 g (yield: 71%).
(2) Synthesis of Sub 1-52
Sub (3)-52 (5.74 g, 21.3 mmol), DMSO (107 mL), and CuI (6.09 g, 32 mmol) were subjected to the synthesis method for Sub 1-1 to give 2.16 g (yield: 38%).
14. Synthesis Example of Sub 1-57
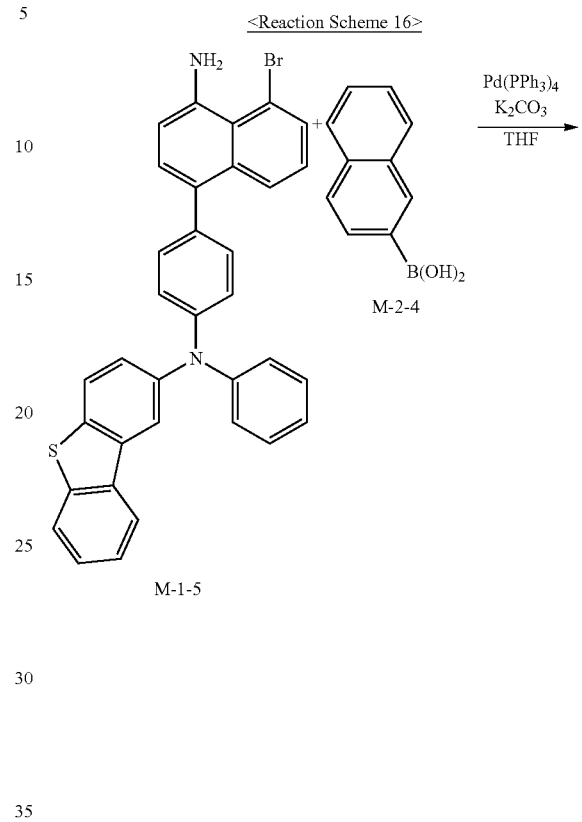
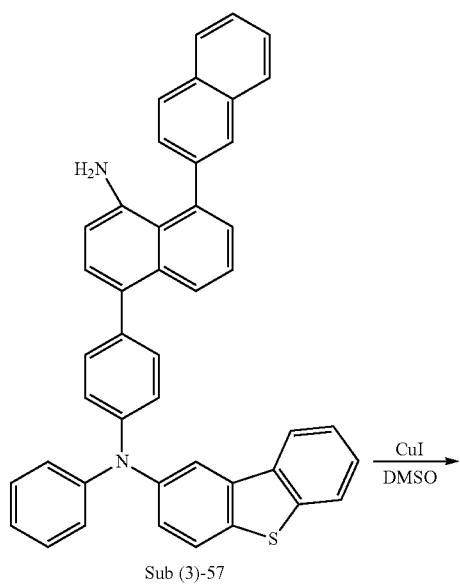

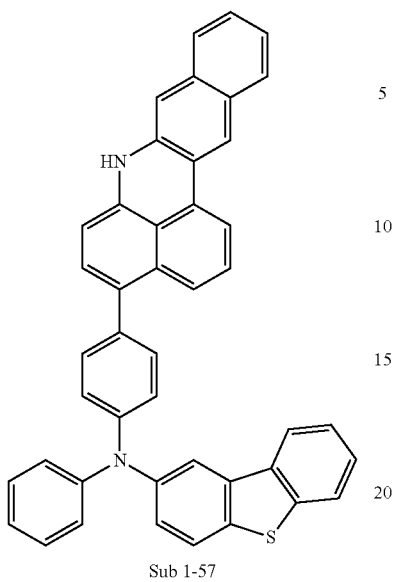

Sub 1-57

$L^2$ = H, n = 1, and m = 0

(1) Synthesis of Sub (3)-57

M-1-5 (17.14 g, 30 mmol), M-2-4 (5.16 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 5.74 g (yield: 65%).

(2) Synthesis of Sub 1-57

Sub (3)-57 (5.74 g, 21.3 mmol), DMSO (46 mL), and CuI (2.65 g, 21 mmol) were subjected to the synthesis method for Sub 1-1 to give 2.29 g (yield: 40%).

15. Synthesis Example of Sub 1-56

<Reaction Scheme 17>

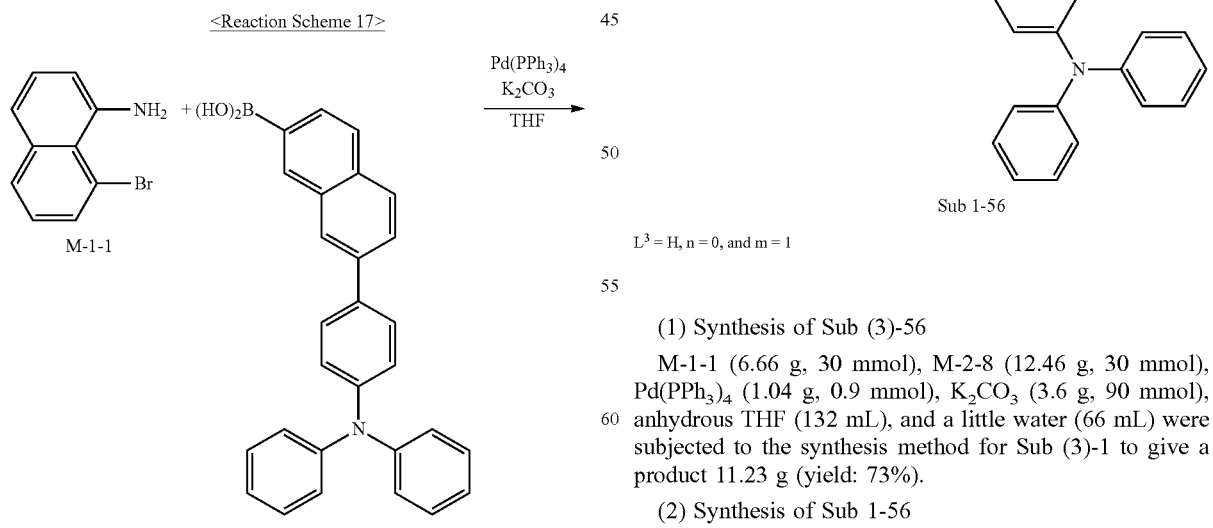

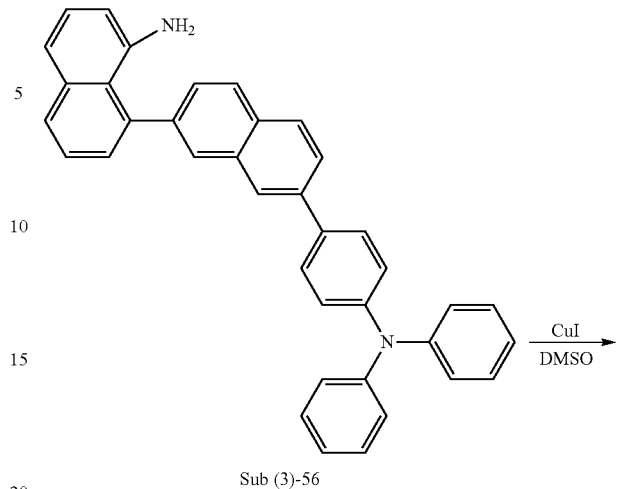

Sub (3)-56

Sub 1-56

$L^3$ = H, n = 0, and m = 1

(1) Synthesis of Sub (3)-56

M-1-1 (6.66 g, 30 mmol), M-2-8 (12.46 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 11.23 g (yield: 73%).

(2) Synthesis of Sub 1-56

Sub (3)-56 (11.23 g, 21.9 mmol), DMSO (109 mL), and CuI (6.26 g, 32.9 mmol) were subjected to the synthesis method for Sub 1-1 to give 4.25 g (yield: 38%).

16. Synthesis Example of Sub 1-60
<Reaction Scheme 18>
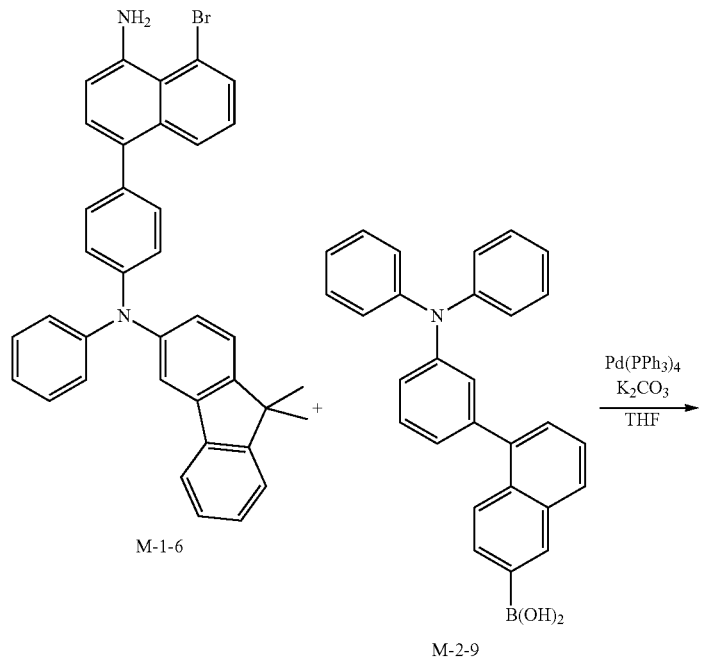
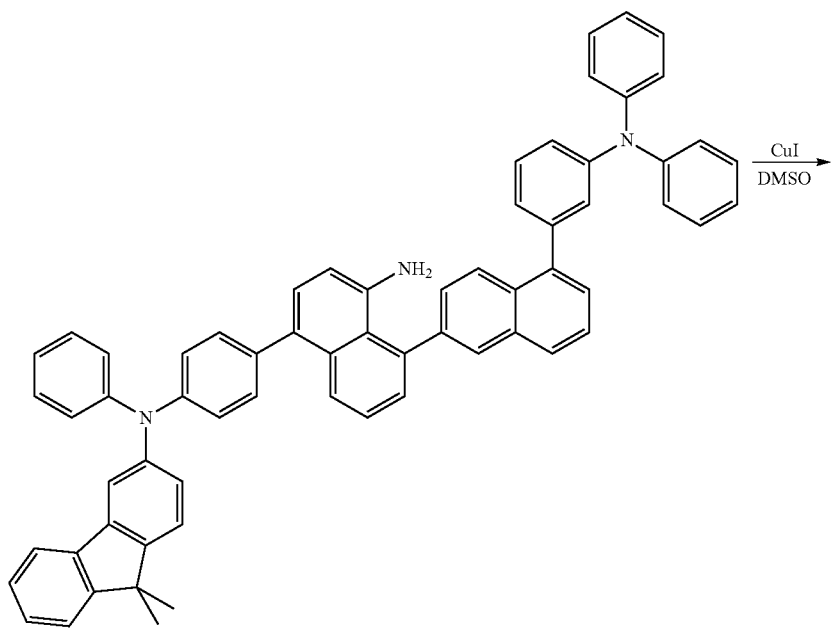

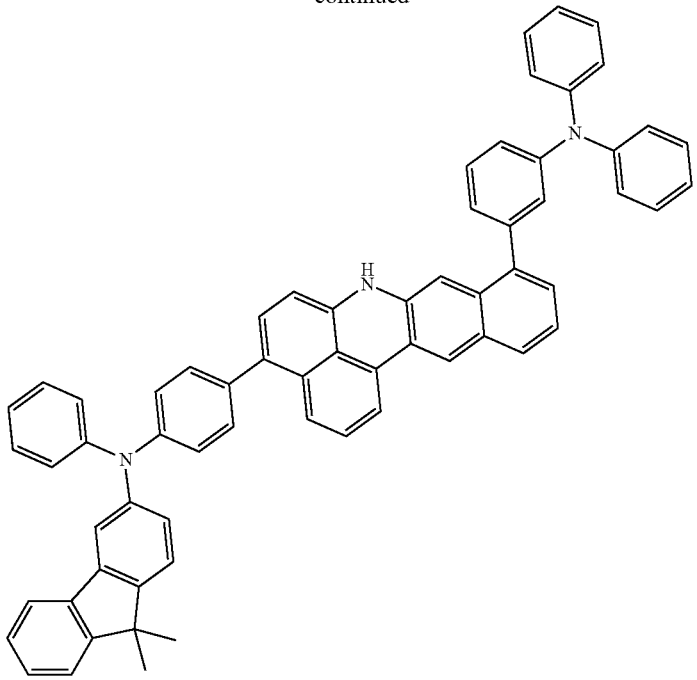

Sub 1-60 n = 1 and m = 1

(1) Synthesis of Sub (3)-60

M-1-1 (17.4 g, 30 mmol), M-2-9 (12.46 g, 30 mmol), Pd(PPh$_3$)$_4$ (1.04 g, 0.9 mmol), K$_2$CO$_3$ (3.6 g, 90 mmol), anhydrous THF (132 mL), and a little water (66 mL) were subjected to the synthesis method for Sub (3)-1 to give a product 18.6 g (yield: 71%).

(2) Synthesis of Sub 1-60

Sub (3)-60 (18.6 g, 21.3 mmol), DMSO (107 mL), and CuI (6.09 g, 32 mmol) were subjected to the synthesis method for Sub 1-1 to give 6.5 g (yield: 35%).

Table 1 below shows FD-MS values of the compounds pertaining to Sub 1.

TABLE 1

| Compound | FD-MS | Compound | FD-MS |
|---|---|---|---|
| Sub 1-1 | m/z = 217.09(C$_{16}$H$_{11}$N = 217.27) | Sub 1-2 | m/z = 700.29(C$_{53}$H$_{36}$N$_2$ = 700.87) |
| Sub 1-3 | m/z = 625.25(C$_{46}$H$_{315}$N$_3$ = 625.76) | Sub 1-4 | m/z = 625.25(C$_{46}$H$_{31}$N$_3$ = 625.76) |
| Sub 1-5 | m/z = 458.18(C$_{34}$H$_{22}$N$_2$ = 458.55) | Sub 1-6 | m/z = 399.11(C$_{28}$H$_{17}$NS = 399.51) |
| Sub 1-7 | m/z = 293.12(C$_{22}$H$_{15}$N = 293.36) | Sub 1-8 | m/z = 566.18(C$_{40}$H$_{26}$N$_2$S = 566.71) |
| Sub 1-9 | m/z = 510.21(C$_{38}$H$_{264}$N$_2$ = 510.63) | Sub 1-10 | m/z = 626.27(C$_{47}$H$_{34}$N$_2$ = 626.79) |
| Sub 1-11 | m/z = 700.29(C$_{53}$H$_{36}$N$_2$ = 700.87) | Sub 1-12 | m/z = 560.23(C$_{42}$H$_{28}$N$_2$ = 560.69) |
| Sub 1-13 | m/z = 642.21(C$_{46}$H$_{30}$N$_2$S = 642.81) | Sub 1-14 | m/z = 700.29(C$_{53}$H$_{36}$N$_2$ = 700.87) |
| Sub 1-15 | m/z = 703.30(C$_{52}$H$_{37}$N$_3$ = 703.87) | Sub 1-16 | m/z = 702.28(C$_{51}$H$_{34}$N$_4$ = 702.84) |
| Sub 1-17 | m/z = 612.26(C$_{46}$H$_{32}$N$_2$ = 612.76) | Sub 1-18 | m/z = 700.29(C$_{53}$H$_{36}$N$_2$ = 700.87) |
| Sub 1-19 | m/z = 566.18(C$_{40}$H$_{26}$N$_2$S = 566.71) | Sub 1-20 | m/z = 536.23(C$_{40}$H$_{28}$N$_2$ = 536.66) |
| Sub 1-21 | m/z = 267.10(C$_{20}$H$_{13}$N = 267.32) | Sub 1-22 | m/z = 510.21(C$_{38}$H$_{26}$N$_2$ = 510.63) |
| Sub 1-23 | m/z = 508.19(C$_{38}$H$_{24}$N$_2$ = 508.61) | Sub 1-24 | m/z = 434.18(C$_{32}$H$_{22}$N$_2$ = 434.53) |
| Sub 1-25 | m/z = 616.20(C$_{44}$H$_{28}$N$_2$S = 616.77) | Sub 1-26 | m/z = 677.28(C$_{50}$H$_{35}$N$_3$ = 677.83) |
| Sub 1-27 | m/z = 662.27(C$_{50}$H$_{34}$N$_2$ = 662.82) | Sub 1-28 | m/z = 750.30(C$_{57}$H$_{38}$N$_2$ = 750.93) |
| Sub 1-29 | m/z = 616.20(C$_{44}$H$_{28}$N$_2$S = 616.77) | Sub 1-30 | m/z = 586.24(C$_{44}$H$_{30}$N$_2$ = 586.72) |
| Sub 1-31 | m/z = 267.10(C$_{20}$H$_{13}$N = 267.32) | Sub 1-32 | m/z = 750.30(C$_{57}$H$_{38}$N$_2$ = 750.93) |
| Sub 1-33 | m/z = 675.27(C$_{50}$H$_{33}$N$_3$ = 675.82) | Sub 1-34 | m/z = 675.27(C$_{50}$H$_{33}$N$_3$ = 675.82) |
| Sub 1-35 | m/z = 508.19(C$_{50}$H$_{32}$N$_2$S = 508.61) | Sub 1-36 | m/z = 616.20(C$_{44}$H$_{28}$N$_2$S = 616.77) |
| Sub 1-37 | m/z = 343.14(C$_{26}$H$_{17}$N = 343.42) | Sub 1-38 | m/z = 600.22(C$_{44}$H$_{28}$N$_2$O = 600.71) |
| Sub 1-39 | m/z = 560.23(C$_{42}$H$_{28}$N$_2$ = 560.69) | Sub 1-40 | m/z = 676.29(C$_{51}$H$_{36}$N$_2$ = 676.84) |
| Sub 1-41 | m/z = 750.30(C$_{57}$H$_{38}$N$_2$ = 750.93) | Sub 1-42 | m/z = 748.29(C$_{57}$H$_{36}$N$_2$ = 748.91) |
| Sub 1-43 | m/z = 610.24(C$_{46}$H$_{30}$N$_2$ = 610.74) | Sub 1-44 | m/z = 692.23(C$_{50}$H$_{32}$N$_2$S = 692.87) |
| Sub 1-45 | m/z = 650.24(C$_{48}$H$_{30}$N$_2$O = 650.76) | Sub 1-46 | m/z = 753.31(C$_{56}$H$_{39}$N$_3$ = 753.93) |
| Sub 1-47 | m/z = 752.29(C$_{55}$H$_{36}$N$_4$ = 752.90) | Sub 1-48 | m/z = 662.27(C$_{50}$H$_{34}$N$_2$ = 662.82) |
| Sub 1-49 | m/z = 750.30(C$_{57}$H$_{38}$N$_2$ = 750.93) | Sub 1-50 | m/z = 616.20(C$_{44}$H$_{28}$N$_2$S = 616.77) |
| Sub 1-51 | m/z = 586.24(C$_{44}$H$_{30}$N$_2$ = 586.72) | Sub 1-52 | m/z = 267.10(C$_{20}$H$_{13}$N = 267.32) |
| Sub 1-53 | m/z = 508.19(C$_{38}$H$_{24}$N$_2$ = 508.61) | Sub 1-54 | m/z = 449.12(C$_{32}$H$_{19}$NS = 449.56) |
| Sub 1-55 | m/z = 343.14(C$_{26}$H$_{17}$N = 343.42) | Sub 1-56 | m/z = 510.21(C$_{38}$H$_{26}$N$_2$ = 510.63) |
| Sub 1-57 | m/z = 616.20(C$_{44}$H$_{28}$N$_2$S = 616.77) | Sub 1-58 | m/z = 637.25(C$_{47}$H$_{31}$N$_3$ = 637.77) |
| Sub 1-59 | m/z = 750.30(C$_{57}$H$_{38}$N$_2$ = 750.93) | Sub 1-60 | m/z = 869.38(C$_{65}$H$_{47}$N$_3$ = 870.09) |

TABLE 1-continued
| Compound | FD-MS | Compound | FD-MS |
|---|---|---|---|
| Sub 1-61 | m/z = 662.27($C_{50}H_{34}N_2$ = 662.82) | Sub 1-62 | m/z = 750.30($C_{57}H_{38}N_2$ = 750.93) |
| Sub 1-63 | m/z = 616.20($C_{44}H_{28}N_2S$ = 616.77) | Sub 1-64 | m/z = 586.24($C_{44}H_{30}N_2$ = 586.72) |
II. Synthesis of Sub 2
Sub 2 of Reaction Scheme 1 above may be synthesized by the following reaction pathway, but is not limited thereto.
The compounds pertaining to Sub 2 may be the following compounds, but are not limited thereto.
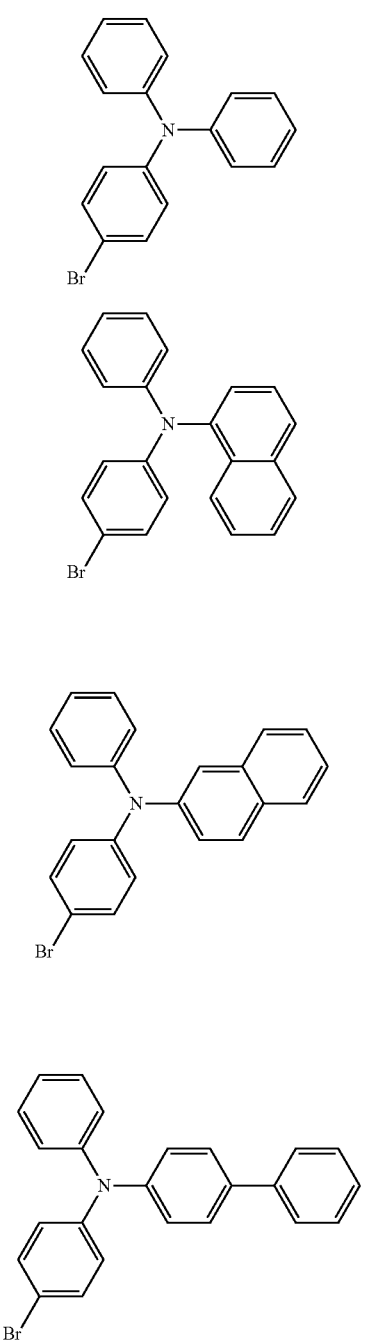
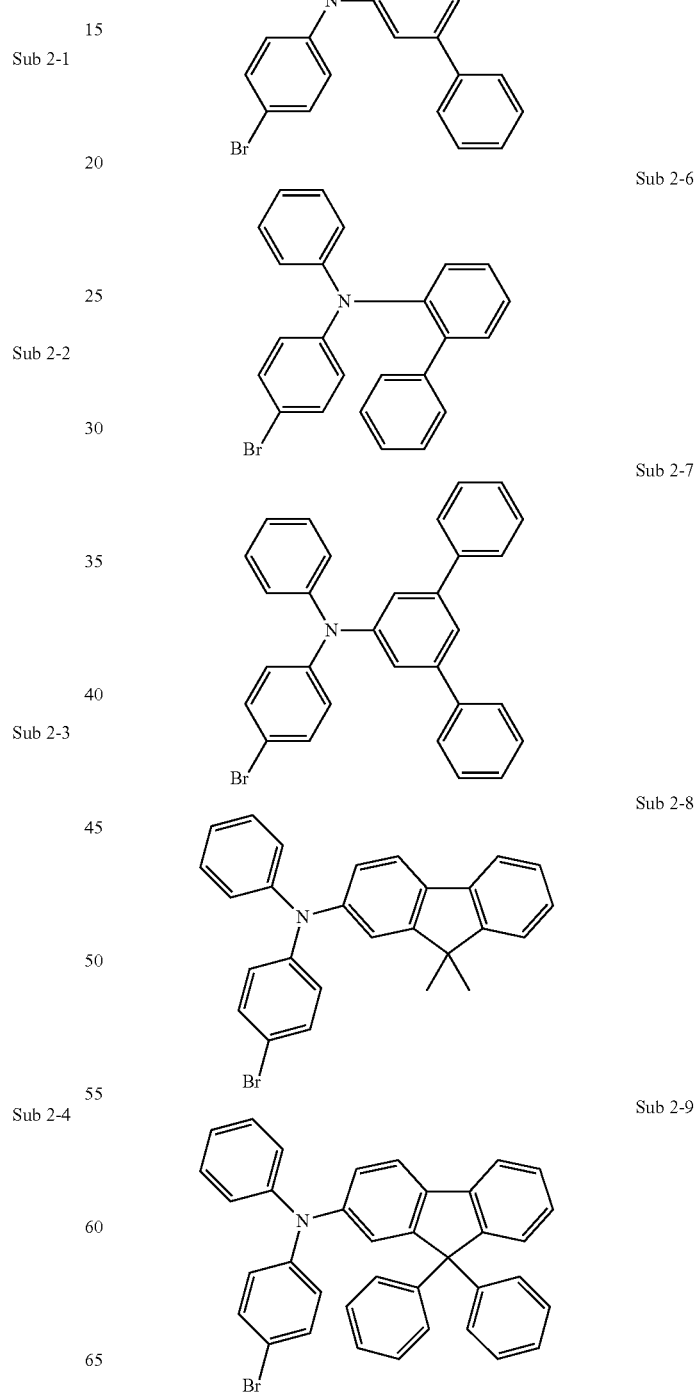

-continued
Sub 2-10
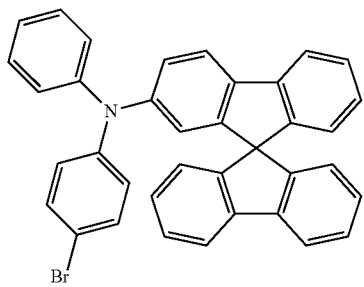
Sub 2-11
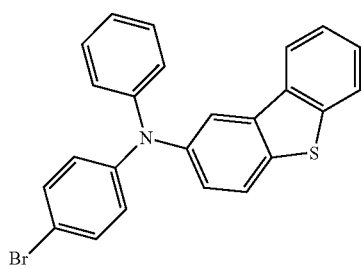
Sub 2-12
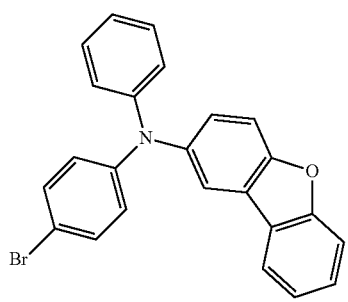
Sub 2-13
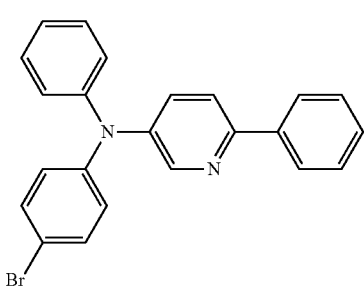
Sub 2-14
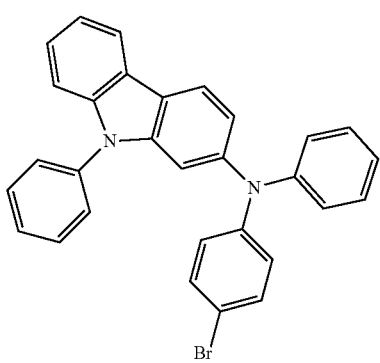
-continued
Sub 2-15
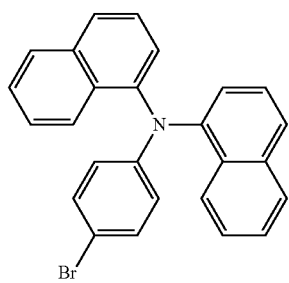
Sub 2-16
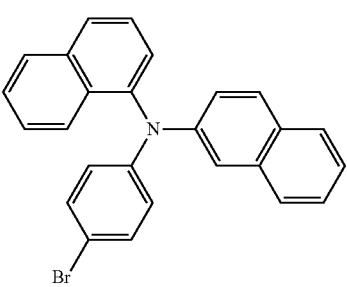
Sub 2-17
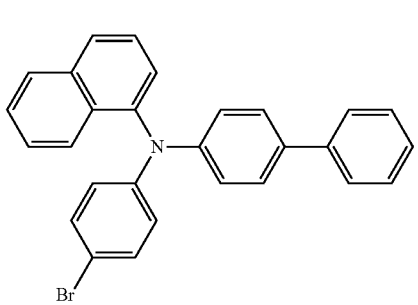
Sub 2-18
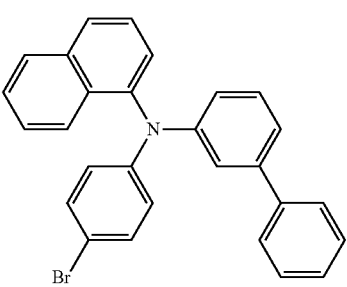
Sub 2-19
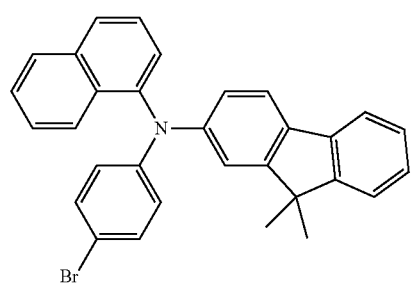

Sub 2-20
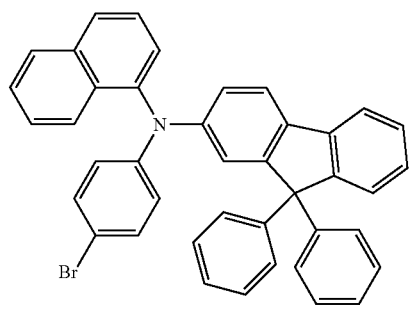
Sub 2-21
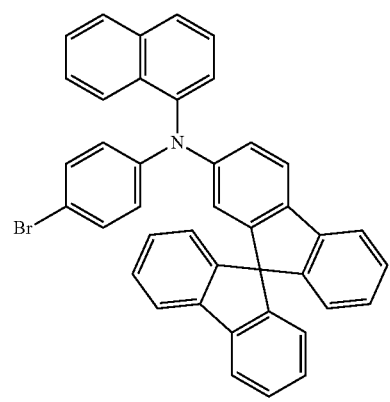
Sub 2-22
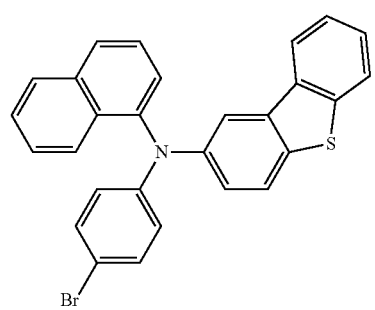
Sub 2-23
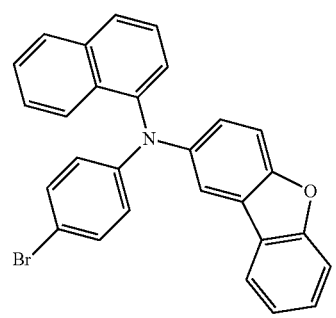
Sub 2-24
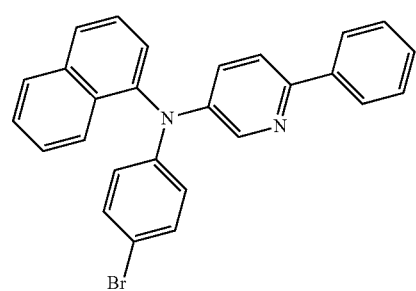
Sub 2-25
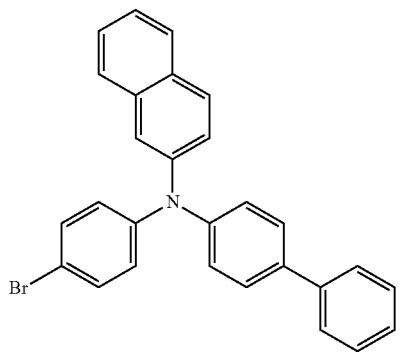
Sub 2-26
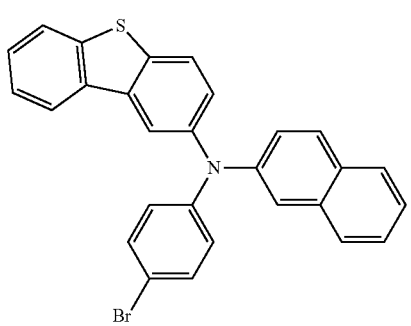
Sub 2-27
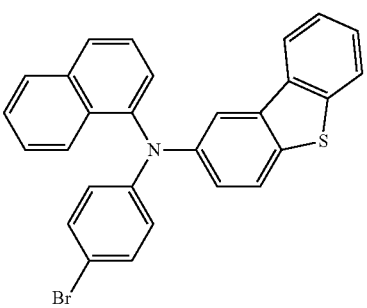
Sub 2-28
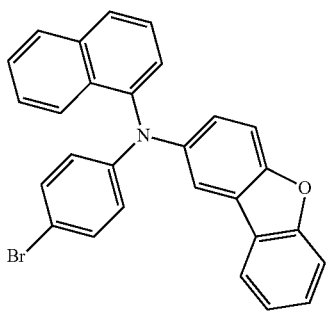
Sub 2-29
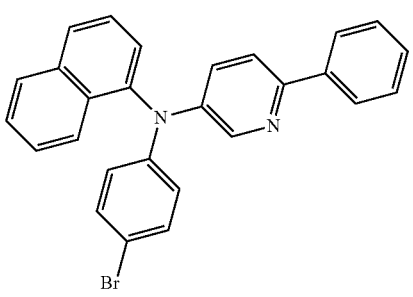

Sub 2-30
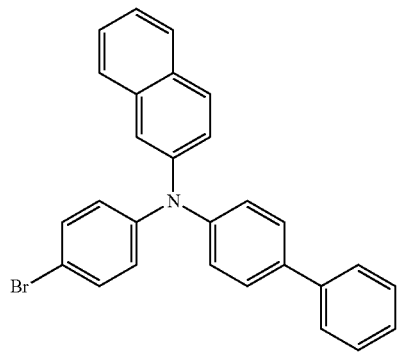
Sub 2-34
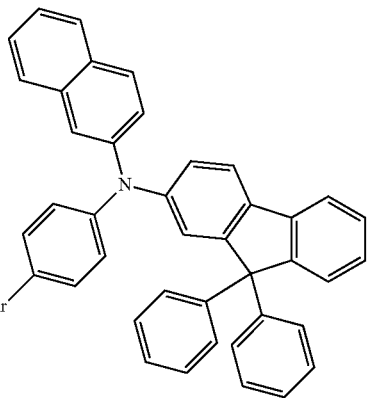
Sub 2-31
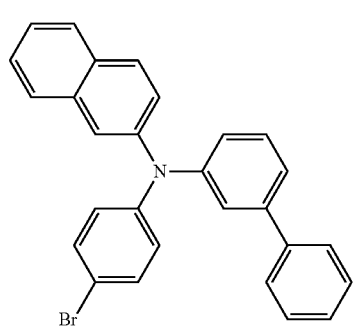
Sub 2-35
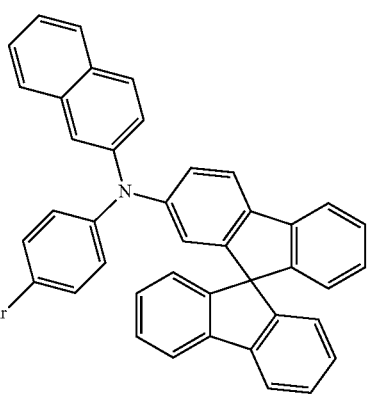
Sub 2-32
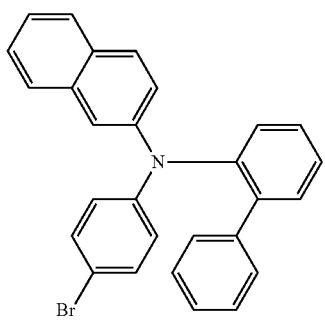
Sub 2-36
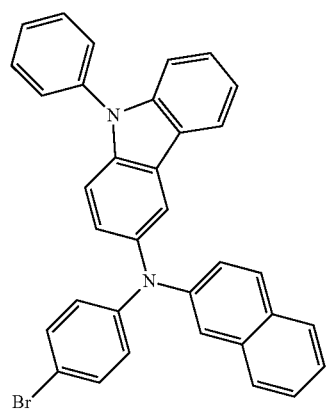
Sub 2-33
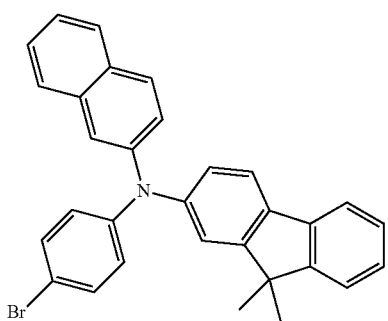
Sub 2-37
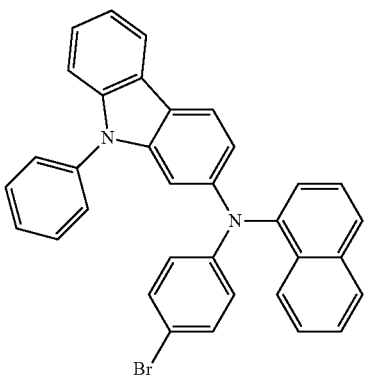

Sub 2-38
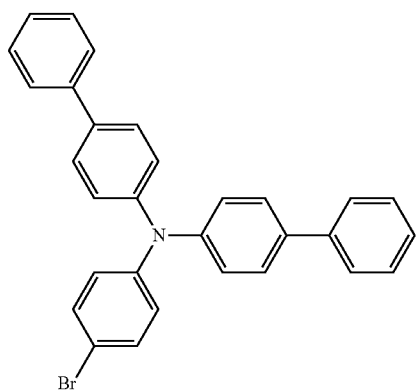
Sub 2-39
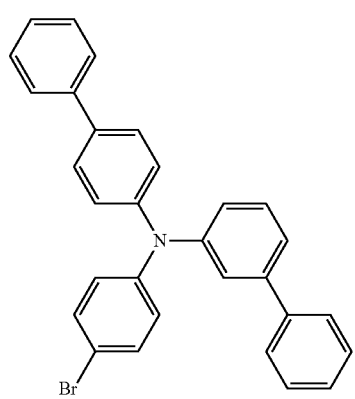
Sub 2-40
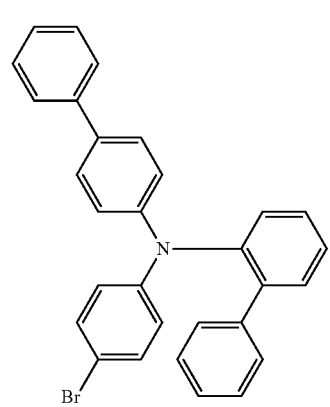
Sub 2-41
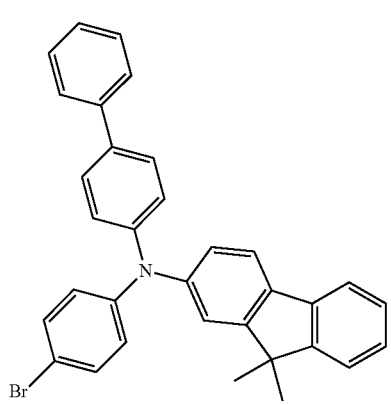
Sub 2-42
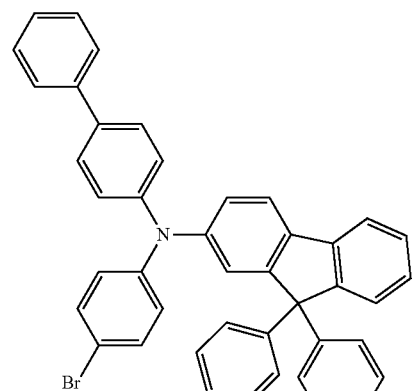
Sub 2-43
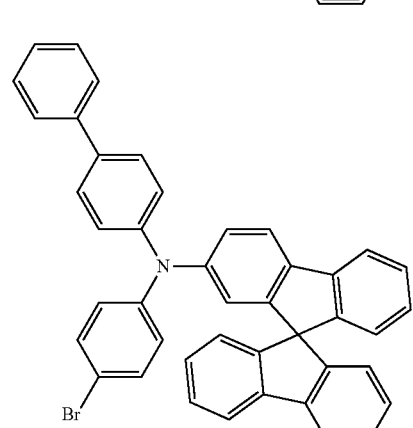
Sub 2-44
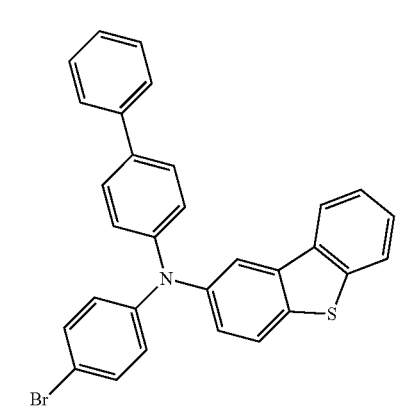
Sub 2-45
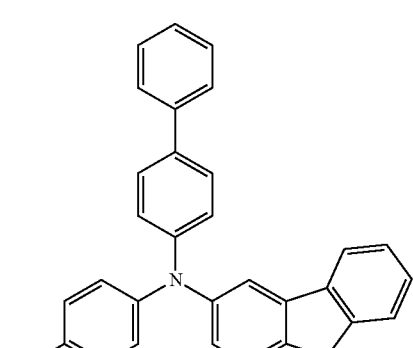

Sub 2-46
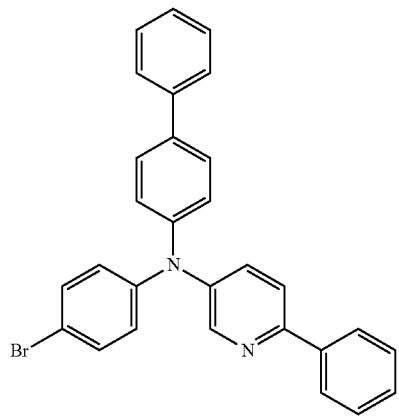
Sub 2-47
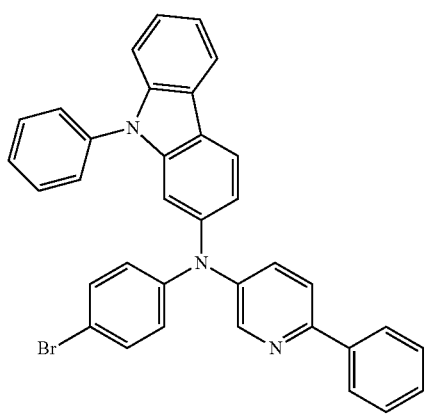
Sub 2-48
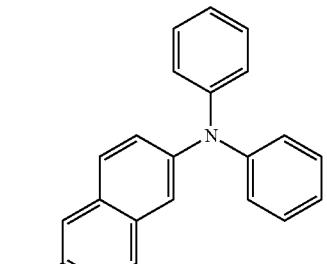
Sub 2-49
Sub 2-50
Sub 2-51
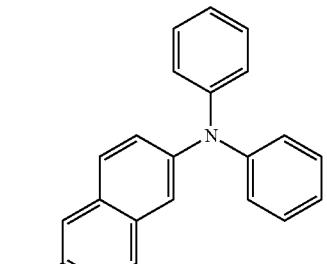
Sub 2-52
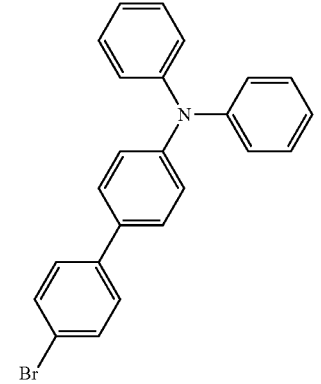
Sub 2-53
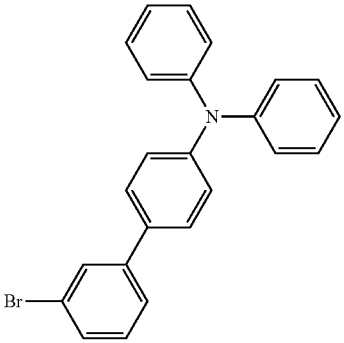
Sub 2-54
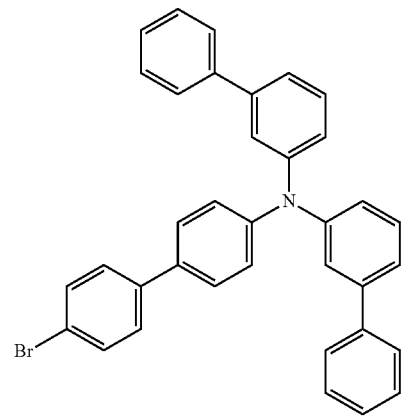

Sub 2-55
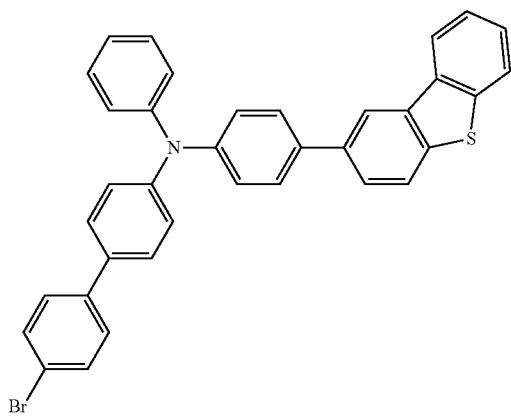
Sub 2-56
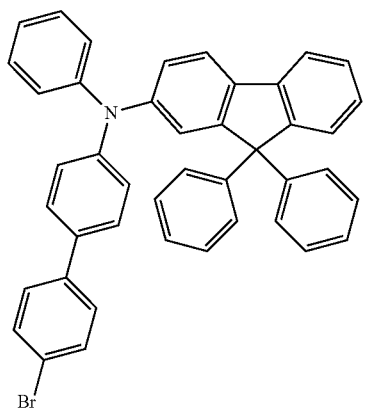
Sub 2-57
Sub 2-58
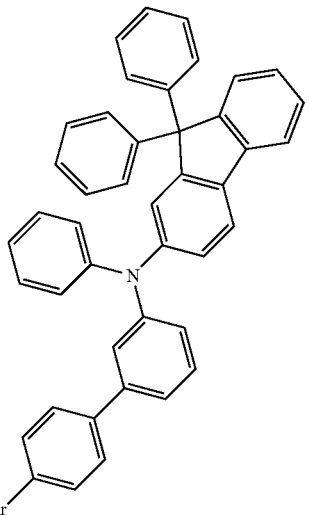
Sub 2-59
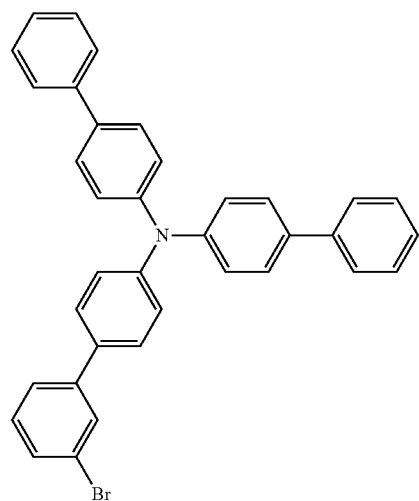
Sub 2-60
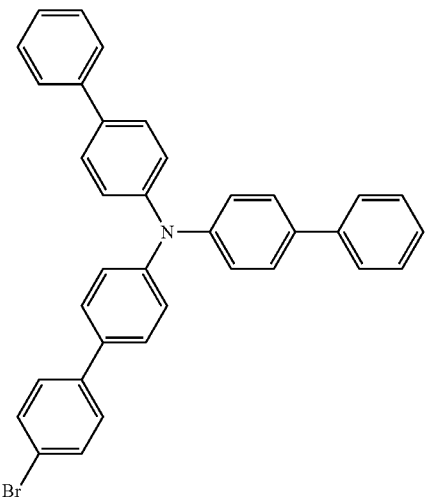

Sub 2-61
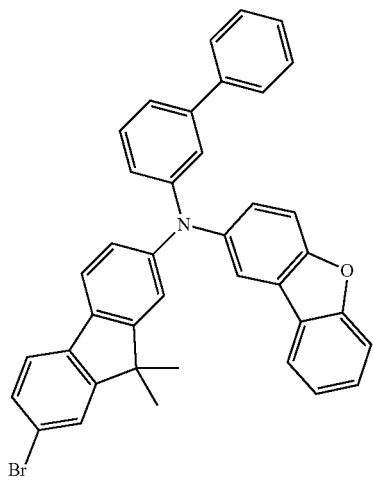
Sub 2-62
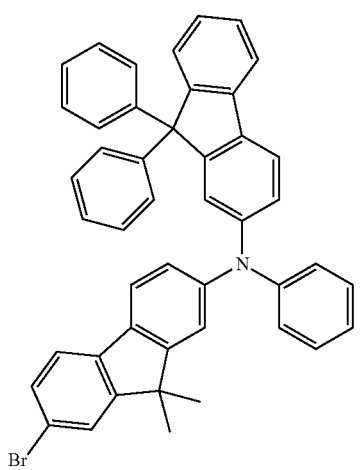
Sub 2-63
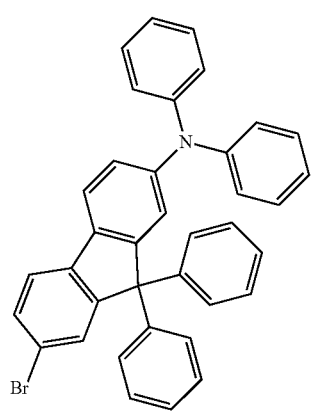
Sub 2-64
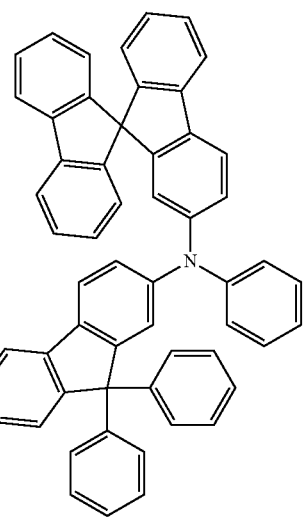
Sub 2-65
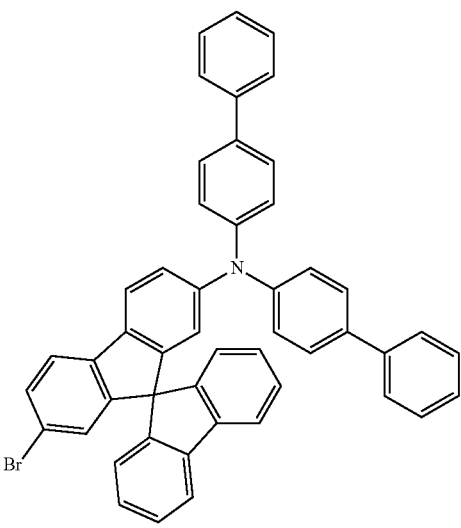
Sub 2-66
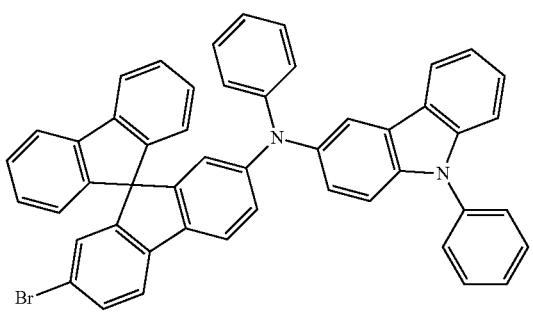
Sub 2-67
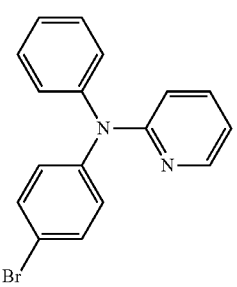

-continued
Sub 2-68
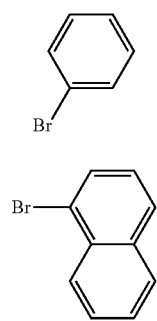
Sub 2-69
Sub 2-70
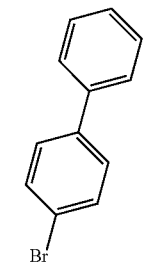
Sub 2-71
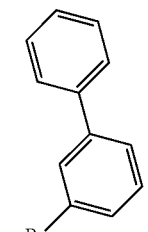
Sub 2-72
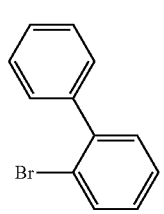
Sub 2-73
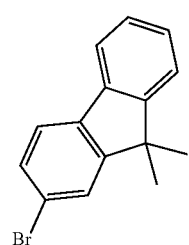
Sub 2-74
-continued
Sub 2-75
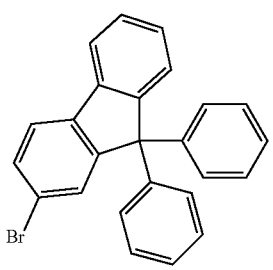
Sub 2-76
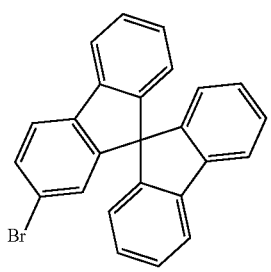
Sub 2-77
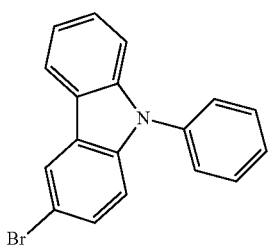
Sub 2-78
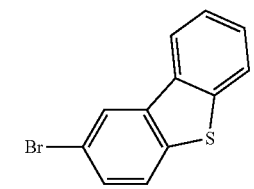
Sub 2-79
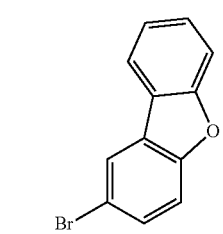
Sub 2-80
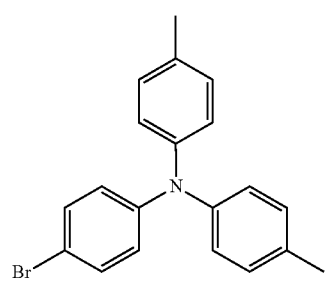

Sub 2-81
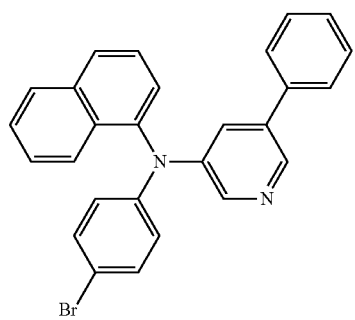
Sub 2-82
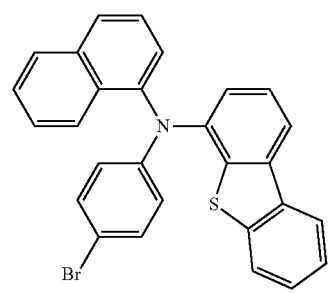
Sub 2-83
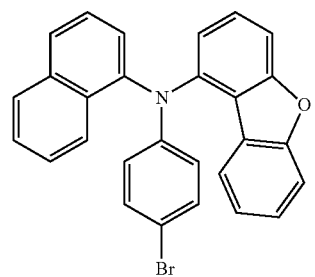
Sub 2-84
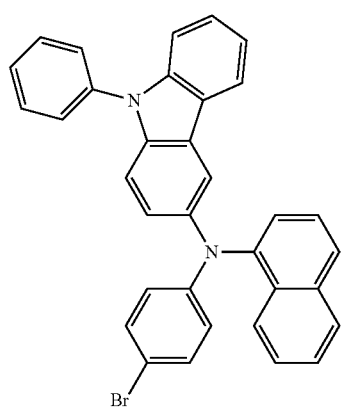
Sub 2-85
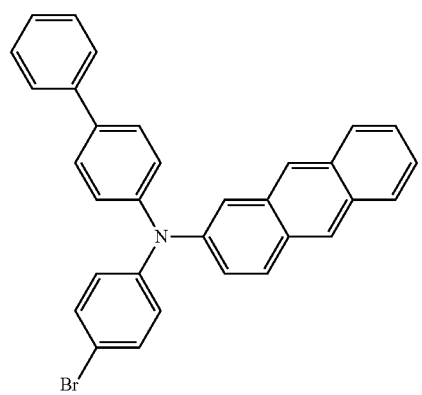
Sub 2-86
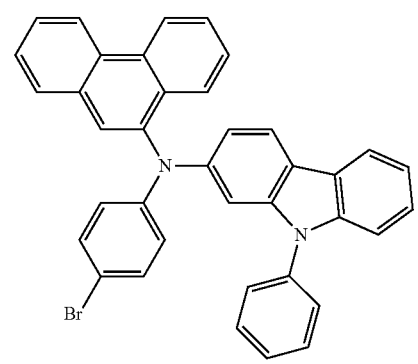
Sub 2-87
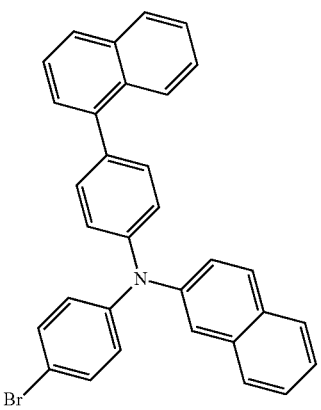
Sub 2-88
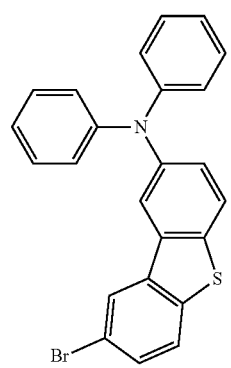

Sub 2-89
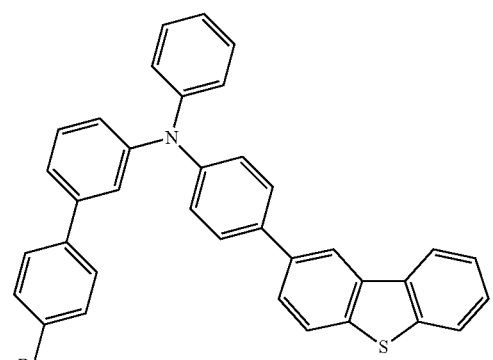
Sub 2-93
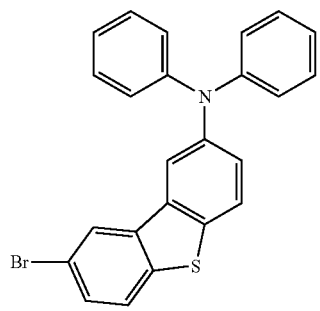
Sub 2-94
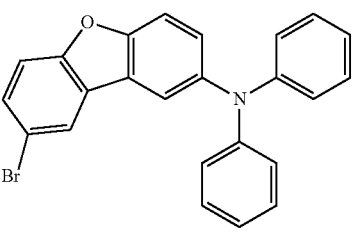
Sub 2-90
Sub 2-91
Sub 2-95
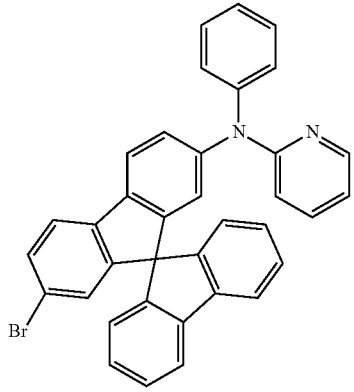
Sub 2-92
Sub 2-96
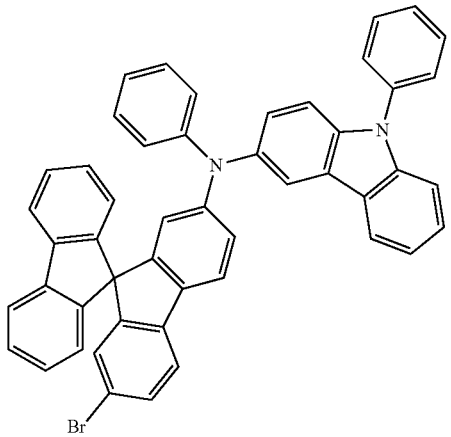

Sub 2-97

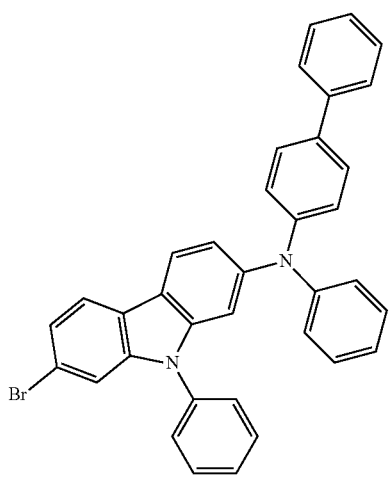

Sub 2-100

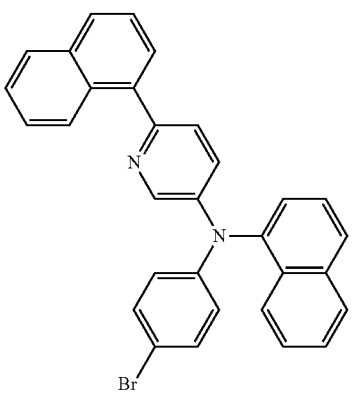

Sub 2-98

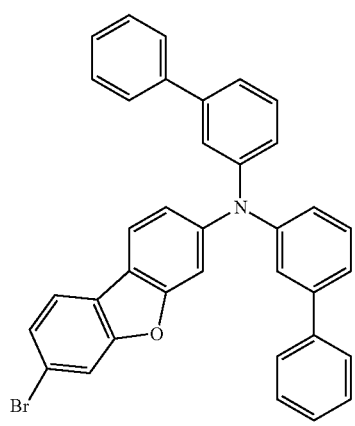

L¹ to L³ are a single bond

Sub 2-99

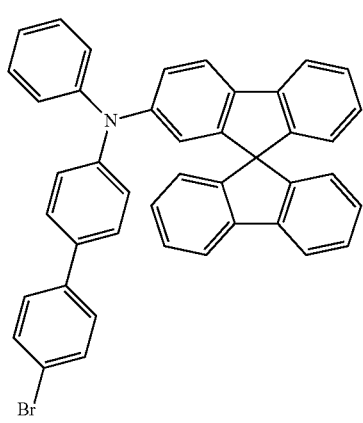

1. Synthesis Example of Sub 2-74

<Reaction Scheme 19>

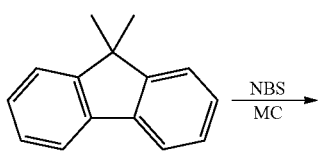

Sub (2)-I-5

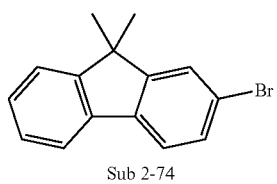

Sub 2-74

After Sub (2)-I-5 (6.8 g, 35 mmol) was dissolved in methylene chloride (123 mL), NBS (N-bromosuccimide) (6.85 g, 38.5 mmol) was slowly added, and then the mixture was stirred at room temperature for 24 hours. Upon completion of the reaction, 5% HCl was added, and then water was added to remove residual NBS. Thereafter, the reaction product was extracted with ether and water, and the organic layer was dried over MgSO₄ and concentrated, and then the resulting organic material was subjected to silica gel column chromatography and recrystallization to give a product 7.46 g (yield: 78%).

2. Synthesis Example of Sub 2-3

<Reaction Scheme 20>

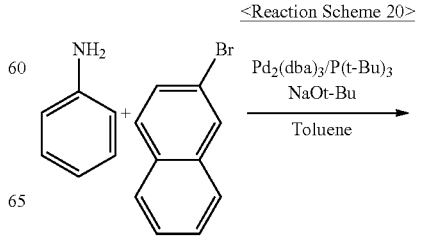

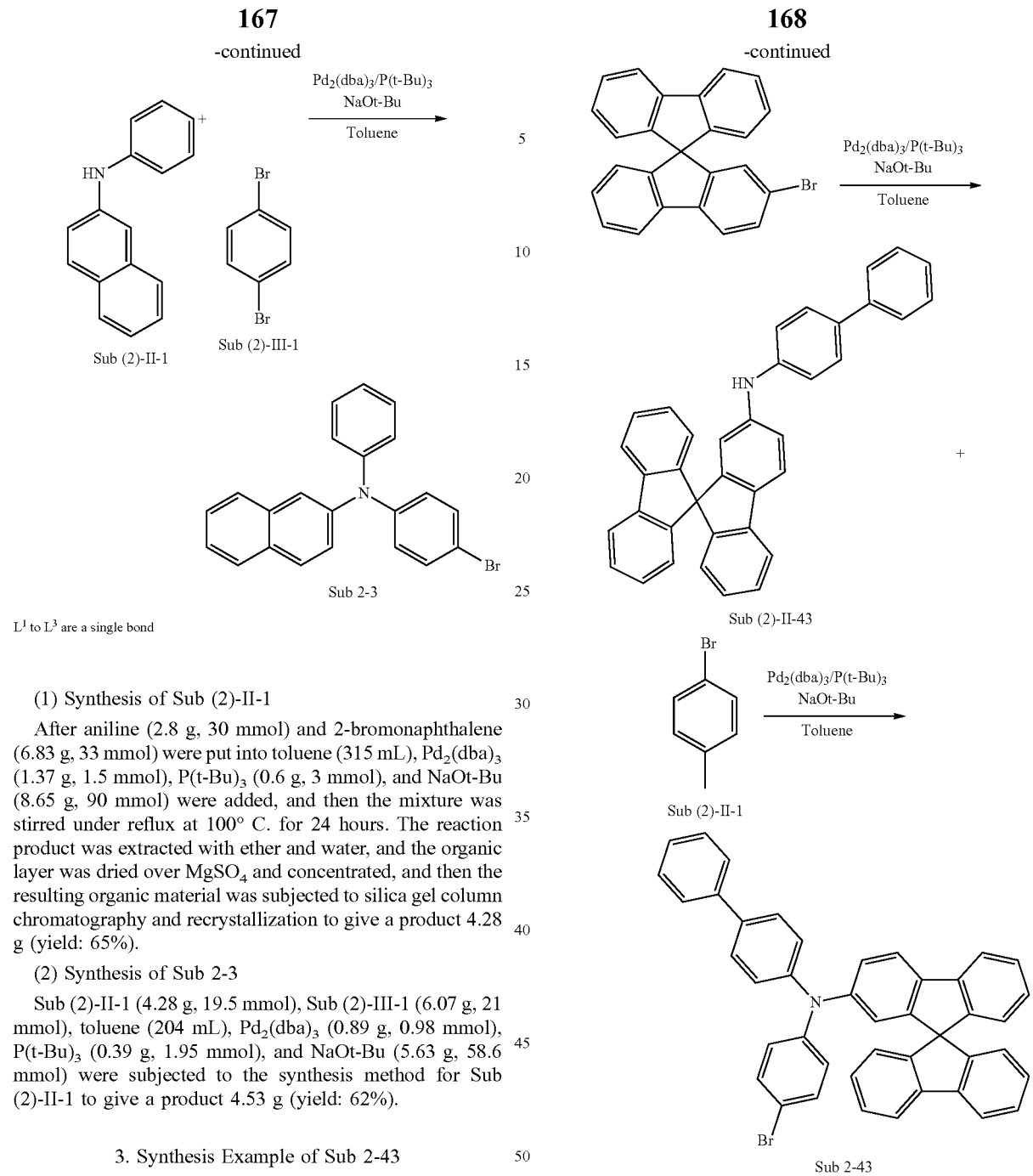

Sub (2)-II-1

Sub (2)-III-1

Sub 2-3

L¹ to L³ are a single bond (1) Synthesis of Sub (2)-II-1

After aniline (2.8 g, 30 mmol) and 2-bromonaphthalene (6.83 g, 33 mmol) were put into toluene (315 mL), Pd$_2$(dba)$_3$ (1.37 g, 1.5 mmol), P(t-Bu)$_3$ (0.6 g, 3 mmol), and NaOt-Bu (8.65 g, 90 mmol) were added, and then the mixture was stirred under reflux at 100° C. for 24 hours. The reaction product was extracted with ether and water, and the organic layer was dried over MgSO$_4$ and concentrated, and then the resulting organic material was subjected to silica gel column chromatography and recrystallization to give a product 4.28 g (yield: 65%).

(2) Synthesis of Sub 2-3

Sub (2)-II-1 (4.28 g, 19.5 mmol), Sub (2)-III-1 (6.07 g, 21 mmol), toluene (204 mL), Pd$_2$(dba)$_3$ (0.89 g, 0.98 mmol), P(t-Bu)$_3$ (0.39 g, 1.95 mmol), and NaOt-Bu (5.63 g, 58.6 mmol) were subjected to the synthesis method for Sub (2)-II-1 to give a product 4.53 g (yield: 62%).

3. Synthesis Example of Sub 2-43

<Reaction Scheme 21> L¹ to L³ are a single bond

Sub (2)-II-43

Sub (2)-II-1

Sub 2-43

(1) Synthesis of Sub (2)-II-43

[1,1'-Biphenyl]-4-amine (5.07 g, 30 mmol), 2-bromo-9,9'-spirobi[fluorene] (13 g, 33 mmol), toluene (315 mL), Pd$_2$(dba)$_3$ (1.37 g, 1.5 mmol), P(t-Bu)$_3$ (0.6 g, 3 mmol), and NaOt-Bu (8.65 g, 90 mmol) were subjected to the synthesis method for Sub (2)-II-1 to give a product 12.2 g (yield: 68%).

(2) Synthesis of Sub 2-43

Sub (2)-II-43 (12.2 g, 25.2 mmol), Sub (2)-III-1 (7.85 g, 27.8 mmol), toluene (204 mL), Pd$_2$(dba)$_3$ (1.16 g, 1.26 mmol), P(t-Bu)$_3$ (0.51 g, 2.5 mmol), and NaOt-Bu (7.27 g, 75.7 mmol) were subjected to the synthesis method for Sub (2)-II-1 to give a product 10.3 g (yield: 64%).

4. Synthesis Example of Sub 2-61

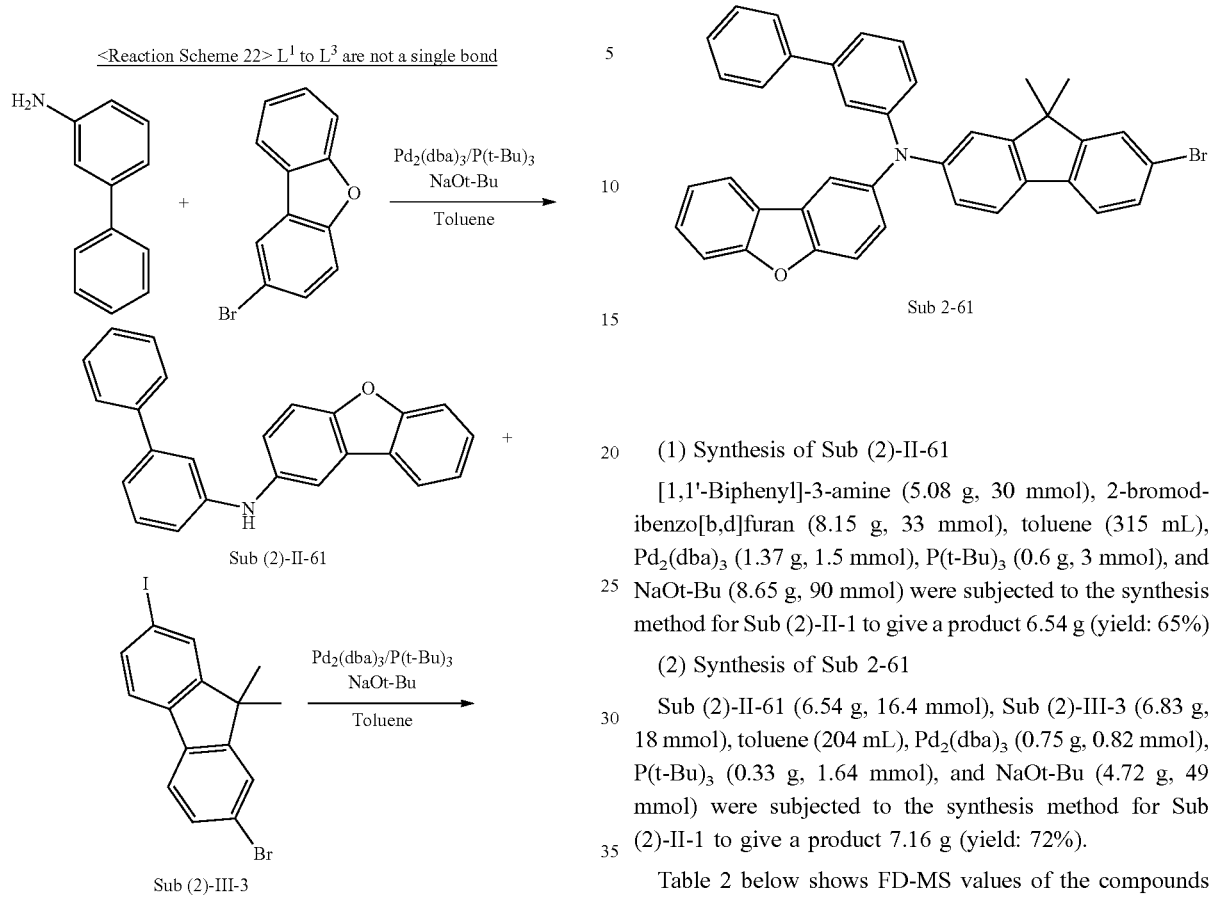

(1) Synthesis of Sub (2)-II-61

[1,1'-Biphenyl]-3-amine (5.08 g, 30 mmol), 2-bromodibenzo[b,d]furan (8.15 g, 33 mmol), toluene (315 mL), $Pd_2(dba)_3$ (1.37 g, 1.5 mmol), $P(t-Bu)_3$ (0.6 g, 3 mmol), and NaOt-Bu (8.65 g, 90 mmol) were subjected to the synthesis method for Sub (2)-II-1 to give a product 6.54 g (yield: 65%)

(2) Synthesis of Sub 2-61

Sub (2)-II-61 (6.54 g, 16.4 mmol), Sub (2)-III-3 (6.83 g, 18 mmol), toluene (204 mL), $Pd_2(dba)_3$ (0.75 g, 0.82 mmol), $P(t-Bu)_3$ (0.33 g, 1.64 mmol), and NaOt-Bu (4.72 g, 49 mmol) were subjected to the synthesis method for Sub (2)-II-1 to give a product 7.16 g (yield: 72%).

Table 2 below shows FD-MS values of the compounds pertaining to Sub 2.

TABLE 2

| Compound | FD-MS | Compound | FD-MS |
|---|---|---|---|
| Sub 2-1 | m/z = 323.03($C_{18}H_{14}BrN$ = 324.21) | Sub 2-2 | m/z = 373.05($C_{22}H_{16}BrN$ = 374.27) |
| Sub 2-3 | m/z = 373.05($C_{22}H_{16}BrN$ = 374.27) | Sub 2-4 | m/z = 399.06($C_{24}H_{18}BrN$ = 400.31) |
| Sub 2-5 | m/z = 399.06($C_{24}H_{18}BrN$ = 400.31) | Sub 2-6 | m/z = 399.06($C_{24}H_{18}BrN$ = 400.31) |
| Sub 2-7 | m/z = 475.09($C_{30}H_{22}BrN$ = 476.41) | Sub 2-8 | m/z = 439.09($C_{27}H_{22}BrN$ = 440.37) |
| Sub 2-9 | m/z = 563.12($C_{37}H_{26}BrN$ = 564.51) | Sub 2-10 | m/z = 561.11($C_{37}H_{24}BrN$ = 562.50) |
| Sub 2-11 | m/z = 429.02($C_{24}H_{16}BrNS$ = 430.36) | Sub 2-12 | m/z = 413.04($C_{24}H_{16}BrNO$ = 414.29) |
| Sub 2-13 | m/z = 400.06($C_{23}H_{17}BrN_2$ = 401.30) | Sub 2-14 | m/z = 488.09($C_{30}H_{21}BrN_2$ = 489.41) |
| Sub 2-15 | m/z = 423.06($C_{26}H_{18}BrN$ = 424.33) | Sub 2-16 | m/z = 423.06($C_{26}H_{18}BrN$ = 424.33) |
| Sub 2-17 | m/z = 449.08($C_{28}H_{20}BrN$ = 450.37) | Sub 2-18 | m/z = 449.08($C_{28}H_{20}BrN$ = 450.37) |
| Sub 2-19 | m/z = 489.11($C_{31}H_{24}BrN$ = 490.43) | Sub 2-20 | m/z = 613.14($C_{41}H_{28}BrN$ = 614.57) |
| Sub 2-21 | m/z = 611.12($C_{41}H_{26}BrN$ = 612.56) | Sub 2-22 | m/z = 479.03($C_{28}H_{18}BrNS$ = 480.42) |
| Sub 2-23 | m/z = 463.06($C_{28}H_{18}BrNO$ = 464.35) | Sub 2-24 | m/z = 450.07($C_{27}H_{19}BrN_2$ = 451.36) |
| Sub 2-25 | m/z = 538.10($C_{34}H_{23}BrN_2$ = 539.46) | Sub 2-26 | m/z = 449.08($C_{28}H_{20}BrN$ = 450.37) |
| Sub 2-27 | m/z = 479.03($C_{28}H_{18}BrNS$ = 480.42) | Sub 2-28 | m/z = 436.06($C_{28}H_{18}BrNO$ = 464.35) |
| Sub 2-29 | m/z = 450.07($C_{27}H_{19}BrN_2$ = 451.36) | Sub 2-30 | m/z = 538.10($C_{34}H_{23}BrN_2$ = 539.46) |
| Sub 2-31 | m/z = 449.08($C_{28}H_{20}BrN$ = 450.37) | Sub 2-32 | m/z = 449.08($C_{28}H_{20}BrN$ = 450.37) |
| Sub 2-33 | m/z = 489.11($C_{31}H_{24}BrN$ = 490.43) | Sub 2-34 | m/z = 613.14($C_{41}H_{28}BrN$ = 614.57) |
| Sub 2-35 | m/z = 611.12($C_{41}H_{26}BrN$ = 612.56) | Sub 2-36 | m/z = 479.03($C_{28}H_{18}BrNS$ = 480.42) |
| Sub 2-37 | m/z = 450.07($C_{27}H_{19}BrN_2$ = 451.36) | Sub 2-38 | m/z = 475.09($C_{30}H_{22}BrN$ = 476.41) |
| Sub 2-39 | m/z = 475.09($C_{30}H_{22}BrN$ = 476.41) | Sub 2-40 | m/z = 475.09($C_{30}H_{22}BrN$ = 476.41) |
| Sub 2-41 | m/z = 515.12($C_{33}H_{26}BrN$ = 516.47) | Sub 2-42 | m/z = 639.16($C_{43}H_{30}BrN$ = 640.61) |
| Sub 2-43 | m/z = 637.14($C_{43}H_{28}BrN$ = 368.59) | Sub 2-44 | m/z = 505.05($C_{30}H_{20}BrNS$ = 506.46) |
| Sub 2-45 | m/z = 489.07($C_{30}H_{20}BrNO$ = 490.39) | Sub 2-46 | m/z = 476.09($C_{29}H_{21}BrN_2$ = 477.39) |
| Sub 2-47 | m/z = 564.12($C_{36}H_{25}BrN_2$ = 565.50) | Sub 2-48 | m/z = 321.02($C_{18}H_{12}BrN$ = 322.20) |
| Sub 2-49 | m/z = 399.06($C_{24}H_{18}BrN$ = 400.31) | Sub 2-50 | m/z = 373.05($C_{22}H_{16}BrN$ = 374.27) |
| Sub 2-51 | m/z = 373.05($C_{22}H_{16}BrN$ = 374.27) | Sub 2-52 | m/z = 399.06($C_{24}H_{18}BrN$ = 400.31) |
| Sub 2-53 | m/z = 399.06($C_{24}H_{18}BrN$ = 400.31) | Sub 2-54 | m/z = 551.12($C_{36}H_{26}BrN$ = 552.50) |
| Sub 2-55 | m/z = 581.08($C_{36}H_{24}BrNS$ = 582.55) | Sub 2-56 | m/z = 639.16($C_{43}H_{30}BrN$ = 640.61) |
| Sub 2-57 | m/z = 637.14($C_{43}H_{28}BrN$ = 638.59) | Sub 2-58 | m/z = 639.16($C_{43}H_{30}BrN$ = 640.61) |
| Sub 2-59 | m/z = 551.12($C_{36}H_{26}BrN$ = 552.50) | Sub 2-60 | m/z = 551.12($C_{36}H_{26}BrN$ = 552.50) |

TABLE 2-continued

| Compound | FD-MS | Compound | FD-MS |
| --- | --- | --- | --- |
| Sub 2-61 | m/z = 605.14($C_{39}H_{28}BrNO$ = 606.55) | Sub 2-62 | m/z = 679.19($C_{46}H_{34}BrN$ = 680.67) |
| Sub 2-63 | m/z = 563.12($C_{37}H_{26}BrN$ = 564.51) | Sub 2-64 | m/z = 801.20($C_{56}H_{36}BrN$ = 802.80) |
| Sub 2-65 | m/z = 713.17($C_{49}H_{32}BrN$ = 714.69) | Sub 2-66 | m/z = 726.17($C_{49}H_{31}BrN_2$ = 727.69) |
| Sub 2-67 | m/z = 324.03($C_{17}H_{13}BrN_2$ = 325.20) | Sub 2-68 | m/z = 155.96($C_6H_5Br$ = 157.01) |
| Sub 2-69 | m/z = 205.97($C_{10}H_7Br$ = 207.07) | Sub 2-70 | m/z = 205.97($C_{10}H_7Br$ = 207.07) |
| Sub 2-71 | m/z = 231.99($C_{12}H_9Br$ = 233.10) | Sub 2-72 | m/z = 231.99($C_{12}H_9Br$ = 233.10) |
| Sub 2-73 | m/z = 231.99($C_{12}H_9Br$ = 233.10) | Sub 2-74 | m/z = 272.02($C_{15}H_{13}Br$ = 273.17) |
| Sub 2-75 | m/z = 396.05($C_{25}H_{17}Br$ = 397.31) | Sub 2-76 | m/z = 394.04($C_{25}H_{15}Br$ = 395.29) |
| Sub 2-77 | m/z = 321.02($C_{18}H_{12}BrN$ = 322.20) | Sub 2-78 | m/z = 261.95($C_{12}H_7BrS$ = 263.15) |
| Sub 2-79 | m/z = 245.97($C_{12}H_7BrO$ = 247.09) | Sub 2-80 | m/z = 351.06($C_{20}H_{18}BrN$ = 352.27) |
| Sub 2-81 | m/z = 450.07($C_{27}H_{19}BrN_2$ = 451.36) | Sub 2-82 | m/z = 479.03($C_{28}H_{18}BrNS$ = 480.42) |
| Sub 2-83 | m/z = 436.06($C_{28}H_{18}BrNO$ = 464.35) | Sub 2-84 | m/z = 538.10($C_{34}H_{23}BrN_2$ = 539.46) |
| Sub 2-85 | m/z = 499.09($C_{32}H_{22}BrN$ = 500.43) | Sub 2-86 | m/z = 588.12(C38H25BrN2 = 589.52) |
| Sub 2-87 | m/z = 499.09($C_{32}H_{22}BrN$ = 500.43) | Sub 2-88 | m/z = 429.02($C_{24}H_{16}BrNS$ = 430.36) |
| Sub 2-89 | m/z = 581.08($C_{36}H_{24}BrNS$ = 582.55) | Sub 2-90 | m/z = 715.19($C_{49}H_{34}BrN$ = 716.70) |
| Sub 2-91 | m/z = 564.12($C_{36}H_{25}BrN_2$ = 565.50) | Sub 2-92 | m/z = 565.10($C_{36}H_{24}BrNO$ = 566.49) |
| Sub 2-93 | m/z = 429.02($C_{24}H_{16}BrNS$ = 430.36) | Sub 2-94 | m/z = 413.04($C_{24}H_{16}BrNO$ = 414.29) |
| Sub 2-95 | m/z = 562.10($C_{36}H_{23}BrN_2$ = 563.49) | Sub 2-96 | m/z = 726.17($C_{49}H_{31}BrN_2$ = 727.69) |
| Sub 2-97 | m/z = 429.02($C_{24}H_{16}BrNS$ = 430.36) | Sub 2-98 | m/z = 413.04($C_{24}H_{16}BrNO$ = 414.29) |
| Sub 2-99 | m/z = 562.10($C_{36}H_{23}BrN_2$ = 563.49) | Sub 2-100 | m/z = 500.09($C_{31}H_{21}BrN_2$ = 501.42) |

III. Synthesis of Final Products

1. Synthesis Example of P 1-8

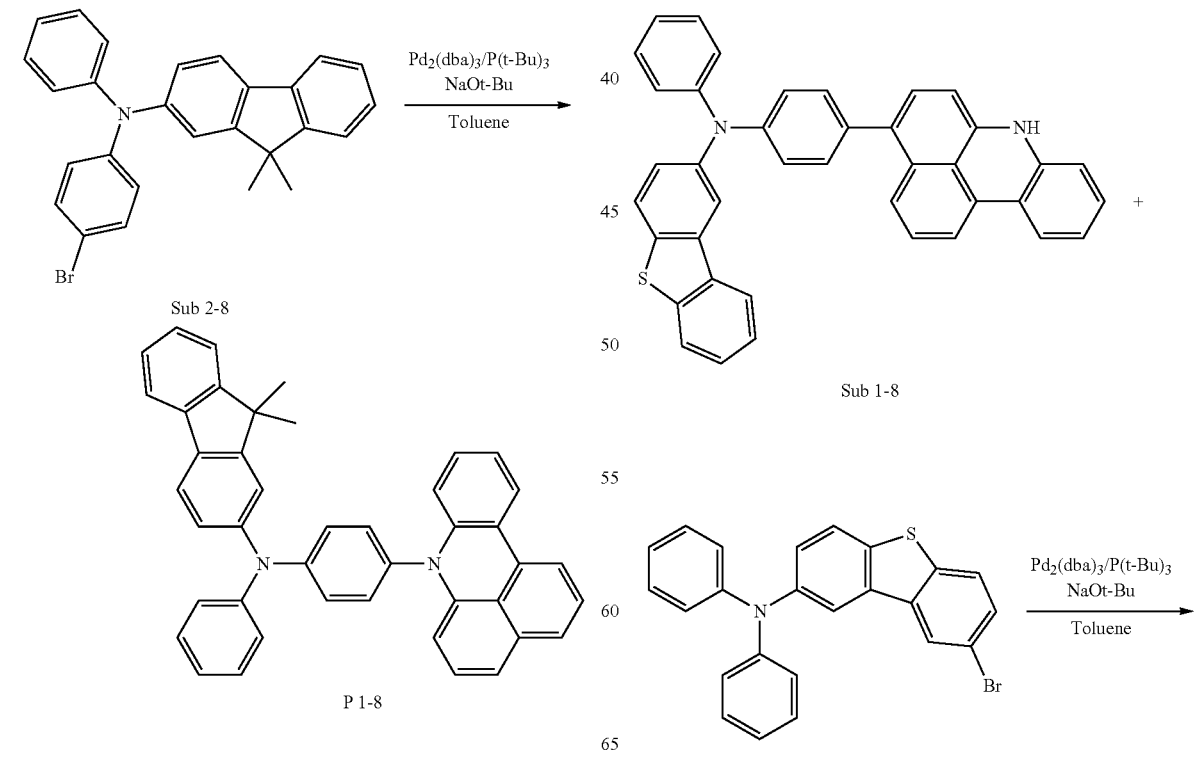

After Sub 1-1 (6.52 g, 30 mmol) and Sub 2-8 (14.5 g, 33 mmol) were dissolved in toluene (315 mL), Pd$_2$(dba)$_3$ (1.37 g, 1.5 mmol), P(t-Bu)$_3$ (0.6 g, 3 mmol), and NaOt-Bu (8.65 g, 90 mmol) were added, and then the mixture was stirred under reflux at 100° C. for 24 hours. The reaction product was extracted with ether and water, and the organic layer was dried over MgSO$_4$ and concentrated, and then the resulting organic material was subjected to silica gel column chromatography and recrystallization to give a product 12.5 g (yield: 72%).

2. Synthesis Example of P 1-75

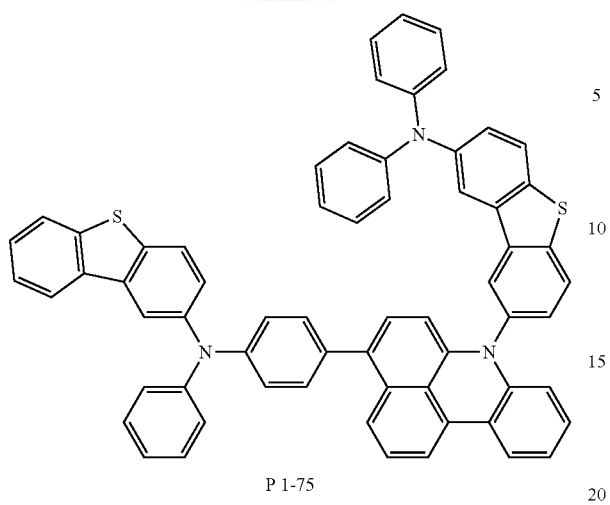

P 1-75

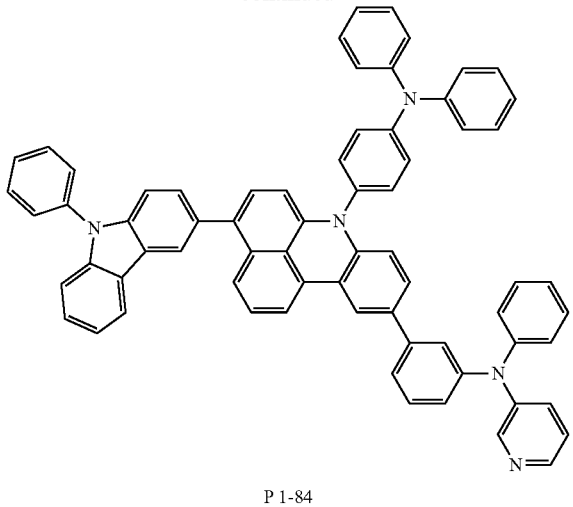

P 1-84

Sub 1-8 (18.5 g, 30 mmol), Sub 2-93 (14.2 g, 33 mmol), toluene (315 mL), Pd$_2$(dba)$_3$ (1.37 g, 1.5 mmol), P(t-Bu)$_3$ (0.61 g, 3 mmol), and NaOt-Bu (8.65 g, 90 mmol) were subjected to the synthesis method for P 1-8 to give a product 18.4 g (yield: 67%).

3. Synthesis Example of P 1-84

Sub 1-16 (21 g, 30 mmol), Sub 2-1 (10.7 g, 33 mmol), toluene (315 mL), Pd$_2$(dba)$_3$ (1.37 g, 1.5 mmol), P(t-Bu)$_3$ (0.61 g, 3 mmol), and NaOt-Bu (8.65 g, 90 mmol) were subjected to the synthesis method for P 1-8 to give a product 17.31 g (yield: 61%).

4. Synthesis Example of P 2-40

<Reaction Scheme 25>

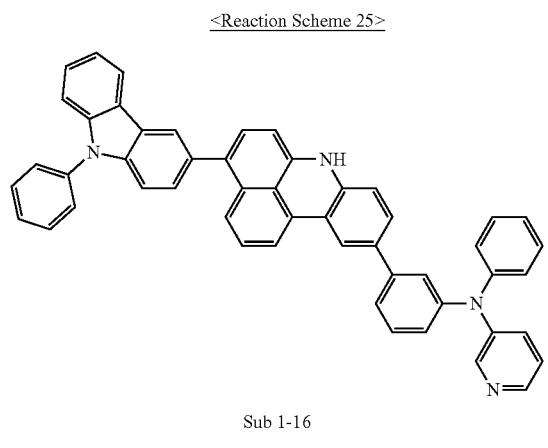

Sub 1-16

<Reaction Scheme 26>

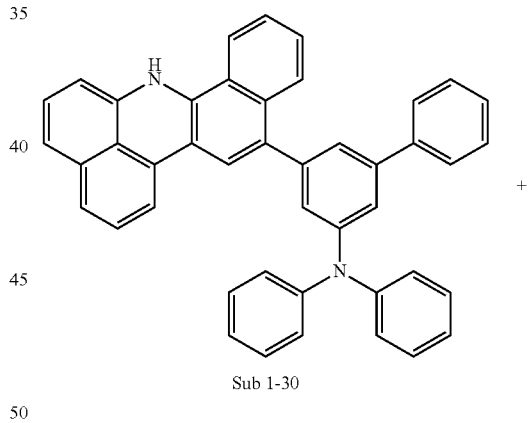

Sub 1-30

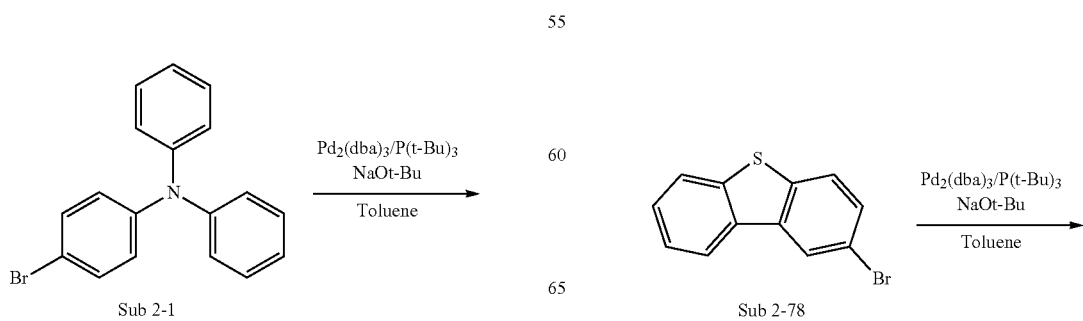

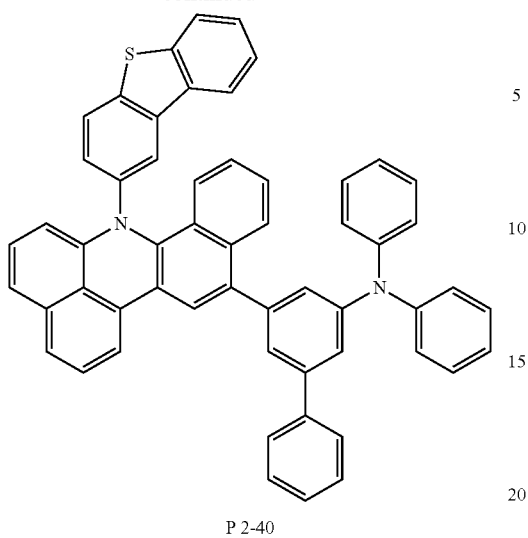

P 2-40

Sub 1-30 (14.7 g, 25 mmol), Sub 2-78 (7.24 g, 27.5 mmol), toluene (263 mL), Pd$_2$(dba)$_3$ (1.14 g, 1.25 mmol), P(t-Bu)$_3$ (0.51 g, 2.5 mmol), and NaOt-Bu (7.21 g, 75 mmol) were subjected to the synthesis method for P 1-8 to give a product 12.5 g (yield: 65%).

5. Synthesis Example of P 2-22

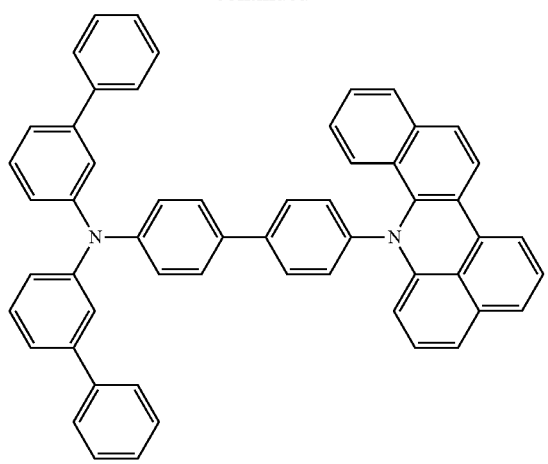

P 2-22

Sub 1-21 (8.02 g, 30 mmol), Sub 2-54 (18.2 g, 33 mmol), toluene (315 mL), Pd$_2$(dba)$_3$ (1.37 g, 1.5 mmol), P(t-Bu)$_3$ (0.61 g, 3 mmol), and NaOt-Bu (8.65 g, 90 mmol) were subjected to the synthesis method for P 1-8 to give a product 15.3 g (yield: 69%).

6. Synthesis Example of P 2-33

<Reaction Scheme 27>

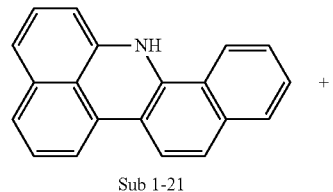

Sub 1-21

<Reaction Scheme 28>

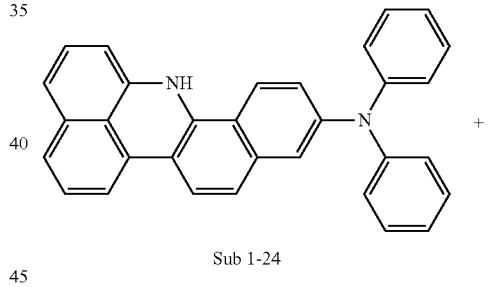

Sub 1-24

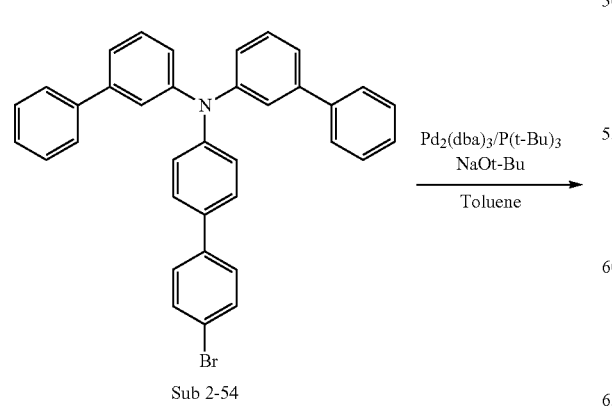

Sub 2-54

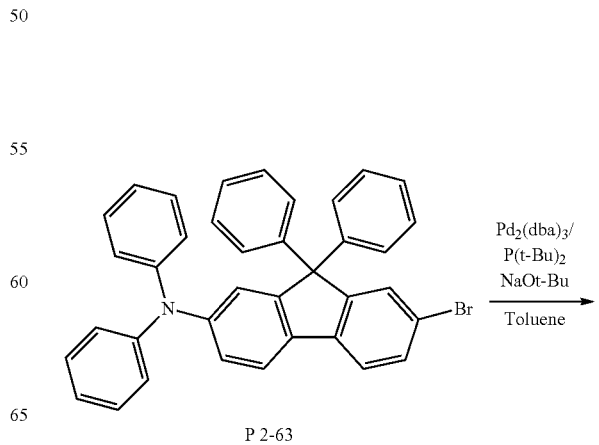

P 2-63

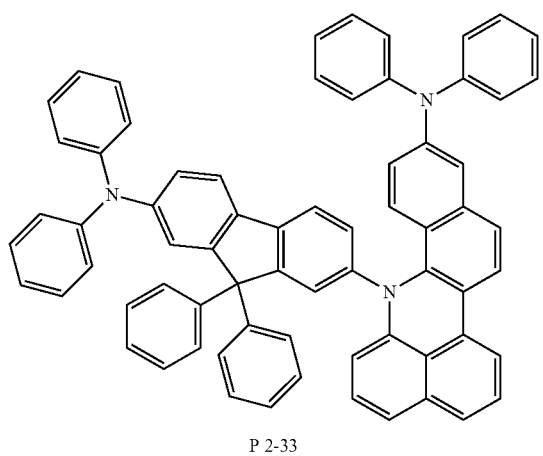

P 2-33

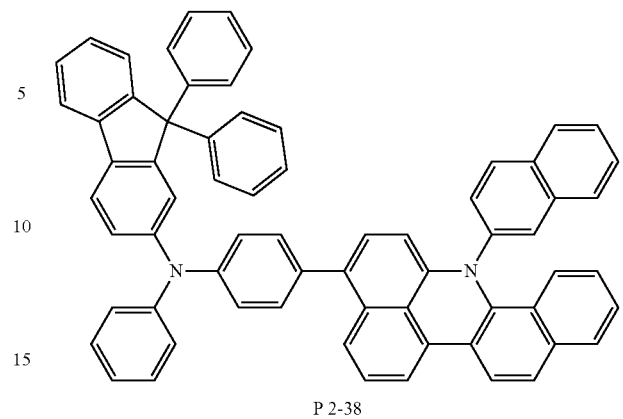

P 2-38

Sub 1-24 (13 g, 30 mmol), Sub 2-63 (18.6 g, 33 mmol), toluene (315 mL), Pd$_2$(dba)$_3$ (1.37 g, 1.5 mmol), P(t-Bu)$_3$ (0.61 g, 3 mmol), and NaOt-Bu (8.65 g, 90 mmol) were subjected to the synthesis method for P 1-8 to give a product 20.1 g (yield: 73%).

7. Synthesis Example of P 2-38

<Reaction Scheme 29>

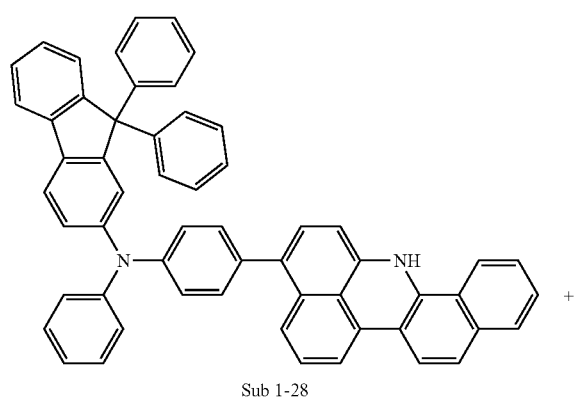

Sub 1-28

Sub 1-28 (18.8 g, 25 mmol), Sub 2-70 (5.7 g, 27.5 mmol), toluene (263 mL), Pd$_2$(dba)$_3$ (1.14 g, 1.25 mmol), P(t-Bu)$_3$ (0.51 g, 2.5 mmol), and NaOt-Bu (7.21 g, 75 mmol) were subjected to the synthesis method for P 1-8 to give a product 15.8 g (yield: 72%).

8. Synthesis Example of P 3-41

<Reaction Scheme 30>

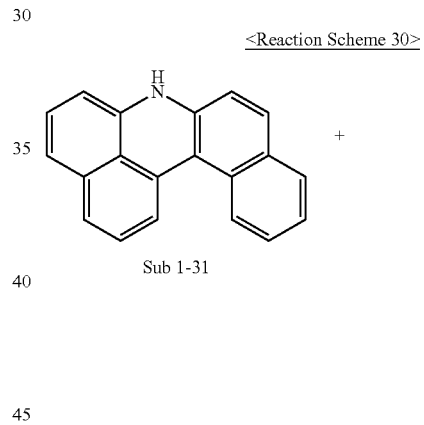

Sub 1-31

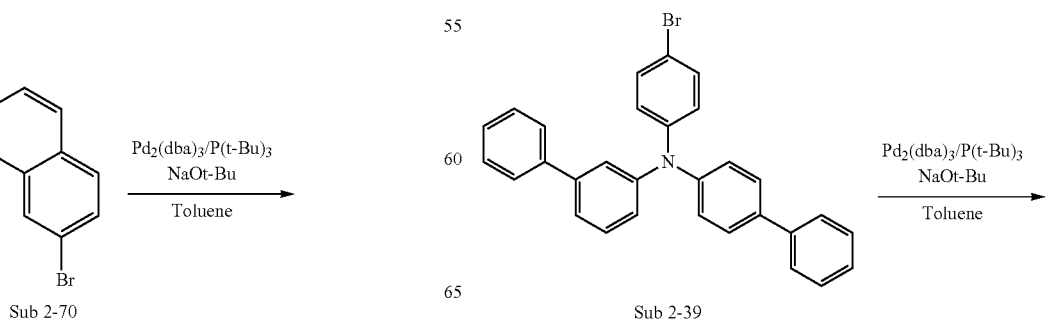

Sub 2-70        Sub 2-39

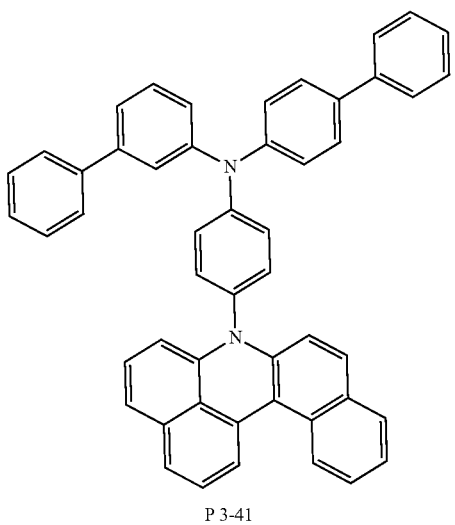

P 3-41

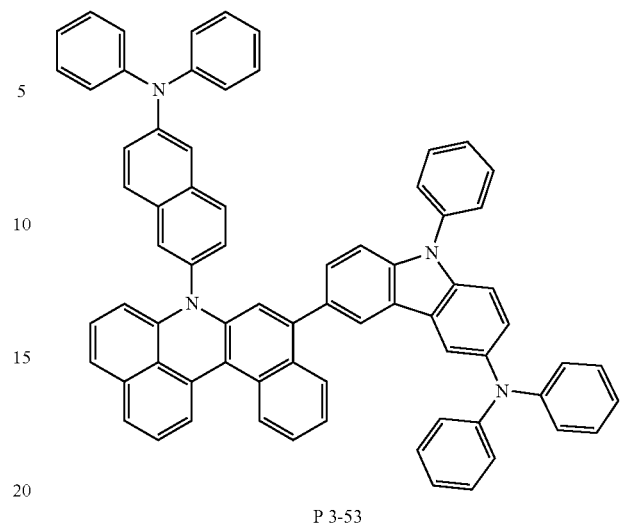

P 3-53

Sub 1-31 (8 g, 30 mmol), Sub 2-39 (15.7 g, 33 mmol), toluene (315 mL), Pd₂(dba)₃ (1.37 g, 1.5 mmol), P(t-Bu)₃ (0.61 g, 3 mmol), and NaOt-Bu (8.65 g, 90 mmol) were subjected to the synthesis method for P 1-8 to give a product 14.5 g (yield: 73%).

9. Synthesis Example of P 3-53

Sub 1-33 (5.3 g, 20 mmol), Sub 2-51 (13.3 g, 22 mmol), toluene (210 mL), Pd₂(dba)₃ (0.92 g, 1 mmol), P(t-Bu)₃ (0.4 g, 2 mmol), and NaOt-Bu (5.77 g, 60 mmol) were subjected to the synthesis method for P 1-8 to give a product 14.2 g (yield: 73%).

10. Synthesis Example of P 3-87

<Reaction Scheme 31>

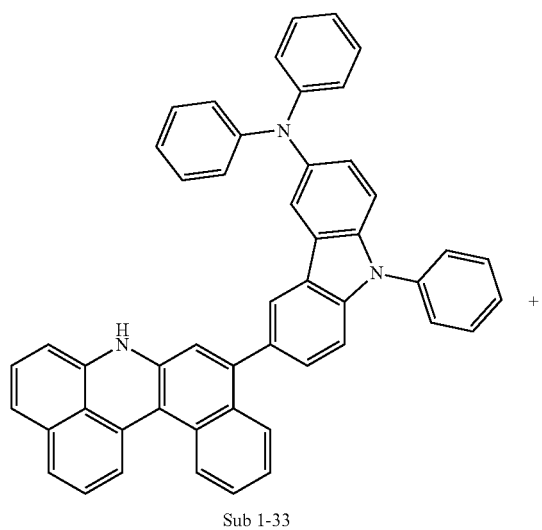

Sub 1-33

<Reaction Scheme 32>

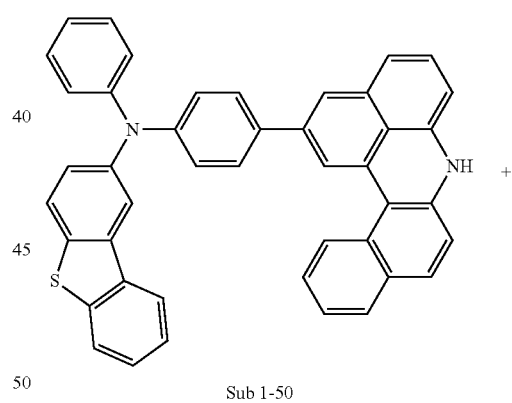

Sub 1-50

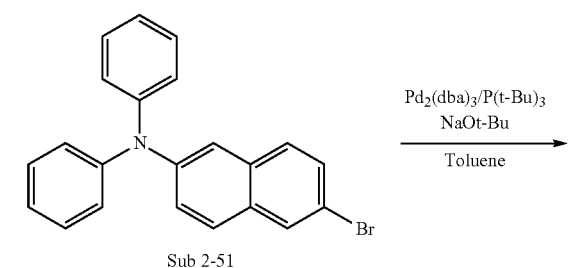

Sub 2-51

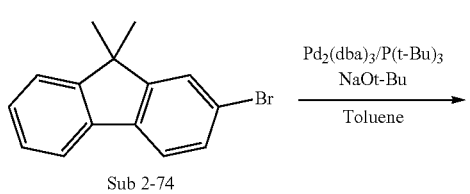

Sub 2-74

-continued
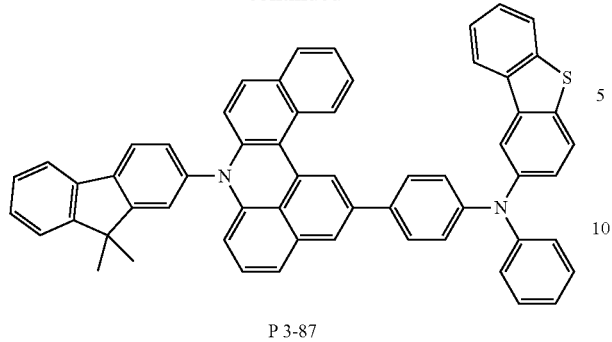
P 3-87
Sub 1-50 (12.3 g, 20 mmol), Sub 2-75 (6 g, 22 mmol), toluene (210 mL), Pd$_2$(dba)$_3$ (0.92 g, 1 mmol), P(t-Bu)$_3$ (0.4 g, 2 mmol), and NaOt-Bu (5.77 g, 60 mmol) were subjected to the synthesis method for P 1-8 to give a product 10.4 g (yield: 64%).
11. Synthesis Example of P 3-84
<Reaction Scheme 33>
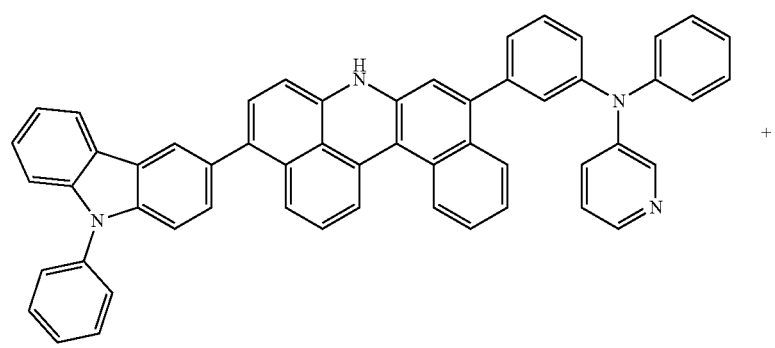
Sub 1-47
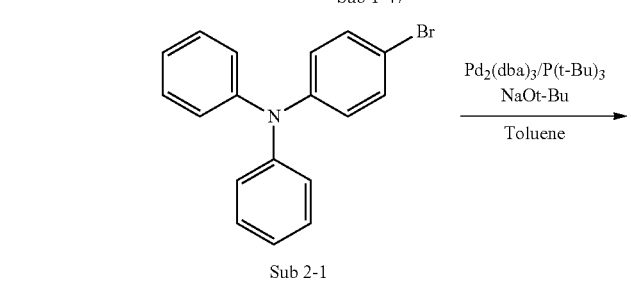
Sub 2-1
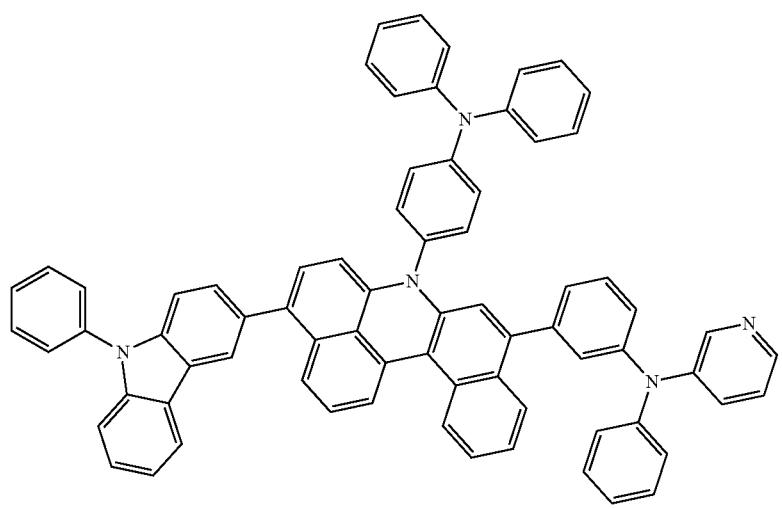
P 3-84

Sub 1-47 (15.1 g, 20 mmol), Sub 2-1 (7.1 g, 22 mmol), toluene (210 mL), Pd₂(dba)₃ (0.92 g, 1 mmol), P(t-Bu)₃ (0.4 g, 2 mmol), and NaOt-Bu (5.77 g, 60 mmol) were subjected to the synthesis method for P 1-8 to give a product 12.2 g (yield: 61%).

12. Synthesis Example of P 4-32

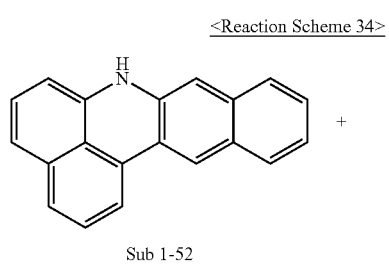

13. Synthesis Example of P 4-45

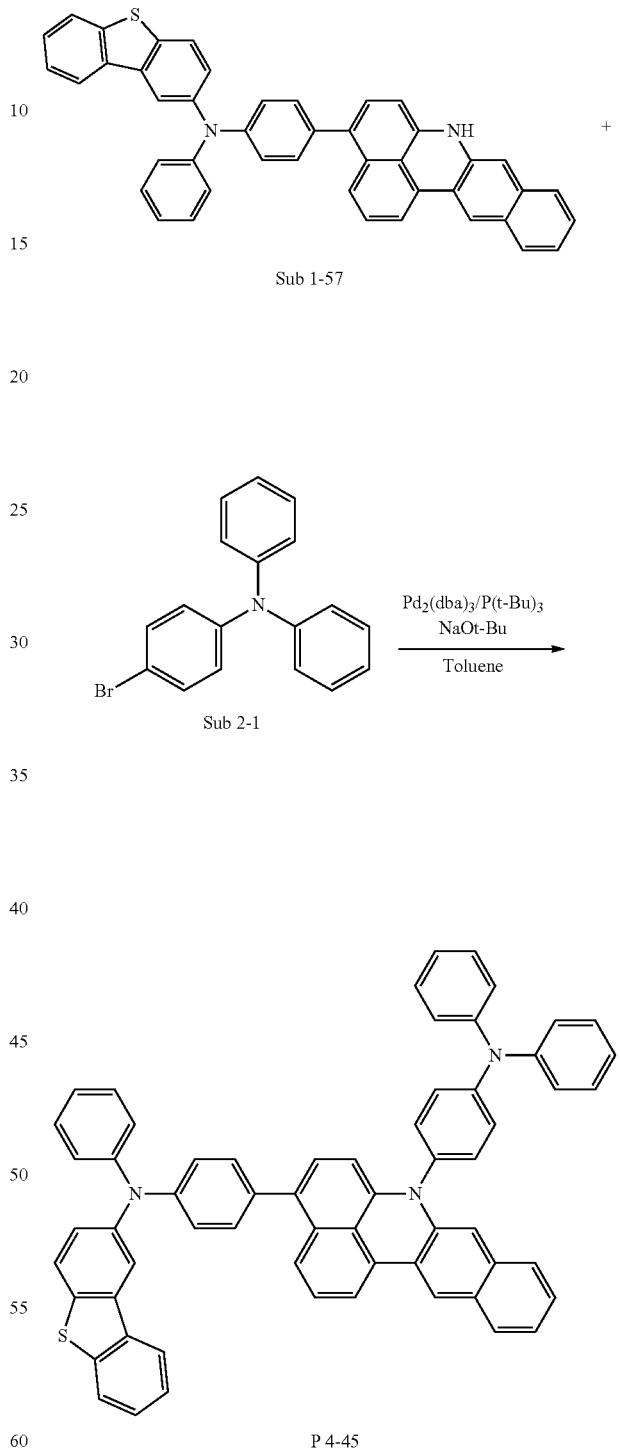

Sub 1-52 (8 g, 30 mmol), Sub 2-55 (19.2 g, 33 mmol), toluene (315 mL), Pd₂(dba)₃ (1.37 g, 1.5 mmol), P(t-Bu)₃ (0.61 g, 3 mmol), and NaOt-Bu (8.65 g, 90 mmol) were subjected to the synthesis method for P 1-8 to give a product 15 g (yield: 65%).

Sub 1-57 (18.5 g, 30 mmol), Sub 2-1 (10.7 g, 33 mmol), toluene (315 mL), Pd₂(dba)₃ (1.37 g, 1.5 mmol), P(t-Bu)₃ (0.61 g, 3 mmol), and NaOt-Bu (8.65 g, 90 mmol) were subjected to the synthesis method for P 1-8 to give a product 16.3 g (yield: 63%).

14. Synthesis Example of P 4-48
<Reaction Scheme 36>
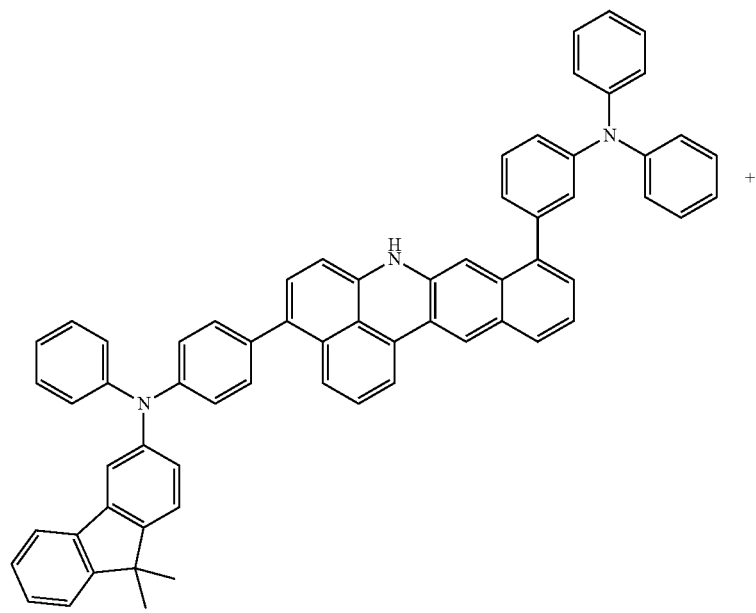
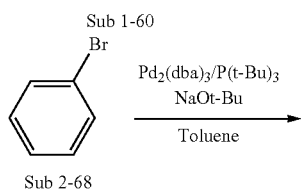
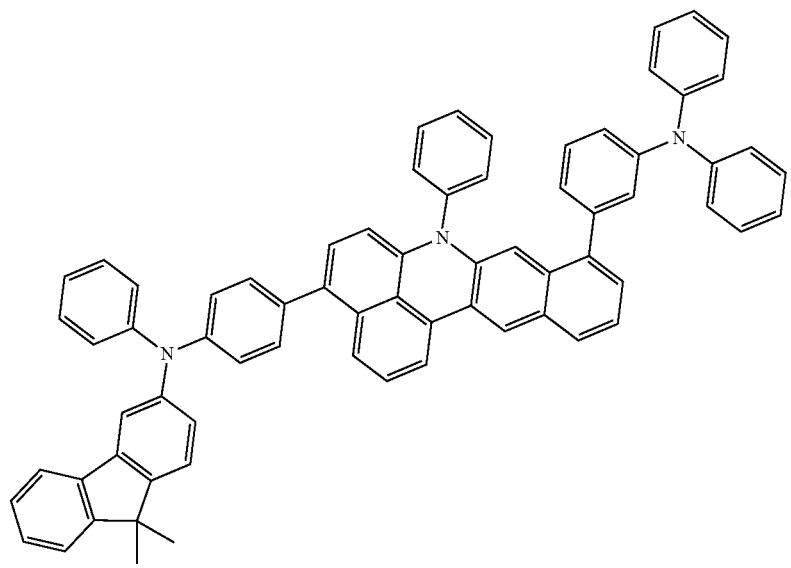
P 4-48
Sub 1-60 (17.4 g, 20 mmol), Sub 2-68 (3.45 g, 22 mmol), toluene (210 mL), Pd$_2$(dba)$_3$ (0.92 g, 1 mmol), P(t-Bu)$_3$ (0.4 g, 2 mmol), and NaOt-Bu (5.77 g, 60 mmol) were subjected to the synthesis method for P 1-8 to give a product 12.3 g (yield: 65%).
Table 3 shows FD-MS values of compounds P 1-1 to P 1-84, P 2-1 to P 2-40, P 3-1 to P 3-88, and P 4-1 to P 4-52 of the present invention prepared by synthesis examples above.

TABLE 3

| Compound | FD-MS | Compound | FD-MS |
| --- | --- | --- | --- |
| P 1-1 | m/z = 460.19($C_{34}H_{24}N_2$ = 460.57) | P 1-2 | m/z = 510.21($C_{38}H_{26}N_2$ = 510.63) |
| P 1-3 | m/z = 510.21($C_{38}H_{26}N_2$ = 510.63) | P 1-4 | m/z = 536.23($C_{40}H_{28}N_2$ = 536.66) |
| P 1-5 | m/z = 536.23($C_{40}H_{28}N_2$ = 536.66) | P 1-6 | m/z = 536.23($C_{40}H_{20}N_2$ = 536.66) |
| P 1-7 | m/z = 612.26($C_{46}H_{32}N_2$ = 612.76) | P 1-8 | m/z = 576.26($C_{43}H_{32}N_2$ = 576.73) |
| P 1-9 | m/z = 700.29($C_{53}H_{36}N_2$ = 700.87) | P 1-10 | m/z = 698.27($C_{53}H_{34}N_2$ = 698.85) |
| P 1-11 | m/z = 566.18($C_{40}H_{26}N_2S$ = 566.71) | P 1-12 | m/z = 550.20($C_{40}H_{26}N_2O$ = 550.65) |
| P 1-13 | m/z = 537.22($C_{39}H_{27}N_3$ = 537.65) | P 1-14 | m/z = 625.25($C_{46}H_{31}N_3$ = 625.76) |
| P 1-15 | m/z = 560.23($C_{42}H_{28}N_2$ = 560.69) | P 1-16 | m/z = 560.23($C_{42}H_{28}N_2$ = 560.69) |
| P 1-17 | m/z = 586.24($C_{44}H_{30}N_2$ = 586.72) | P 1-18 | m/z = 586.24($C_{44}H_{30}N_2$ = 586.72) |
| P 1-19 | m/z = 626.27($C_{47}H_{34}N_2$ = 626.79) | P 1-20 | m/z = 750.30($C_{57}H_{38}N_2$ = 750.93) |
| P 1-21 | m/z = 748.29($C_{57}H_{36}N_2$ = 748.91) | P 1-22 | m/z = 616.20($C_{44}H_{28}N_2S$ = 616.77) |
| P 1-23 | m/z = 600.22($C_{44}H_{28}N_2O$ = 600.71) | P 1-24 | m/z = 587.24($C_{43}H_{29}N_3$ = 587.71) |
| P 1-25 | m/z = 675.27($C_{50}H_{33}N_3$ = 675.82) | P 1-26 | m/z = 586.24($C_{44}H_{30}N_2$ = 586.72) |
| P 1-27 | m/z = 616.20($C_{44}H_{28}N_2S$ = 616.77) | P 1-28 | m/z = 600.22($C_{44}H_{28}N_2O$ = 600.71) |
| P 1-29 | m/z = 587.24($C_{43}H_{29}N_3$ = 587.71) | P 1-30 | m/z = 675.27($C_{50}H_{33}N_3$ = 675.82) |
| P 1-31 | m/z = 586.24($C_{44}H_{30}N_2$ = 586.72) | P 1-32 | m/z = 586.24($C_{44}H_{30}N_2$ = 586.72) |
| P 1-33 | m/z = 626.27($C_{47}H_{34}N_2$ = 626.79) | P 1-34 | m/z = 750.30($C_{57}H_{38}N_2$ = 750.93) |
| P 1-35 | m/z = 748.29($C_{57}H_{36}N_2$ = 748.91) | P 1-36 | m/z = 616.20($C_{44}H_{28}N_2S$ = 616.77) |
| P 1-37 | m/z = 626.27($C_{50}H_{33}N_3$ = 626.82) | P 1-38 | m/z = 587.24($C_{43}H_{29}N_3$ = 587.71) |
| P 1-39 | m/z = 636.26($C_{48}H_{32}N_2$ = 636.78) | P 1-40 | m/z = 612.26($C_{46}H_{32}N_2$ = 612.76) |
| P 1-41 | m/z = 612.26($C_{46}H_{32}N_2$ = 612.76) | P 1-42 | m/z = 612.26($C_{46}H_{32}N_2$ = 612.76) |
| P 1-43 | m/z = 652.29($C_{49}H_{36}N_2$ = 652.82) | P 1-44 | m/z = 776.32($C_{59}H_{40}N_2$ = 776.96) |
| P 1-45 | m/z = 774.30($C_{59}H_{38}N_2$ = 774.95) | P 1-46 | m/z = 642.21($C_{46}H_{30}N_2S$ = 642.81) |
| P 1-47 | m/z = 626.24($C_{46}H_{30}N_2O$ = 626.74) | P 1-48 | m/z = 613.25($C_{45}H_{31}N_3$ = 613.75) |
| P 1-49 | m/z = 701.28($C_{52}H_{35}N_3$ = 701.85) | P 1-50 | m/z = 458.18($C_{34}H_{22}N_2$ = 458.55) |
| P 1-51 | m/z = 536.23($C_{40}H_{28}N_2$ = 536.66) | P 1-52 | m/z = 993.41($C_{75}H_{51}N_3$ = 994.23) |
| P 1-53 | m/z = 918.37($C_{68}H_{46}N_4$ = 919.12) | P 1-54 | m/z = 944.39($C_{70}H_{48}N_4$ = 945.16) |
| P 1-55 | m/z = 777.31($C_{58}H_{39}N_3$ = 777.95) | P 1-56 | m/z = 758.28($C_{55}H_{38}N_2S$ = 758.97) |
| P 1-57 | m/z = 776.32($C_{59}H_{40}N_2$ = 776.96) | P 1-58 | m/z = 688.29($C_{52}H_{36}N_2$ = 688.86) |
| P 1-59 | m/z = 688.29($C_{52}H_{36}N_2$ = 688.86) | P 1-60 | m/z = 776.32($C_{59}H_{40}N_2$ = 776.96) |
| P 1-61 | m/z = 774.30($C_{59}H_{38}N_2$ = 774.95) | P 1-62 | m/z = 718.24($C_{52}H_{34}N_2S$ = 718.90) |
| P 1-63 | m/z = 688.29($C_{52}H_{36}N_2$ = 688.86) | P 1-64 | m/z = 776.32($C_{59}H_{40}N_2$ = 776.96) |
| P 1-65 | m/z = 774.30($C_{59}H_{38}N_2$ = 774.95) | P 1-66 | m/z = 718.24($C_{52}H_{34}N_2S$ = 718.90) |
| P 1-67 | m/z = 742.30($C_{55}H_{38}N_2O$ = 742.90) | P 1-68 | m/z = 816.35($C_{62}H_{44}N_2$ = 817.03) |
| P 1-69 | m/z = 852.35($C_{65}H_{44}N_2$ = 853.06) | P 1-70 | m/z = 938.37($C_{72}H_{46}N_2$ = 939.15) |
| P 1-71 | m/z = 850.33($C_{65}H_{42}N_2$ = 851.04) | P 1-72 | m/z = 863.33($C_{65}H_{41}N_3$ = 864.04) |
| P 1-73 | m/z = 701.28($C_{52}H_{35}N_3$ = 701.85) | P 1-74 | m/z = 702.27($C_{52}H_{34}N_2O$ = 702.84) |
| P 1-75 | m/z = 915.27($C_{64}H_{41}N_3S_2$ = 916.16) | P 1-76 | m/z = 843.32($C_{62}H_{41}N_3O$ = 844.01) |
| P 1-77 | m/z = 869.38($C_{65}H_{47}N_3$ = 870.09) | P 1-78 | m/z = 943.39($C_{71}H_{49}N_3$ = 944.17) |
| P 1-79 | m/z = 941.38($C_{71}H_{47}N_3$ = 942.15) | P 1-80 | m/z = 803.33($C_{60}H_{41}N_3$ = 803.99) |
| P 1-81 | m/z = 885.32($C_{64}H_{43}N_3S$ = 886.11) | P 1-82 | m/z = 943.39($C_{71}H_{49}N_3$ = 944.17) |
| P 1-83 | m/z = 974.43($C_{72}H_{54}N_4$ = 975.23) | P 1-84 | m/z = 945.38($C_{69}H_{47}N_5$ = 946.14) |
| P 2-1 | m/z = 510.21($C_{38}H_{26}N_2$ = 510.63) | P 2-2 | m/z = 560.23($C_{42}H_{28}N_2$ = 560.69) |
| P 2-3 | m/z = 560.23($C_{42}H_{28}N_2$ = 560.69) | P 2-4 | m/z = 586.24($C_{44}H_{30}N_2$ = 586.72) |
| P 2-5 | m/z = 586.24($C_{44}H_{30}N_2$ = 586.72) | P 2-6 | m/z = 586.24($C_{44}H_{30}N_2$ = 586.72) |
| P 2-7 | m/z = 662.27($C_{50}H_{34}N_2$ = 662.82) | P 2-8 | m/z = 626.27($C_{47}H_{34}N_2$ = 626.73) |
| P 2-9 | m/z = 750.93($C_{57}H_{38}N_2$ = 777.95) | P 2-10 | m/z = 748.29($C_{57}H_{36}N_2$ = 748.91) |
| P 2-11 | m/z = 616.20($C_{44}H_{28}N_2S$ = 616.77) | P 2-12 | m/z = 600.22($C_{44}H_{28}N_2O$ = 600.71) |
| P 2-13 | m/z = 587.24($C_{43}H_{29}N_3$ = 587.71) | P 2-14 | m/z = 675.27($C_{50}H_{33}N_3$ = 675.82) |
| P 2-15 | m/z = 636.26($C_{48}H_{32}N_2$ = 636.78) | P 2-16 | m/z = 869.38($C_{65}H_{47}N_3$ = 870.09) |
| P 2-17 | m/z = 508.19($C_{38}H_{24}N_2$ = 508.61) | P 2-18 | m/z = 586.24($C_{44}H_{30}N_2$ = 586.72) |
| P 2-19 | m/z = 751.30($C_{56}H_{37}N_3$ = 751.91) | P 2-20 | m/z = 754.31($C_{55}H_{38}N_4$ = 754.92) |
| P 2-21 | m/z = 1099.40($C_{81}H_{53}N_3S$ = 1100.37) | P 2-22 | m/z = 738.30($C_{56}H_{38}N_2$ = 738.91) |
| P 2-23 | m/z = 738.30($C_{56}H_{38}N_2$ = 738.91) | P 2-24 | m/z = 826.33($C_{63}H_{42}N_2$ = 827.02) |
| P 2-25 | m/z = 824.32($C_{63}H_{40}N_2$ = 825.01) | P 2-26 | m/z = 768.26($C_{56}H_{36}N_2S$ = 768.96) |
| P 2-27 | m/z = 738.30($C_{56}H_{38}N_2$ = 738.91) | P 2-28 | m/z = 826.33($C_{63}H_{42}N_2$ = 827.02) |
| P 2-29 | m/z = 824.32($C_{63}H_{40}N_2$ = 825.01) | P 2-30 | m/z = 768.26($C_{56}H_{36}N_2S$ = 768.96) |
| P 2-31 | m/z = 792.31($C_{59}H_{40}N_2O$ = 792.96) | P 2-32 | m/z = 866.37($C_{66}H_{46}N_2$ = 867.08) |
| P 2-33 | m/z = 917.38($C_{69}H_{47}N_3$ = 918.13) | P 2-34 | m/z = 988.38($C_{76}H_{48}N_2$ = 989.21) |
| P 2-35 | m/z = 900.35($C_{69}H_{44}N_2$ = 901.10) | P 2-36 | m/z = 913.35($C_{69}H_{43}N_3$ = 914.10) |
| P 2-37 | m/z = 738.30($C_{56}H_{38}N_2$ = 738.91) | P 2-38 | m/z = 876.35($C_{67}H_{44}N_2$ = 877.08) |
| P 2-39 | m/z = 808.29($C_{59}H_{40}N_2S$ = 809.03) | P 2-40 | m/z = 768.26($C_{56}H_{36}N_2S$ = 768.96) |
| P 3-1 | m/z = 510.21($C_{38}H_{26}N_2$ = 510.63) | P 3-2 | m/z = 560.23($C_{42}H_{28}N_2$ = 560.69) |
| P 3-3 | m/z = 560.23($C_{42}H_{28}N_2$ = 560.69) | P 3-4 | m/z = 586.24($C_{44}H_{30}N_2$ = 586.72) |
| P 3-5 | m/z = 586.24($C_{44}H_{30}N_2$ = 586.72) | P 3-6 | m/z = 586.24($C_{44}H_{30}N_2$ = 586.72) |
| P 3-7 | m/z = 662.27($C_{50}H_{34}N_2$ = 662.82) | P 3-8 | m/z = 626.27($C_{47}H_{34}N_2$ = 626.79) |
| P 3-9 | m/z = 750.30($C_{57}H_{38}N_2$ = 750.93) | P 3-10 | m/z = 748.29($C_{57}H_{36}N_2$ = 748.91) |
| P 3-11 | m/z = 616.20($C_{44}H_{28}N_2S$ = 616.77) | P 3-12 | m/z = 600.22($C_{44}H_{28}N_2O$ = 600.71) |
| P 3-13 | m/z = 587.24($C_{43}H_{29}N_3$ = 587.71) | P 3-14 | m/z = 675.27($C_{50}H_{33}N_3$ = 675.82) |
| P 3-15 | m/z = 610.24($C_{46}H_{30}N_2$ = 610.74) | P 3-16 | m/z = 610.24($C_{46}H_{30}N_2$ = 610.74) |
| P 3-17 | m/z = 636.26($C_{48}H_{32}N_2$ = 636.78) | P 3-18 | m/z = 636.26($C_{48}H_{32}N_2$ = 636.78) |
| P 3-19 | m/z = 676.29($C_{51}H_{36}N_2$ = 676.84) | P 3-20 | m/z = 800.32($C_{61}H_{40}N_2$ = 800.98) |
| P 3-21 | m/z = 798.30($C_{61}H_{38}N_2$ = 798.97) | P 3-22 | m/z = 666.21($C_{48}H_{30}N_2S$ = 666.83) |
| P 3-23 | m/z = 650.24($C_{48}H_{30}N_2O$ = 650.76) | P 3-24 | m/z = 637.25($C_{47}H_{31}N_3$ = 637.77) |
| P 3-25 | m/z = 725.28($C_{54}H_{35}N_3$ = 725.88) | P 3-26 | m/z = 686.27($C_{52}H_{34}N_2$ = 686.84) |
| P 3-27 | m/z = 666.21($C_{48}H_{30}N_2S$ = 666.83) | P 3-28 | m/z = 650.24($C_{48}H_{30}N_2O$ = 650.76) |
| P 3-29 | m/z = 687.27($C_{51}H_{33}N_3$ = 687.83) | P 3-30 | m/z = 775.30($C_{58}H_{37}N_3$ = 775.93) |
| P 3-31 | m/z = 636.26($C_{48}H_{32}N_2$ = 636.78) | P 3-32 | m/z = 636.26($C_{48}H_{32}N_2$ = 636.78) |

TABLE 3-continued

| Compound | FD-MS | Compound | FD-MS |
|---|---|---|---|
| P 3-33 | m/z = 676.29($C_{51}H_{36}N_2$ = 676.84) | P 3-34 | m/z = 800.32($C_{61}H_{40}N_2$ = 800.98) |
| P 3-35 | m/z = 798.30($C_{61}H_{38}N_2$ = 798.97) | P 3-36 | m/z = 666.21($C_{48}H_{30}N_2S$ = 666.83) |
| P 3-37 | m/z = 725.28($C_{54}H_{35}N_3$ = 725.88) | P 3-38 | m/z = 637.25($C_{47}H_{31}N_3$ = 637.77) |
| P 3-39 | m/z = 636.26($C_{48}H_{32}N_2$ = 636.78) | P 3-40 | m/z = 662.27($C_{50}H_{34}N_2$ = 662.82) |
| P 3-41 | m/z = 662.27($C_{50}H_{34}N_2$ = 662.82) | P 3-42 | m/z = 602.27($C_{50}H_{34}N_2$ = 662.82) |
| P 3-43 | m/z = 702.30($C_{53}H_{38}N_2$ = 702.88) | P 3-44 | m/z = 826.33($C_{63}H_{42}N_2$ = 827.02) |
| P 3-45 | m/z = 824.32($C_{63}H_{40}N_2$ = 825.01) | P 3-46 | m/z = 692.23($C_{50}H_{32}N_2S$ = 692.87) |
| P 3-47 | m/z = 676.25($C_{50}H_{32}N_2O$ = 676.80) | P 3-48 | m/z = 663.27($C_{49}H_{33}N_3$ = 663.81) |
| P 3-49 | m/z = 751.30($C_{56}H_{37}N_3$ = 751.91) | P 3-50 | m/z = 508.19($C_{38}H_{24}N_2$ = 508.61) |
| P 3-51 | m/z = 586.24($C_{44}H_{30}N_2$ = 586.72) | P 3-52 | m/z = 1043.42($C_{79}H_{53}N_3$ = 1044.29) |
| P 3-53 | m/z = 968.39($C_{72}H_{48}N_4$ = 969.18) | P 3-54 | m/z = 994.40($C_{74}H_{50}N_4$ = 995.22) |
| P 3-55 | m/z = 827.33($C_{62}H_{41}N_3$ = 828.01) | P 3-56 | m/z = 975.36($C_{71}H_{49}N_3S$ = 976.23) |
| P 3-57 | m/z = 826.33($C_{63}H_{42}N_2$ = 827.02) | P 3-58 | m/z = 738.30($C_{56}H_{38}N_2$ = 738.91) |
| P 3-59 | m/z = 738.30($C_{56}H_{38}N_2$ = 738.91) | P 3-60 | m/z = 826.33($C_{63}H_{42}N_2$ = 827.02) |
| P 3-61 | m/z = 824.32($C_{63}H_{40}N_2$ = 825.01) | P 3-62 | m/z = 768.26($CC_{56}H_{36}N_2S$ = 768.96) |
| P 3-63 | m/z = 738.30($C_{56}H_{38}N_2$ = 738.91) | P 3-64 | m/z = 826.33($C_{63}H_{42}N_2$ = 827.02) |
| P 3-65 | m/z = 824.32($C_{63}H_{40}N_2$ = 825.01) | P 3-66 | m/z = 768.26($C_{56}H_{36}N_2S$ = 768.96) |
| P 3-67 | m/z = 792.31($C_{59}H_{40}N_2O$ = 792.96) | P 3-68 | m/z = 866.37($C_{66}H_{46}N_2$ = 867.08) |
| P 3-69 | m/z = 902.37($C_{69}H_{46}N_2$ = 903.12) | P 3-70 | m/z = 988.38($C_{76}H_{48}N_2$ = 989.21) |
| P 3-71 | m/z = 900.35($C_{69}H_{44}N_2$ = 901.10) | P 3-72 | m/z = 913.35($C_{69}H_{43}N_3$ = 914.10) |
| P 3-73 | m/z = 751.30($C_{56}H_{37}N_3$ = 751.91) | P 3-74 | m/z = 752.28($C_{56}H_{36}N_2O$ = 752.90) |
| P 3-75 | m/z = 965.29($C_{68}H_{43}N_3S_2$ = 966.22) | P 3-76 | m/z = 893.34($C_{66}H_{43}N_3O$ = 894.07) |
| P 3-77 | m/z = 919.39($C_{69}H_{49}N_3$ = 920.15) | P 3-78 | m/z = 993.41($C_{75}H_{51}N_3$ = 994.23) |
| P 3-79 | m/z = 991.39($C_{75}H_{49}N_3$ = 992.21) | P 3-80 | m/z = 853.35($C_{64}H_{43}N_3$ = 854.05) |
| P 3-81 | m/z = 935.33($C_{68}H_{45}N_3S$ = 936.17) | P 3-82 | m/z = 843.32($C_{62}H_{41}N_3O$ = 844.01) |
| P 3-83 | m/z = 1024.45($C_{76}H_{56}N_4$ = 1025.28) | P 3-84 | m/z = 995.40($C_{73}H_{49}N_5$ = 996.20) |
| P 3-85 | m/z = 738.30($C_{56}H_{38}N_2$ = 738.91) | P 3-86 | m/z = 876.35($C_{67}H_{44}N_2$ = 877.08) |
| P 3-87 | m/z = 808.29($C_{59}H_{40}N_2S$ = 809.03) | P 3-88 | m/z = 768.26($C_{56}H_{36}N_2S$ = 768.96) |
| P 4-1 | m/z = 510.21($C_{38}H_{26}N_2$ = 510.63) | P 4-2 | m/z = 560.23($C_{42}H_{28}N_2$ = 560.69) |
| P 4-3 | m/z = 560.23($C_{42}H_{28}N_2$ = 560.69) | P 4-4 | m/z = 586.24($C_{44}H_{30}N_2$ = 586.72) |
| P 4-5 | m/z = 586.24($C_{44}H_{30}N_2$ = 586.72) | P 4-6 | m/z = 586.24($C_{44}H_{30}N_2$ = 586.72) |
| P 4-7 | m/z = 626.27($C_{47}H_{34}N_2$ = 626.79) | P 4-8 | m/z = 750.30($C_{44}H_{28}N_2S$ = 750.93) |
| P 4-9 | m/z = 748.29($C_{57}H_{36}N_2$ = 748.91) | P 4-10 | m/z = 616.20($C_{44}H_{28}N_2S$ = 616.77) |
| P 4-11 | m/z = 600.22($C_{44}H_{28}N_2O$ = 600.71) | P 4-12 | m/z = 587.24($C_{43}H_{29}N_3$ = 587.71) |
| P 4-13 | m/z = 675.27($C_{50}H_{33}N_3$ = 675.82) | P 4-14 | m/z = 676.29($C_{51}H_{36}N_2$ = 676.84) |
| P 4-15 | m/z = 800.32($C_{61}H_{40}N_2$ = 800.98) | P 4-16 | m/z = 798.30($C_{61}H_{38}N_2$ = 798.97) |
| P 4-17 | m/z = 666.21($C_{48}H_{30}N_2S$ = 666.83) | P 4-18 | m/z = 650.24($C_{48}H_{30}N_2O$ = 650.76) |
| P 4-19 | m/z = 637.25($C_{47}H_{31}N_3$ = 637.77) | P 4-20 | m/z = 725.28($C_{54}H_{35}N_3$ = 725.88) |
| P 4-21 | m/z = 666.21($C_{48}H_{30}N_2S$ = 666.83) | P 4-22 | m/z = 650.24($C_{48}H_{30}N_2O$ = 650.76) |
| P 4-23 | m/z = 508.19($C_{38}H_{24}N_2$ = 508.61) | P 4-24 | m/z = 586.24($C_{44}H_{30}N_2$ = 586.72) |
| P 4-25 | m/z = 751.30($C_{56}H_{37}N_3$ = 751.91) | P 4-26 | m/z = 808.29($C_{59}H_{40}N_2S$ = 809.03) |
| P 4-27 | m/z = 826.33($C_{63}H_{42}N_2$ = 827.02) | P 4-28 | m/z = 738.30($C_{56}H_{38}N_2$ = 738.91) |
| P 4-29 | m/z = 738.30($C_{56}H_{38}N_2$ = 738.91) | P 4-30 | m/z = 826.33($C_{63}H_{42}N_2$ = 827.02) |
| P 4-31 | m/z = 824.32($C_{63}H_{40}N_2$ = 825.01) | P 4-32 | m/z = 768.26($C_{56}H_{36}N_2S$ = 768.96) |
| P 4-33 | m/z = 738.30($C_{56}H_{38}N_2$ = 738.91) | P 4-34 | m/z = 826.33($C_{63}H_{42}N_2$ = 827.02) |
| P 4-35 | m/z = 824.32($C_{63}H_{40}N_2$ = 825.01) | P 4-36 | m/z = 768.26($C_{56}H_{36}N_2S$ = 768.96) |
| P 4-37 | m/z = 792.31($C_{59}H_{40}N_2O$ = 792.96) | P 4-38 | m/z = 880.38($C_{67}H_{48}N_2$ = 881.11) |
| P 4-39 | m/z = 902.37($C_{69}H_{46}N_2$ = 903.12) | P 4-40 | m/z = 988.38($C_{76}H_{48}N_2$ = 989.21) |
| P 4-41 | m/z = 992.39($C_{74}H_{48}N_4$ = 993.20) | P 4-42 | m/z = 913.35($C_{69}H_{43}N_3$ = 914.10) |
| P 4-43 | m/z = 751.30($C_{56}H_{37}N_3$ = 751.91) | P 4-44 | m/z = 752.28($C_{56}H_{36}N_2O$ = 752.90) |
| P 4-45 | m/z = 859.30($C_{62}H_{41}N_3S$ = 860.07) | P 4-46 | m/z = 880.36($C_{65}H_{44}N_4$ = 881.07) |
| P 4-47 | m/z = 993.11($C_{75}H_{51}N_3$ = 994.23) | P 4-48 | m/z = 945.41($C_{71}H_{51}N_3$ = 946.18) |
| P 4-49 | m/z = 738.30($C_{56}H_{38}N_2$ = 738.91) | P 4-50 | m/z = 876.35($C_{67}H_{44}N_2$ = 877.08) |
| P 4-51 | m/z = 808.29($C_{59}H_{40}N_2S$ = 809.03) | P 4-52 | m/z = 768.26($C_{56}H_{36}N_2S$ = 768.96) |

MANUFACTURING AND EVALUATION OF ORGANIC ELECTRONIC ELEMENT

[Example 1] Green Organic Light Emitting Diode (Hole Transport Layer)

An organic light emitting diode was manufactured by an ordinary method using the compound of the present invention as a material for a hole transport layer. First, 4,4',4"-Tris[2-naphthyl(phenyl)amino]triphenylamine (hereinafter, abbreviated as "2-TNATA") was vacuum-deposited to a thickness of 60 nm on an ITO layer (anode) formed on a galas substrate to form a hole injection layer, and then, compound P 1-1 of the present invention was vacuum-deposited to a thickness of 60 nm on the hole injection layer to form a hole transport layer. Subsequently, 4,4'-N,N'-dicarbazole-biphenyl (hereinafter, abbreviated as "CBP") as a host material and tris(2-phenylpyridine)-iridium (hereinafter, abbreviated as "Ir(ppy)₃") as a dopant material were doped at a weight ratio of 90:10 and thus vacuum-deposited to a thickness of 30 nm on the hole transport layer to form a light emitting layer. Then, a film of (1,1'-bisphenyl)-4-olato)bis(2-methyl-8-quinolinolato) aluminum (hereinafter, abbreviated as "BAlq") was vacuum-deposited to a thickness of 10 nm on the light emitting layer to form a hole blocking layer, and tris(8-quinolinolato)aluminum (hereinafter abbreviated as "Alq₃") was vacuum-deposited to a thickness of 40 nm on the hole blocking layer to form an electron transport layer. Thereafter, LiF as a halogenated alkali metal was deposited to a thickness of 0.2 nm to form an electron injection layer, and then Al was deposited to a thickness of 150 nm to form a cathode, and ultimately, an organic light emitting diode was manufactured.

[Example 2] to [Example 176] Green Organic Light Emitting Diode (Hole Transport Layer)

Organic light emitting diodes were manufactured by the same method as in Example 1 except that, instead of inventive compound P 1-1, the inventive compounds shown in table 4 below were used as a material for a hole transport layer.

Comparative Example 1

As for comparative example 1, an organic light emitting diode was manufactured by the same method as in Example 1 except that, instead of inventive compound P 1-1, comparative compound 1 below was used as a material for a hole transport layer.

<Comparative Example 1>

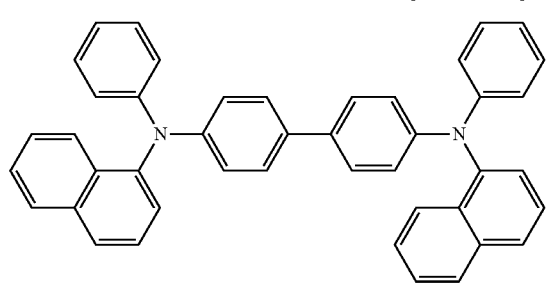

Comparative Example 2

As for comparative example 2, an organic light emitting diode was manufactured by the same method as in Example 1 except that, instead of inventive compound P 1-1, comparative compound 2 below was used as a material for a hole transport layer.

<Comparative Example 2>

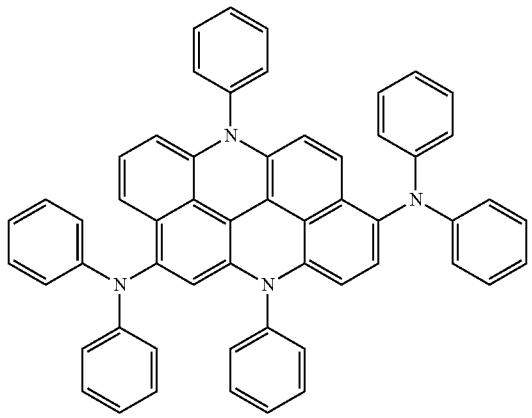

A forward bias DC voltage was applied to each of the manufactured organic light emitting diodes of the examples and comparative examples to measure electroluminescent (EL) characteristics thereof by PR-650 from Photoresearch Company, and on the basis of the measurement results, the T95 lifetime was measured by lifetime measuring equipment from Mcscience Company at a standard brightness of 5000 cd/m$^2$. Table 4 below shows the manufacturing of elements and evaluation results thereof.

TABLE 4

| | | \multicolumn{7}{c}{Manufacturing and testing of green organic light emitting diode (hole transport layer).} |
| | Compound | Driving Voltage | Current Density (mA/cm2) | Brightness (cd/m$_2$) | Efficiency (cd/A) | Lifetime T(95) | CIE X | CIE Y |
| --- | --- | --- | --- | --- | --- | --- | --- | --- |
| Comparative Example (1) | Comparative Compound 1 | 6.1 | 21.7 | 5000.0 | 23.0 | 56.1 | 0.33 | 0.61 |
| Comparative Example (2) | Comparative Compound 2 | 5.9 | 14.6 | 5000.0 | 34.2 | 72.5 | 0.33 | 0.63 |
| Example (1) | Compound (P 1-1) | 5.7 | 12.1 | 5000.0 | 41.4 | 124.3 | 0.32 | 0.63 |
| Example (2) | Compound (P 1-2) | 5.6 | 12.4 | 5000.0 | 40.4 | 124.6 | 0.32 | 0.63 |
| Example (3) | Compound (P 1-3) | 5.6 | 12.5 | 5000.0 | 40.0 | 123.1 | 0.32 | 0.63 |
| Example (4) | Compound (P 1-4) | 5.7 | 12.3 | 5000.0 | 40.8 | 123.0 | 0.33 | 0.61 |
| Example (5) | Compound (P 1-5) | 5.7 | 12.1 | 5000.0 | 41.3 | 123.1 | 0.32 | 0.62 |
| Example (6) | Compound (P 1-6) | 5.6 | 12.3 | 5000.0 | 40.6 | 123.5 | 0.32 | 0.62 |
| Example (7) | Compound (P 1-7) | 5.5 | 12.1 | 5000.0 | 41.3 | 124.5 | 0.32 | 0.62 |
| Example (8) | Compound (P 1-8) | 5.6 | 12.0 | 5000.0 | 41.5 | 123.2 | 0.32 | 0.61 |
| Example (9) | Compound (P 1-9) | 5.6 | 12.3 | 5000.0 | 40.7 | 123.4 | 0.33 | 0.62 |
| Example (10) | Compound (P 1-10) | 5.5 | 12.2 | 5000.0 | 41.0 | 124.2 | 0.32 | 0.61 |
| Example (11) | Compound (P 1-11) | 5.7 | 12.1 | 5000.0 | 41.2 | 124.3 | 0.32 | 0.62 |
| Example (12) | Compound (P 1-12) | 5.6 | 12.3 | 5000.0 | 40.6 | 124.6 | 0.32 | 0.61 |

TABLE 4-continued

Manufacturing and testing of green organic light emitting diode (hole transport layer).

|  | Compound | Driving Voltage | Current Density (mA/cm2) | Brightness (cd/m$_2$) | Efficiency (cd/A) | Lifetime T(95) | CIE X | CIE Y |
|---|---|---|---|---|---|---|---|---|
| Example (13) | Compound (P 1-33) | 5.6 | 12.1 | 5000.0 | 41.3 | 124.7 | 0.33 | 0.61 |
| Example (14) | Compound (P 1-34) | 5.5 | 12.1 | 5000.0 | 41.3 | 123.9 | 0.33 | 0.61 |
| Example (15) | Compound (P 1-35) | 5.7 | 12.4 | 5000.0 | 40.3 | 124.8 | 0.33 | 0.62 |
| Example (16) | Compound (P 1-36) | 5.5 | 12.0 | 5000.0 | 41.6 | 124.6 | 0.32 | 0.62 |
| Example (17) | Compound (P 1-40) | 5.5 | 12.4 | 5000.0 | 40.2 | 123.1 | 0.32 | 0.62 |
| Example (18) | Compound (P 1-41) | 5.7 | 11.9 | 5000.0 | 41.9 | 124.0 | 0.33 | 0.62 |
| Example (19) | Compound (P 1-42) | 5.6 | 12.0 | 5000.0 | 41.7 | 124.2 | 0.32 | 0.62 |
| Example (20) | Compound (P 1-43) | 5.6 | 12.5 | 5000.0 | 40.1 | 124.7 | 0.33 | 0.61 |
| Example (21) | Compound (P 1-44) | 5.6 | 12.2 | 5000.0 | 41.1 | 124.9 | 0.33 | 0.61 |
| Example (22) | Compound (P 1-45) | 5.5 | 12.2 | 5000.0 | 41.1 | 123.1 | 0.32 | 0.63 |
| Example (23) | Compound (P 1-46) | 5.7 | 12.1 | 5000.0 | 41.2 | 124.3 | 0.33 | 0.63 |
| Example (24) | Compound (P 1-47) | 5.7 | 12.3 | 5000.0 | 40.7 | 124.6 | 0.33 | 0.62 |
| Example (25) | Compound (P 1-50) | 5.5 | 12.0 | 5000.0 | 41.6 | 124.9 | 0.32 | 0.61 |
| Example (26) | Compound (P 1-51) | 5.5 | 12.3 | 5000.0 | 40.5 | 123.8 | 0.32 | 0.62 |
| Example (27) | Compound (P 1-52) | 5.5 | 13.0 | 5000.0 | 38.6 | 120.4 | 0.33 | 0.61 |
| Example (28) | Compound (P 1-57) | 5.7 | 12.3 | 5000.0 | 40.7 | 124.3 | 0.33 | 0.61 |
| Example (29) | Compound (P 1-58) | 5.5 | 11.9 | 5000.0 | 41.9 | 123.1 | 0.33 | 0.62 |
| Example (30) | Compound (P 1-59) | 5.4 | 11.6 | 5000.0 | 43.0 | 126.2 | 0.33 | 0.62 |
| Example (31) | Compound (P 1-60) | 5.5 | 12.1 | 5000.0 | 41.4 | 123.3 | 0.32 | 0.62 |
| Example (32) | Compound (P 1-61) | 5.6 | 12.3 | 5000.0 | 40.7 | 124.0 | 0.32 | 0.62 |
| Example (33) | Compound (P 1-62) | 5.6 | 12.0 | 5000.0 | 41.8 | 124.1 | 0.32 | 0.61 |
| Example (34) | Compound (P 1-63) | 5.7 | 12.1 | 5000.0 | 41.2 | 124.1 | 0.33 | 0.61 |
| Example (35) | Compound (P 1-64) | 5.7 | 12.0 | 5000.0 | 41.6 | 123.1 | 0.32 | 0.61 |
| Example (36) | Compound (P 1-65) | 5.7 | 12.0 | 5000.0 | 41.7 | 124.1 | 0.32 | 0.62 |
| Example (37) | Compound (P 1-66) | 5.6 | 12.5 | 5000.0 | 40.1 | 124.2 | 0.33 | 0.61 |
| Example (38) | Compound (P 1-67) | 5.7 | 12.4 | 5000.0 | 40.4 | 124.3 | 0.33 | 0.62 |
| Example (39) | Compound (P 1-68) | 5.6 | 12.5 | 5000.0 | 40.0 | 123.6 | 0.33 | 0.62 |
| Example (40) | Compound (P 1-69) | 5.5 | 12.3 | 5000.0 | 40.5 | 123.1 | 0.32 | 0.62 |
| Example (41) | Compound (P 1-70) | 5.6 | 12.0 | 5000.0 | 41.8 | 124.8 | 0.33 | 0.61 |
| Example (42) | Compound (P 1-71) | 5.5 | 12.2 | 5000.0 | 41.0 | 123.5 | 0.33 | 0.62 |
| Example (43) | Compound (P 1-72) | 5.5 | 12.0 | 5000.0 | 41.7 | 124.3 | 0.33 | 0.63 |
| Example (44) | Compound (P 1-75) | 5.6 | 13.0 | 5000.0 | 38.5 | 118.9 | 0.33 | 0.61 |
| Example (45) | Compound (P 1-76) | 5.6 | 13.1 | 5000.0 | 38.2 | 118.1 | 0.33 | 0.61 |
| Example (46) | Compound (P 1-77) | 5.7 | 13.0 | 5000.0 | 38.5 | 120.1 | 0.32 | 0.61 |
| Example (47) | Compound (P 1-78) | 5.7 | 13.0 | 5000.0 | 38.6 | 120.4 | 0.33 | 0.62 |
| Example (48) | Compound (P 1-79) | 5.6 | 13.1 | 5000.0 | 38.2 | 119.1 | 0.33 | 0.63 |

TABLE 4-continued

Manufacturing and testing of green organic light emitting diode (hole transport layer).

| | Compound | Driving Voltage | Current Density (mA/cm2) | Brightness (cd/m$_2$) | Efficiency (cd/A) | Lifetime T(95) | CIE X | CIE Y |
|---|---|---|---|---|---|---|---|---|
| Example (49) | Compound (P 1-80) | 5.6 | 13.5 | 5000.0 | 37.1 | 116.8 | 0.32 | 0.62 |
| Example (50) | Compound (P 1-81) | 5.6 | 13.3 | 5000.0 | 37.7 | 117.2 | 0.32 | 0.62 |
| Example (51) | Compound (P 1-82) | 5.5 | 13.5 | 5000.0 | 37.0 | 117.3 | 0.32 | 0.61 |
| Example (52) | Compound (P 1-83) | 5.7 | 12.2 | 5000.0 | 40.9 | 115.4 | 0.32 | 0.62 |
| Example (53) | Compound (P 1-84) | 5.6 | 14.1 | 5000.0 | 35.5 | 115.2 | 0.32 | 0.62 |
| Example (54) | Compound (P 2-1) | 5.6 | 12.4 | 5000.0 | 40.4 | 124.0 | 0.32 | 0.62 |
| Example (55) | Compound (P 2-2) | 5.6 | 12.2 | 5000.0 | 41.0 | 123.5 | 0.32 | 0.62 |
| Example (56) | Compound (P 2-3) | 5.6 | 12.4 | 5000.0 | 40.2 | 123.8 | 0.33 | 0.62 |
| Example (57) | Compound (P 2-4) | 5.7 | 12.2 | 5000.0 | 41.1 | 125.0 | 0.32 | 0.61 |
| Example (58) | Compound (P 2-5) | 5.6 | 12.2 | 5000.0 | 41.0 | 124.6 | 0.32 | 0.61 |
| Example (59) | Compound (P 2-6) | 5.5 | 12.2 | 5000.0 | 41.0 | 124.5 | 0.32 | 0.63 |
| Example (60) | Compound (P 2-7) | 5.6 | 12.2 | 5000.0 | 41.1 | 123.6 | 0.33 | 0.62 |
| Example (61) | Compound (P 2-8) | 5.6 | 12.0 | 5000.0 | 41.6 | 124.9 | 0.32 | 0.61 |
| Example (62) | Compound (P 2-9) | 5.5 | 12.3 | 5000.0 | 40.5 | 124.6 | 0.32 | 0.62 |
| Example (63) | Compound (P 2-10) | 5.6 | 12.4 | 5000.0 | 40.5 | 123.5 | 0.33 | 0.62 |
| Example (64) | Compound (P 2-11) | 5.6 | 12.2 | 5000.0 | 40.8 | 123.9 | 0.32 | 0.62 |
| Example (65) | Compound (P 2-12) | 5.7 | 12.5 | 5000.0 | 40.1 | 123.4 | 0.32 | 0.62 |
| Example (66) | Compound (P 2-13) | 5.6 | 12.4 | 5000.0 | 40.3 | 123.4 | 0.32 | 0.63 |
| Example (67) | Compound (P 2-14) | 5.5 | 12.0 | 5000.0 | 41.6 | 123.3 | 0.33 | 0.62 |
| Example (68) | Compound (P 2-15) | 5.7 | 12.4 | 5000.0 | 40.2 | 123.5 | 0.32 | 0.62 |
| Example (69) | Compound (P 2-16) | 5.6 | 13.5 | 5000.0 | 36.9 | 116.5 | 0.33 | 0.61 |
| Example (70) | Compound (P 2-17) | 5.6 | 12.4 | 5000.0 | 40.4 | 124.8 | 0.33 | 0.62 |
| Example (71) | Compound (P 2-18) | 5.7 | 12.3 | 5000.0 | 40.8 | 124.4 | 0.33 | 0.63 |
| Example (72) | Compound (P 2-19) | 5.6 | 13.3 | 5000.0 | 37.5 | 117.1 | 0.33 | 0.62 |
| Example (73) | Compound (P 2-20) | 5.5 | 12.0 | 5000.0 | 41.5 | 123.9 | 0.32 | 0.62 |
| Example (74) | Compound (P 2-21) | 5.6 | 13.3 | 5000.0 | 37.5 | 117.1 | 0.32 | 0.63 |
| Example (75) | Compound (P 2-23) | 5.6 | 14.0 | 5000.0 | 35.8 | 115.4 | 0.33 | 0.62 |
| Example (76) | Compound (P 2-24) | 5.6 | 12.3 | 5000.0 | 40.5 | 123.2 | 0.32 | 0.61 |
| Example (77) | Compound (P 2-25) | 5.6 | 12.0 | 5000.0 | 41.7 | 124.7 | 0.33 | 0.62 |
| Example (78) | Compound (P 2-26) | 5.6 | 12.3 | 5000.0 | 40.6 | 124.4 | 0.33 | 0.62 |
| Example (79) | Compound (P 2-27) | 5.5 | 11.9 | 5000.0 | 41.9 | 124.5 | 0.33 | 0.62 |
| Example (80) | Compound (P 2-28) | 5.6 | 12.3 | 5000.0 | 40.6 | 124.5 | 0.32 | 0.63 |
| Example (81) | Compound (P 2-29) | 5.6 | 12.4 | 5000.0 | 40.2 | 124.4 | 0.32 | 0.63 |
| Example (82) | Compound (P 2-30) | 5.6 | 12.1 | 5000.0 | 41.2 | 124.8 | 0.33 | 0.63 |
| Example (83) | Compound (P 2-31) | 5.6 | 12.4 | 5000.0 | 40.2 | 123.7 | 0.33 | 0.63 |
| Example (84) | Compound (P 2-32) | 5.6 | 12.4 | 5000.0 | 40.3 | 123.8 | 0.32 | 0.62 |

TABLE 4-continued

Manufacturing and testing of green organic light emitting diode (hole transport layer).

|  | Compound | Driving Voltage | Current Density (mA/cm2) | Brightness (cd/m$_2$) | Efficiency (cd/A) | Lifetime T(95) | CIE X | CIE Y |
|---|---|---|---|---|---|---|---|---|
| Example (85) | Compound (P 2-33) | 5.6 | 12.0 | 5000.0 | 41.8 | 123.2 | 0.33 | 0.61 |
| Example (86) | Compound (P 2-34) | 5.7 | 12.2 | 5000.0 | 40.8 | 124.0 | 0.32 | 0.62 |
| Example (87) | Compound (P 2-35) | 5.5 | 12.4 | 5000.0 | 40.2 | 123.2 | 0.32 | 0.63 |
| Example (88) | Compound (P 2-36) | 5.6 | 12.0 | 5000.0 | 41.5 | 124.0 | 0.32 | 0.62 |
| Example (89) | Compound (P 2-39) | 5.6 | 12.6 | 5000.0 | 39.8 | 121.0 | 0.33 | 0.62 |
| Example (90) | Compound (P 2-40) | 5.5 | 12.6 | 5000.0 | 39.7 | 121.9 | 0.33 | 0.61 |
| Example (91) | Compound (P 3-1) | 5.7 | 12.3 | 5000.0 | 40.6 | 124.0 | 0.32 | 0.63 |
| Example (92) | Compound (P 3-2) | 5.5 | 12.3 | 5000.0 | 40.7 | 123.4 | 0.33 | 0.62 |
| Example (93) | Compound (P 3-3) | 5.5 | 12.2 | 5000.0 | 41.1 | 124.3 | 0.33 | 0.61 |
| Example (94) | Compound (P 3-4) | 5.7 | 12.1 | 5000.0 | 41.2 | 123.8 | 0.32 | 0.61 |
| Example (95) | Compound (P 3-5) | 5.7 | 12.5 | 5000.0 | 40.1 | 124.7 | 0.33 | 0.61 |
| Example (96) | Compound (P 3-6) | 5.6 | 12.2 | 5000.0 | 41.1 | 123.4 | 0.32 | 0.62 |
| Example (97) | Compound (P 3-7) | 5.5 | 12.1 | 5000.0 | 41.2 | 124.5 | 0.33 | 0.62 |
| Example (98) | Compound (P 3-8) | 5.5 | 12.2 | 5000.0 | 40.9 | 124.8 | 0.32 | 0.63 |
| Example (99) | Compound (P 3-9) | 5.6 | 12.2 | 5000.0 | 41.1 | 123.5 | 0.33 | 0.62 |
| Example (100) | Compound (P 3-10) | 5.6 | 12.5 | 5000.0 | 40.0 | 124.1 | 0.32 | 0.62 |
| Example (101) | Compound (P 3-11) | 5.6 | 12.2 | 5000.0 | 40.8 | 123.7 | 0.33 | 0.61 |
| Example (102) | Compound (P 3-12) | 5.6 | 12.5 | 5000.0 | 40.1 | 124.3 | 0.33 | 0.62 |
| Example (103) | Compound (P 3-13) | 5.6 | 12.4 | 5000.0 | 40.2 | 123.4 | 0.33 | 0.62 |
| Example (104) | Compound (P 3-14) | 5.5 | 11.9 | 5000.0 | 41.9 | 124.1 | 0.32 | 0.63 |
| Example (105) | Compound (P 3-15) | 5.6 | 12.5 | 5000.0 | 40.0 | 123.3 | 0.33 | 0.63 |
| Example (106) | Compound (P 3-16) | 5.6 | 12.2 | 5000.0 | 41.0 | 124.1 | 0.33 | 0.63 |
| Example (107) | Compound (P 3-17) | 5.5 | 12.5 | 5000.0 | 40.0 | 124.1 | 0.32 | 0.62 |
| Example (108) | Compound (P 3-18) | 5.6 | 11.9 | 5000.0 | 41.9 | 124.9 | 0.32 | 0.62 |
| Example (109) | Compound (P 3-19) | 5.6 | 12.3 | 5000.0 | 40.7 | 123.9 | 0.33 | 0.62 |
| Example (110) | Compound (P 3-20) | 5.7 | 12.4 | 5000.0 | 40.2 | 124.3 | 0.32 | 0.63 |
| Example (111) | Compound (P 3-21) | 5.5 | 12.1 | 5000.0 | 41.2 | 124.2 | 0.33 | 0.62 |
| Example (112) | Compound (P 3-22) | 5.6 | 12.2 | 5000.0 | 41.1 | 123.6 | 0.32 | 0.62 |
| Example (113) | Compound (P 3-23) | 5.7 | 12.2 | 5000.0 | 40.9 | 124.8 | 0.33 | 0.62 |
| Example (114) | Compound (P 3-24) | 5.5 | 12.5 | 5000.0 | 40.1 | 123.6 | 0.33 | 0.62 |
| Example (115) | Compound (P 3-33) | 5.5 | 12.2 | 5000.0 | 41.0 | 124.3 | 0.32 | 0.61 |
| Example (116) | Compound (P 3-34) | 5.7 | 11.9 | 5000.0 | 41.9 | 123.5 | 0.33 | 0.61 |
| Example (117) | Compound (P 3-35) | 5.5 | 12.5 | 5000.0 | 40.0 | 124.3 | 0.32 | 0.62 |
| Example (118) | Compound (P 3-36) | 5.6 | 12.1 | 5000.0 | 41.4 | 123.4 | 0.32 | 0.63 |
| Example (119) | Compound (P 3-40) | 5.6 | 12.5 | 5000.0 | 40.1 | 123.1 | 0.32 | 0.61 |
| Example (120) | Compound (P 3-43) | 5.6 | 12.2 | 5000.0 | 41.0 | 124.5 | 0.32 | 0.62 |

TABLE 4-continued

Manufacturing and testing of green organic light emitting diode (hole transport layer).

| | Compound | Driving Voltage | Current Density (mA/cm2) | Brightness (cd/m$_2$) | Efficiency (cd/A) | Lifetime T(95) | CIE X | CIE Y |
|---|---|---|---|---|---|---|---|---|
| Example (121) | Compound (P 3-44) | 5.5 | 12.3 | 5000.0 | 40.8 | 124.7 | 0.33 | 0.63 |
| Example (122) | Compound (P 3-45) | 5.5 | 12.2 | 5000.0 | 40.9 | 123.4 | 0.33 | 0.63 |
| Example (123) | Compound (P 3-46) | 5.7 | 12.4 | 5000.0 | 40.2 | 124.0 | 0.33 | 0.61 |
| Example (124) | Compound (P 3-50) | 5.5 | 12.1 | 5000.0 | 41.4 | 123.4 | 0.33 | 0.62 |
| Example (125) | Compound (P 3-51) | 5.5 | 12.2 | 5000.0 | 40.9 | 123.6 | 0.32 | 0.62 |
| Example (126) | Compound (P 3-52) | 5.7 | 13.1 | 5000.0 | 38.0 | 118.7 | 0.32 | 0.62 |
| Example (127) | Compound (P 3-56) | 5.7 | 13.3 | 5000.0 | 37.7 | 117.5 | 0.33 | 0.61 |
| Example (128) | Compound (P 3-57) | 5.7 | 12.4 | 5000.0 | 40.2 | 123.9 | 0.33 | 0.63 |
| Example (129) | Compound (P 3-58) | 5.6 | 12.0 | 5000.0 | 41.6 | 124.5 | 0.33 | 0.62 |
| Example (130) | Compound (P 3-59) | 5.6 | 12.3 | 5000.0 | 40.5 | 124.6 | 0.33 | 0.62 |
| Example (131) | Compound (P 3-60) | 5.5 | 12.1 | 5000.0 | 41.4 | 123.1 | 0.32 | 0.63 |
| Example (132) | Compound (P 3-63) | 5.6 | 12.4 | 5000.0 | 40.4 | 123.3 | 0.32 | 0.61 |
| Example (133) | Compound (P 3-64) | 5.6 | 12.4 | 5000.0 | 40.2 | 124.7 | 0.32 | 0.62 |
| Example (134) | Compound (P 3-65) | 5.6 | 12.0 | 5000.0 | 41.7 | 123.5 | 0.32 | 0.62 |
| Example (135) | Compound (P 3-66) | 5.7 | 12.3 | 5000.0 | 40.7 | 123.5 | 0.32 | 0.61 |
| Example (136) | Compound (P 3-67) | 5.6 | 11.9 | 5000.0 | 41.9 | 124.1 | 0.32 | 0.62 |
| Example (137) | Compound (P 3-68) | 5.5 | 12.1 | 5000.0 | 41.2 | 124.5 | 0.32 | 0.62 |
| Example (138) | Compound (P 3-69) | 5.6 | 12.2 | 5000.0 | 40.9 | 123.5 | 0.32 | 0.62 |
| Example (139) | Compound (P 3-70) | 5.5 | 12.4 | 5000.0 | 40.4 | 124.4 | 0.32 | 0.63 |
| Example (140) | Compound (P 3-71) | 5.6 | 12.1 | 5000.0 | 41.4 | 123.6 | 0.32 | 0.62 |
| Example (141) | Compound (P 3-72) | 5.7 | 12.0 | 5000.0 | 41.6 | 123.7 | 0.33 | 0.61 |
| Example (142) | Compound (P 3-73) | 5.7 | 11.9 | 5000.0 | 41.9 | 123.7 | 0.32 | 0.61 |
| Example (143) | Compound (P 3-74) | 5.5 | 12.3 | 5000.0 | 40.5 | 124.7 | 0.33 | 0.63 |
| Example (144) | Compound (P 3-75) | 5.6 | 13.4 | 5000.0 | 37.3 | 116.2 | 0.33 | 0.63 |
| Example (145) | Compound (P 3-76) | 5.6 | 13.2 | 5000.0 | 37.9 | 118.1 | 0.33 | 0.62 |
| Example (146) | Compound (P 3-77) | 5.5 | 13.1 | 5000.0 | 38.0 | 119.2 | 0.32 | 0.62 |
| Example (147) | Compound (P 3-78) | 5.5 | 13.5 | 5000.0 | 36.9 | 117.0 | 0.33 | 0.62 |
| Example (148) | Compound (P 3-79) | 5.7 | 13.3 | 5000.0 | 37.5 | 116.5 | 0.32 | 0.61 |
| Example (149) | Compound (P 3-80) | 5.7 | 13.4 | 5000.0 | 37.3 | 117.0 | 0.32 | 0.62 |
| Example (150) | Compound (P 3-81) | 5.6 | 13.4 | 5000.0 | 37.3 | 117.4 | 0.33 | 0.63 |
| Example (151) | Compound (P 3-82) | 5.6 | 13.4 | 5000.0 | 37.4 | 117.0 | 0.33 | 0.61 |
| Example (152) | Compound (P 3-83) | 5.6 | 14.2 | 5000.0 | 35.3 | 115.2 | 0.32 | 0.61 |
| Example (153) | Compound (P 3-84) | 5.7 | 14.0 | 5000.0 | 35.7 | 115.5 | 0.33 | 0.61 |
| Example (154) | Compound (P 4-1) | 5.6 | 11.9 | 5000.0 | 41.9 | 123.3 | 0.32 | 0.62 |
| Example (155) | Compound (P 4-2) | 5.5 | 12.1 | 5000.0 | 41.5 | 124.8 | 0.33 | 0.62 |
| Example (156) | Compound (P 4-3) | 5.7 | 12.4 | 5000.0 | 40.4 | 124.5 | 0.32 | 0.61 |

TABLE 4-continued

Manufacturing and testing of green organic light emitting diode (hole transport layer).

| | Compound | Driving Voltage | Current Density (mA/cm2) | Brightness (cd/m$_2$) | Efficiency (cd/A) | Lifetime T(95) | CIE X | CIE Y |
|---|---|---|---|---|---|---|---|---|
| Example (157) | Compound (P 4-4) | 5.5 | 12.2 | 5000.0 | 41.1 | 123.7 | 0.33 | 0.63 |
| Example (158) | Compound (P 4-5) | 5.5 | 12.0 | 5000.0 | 41.8 | 124.8 | 0.33 | 0.63 |
| Example (159) | Compound (P 4-6) | 5.7 | 12.2 | 5000.0 | 41.2 | 123.9 | 0.33 | 0.62 |
| Example (160) | Compound (P 4-7) | 5.6 | 12.4 | 5000.0 | 40.2 | 125.0 | 0.33 | 0.61 |
| Example (161) | Compound (P 4-8) | 5.6 | 11.9 | 5000.0 | 41.9 | 124.4 | 0.32 | 0.62 |
| Example (162) | Compound (P 4-14) | 5.5 | 12.1 | 5000.0 | 41.2 | 123.0 | 0.32 | 0.63 |
| Example (163) | Compound (P 4-15) | 5.7 | 11.9 | 5000.0 | 41.9 | 124.4 | 0.33 | 0.61 |
| Example (164) | Compound (P 4-16) | 5.7 | 11.9 | 5000.0 | 41.9 | 124.0 | 0.33 | 0.62 |
| Example (165) | Compound (P 4-23) | 5.6 | 12.3 | 5000.0 | 40.5 | 123.7 | 0.32 | 0.62 |
| Example (166) | Compound (P 4-24) | 5.6 | 12.4 | 5000.0 | 40.3 | 125.0 | 0.32 | 0.63 |
| Example (167) | Compound (P 4-28) | 5.7 | 12.4 | 5000.0 | 40.2 | 124.8 | 0.32 | 0.62 |
| Example (168) | Compound (P 4-29) | 5.5 | 12.3 | 5000.0 | 40.6 | 124.0 | 0.32 | 0.61 |
| Example (169) | Compound (P 4-30) | 5.6 | 12.0 | 5000.0 | 41.5 | 115.5 | 0.33 | 0.62 |
| Example (170) | Compound (P 4-32) | 5.7 | 12.1 | 5000.0 | 41.3 | 123.9 | 0.33 | 0.62 |
| Example (171) | Compound (P 4-33) | 5.7 | 12.5 | 5000.0 | 40.1 | 124.7 | 0.33 | 0.61 |
| Example (172) | Compound (P 4-34) | 5.6 | 12.2 | 5000.0 | 41.0 | 123.5 | 0.33 | 0.61 |
| Example (173) | Compound (P 4-35) | 5.5 | 12.3 | 5000.0 | 40.8 | 123.8 | 0.33 | 0.63 |
| Example (174) | Compound (P 4-36) | 5.6 | 12.1 | 5000.0 | 41.4 | 125.0 | 0.32 | 0.61 |
| Example (175) | Compound (P 4-38) | 5.7 | 11.9 | 5000.0 | 41.9 | 124.6 | 0.32 | 0.61 |
| Example (176) | Compound (P 4-39) | 5.7 | 12.2 | 5000.0 | 40.9 | 124.6 | 0.32 | 0.62 |

As can be seen from the results of table 4 above, it was verified that the organic light emitting diodes using the inventive compounds as a material for a hole transport layer showed a low driving voltage, comparatively high efficiency, and a high lifetime compared with comparative compound 1 and comparative compound 2.

Especially, comparative compound 2, which has a similar structure to the inventive compounds of the present invention in view of a core region, showed comparatively high efficiency, but showed a significantly lower lifetime compared with the inventive compounds of the present invention.

The reason is determined that the element lifetime of comparative compound 2 showed a similar pattern to those of the inventive compounds of the present invention at the initial stage of element driving and then was rapidly decreased, and in most cases, the decrease in the element lifetime occurs due to joule heat (the occurrence of thermal damage) or the charge unbalance in the light emitting layer. As can also be seen from the measurement results of the elements using the inventive compounds of the present invention, the functional difference depending on the number of amine groups binding to a core of the inventive compound of the present invention can be found. It is determined that the increase in the number of amine groups induces more rotation points in the molecule, resulting in a reduction in packing density, causing a deterioration in hole mobility.

[Example 177] Green Organic Light Emitting Diode (Auxiliary Light Emitting Layer)

First, a film of (naphthalen-2-yl)-$N^4$,$N^4$-bis (4-(naphthalen-2-yl(phenyl)amino)phenyl)-$N^1$-phenylbenzene-1,4-diamine (hereinafter, abbreviated as "2-TNATA") was vacuum-deposited on an ITO layer (anode) formed on a galas substrate, to form a hole injection layer with a thickness nm. Then, 4,4-bis[N-(1-naphthyl)-N-phenylamino]biphenyl (hereinafter, abbreviated as "-NPD") as a hole transport compound was vacuum-deposited to a thickness of 60 nm on the film to form a hole transport layer. Then, compound P 1-59 above as a material for an auxiliary light emitting layer was vacuum-deposited to a thickness of 20 nm to form an auxiliary light emitting layer. After the auxiliary light emitting layer was formed, CBP [4,4'-N,N'-dicarbazole-biphenyl] as a host material and Ir(ppy)$_3$ [tris(2-phenylpyridine)-iridium] as a dopant material were doped at a weight ratio of 95:5 on the auxiliary light emitting layer, so that, a light emitting layer with a thickness of 30 nm was deposited on the auxiliary light emitting layer. Then, (1.1'-bisphenyl)-4-olato)bis(2-methyl-8-quinolinolato) aluminum (hereinafter abbreviated as "BAlq") was vacuum-deposited to a thickness of 10 nm for a hole blocking layer, and a film of tris(8-quinolinol)aluminum (hereinafter abbreviated as "Alq$_3$") was formed with a thickness of 40 nm for an electron transport layer. Thereafter, LiF as halogenated alkali metal was deposited to a thickness of 0.2 nm for an electron injection layer, and then Al was deposited to a thickness of 150 nm and used as a cathode, and ultimately, an organic light emitting diode was manufactured.

[Example 178] to [Example 204] Green Organic Light Emitting Diode (Auxiliary Light Emitting Layer)

Organic light emitting diodes were manufactured by the same method as in Example 177 except that, instead of inventive compound P 1-59, the inventive compounds shown in table 5 below were used as a material for an auxiliary light emitting layer.

Comparative Example 3

As for comparative example 3, an organic light emitting diode was manufactured by the same method as in Example 177 except that the auxiliary light emitting layer was not used.

Comparative Example 4

As for comparative example 4, an organic light emitting diode was manufactured by the same method as in Example 177 except that, instead of inventive compound P 1-59, comparative compound 1 above was used.

Comparative Example 5

As for comparative example 5, an organic light emitting diode was manufactured by the same method as in Example 177 except that, instead of inventive compound P 1-59, comparative compound 2 above was used.

A forward bias DC voltage was applied to each of the manufactured organic light emitting diodes of the examples and comparative examples to measure electroluminescent (EL) characteristics thereof by PR-650 from Photoresearch Company, and on the basis of the measurement results, the T95 lifetime was measured by lifetime measuring equipment from Mcscience Company at a standard brightness of 5000 cd/m$^2$. Table 5 below shows the manufacturing of elements and evaluation results thereof.

TABLE 5

Manufacturing and testing of green organic light emitting diode (auxiliary light emitting layer).

|  | Compound | Driving Voltage | Current Density (mA/cm2) | Brightness (cd/m2) | Efficiency (cd/A) | Lifetime T(95) | CIE X | Y |
|---|---|---|---|---|---|---|---|---|
| Comparative Example (3) | — | 6.1 | 21.7 | 5000.0 | 23.0 | 56.1 | 0.33 | 0.61 |
| Comparative Example (4) | Comparative Compound 1 | 6.2 | 14.2 | 5000.0 | 35.3 | 79.4 | 0.33 | 0.61 |
| Comparative Example (5) | Comparative Compound 2 | 6.1 | 12.7 | 5000.0 | 39.3 | 91.6 | 0.33 | 0.61 |
| Example (177) | Compound (P 1-59) | 5.5 | 10.5 | 5000.0 | 49.4 | 139.8 | 0.32 | 0.62 |
| Example (178) | Compound (P 1-61) | 5.8 | 10.8 | 5000.0 | 47.5 | 137.8 | 0.33 | 0.62 |
| Example (179) | Compound (P 1-62) | 5.7 | 10.0 | 5000.0 | 47.9 | 137.5 | 0.32 | 0.61 |
| Example (180) | Compound (P 1-63) | 5.8 | 10.1 | 5000.0 | 47.7 | 136.4 | 0.32 | 0.62 |
| Example (181) | Compound (P 1-65) | 5.8 | 10.9 | 5000.0 | 47.6 | 139.7 | 0.33 | 0.62 |
| Example (182) | Compound (P 1-69) | 5.6 | 10.7 | 5000.0 | 48.1 | 134.2 | 0.33 | 0.61 |
| Example (183) | Compound (P 1-71) | 5.6 | 10.6 | 5000.0 | 47.2 | 137.0 | 0.32 | 0.62 |
| Example (184) | Compound (P 1-78) | 5.6 | 11.6 | 5000.0 | 49.0 | 136.2 | 0.32 | 0.62 |
| Example (185) | Compound (P 2-24) | 5.8 | 11.7 | 5000.0 | 47.8 | 136.0 | 0.32 | 0.61 |
| Example (186) | Compound (P 2-25) | 5.8 | 11.3 | 5000.0 | 47.6 | 138.3 | 0.32 | 0.61 |
| Example (187) | Compound (P 2-27) | 5.7 | 12.1 | 5000.0 | 47.5 | 137.4 | 0.33 | 0.61 |
| Example (188) | Compound (P 3-58) | 5.7 | 11.4 | 5000.0 | 47.4 | 139.7 | 0.33 | 0.62 |
| Example (189) | Compound (P 3-59) | 5.7 | 11.4 | 5000.0 | 48.2 | 138.2 | 0.32 | 0.62 |
| Example (190) | Compound (P 3-60) | 5.6 | 11.6 | 5000.0 | 47.3 | 140.0 | 0.33 | 0.61 |

TABLE 5-continued

Manufacturing and testing of green organic light emitting diode (auxiliary light emitting layer).

| | Compound | Driving Voltage | Current Density (mA/cm2) | Brightness (cd/m2) | Efficiency (cd/A) | Lifetime T(95) | CIE X | CIE Y |
|---|---|---|---|---|---|---|---|---|
| Example (191) | Compound (P 3-61) | 5.6 | 12.1 | 5000.0 | 48.8 | 136.8 | 0.33 | 0.61 |
| Example (192) | Compound (P 3-63) | 5.6 | 11.3 | 5000.0 | 47.4 | 134.9 | 0.33 | 0.62 |
| Example (193) | Compound (P 3-64) | 5.7 | 12.1 | 5000.0 | 48.9 | 139.9 | 0.32 | 0.62 |
| Example (194) | Compound (P 3-65) | 5.7 | 11.7 | 5000.0 | 47.9 | 135.4 | 0.33 | 0.61 |
| Example (195) | Compound (P 3-67) | 5.7 | 11.9 | 5000.0 | 48.1 | 139.3 | 0.32 | 0.62 |
| Example (196) | Compound (P 3-68) | 5.6 | 12.5 | 5000.0 | 48.8 | 134.6 | 0.32 | 0.61 |
| Example (197) | Compound (P 3-69) | 5.7 | 11.4 | 5000.0 | 45.2 | 128.1 | 0.33 | 0.61 |
| Example (198) | Compound (P 4-28) | 5.7 | 11.7 | 5000.0 | 48.1 | 137.2 | 0.33 | 0.62 |
| Example (199) | Compound (P 4-29) | 5.6 | 11.7 | 5000.0 | 48.2 | 138.6 | 0.33 | 0.61 |
| Example (200) | Compound (P 4-30) | 5.8 | 12.4 | 5000.0 | 48.7 | 135.9 | 0.33 | 0.61 |
| Example (201) | Compound (P 4-32) | 5.7 | 12.1 | 5000.0 | 48.4 | 137.5 | 0.33 | 0.62 |
| Example (202) | Compound (P 4-33) | 5.8 | 11.3 | 5000.0 | 48.0 | 134.2 | 0.33 | 0.61 |
| Example (203) | Compound (P 4-36) | 5.8 | 12.3 | 5000.0 | 49.0 | 135.6 | 0.33 | 0.61 |
| Example (204) | Compound (P 4-39) | 5.6 | 11.3 | 5000.0 | 47.3 | 135.6 | 0.33 | 0.61 |

[Example 205[ Red Organic Light Emitting Diode (Auxiliary Light Emitting Layer)

First, a film of $N^1$-(naphthalen-2-yl)-$N^4$,$N^4$-bis (4-(naphthalen-2-yl(phenyl)amino)phenyl)-$N^1$-phenylbenzene-1,4-diamine (hereinafter, abbreviated as "2-TNATA") was vacuum-deposited on an ITO layer (anode) formed on a galas substrate, to form a hole injection layer with a thickness nm. Then, 4,4-bis[N-(1-naphthyl)-N-phenylamino]biphenyl (hereinafter, abbreviated as "-NPD") as a hole transport compound was vacuum-deposited to a thickness of 20 nm on the film to form a hole transport layer. Then, compound P 1-52 of the present invention as a material for an auxiliary light emitting layer was vacuum-deposited to a thickness of 60 nm to form an auxiliary light emitting layer. After the auxiliary light emitting layer was formed, CBP [4,4'-N,N'-dicarbazole-biphenyl] as a host material and $(piq)_2$ Ir(acac) [bis-(1-phenylisoquinolyl)iridium(III) acetylacetonate] as a dopant material were doped at a weight ratio of 95:5 on the auxiliary light emitting layer, so that, a light emitting layer with a thickness of 30 nm was deposited on the auxiliary light emitting layer. Then, (1.1'-bisphenyl)-4-olato)bis(2-methyl-8-quinolinolato)aluminum (hereinafter abbreviated as "BAlq") was vacuum-deposited to a thickness of 10 nm for a hole blocking layer, and a film of tris(8-quinolinol)aluminum (hereinafter abbreviated as "$Alq_3$") was formed with a thickness of 40 nm for an electron transport layer. Thereafter, LiF as halogenated alkali metal was deposited to a thickness of 0.2 nm for an electron injection layer, and then Al was deposited to a thickness of 150 nm and used as a cathode, and ultimately, an organic light emitting diode was manufactured.

[Example 206] to [Example 222] Red Organic Light Emitting Diode (Auxiliary Light Emitting Layer)

Organic light emitting diodes were manufactured by the same method as in Example 205 except that, instead of inventive compound P 1-52, the inventive compounds shown in table 6 below were used as a material for an auxiliary light emitting layer.

Comparative Example 6

As for comparative example 6, an organic light emitting diode was manufactured by the same method as in Example 205 except that the auxiliary light emitting layer was not used.

Comparative Example 7

As for comparative example 7, an organic light emitting diode was manufactured by the same method as in Example 205 except that, instead of inventive compound P 1-52, comparative compound 1 above was used.

Comparative Example 8

As for comparative example 8, an organic light emitting diode was manufactured by the same method as in Example 205 except that, instead of inventive compound P 1-52, comparative compound 2 above was used.

A forward bias DC voltage was applied to each of the manufactured organic light emitting diodes of the examples and comparative examples to measure electroluminescent (EL) characteristics thereof by PR-650 from Photoresearch Company, and on the basis of the measurement results, the T95 lifetime was measured by lifetime measuring equipment from Mcscience Company at a standard brightness of 2500 cd/m². Table 6 below shows the manufacturing of elements and evaluation results thereof.

TABLE 6

Manufacturing and testing of red organic light emitting diode (auxiliary light emitting layer).

| | Compound | Driving Voltage | Current Density (mA/cm2) | Brightness (cd/m2) | Efficiency (cd/A) | Lifetime T(95) | CIE X | CIE Y |
|---|---|---|---|---|---|---|---|---|
| Comparative Example (6) | — | 5.9 | 34.7 | 2500 | 7.2 | 63.5 | 0.65 | 0.31 |
| Comparative Example (7) | Comparative Compound 1 | 5.9 | 27.8 | 2500 | 9 | 65.2 | 0.65 | 0.31 |
| Comparative Example (8) | Comparative Compound 2 | 6.4 | 26.9 | 2500 | 9.3 | 75.6 | 0.65 | 0.34 |
| Example (205) | Compound (P 1-52) | 5.7 | 20.0 | 2500 | 12.5 | 127.0 | 0.65 | 0.33 |
| Example (206) | Compound (P 1-54) | 5.6 | 20.5 | 2500 | 12.2 | 131.9 | 0.65 | 0.32 |
| Example (207) | Compound (P 1-78) | 5.6 | 20.3 | 2500 | 12.3 | 135.8 | 0.66 | 0.33 |
| Example (208) | Compound (P 2-19) | 5.8 | 20.5 | 2500 | 12.2 | 125.1 | 0.66 | 0.31 |
| Example (209) | Compound (P 2-33) | 5.8 | 20.0 | 2500 | 12.5 | 128.2 | 0.66 | 0.32 |
| Example (210) | Compound (P 2-38) | 5.7 | 19.7 | 2500 | 12.7 | 135.1 | 0.65 | 0.31 |
| Example (211) | Compound (P 2-39) | 5.8 | 18.9 | 2500 | 13.2 | 137.0 | 0.66 | 0.33 |
| Example (212) | Compound (P 3-52) | 5.6 | 19.5 | 2500 | 12.8 | 125.8 | 0.65 | 0.33 |
| Example (213) | Compound (P 3-62) | 5.7 | 17.9 | 2500 | 14 | 141.9 | 0.66 | 0.33 |
| Example (214) | Compound (P 3-76) | 5.7 | 19.5 | 2500 | 12.8 | 123.2 | 0.66 | 0.33 |
| Example (215) | Compound (P 3-77) | 5.7 | 20.0 | 2500 | 12.5 | 126.5 | 0.65 | 0.33 |
| Example (216) | Compound (P 3-80) | 5.7 | 20.3 | 2500 | 12.3 | 122.3 | 0.66 | 0.31 |
| Example (217) | Compound (P 3-86) | 5.7 | 19.5 | 2500 | 12.8 | 139.5 | 0.65 | 0.33 |
| Example (218) | Compound (P 3-88) | 5.8 | 19.1 | 2500 | 13.1 | 139.1 | 0.65 | 0.32 |
| Example (219) | Compound (P 4-45) | 5.8 | 20.8 | 2500 | 12 | 120.4 | 0.66 | 0.32 |
| Example (220) | Compound (P 4-47) | 5.6 | 20.5 | 2500 | 12.2 | 121.9 | 0.66 | 0.32 |
| Example (221) | Compound (P 4-50) | 5.7 | 19.2 | 2500 | 13 | 135.5 | 0.66 | 0.32 |
| Example (222) | Compound (P 4-52) | 5.8 | 19.8 | 2500 | 12.6 | 139.8 | 0.65 | 0.33 |

[Example 223] Blue Organic Light Emitting Diode (Auxiliary Light Emitting Layer)

First, a film of $N^1$-(naphthalen-2-yl)-$N^4$,$N^4$-bis(4-(naphthalen-2-yl (phenyl) amino) phenyl)-$N^1$-phenylbenzene-1,4-diamine (hereinafter, abbreviated as "2-TNATA") was vacuum-deposited on an ITO layer (anode) formed on a galas substrate, to form a hole injection layer with a thickness nm. Then, 4,4-bis[N-(1-naphthyl)-N-phenylamino]biphenyl (hereinafter, abbreviated as "-NPD") as a hole transport compound was vacuum-deposited to a thickness of 60 nm on the film to form a hole transport layer. Then, compound P 1-4 of the present invention as a material for an auxiliary light emitting layer was vacuum-deposited to a thickness of 20 nm to form an auxiliary light emitting layer. After the auxiliary light emitting layer was formed, 9,10-di (naphthalen-2-yl)anthracene as a host material and BD-052X(Idemitsu kosan) as a dopant material were doped at a weight ratio of 93:7 on the auxiliary light emitting layer, so that, a light emitting layer with a thickness of 30 nm was deposited on the auxiliary light emitting layer. Then, (1.1'-bisphenyl)-4-olato)bis(2-methyl-8-quinolinolato)aluminum (hereinafter abbreviated as "BAlq") was vacuum-deposited to a thickness of 10 nm for a hole blocking layer, and a film of tris(8-quinolinol)aluminum (hereinafter abbreviated as "Alq$_3$,") was formed with a thickness of 40 nm for an electron transport layer. Thereafter, LiF as halogenated alkali metal was deposited to a thickness of 0.2 nm for an electron injection layer, and then Al was deposited to a thickness of 150 nm and used as a cathode, and ultimately, an organic light emitting diode was manufactured.

[Example 224] to [Example 275] Blue Organic Light Emitting Diode (Auxiliary Light Emitting Layer)

Organic light emitting diodes were manufactured by the same method as in Example 223 except that, instead of inventive compound P 1-4, the inventive compounds shown in table 7 below were used as a material for an auxiliary light emitting layer.

Comparative Example 9

As for comparative example 9, an organic light emitting diode was manufactured by the same method as in Example 223 except that the auxiliary light emitting layer was not used.

Comparative Example 10

As for comparative example 10, an organic light emitting diode was manufactured by the same method as in Example 223 except that, instead of inventive compound P 1-4, comparative compound 1 above was used.

Comparative Example 11

As for comparative example 11, an organic light emitting diode was manufactured by the same method as in Example 223 except that, instead of inventive compound P 1-4, comparative compound 2 above was used.

A forward bias DC voltage was applied to each of the manufactured organic light emitting diodes of the examples and comparative examples to measure electroluminescent (EL) characteristics thereof by PR-650 from Photoresearch Company, and as a result of measurement, the T95 lifetime was measured by lifetime measuring equipment from Mcscience Company at a standard brightness of 500 cd/m$^2$. Table 7 below shows the manufacturing of elements and evaluation results thereof.

TABLE 7

Manufacturing and testing of blue organic light emitting diode (auxiliary light emitting layer).

| | Compound | Driving Voltage | Current Density (mA/cm2) | Brightness (cd/m2) | Efficiency (cd/A) | Lifetime T(95) | CIE X | CIE Y |
|---|---|---|---|---|---|---|---|---|
| Comparative Example (9) | — | 5.9 | 15.2 | 500.0 | 3.3 | 62.7 | 0.14 | 0.11 |
| Comparative Example (10) | Comparative Compound 1 | 6.0 | 10.6 | 500.0 | 4.7 | 68.5 | 0.14 | 0.11 |
| Comparative Example (11) | Comparative Compound 2 | 6.2 | 9.8 | 500.0 | 5.1 | 99.2 | 0.14 | 0.12 |
| Example (223) | Compound (P 1-4) | 5.5 | 7.2 | 500.0 | 7.0 | 132.9 | 0.14 | 0.12 |
| Example (224) | Compound (P 1-5) | 5.8 | 8.0 | 500.0 | 6.3 | 141.4 | 0.14 | 0.11 |
| Example (225) | Compound (P 1-6) | 5.6 | 8.6 | 500.0 | 5.8 | 144.8 | 0.14 | 0.11 |
| Example (226) | Compound (P 1-7) | 5.7 | 8.0 | 500.0 | 6.3 | 133.4 | 0.14 | 0.11 |
| Example (227) | Compound (P 1-8) | 5.8 | 9.1 | 500.0 | 5.5 | 130.6 | 0.14 | 0.12 |
| Example (228) | Compound (P 1-9) | 5.7 | 8.3 | 500.0 | 6.0 | 141.8 | 0.14 | 0.12 |
| Example (229) | Compound (P 1-10) | 5.6 | 7.3 | 500.0 | 6.9 | 134.0 | 0.14 | 0.12 |
| Example (230) | Compound (P 1-15) | 5.6 | 7.6 | 500.0 | 6.6 | 135.0 | 0.14 | 0.12 |
| Example (231) | Compound (P 1-18) | 5.5 | 7.3 | 500.0 | 6.8 | 141.4 | 0.14 | 0.11 |
| Example (232) | Compound (P 1-27) | 5.6 | 8.3 | 500.0 | 6.0 | 137.1 | 0.14 | 0.11 |
| Example (233) | Compound (P 1-28) | 5.6 | 8.4 | 500.0 | 5.9 | 135.5 | 0.14 | 0.11 |
| Example (234) | Compound (P 1-39) | 5.7 | 8.9 | 500.0 | 5.6 | 133.7 | 0.14 | 0.11 |
| Example (235) | Compound (P 1-40) | 5.7 | 7.9 | 500.0 | 6.3 | 131.3 | 0.14 | 0.11 |
| Example (236) | Compound (P 1-41) | 5.6 | 7.9 | 500.0 | 6.3 | 141.7 | 0.14 | 0.11 |
| Example (237) | Compound (P 1-43) | 5.7 | 8.7 | 500.0 | 5.7 | 138.2 | 0.14 | 0.12 |
| Example (238) | Compound (P 1-44) | 5.5 | 7.8 | 500.0 | 6.4 | 130.8 | 0.14 | 0.12 |
| Example (239) | Compound (P 1-45) | 5.6 | 8.4 | 500.0 | 6.0 | 137.9 | 0.14 | 0.12 |
| Example (240) | Compound (P 1-46) | 5.5 | 8.0 | 500.0 | 6.3 | 138.9 | 0.14 | 0.12 |
| Example (241) | Compound (P 1-47) | 5.6 | 7.3 | 500.0 | 6.9 | 140.4 | 0.14 | 0.12 |
| Example (242) | Compound (P 1-52) | 5.5 | 8.4 | 500.0 | 6.0 | 133.6 | 0.14 | 0.11 |
| Example (243) | Compound (P 1-54) | 5.8 | 8.8 | 500.0 | 5.7 | 126.6 | 0.14 | 0.12 |
| Example (244) | Compound (P 2-2) | 5.6 | 8.0 | 500.0 | 6.2 | 141.3 | 0.14 | 0.11 |

TABLE 7-continued

Manufacturing and testing of blue organic light emitting diode (auxiliary light emitting layer).

|  | Compound | Driving Voltage | Current Density (mA/cm2) | Brightness (cd/m2) | Efficiency (cd/A) | Lifetime T(95) | CIE X | CIE Y |
|---|---|---|---|---|---|---|---|---|
| Example (245) | Compound (P 2-8) | 5.7 | 7.2 | 500.0 | 6.9 | 140.0 | 0.14 | 0.11 |
| Example (246) | Compound (P 2-9) | 5.8 | 8.6 | 500.0 | 5.8 | 136.1 | 0.14 | 0.12 |
| Example (247) | Compound (P 2-10) | 5.7 | 7.5 | 500.0 | 6.6 | 134.5 | 0.14 | 0.11 |
| Example (248) | Compound (P 2-11) | 5.6 | 8.3 | 500.0 | 6.0 | 141.0 | 0.14 | 0.11 |
| Example (249) | Compound (P 2-12) | 5.6 | 8.0 | 500.0 | 6.3 | 136.2 | 0.14 | 0.11 |
| Example (250) | Compound (P 3-4) | 5.5 | 7.3 | 500.0 | 6.9 | 140.2 | 0.14 | 0.12 |
| Example (251) | Compound (P 3-7) | 5.6 | 8.0 | 500.0 | 6.2 | 131.4 | 0.14 | 0.12 |
| Example (252) | Compound (P 3-11) | 5.6 | 8.1 | 500.0 | 6.1 | 137.6 | 0.14 | 0.12 |
| Example (253) | Compound (P 3-12) | 5.7 | 9.1 | 500.0 | 5.5 | 133.9 | 0.14 | 0.12 |
| Example (254) | Compound (P 3-15) | 5.7 | 7.4 | 500.0 | 6.8 | 137.2 | 0.14 | 0.11 |
| Example (255) | Compound (P 3-16) | 5.6 | 7.7 | 500.0 | 6.5 | 136.3 | 0.14 | 0.11 |
| Example (256) | Compound (P 3-17) | 5.7 | 7.5 | 500.0 | 6.7 | 144.8 | 0.14 | 0.12 |
| Example (257) | Compound (P 3-26) | 5.5 | 7.2 | 500.0 | 7.0 | 137.2 | 0.14 | 0.11 |
| Example (258) | Compound (P 3-28) | 5.6 | 8.2 | 500.0 | 6.1 | 136.3 | 0.14 | 0.11 |
| Example (259) | Compound (P 3-40) | 5.5 | 8.6 | 500.0 | 5.8 | 132.9 | 0.14 | 0.12 |
| Example (260) | Compound (P 3-41) | 5.6 | 7.2 | 500.0 | 6.9 | 138.4 | 0.14 | 0.12 |
| Example (261) | Compound (P 3-43) | 5.7 | 7.7 | 500.0 | 6.5 | 144.3 | 0.14 | 0.11 |
| Example (262) | Compound (P 3-44) | 5.6 | 8.8 | 500.0 | 5.7 | 143.5 | 0.14 | 0.12 |
| Example (263) | Compound (P 3-46) | 5.8 | 8.4 | 500.0 | 6.0 | 132.1 | 0.14 | 0.11 |
| Example (264) | Compound (P 3-47) | 5.6 | 9.0 | 500.0 | 5.5 | 137.7 | 0.14 | 0.11 |
| Example (265) | Compound (P 4-1) | 5.7 | 7.4 | 500.0 | 6.7 | 130.8 | 0.14 | 0.11 |
| Example (266) | Compound (P 4-2) | 5.6 | 7.5 | 500.0 | 6.7 | 141.9 | 0.14 | 0.12 |
| Example (267) | Compound (P 4-8) | 5.8 | 8.6 | 500.0 | 5.8 | 143.5 | 0.14 | 0.11 |
| Example (268) | Compound (P 4-10) | 5.8 | 8.8 | 500.0 | 5.7 | 142.6 | 0.14 | 0.12 |
| Example (269) | Compound (P 4-11) | 5.7 | 7.6 | 500.0 | 6.6 | 135.3 | 0.14 | 0.11 |
| Example (270) | Compound (P 4-14) | 5.6 | 8.5 | 500.0 | 5.9 | 130.5 | 0.14 | 0.11 |
| Example (271) | Compound (P 4-15) | 5.6 | 8.0 | 500.0 | 6.2 | 134.8 | 0.14 | 0.12 |
| Example (272) | Compound (P 4-17) | 5.7 | 7.3 | 500.0 | 6.8 | 136.8 | 0.14 | 0.11 |
| Example (273) | Compound (P 4-18) | 5.7 | 7.4 | 500.0 | 6.8 | 134.2 | 0.14 | 0.11 |
| Example (274) | Compound (P 4-21) | 5.6 | 7.7 | 500.0 | 6.5 | 136.4 | 0.14 | 0.12 |
| Example (275) | Compound (P 4-22) | 5.7 | 7.3 | 500.0 | 6.8 | 135.1 | 0.14 | 0.11 |

[Example 276] Green Organic Light Emitting Diode (Hole Transport Layer+Auxiliary Light Emitting Layer)

An organic light emitting diode was manufactured by an ordinary method using the compound of the present invention as a material for a hole transport layer. First, a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, abbreviated as "2-TNATA") was vacuum-deposited on an ITO layer (anode} formed on a galas substrate, to form a hole injection layer with a thickness 60 nm. Then, compound P 1-40 of the present invention was vacuum-deposited to a thickness of 60 nm on the hole injection layer to form a hole transport layer. Then, the inventive compound (among compound P 1-59 and 12 kinds of other compounds) as a material for an auxiliary light emitting layer was vacuum-deposited to a thickness of 20 nm to form an auxiliary light emitting layer. After the auxiliary light emitting layer was formed, CBP [4,4'-N,N'-dicarbazole-biphenyl] as a host material and Ir(ppy)₃ [tris(2-phenylpyridine)-iridium] as a dopant material were doped at a weight ratio of 95:5 on the auxiliary light emitting layer, so that, a light emitting layer with a thickness of 30 nm was deposited on the auxiliary light emitting layer. Then, (1.1'-bisphenyl)-4-olato)bis(2-methyl-8-quinolinolato) aluminum (hereinafter abbreviated as "BAlq") was vacuum-deposited to a thickness of 10 nm for a hole blocking layer, and a film of tris(8-quinolinol) aluminum (hereinafter abbreviated as "Alq₃") was formed with a thickness of 40 nm for an electron transport layer. Thereafter, LiF as halogenated alkali metal was deposited to a thickness of 0.2 nm for an electron injection layer, and then Al was deposited to a thickness of 150 nm and used as a cathode, and ultimately, an organic light emitting diode was manufactured.

[Example 277] to [Example 288] Green Organic Light Emitting Diode (Hole Transport Layer+Auxiliary Light Emitting Layer)

Organic light emitting diodes were manufactured by the same method as in Example 276 except that, instead of inventive compound P 1-59, the inventive compounds shown in table 8 below were used as a material for an auxiliary light emitting layer.

A forward bias DC voltage was applied to each of the manufactured organic light emitting diodes of the examples and comparative examples to measure electroluminescent (EL) characteristics thereof by PR-650 from Photoresearch Company, and on the basis of the measurement results, the T95 lifetime was measured by lifetime measuring equipment from Mcscience Company at a standard brightness of 5000 cd/m². Table 8 below shows the manufacturing of elements and evaluation results thereof.

TABLE 8

Manufacturing and testing of green organic light emitting diode (hole transport layer + auxiliary light emitting layer.

| | Auxiliary Light Emitting Layer Compound | Driving Voltage | Current Density (mA/cm2) | Brightness (cd/m2) | Efficiency (cd/A) | Lifetime T(95) | CIE X | CIE Y |
|---|---|---|---|---|---|---|---|---|
| Example (276) | Compound (P 1-59) | 5.7 | 1.0 | 500.0 | 49.6 | 154.9 | 0.33 | 0.61 |
| Example (277) | Compound (P 1-61) | 5.6 | 1.0 | 500.0 | 48.0 | 153.7 | 0.32 | 0.62 |
| Example (278) | Compound (P 1-62) | 5.8 | 1.0 | 500.0 | 48.4 | 149.6 | 0.33 | 0.62 |
| Example (279) | Compound (P 1-63) | 5.8 | 1.0 | 500.0 | 49.0 | 153.4 | 0.32 | 0.61 |
| Example (280) | Compound (P 1-69) | 5.6 | 1.0 | 500.0 | 48.8 | 153.6 | 0.32 | 0.62 |
| Example (281) | Compound (P 1-71) | 5.6 | 1.0 | 500.0 | 48.1 | 151.1 | 0.33 | 0.62 |
| Example (282) | Compound (P 1-78) | 5.7 | 1.0 | 500.0 | 48.8 | 153.0 | 0.33 | 0.61 |
| Example (283) | Compound (P 2-24) | 5.7 | 1.0 | 500.0 | 48.8 | 153.6 | 0.32 | 0.62 |
| Example (284) | Compound (P 2-25) | 5.8 | 1.0 | 500.0 | 48.8 | 152.1 | 0.32 | 0.62 |
| Example (285) | Compound (P 2-27) | 5.6 | 1.0 | 500.0 | 48.8 | 151.5 | 0.32 | 0.61 |
| Example (286) | Compound (P 3-58) | 5.5 | 1.0 | 500.0 | 48.9 | 151.7 | 0.32 | 0.61 |
| Example (287) | Compound (P 3-59) | 5.6 | 1.0 | 500.0 | 48.5 | 150.7 | 0.33 | 0.61 |
| Example (288) | Compound (P 3-60) | 5.5 | 1.0 | 500.0 | 48.3 | 152.5 | 0.33 | 0.62 |

As can be seen from the results of tables 5, 6, 7, and 8, it can be verified that the use of the inventive materials for the organic light emitting diode for an auxiliary light emitting layer significantly improved the light emission efficiency and lifetime, and it can be verified that the use of the inventive compounds for a hole injection layer and an auxiliary light emitting layer significantly improved the lifetime of the organic light emitting diodes.

In other words, it can be verified that the efficiency and lifetime were improved when the auxiliary light emitting layer was used than when the auxiliary light emitting layer was not used, and it can be verified that a higher efficiency and a higher lifetime were showed when the inventive compounds of the present invention, rather than comparative compounds 1 and 2, were used for the auxiliary light emitting layer.

The reason that the use of the inventive compounds of the present invention for an auxiliary light emitting layer induced higher increased efficiency is determined that deep HOMO energy levels reduce the excessive supply of holes into the light emitting layer, thereby increasing the charge balance in the light emitting layer and reducing the entry of excessive holes into the electron transport layer, thus increasing the efficiency.

It is also determined that the auxiliary light emitting layer has a relatively high T1 value, thereby preventing the entry of excessive electrons into the hole transport layer, thus reducing the deterioration in color purity and the thermal damage caused by light emission in the hole transport layer, leading to an increase in the lifetime.

From the results of comparative examples 4, 5, 7, 8, 10, and 11 using comparative compounds 1 and 2 for an auxiliary light emitting layer, it can be verified that comparative examples 4, 5, 7, 8, 10, and 11 showed small increases in efficiency and lifetime but an increasing driving voltage compared with when the auxiliary light emitting layer was not used.

Last, it can be seen verified through the comparison between tables 5 and 8 that the lifetime was increased when inventive compound P 1-40 of the present invention was used for the hole transport layer and inventive compound P 1-59 and 12 other inventive compounds were used for the auxiliary light emitting layer than when comparative compound 1 was used for the hole transport layer.

In addition, the characteristics of elements have been described in view of a hole transport layer and an auxiliary light emitting layer in the foregoing evaluation results of the manufacturing of elements, but ordinarily, the materials used for a hole injection layer and an auxiliary light emitting layer may be used alone or in a mixture with other materials, for the foregoing organic material layer for layers of an organic electronic element, such as an electron transport layer, an electron injection layer, a hole injection layer, and a light emitting layer. Therefore, for the foregoing reasons, the inventive compounds may be used alone or in a mixture with other materials, for, in addition to the hole transport layer and the auxiliary light emitting layer, the other layers of an organic material layer, for example, an electron transport layer, an electron injection layer, a hole injection layer, and a light emitting layer.

Although exemplary embodiments of the present invention have been described for illustrative purposes, a person skilled in the art will appreciate that various modifications, additions, and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

EXPLANATION OF NUMERICAL REFERENCES

100: organic electronic element
110: substrate
120: first electrode
130: hole injection layer
140: hole transport layer
141: buffer layer
150: light emitting layer
151: auxiliary light emitting layer
160: electron transport layer
170: electron injection layer
180: second electrode

What is claimed is:

1. A compound represented by Formula 2:

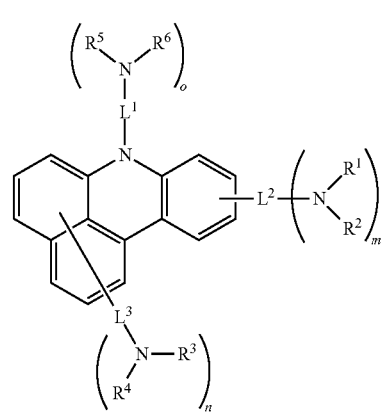

<Formula 2> wherein in Formula 2, $R^1$ to $R^2$ are the same or different from each other, and are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_3$-$C_{60}$ aliphatic group and a $C_6$-$C_{60}$ aromatic group, a $C_1$-$C_{50}$ alkyl group, a $C_2$-$C_{20}$ alkenyl group, a $C_2$-$C_{20}$ alkynyl group, $C_1$-$C_{30}$ alkoxyl group, a $C_6$-$C_{30}$ aryloxy group, and $-L'-N(R_a)(R_b)$, wherein $R^1$ and $R^2$ may bind to each other to form a ring, with the proviso that a biphenyl, a dibenzofuran, a dibenzothiophene, and fluorene groups are excluded from $R^1$ and $R^2$;

$R^3$ to $R^6$ are the same or different from each other, and are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a fused ring group of a $C_3$-$C_{60}$ aliphatic group, and a $C_6$-$C_{60}$ aromatic group, a $C_1$-$C_{50}$ alkyl group, a $C_2$-$C_{20}$ alkenyl group, a $C_2$-$C_{20}$ alkynyl group, $C_{-1}$-$C_{30}$ alkoxyl group, a $C_6$-$C_{30}$ aryloxy group, and $-L'-N(R_a)(R_b)$, wherein $R^3$ and $R^4$ or $R^5$ and $R^6$ may bind to each other to form a ring:

L' is selected from the group consisting of a single bond, a $C_6$-$C_{60}$ arylene group, a fluorenylene group, a fused ring group of a $C_3$-$C_{60}$ aliphatic group and a $C_6$-$C_{60}$ aromatic group, and a $C_2$-$C_{60}$ heterocyclic group;

$R_a$ and $R_b$ are each independently selected from the group consisting of a $C_6$-$C_{60}$ aryl group, a fluorenyl group, a fused ring group of a $C_3$-$C_{60}$ aliphatic group and a $C_6$-$C_{60}$ aromatic group, and a $C_2$-$C_{60}$ heterocyclic group containing at least one heteroatom of O, N, S, Si, and P;

o, m, and n are each independently 0 or 1, m+n≤1, and m+n+o≥1;

as for $L^1$ to $L^3$, when o, m, and n are each 0, $L^1$, $L^2$, and $L^3$ are each independently selected from the group consisting of hydrogen, an aryl group, a fluorenyl group, and a $C_2$-$C_{60}$ heterocyclic group containing at least one heteroatom of O, N, S, Si, and P; and when o, m, and n are each 1, $L^1$, $L^2$, and $L^3$ are each independently selected from the group consisting of a single bond, a arylene group, a fluorenylene group, a fused ring group of a $C_3$-$C_{60}$ aliphatic group and a $C_6$-$C_{60}$ aromatic group, and a $C_2$-$C_{60}$ divalent heterocyclic group containing at least one heteroatom of O, N, S, Si, and P; and the aryl group, fluorenyl group, heterocyclic group, fused ring group, alkyl group, alkenyl group, alkynyl group, alkoxyl group, aryloxy group, arylene group, and fluorenylene group may be each substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound of claim 1, wherein the compound is one of the following compounds:

P 1-2
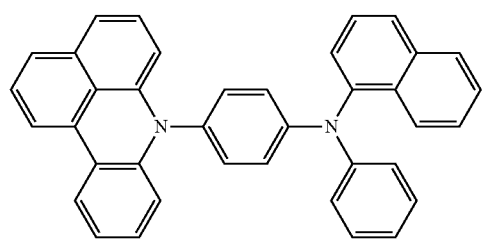

P 1-3
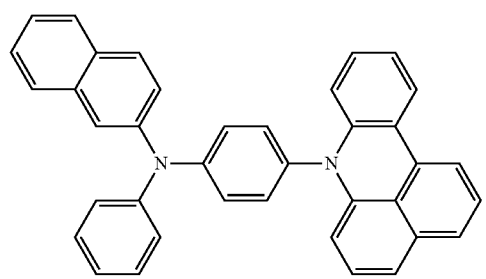

P 1-4
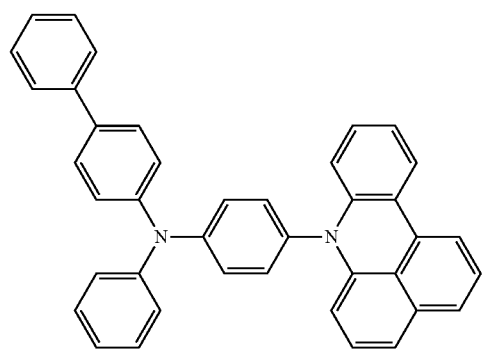

P 1-5
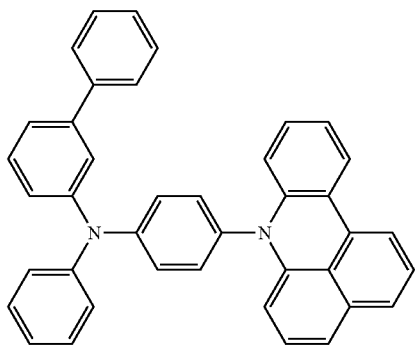

P 1-6
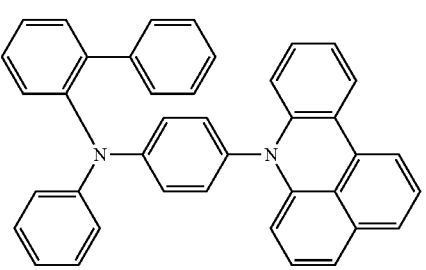

P 1-7
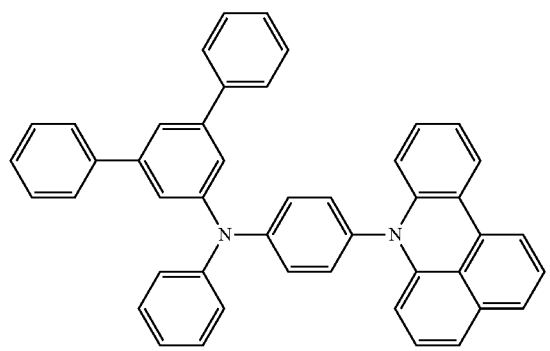

P 1-8
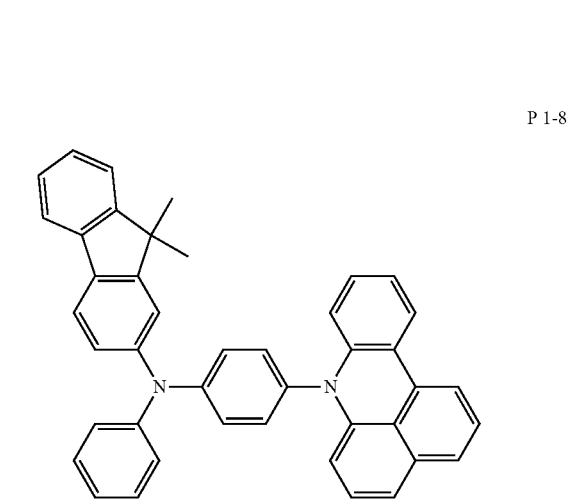

P 1-9
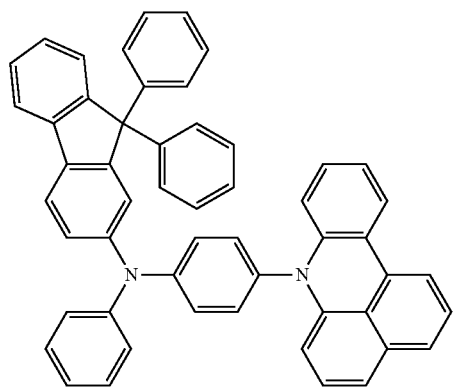
P 1-10
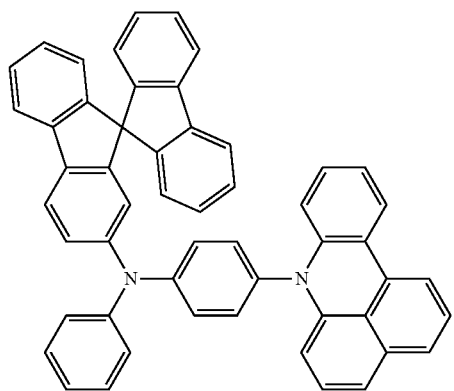
P 1-11
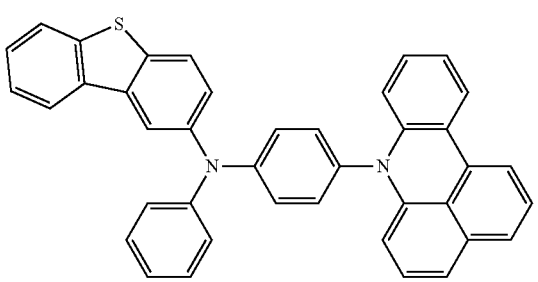
P 1-12
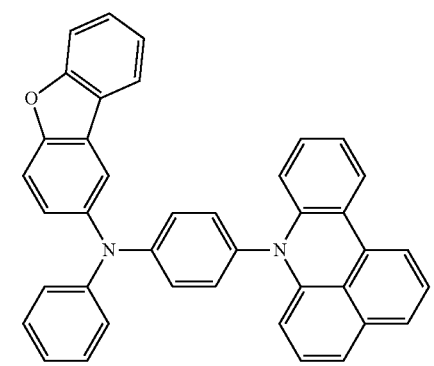
P 1-13
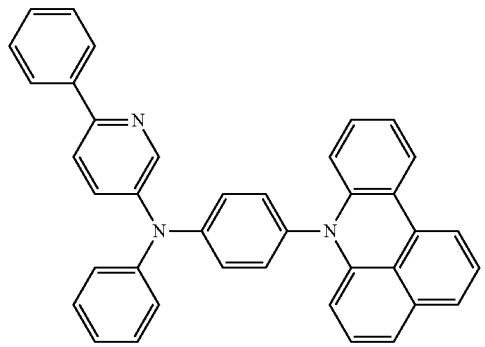
P 1-14
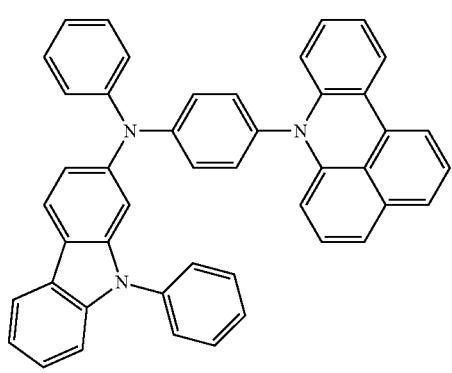
P 1-15
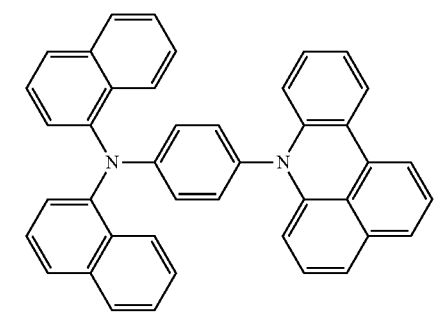
P 1-16
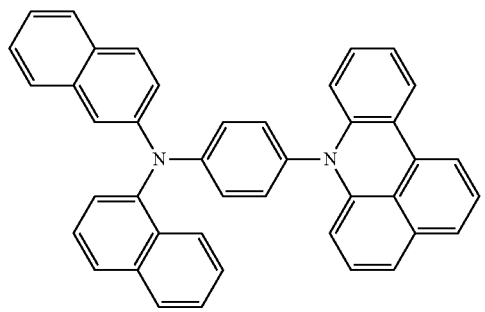

P 1-17
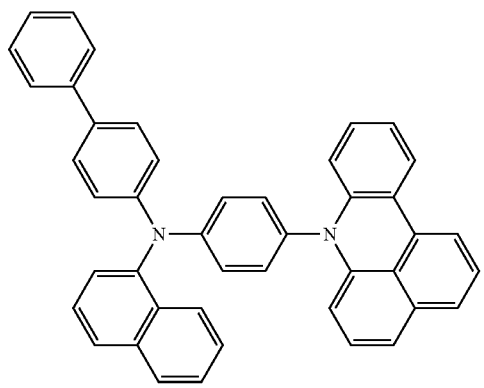
P 1-18
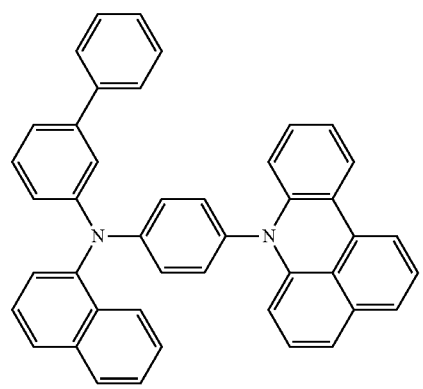
P 1-19
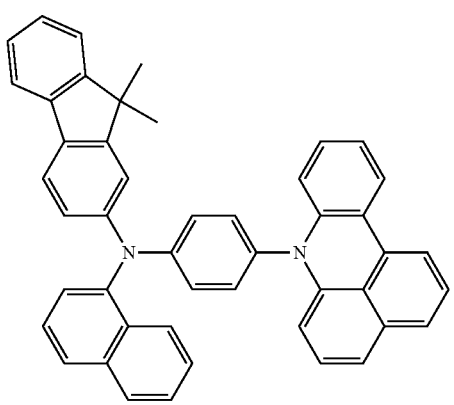
P 1-20
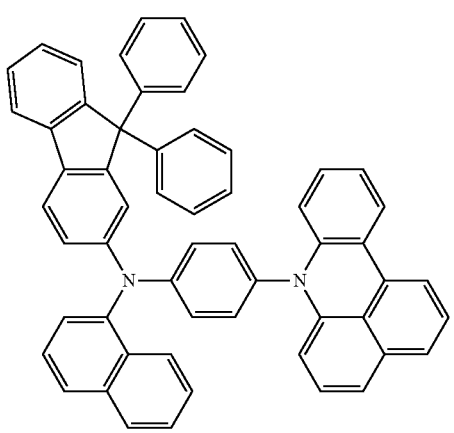
P 1-21
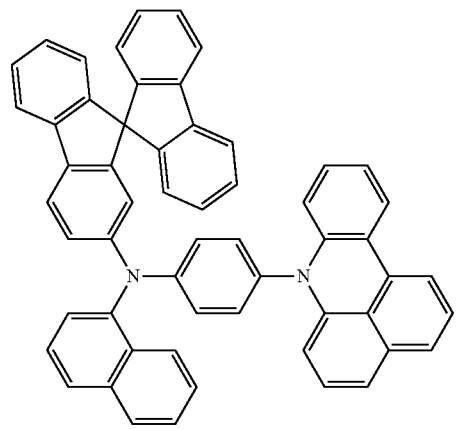
P 1-22
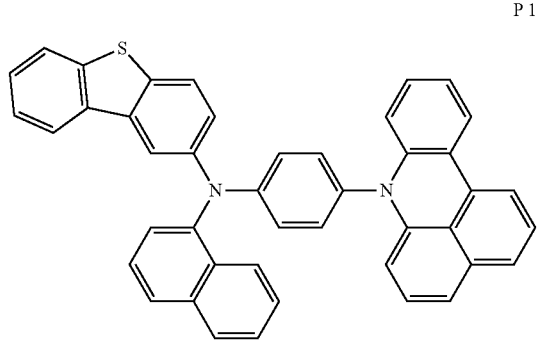
P 1-23
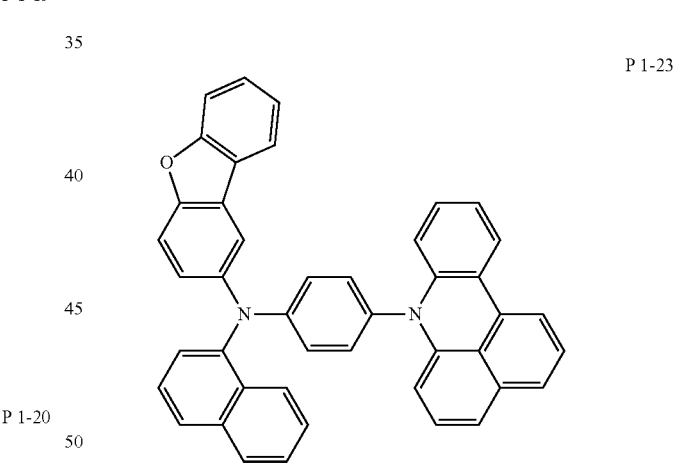
P 1-24
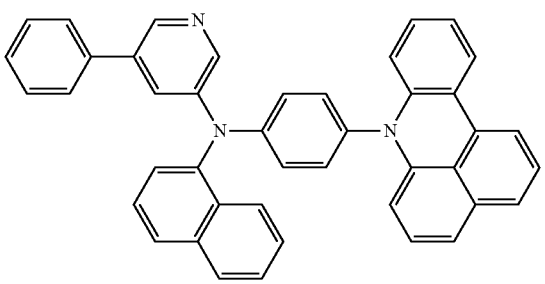

-continued
P 1-25
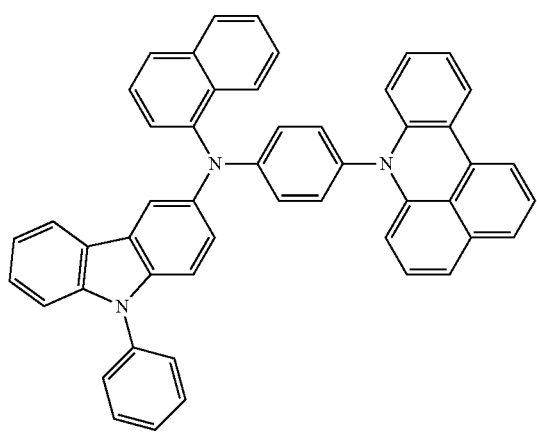
P 1-26
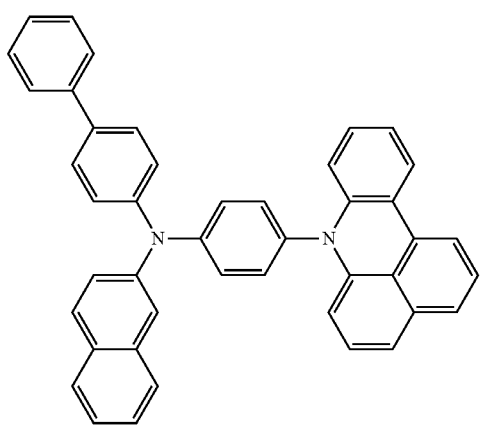
P 1-27
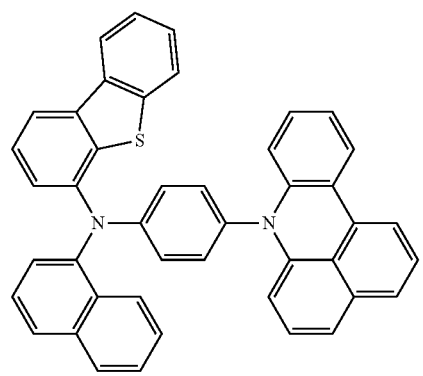
P 1-28
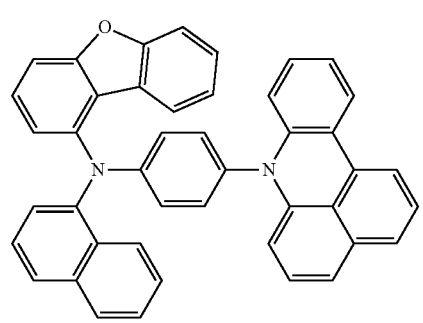
P 1-29
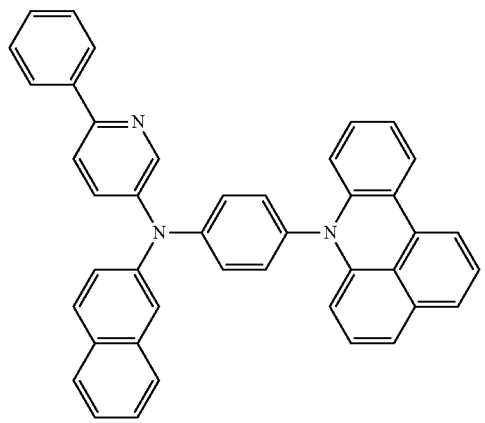
P 1-30
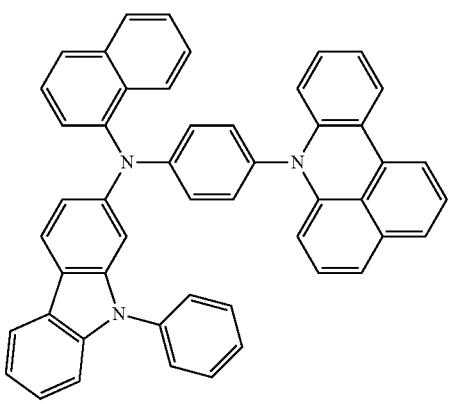
P 1-31
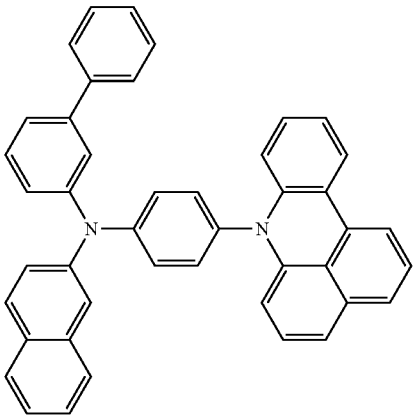
P 1-32
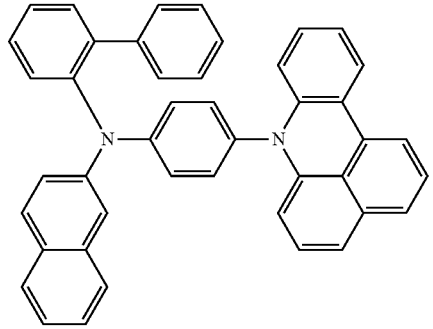

P 1-33
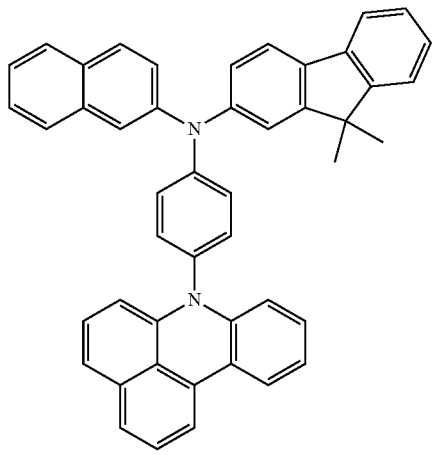
P 1-34
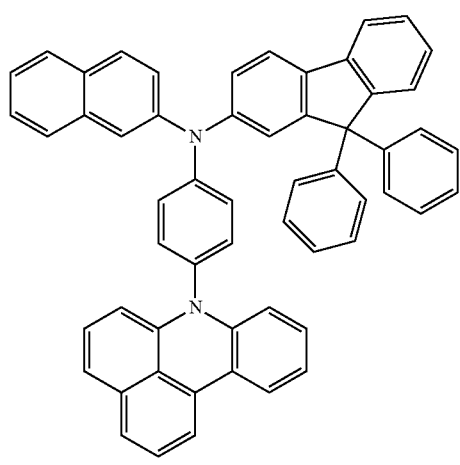
P 1-35
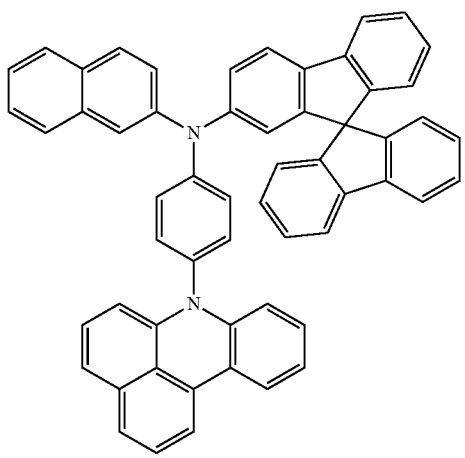
P 1-36
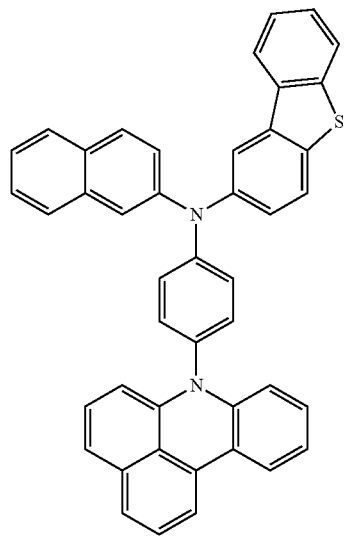
P 1-37
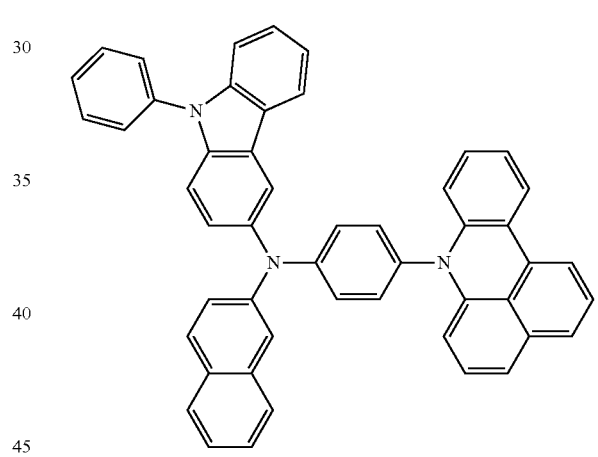
P 1-38
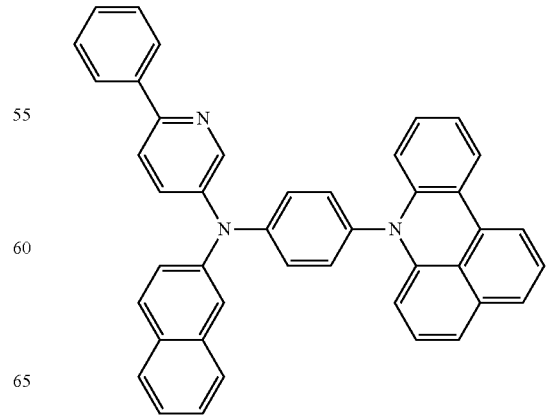

-continued
P 1-39
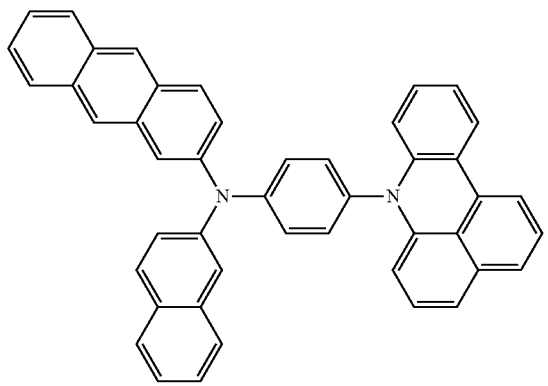
P 1-40
P 1-42
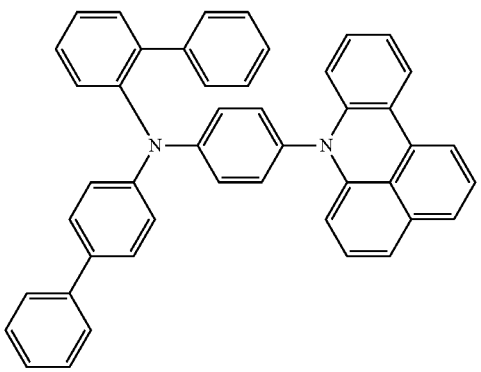
P 1-43
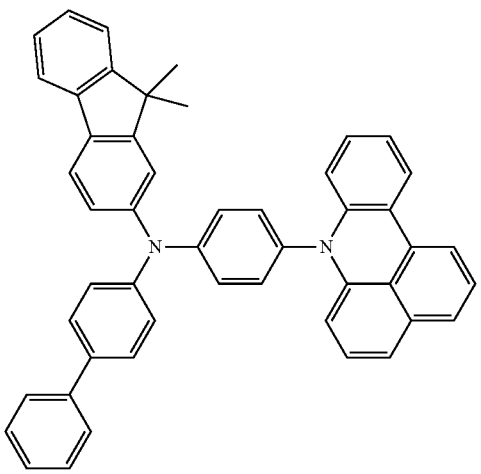
P 1-41
P 1-44
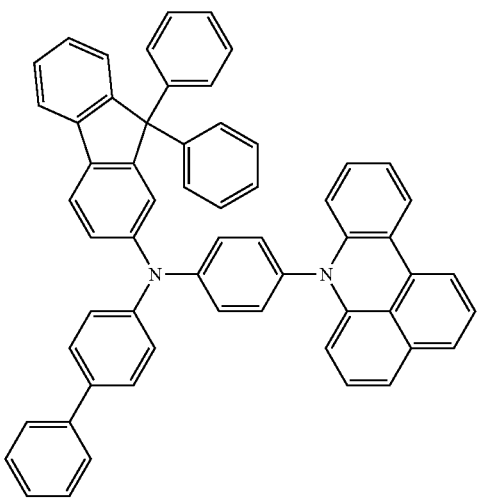

P 1-45
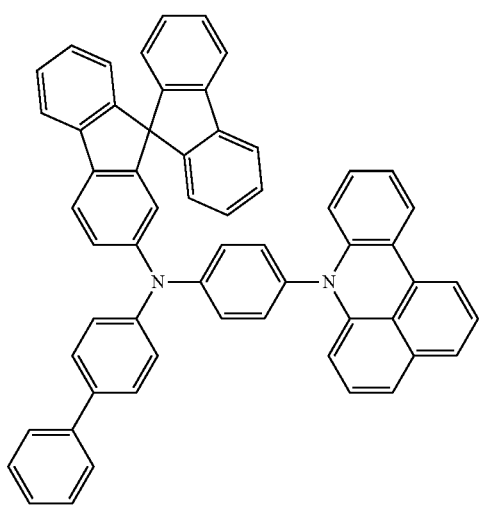
P 1-46
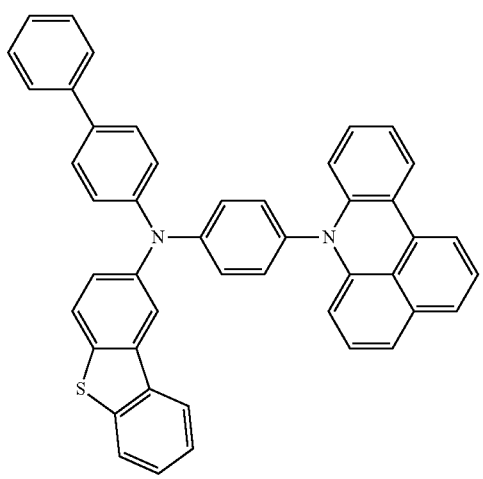
P 1-47
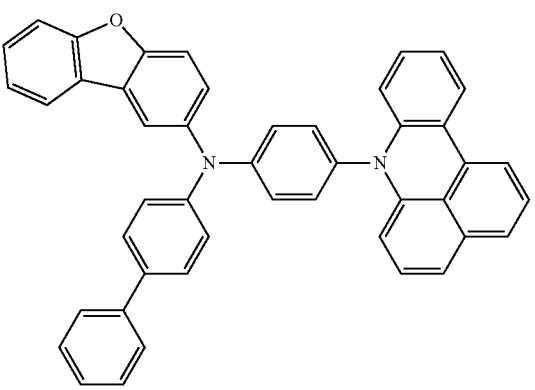
P 1-48
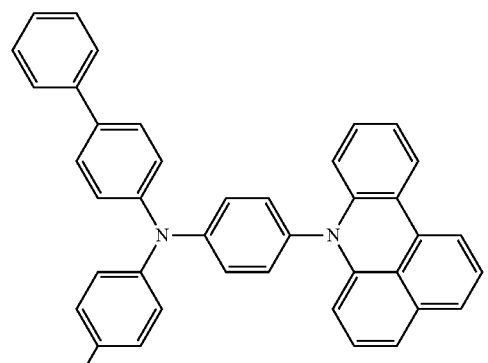
P 1-49
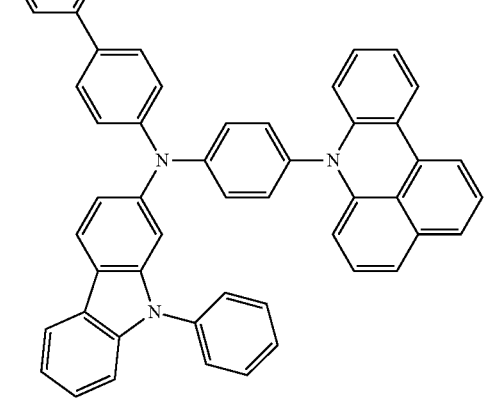
P 1-50
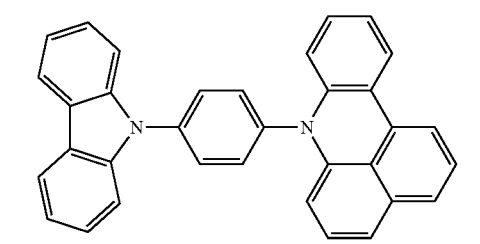
P 1-51
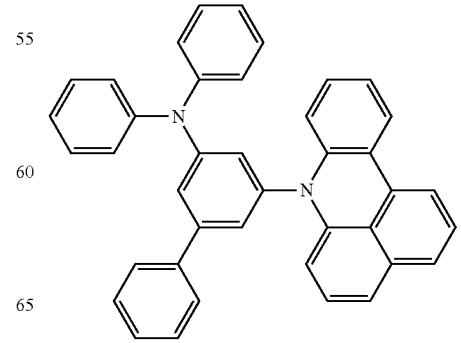

P 1-52
P 1-53
P 1-54
P 1-55
P 1-56
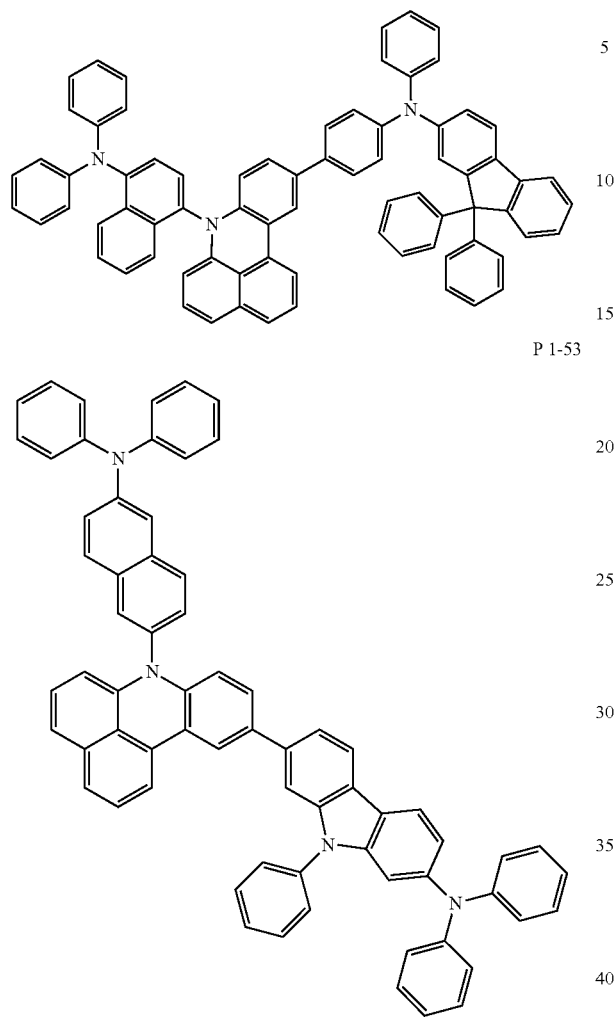
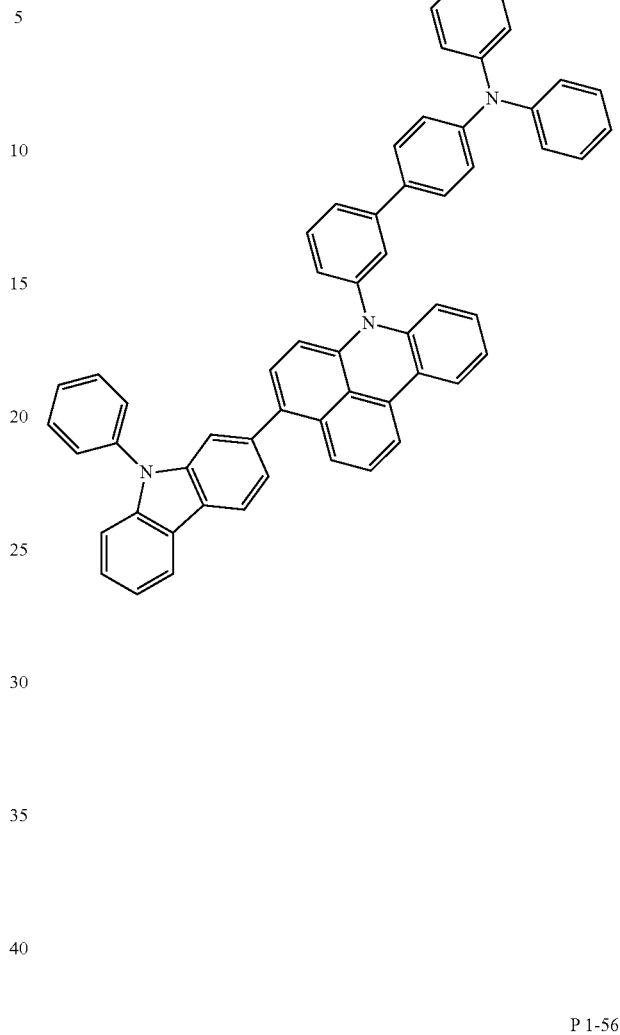
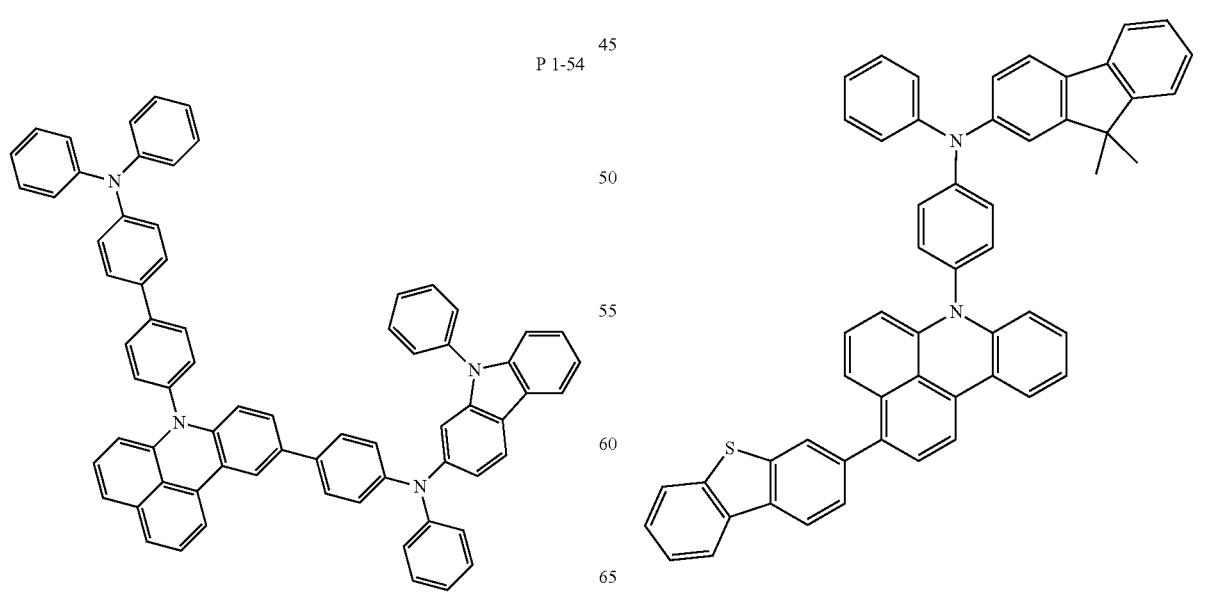

P 1-57
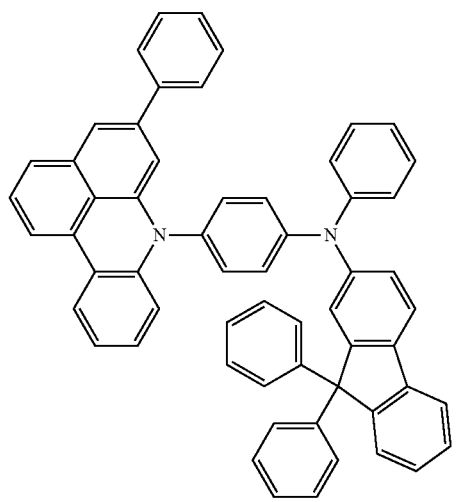
P 1-60
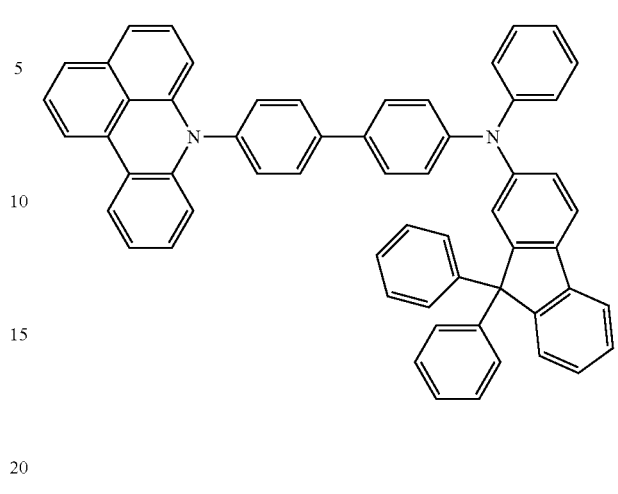
P 1-58
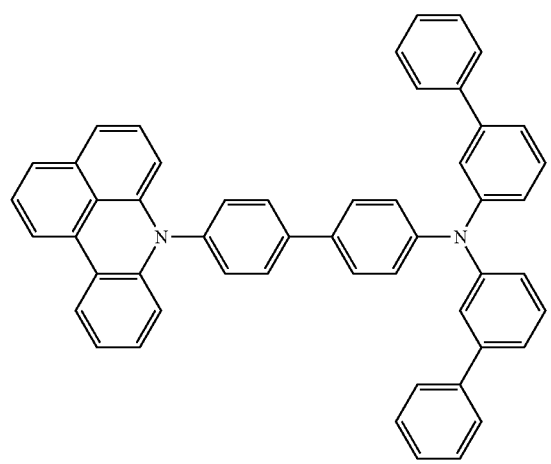
P 1-61
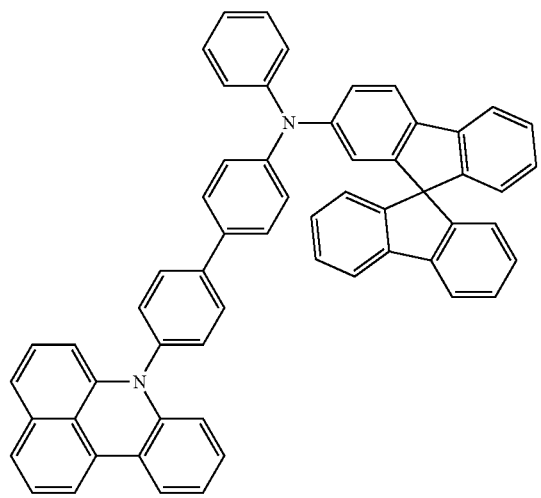
P 1-59
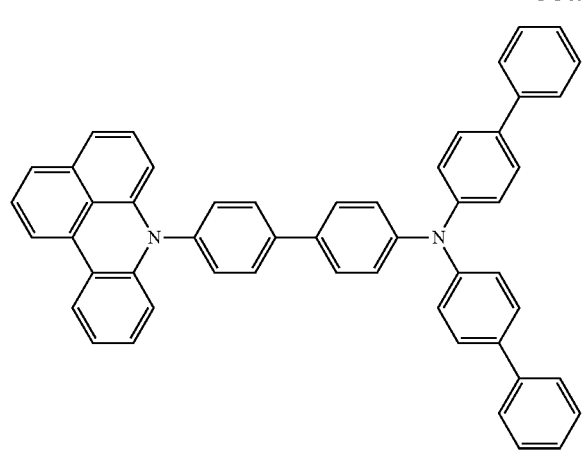
P 1-62
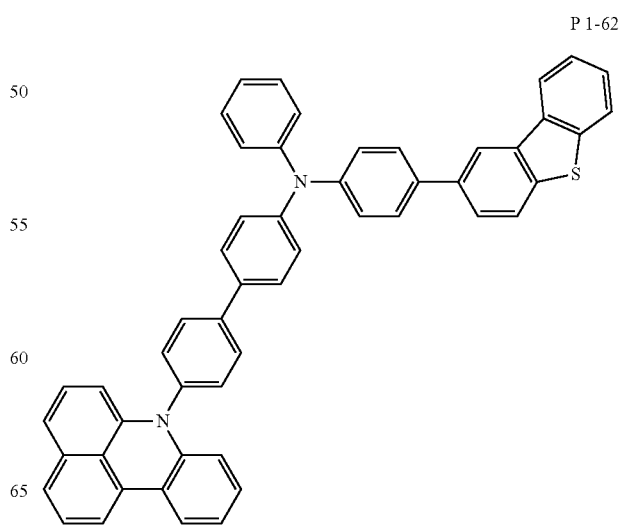

235
-continued
P 1-63
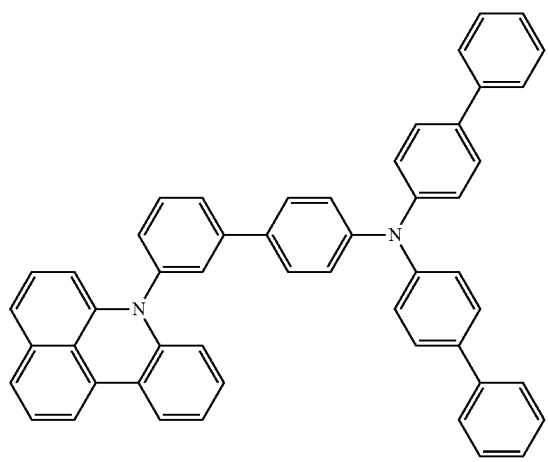
P 1-64
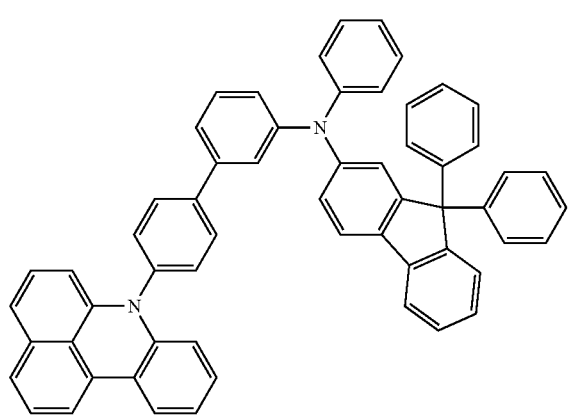
P 1-65
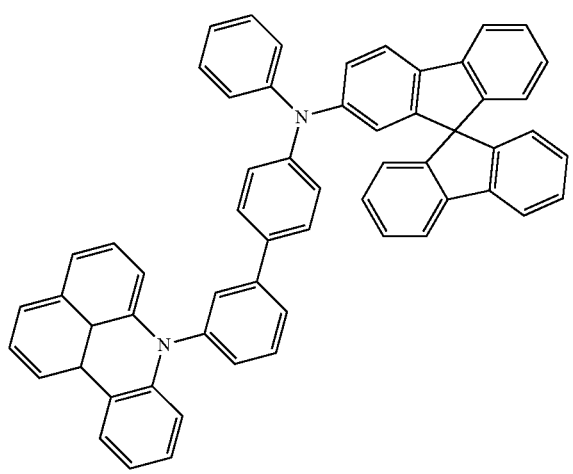
236
-continued
P 1-66
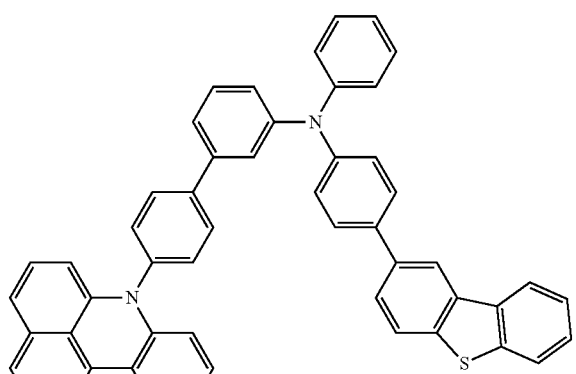
P 1-67
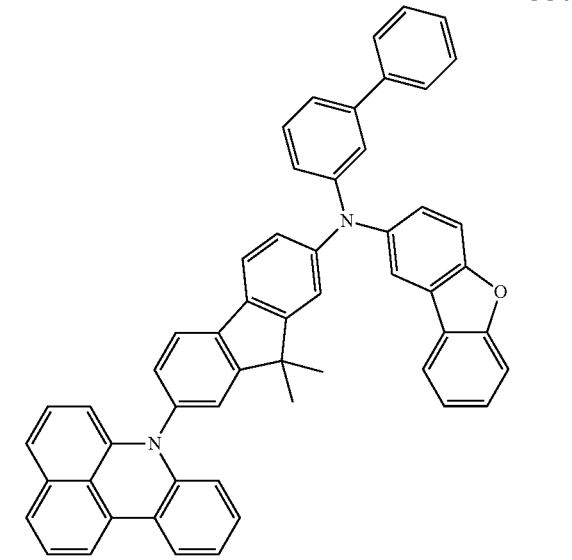
P 1-68
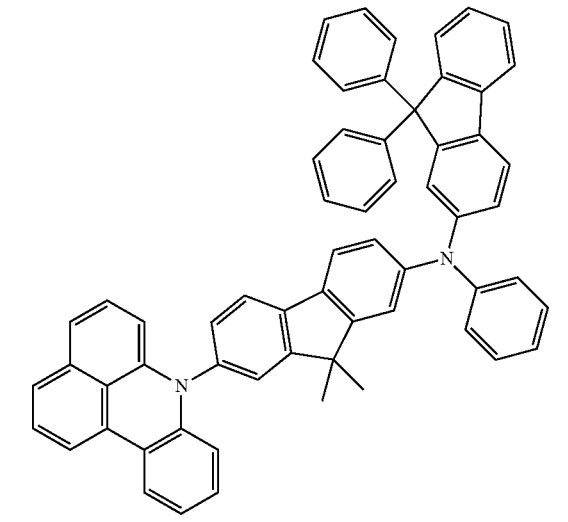

P 1-69
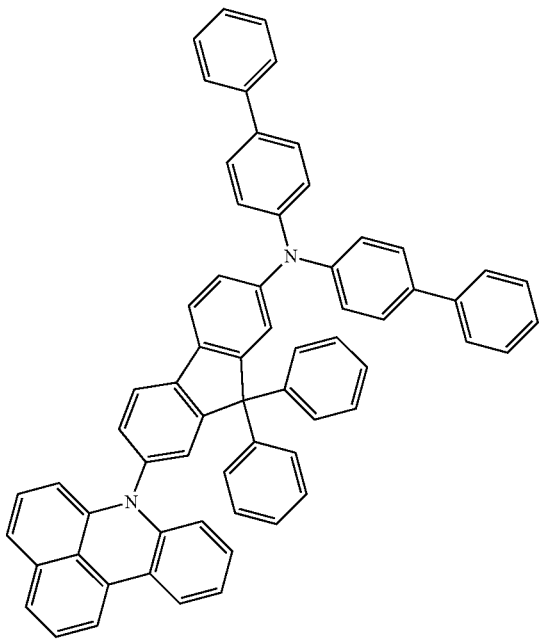
P 1-70
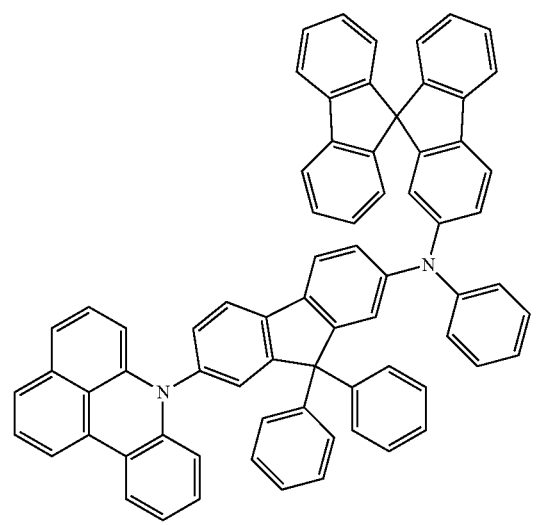
P 1-71
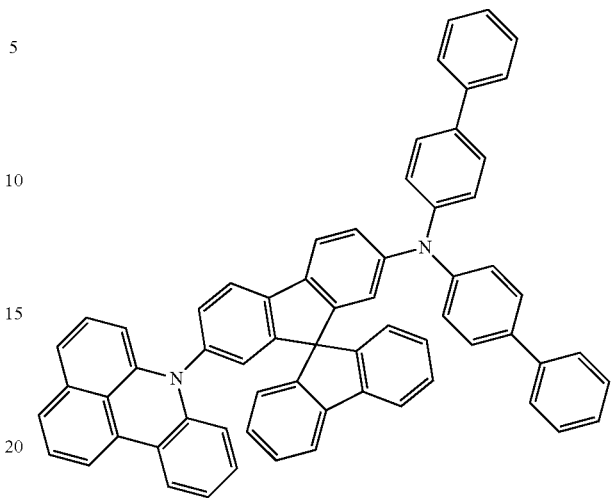
P 1-72
P 1-73
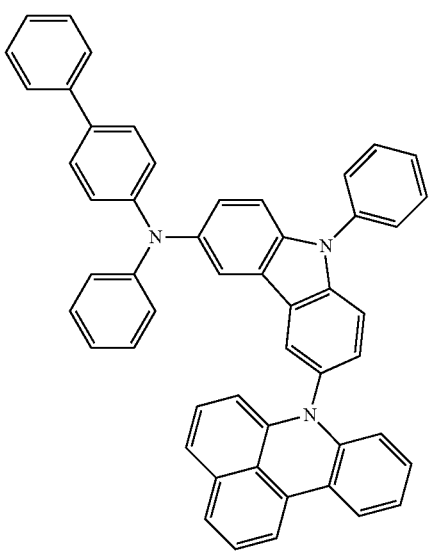

P 1-74
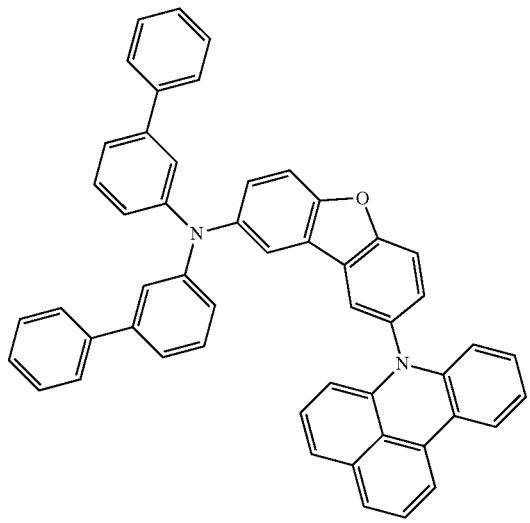
P 1-75
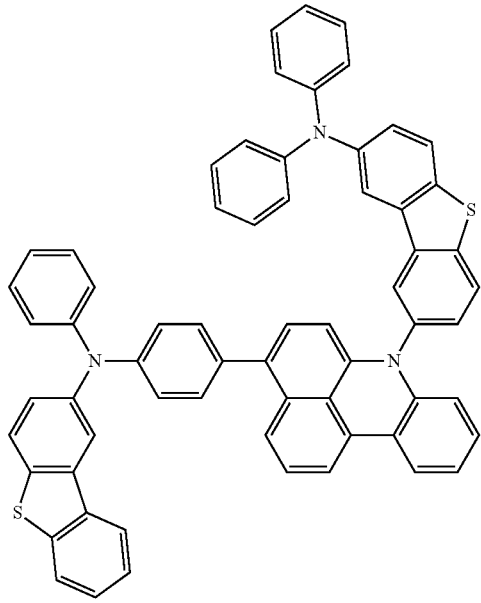
P 1-76
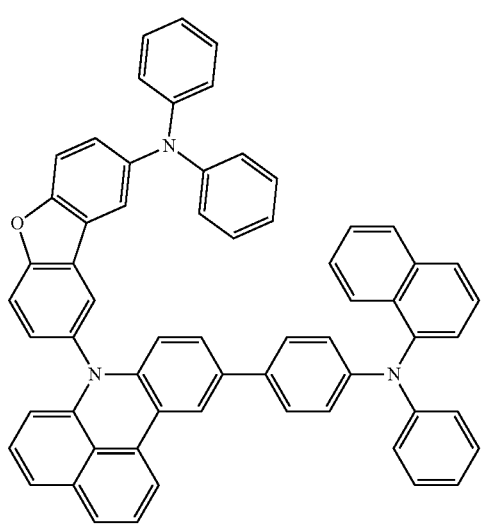
P 1-77
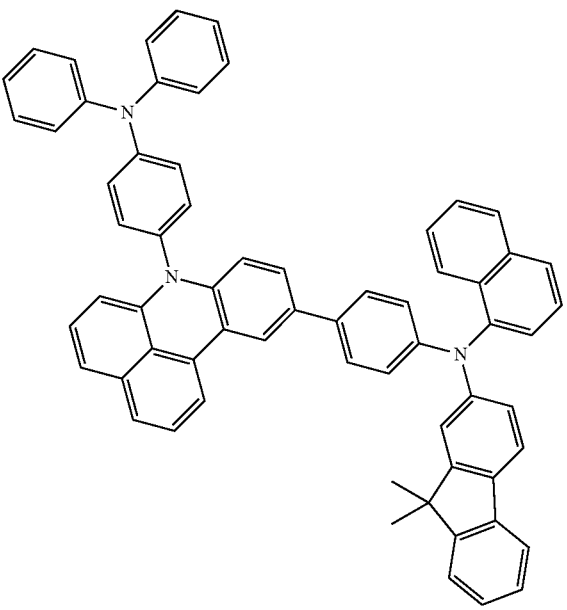
P 1-78
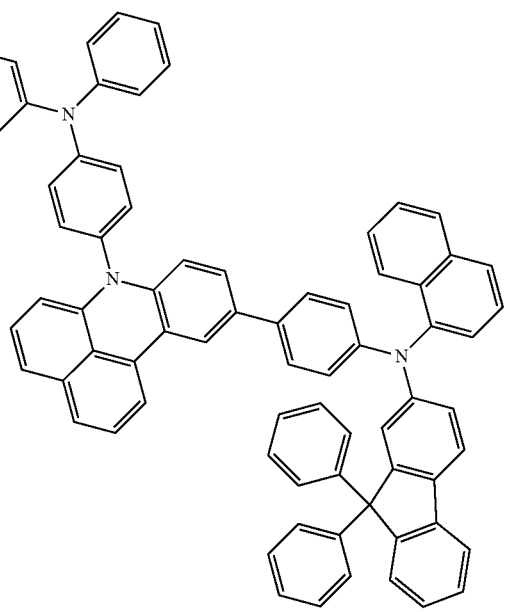

P 1-79

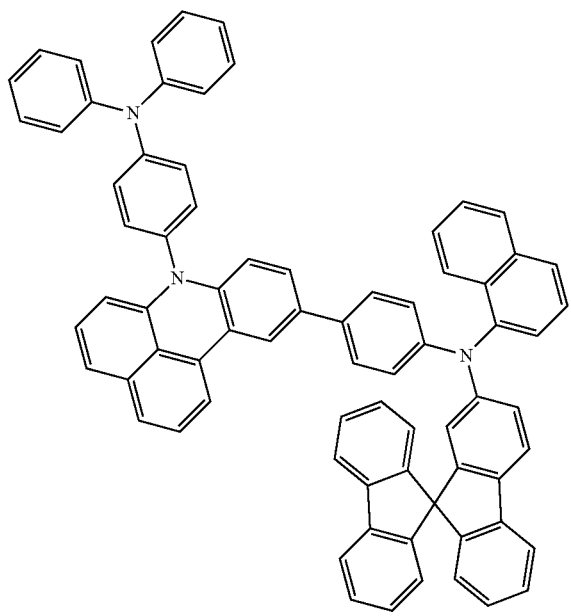

P 1-80

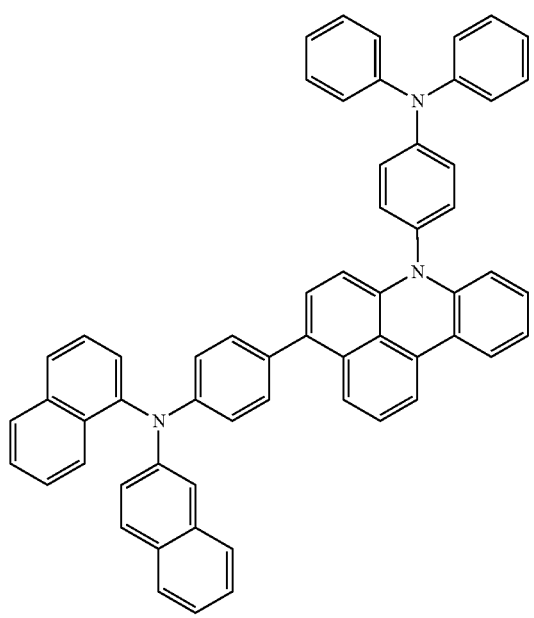

P 1-81

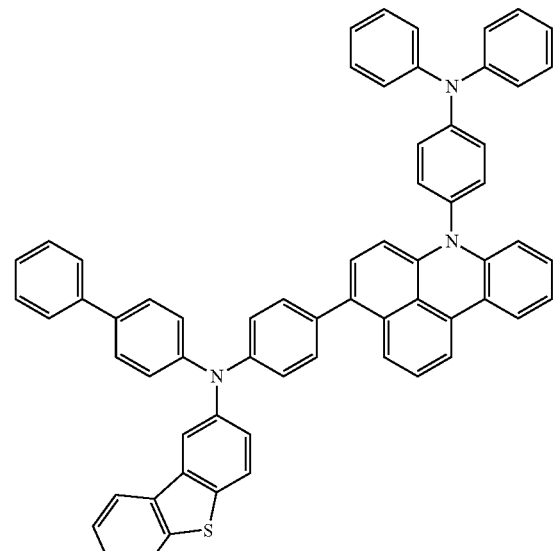

P 1-82

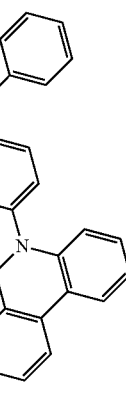

3. An organic electronic element, comprising:
a first electrode;
a second electrode; and
an organic material layer positioned between the first electrode and the second electrode, and containing the compound of claim 1.

4. The organic electronic element of claim 3, wherein the compound is contained in at least one of a hole injection layer, a hole transport layer, an auxiliary light emitting layer, and a light emitting layer of the organic material layer, the compound being a homogeneous compound or heterogeneous compounds of two or more kinds.

5. The organic electronic element of claim 3, further comprising a light efficiency improving layer formed on at least one of one surface of the first electrode and one surface of the second electrode, which are opposite to the organic material layer.

6. The organic electronic element of claim 3, wherein the organic material layer is formed by a spin coating process, a nozzle printing process, an inkjet printing process, a slot coating process, a dip coating process, or a roll-to-roll process.

7. An electronic device, comprising:
   a display device comprising the organic electronic element of claim 3, and
   a controller driving the display device.

8. The electronic device of claim 7, wherein the organic electronic element is one of an organic light emitting diode, an organic solar cell, an organic photo conductor, an organic transistor, and an element for a monochromatic or white illumination.

\* \* \* \* \*